(12) United States Patent
Bretschneider et al.

(10) Patent No.: US 7,238,697 B2
(45) Date of Patent: Jul. 3, 2007

(54) PYRIDYLPYRIMIDINES FOR USE AS PESTICIDES

(75) Inventors: Thomas Bretschneider, Lohmar (DE); Mazen Es-Sayed, Langenfeld (DE); Rüdiger Fischer, Pulheim (DE); Fritz Maurer, Monheim (DE); Christoph Erdelen, Leichlingen (DE); Peter Lösel, Leverkusen (DE)

(73) Assignee: Bayer CropScience AG, Monheim am Rhein (DE)

( * ) Notice: Subject to any disclaimer, the term of this patent is extended or adjusted under 35 U.S.C. 154(b) by 322 days.

(21) Appl. No.: 10/468,526

(22) PCT Filed: Feb. 11, 2002

(86) PCT No.: PCT/EP02/01403

§ 371 (c)(1),
(2), (4) Date: Aug. 19, 2003

(87) PCT Pub. No.: WO02/067684

PCT Pub. Date: Sep. 6, 2002

(65) Prior Publication Data

US 2004/0077641 A1  Apr. 22, 2004

(30) Foreign Application Priority Data

Feb. 22, 2001  (DE) ................ 101 08 481

(51) Int. Cl.
- C07D 401/04 (2006.01)
- C07D 401/14 (2006.01)
- C07D 405/14 (2006.01)
- A01N 43/54 (2006.01)
- A01N 43/647 (2006.01)

(52) U.S. Cl. ............ 514/256; 514/274; 514/275; 544/315; 544/318; 544/331; 544/333

(58) Field of Classification Search ............ 544/315, 544/318, 331, 333; 514/256, 274, 275
See application file for complete search history.

(56) References Cited

U.S. PATENT DOCUMENTS

| 3,910,910 A | 10/1975 | Santilli et al. ............ 260/251 R |
| 5,231,097 A | 7/1993 | Klausener et al. ........... 514/256 |

FOREIGN PATENT DOCUMENTS

| DE | 4031798 | 4/1992 |
| JP | 52-71481 | 6/1977 |
| WO | 94/29268 | 12/1994 |
| WO | WO 96/33972 | * 10/1996 |
| WO | 00/61586 | 10/2000 |
| WO | 01/84849 | 11/2001 |

OTHER PUBLICATIONS

J. Chem., Dalton Trans. (month unavailable) 1999, pp. 3095-3101, Hassan Aït-Haddou et al "New ruthenium(II) heteroleptic complexes containing the 4-(2-pyridyl)pyrimidine ligand with amine and amino acid substituents".
Tetrahedron Letters, 40, (month unavailable) 1999, pp. 4779-4782, Fen Wang et al, "A Convenient Set of Bidentate Pyridine Ligands for Combinatorial Synthesis".
Eur. J. Org. Chem., (month unavailable) 1998, pp. 2907-2912, Elena Bejan et al, "Enaminones in the Synthesis of New Polyaza Heterocycles".
J. Am. Chem. Soc., vol. 73, Dec. 1951, pp. 5614-5616, Robert Levine et al, "The Relative Reactivities of the Isomeric Methyl Pyridinecarboxylates in the Acylation of Certain Ketones. The Synthesis of β-Diketones Containing Pyridine Rings".
Chem. Ind. 37, Oct. 1985, pp. 730-732, Harry R. Ungerer, Schiffsfarben—eine Spezialität der seenanhen Lackindustrie.
**Patent Abstracts of Japan, vol. 17, No. 532 (P-1619), Sep. 24, 1993 & JP 05 143796 A (Ikuo Nagata), Jun. 11, 1993 Zweite Verbindung in der linken Spalte Seite 877.
**Sar et al.: "Synthesis Oxidation and Claisen Rearrangement of 4-(Allyloxy)phenyl-1,4-dihydropyridines and -pyrimidines" Ach Models Chem., Bd. 131, Nr. 3-4, 1994, Seiten 363-376, XP001070105 Verbindung 11h Seite 366.
**Corona Del L et al: "Synthesis and in Vitro Study of Platelet Antiaggregant Activity of 2(4)-Imidazol-1-YL-4(2)-Cycloalkylamino Pyrimidines" European Journal of Medicinal Chemistry, Editions Scientifique Elsevier, Paris, FR, Bd. 26, 1991, Seiten 729-733, XP002064599 ISSN: 0223-5234 Erste Verbindung in Scheme 2 Seite 730.

* cited by examiner

Primary Examiner—Deepak Rao
(74) Attorney, Agent, or Firm—Richard E. L. Henderson

(57) ABSTRACT

The present invention relates to novel pyridylpyrimidines of the formula

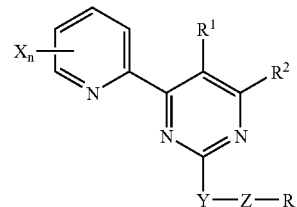

in which $R^1$, $R^2$, X, n, Y, Z and R have the meanings given in the disclosure, to a plurality of processes for preparing these compounds, and to their use for controlling pests. This invention further relates to novel intermediates and process for their preparation.

30 Claims, No Drawings

PYRIDYLPYRIMIDINES FOR USE AS PESTICIDES

The present patent application has been filed under 35 U.S.C. 371 as a national stage application of PCT/EP02/01403, filed Feb. 11, 2002, which was published in German as International Patent Publication WO 02/067684 on Sep. 6, 2002, and is entitled to the right of priority of German Patent Application 101 08 481.1, filed Feb. 22, 2001.

The present invention relates to novel pyridylpyrimidines, to a plurality of processes for their preparation and to their use as pesticides.

It is already known that certain pyridylpyrimidine derivatives have pharmaceutical action (cf. JP 52-71481). Other compounds of this type have been described as intermediates for fungicidally active compounds (cf. EP 0 471 261 B1). Still other derivatives are known as complex ligands (cf. J. Chem. Soc., Dalton Trans. 1999, 3095-3101, Tetrahedron Lett. 1999, 40, 4779-4782) or are used for synthesizing polycyclic heterocycles (cf. Eur. J. Org. Chem. 1998, 2907-2912). Insecticidally active pyridylpyrimidines have hitherto not been disclosed.

This invention now provides novel substituted pyridylpyrimidines of the formula (I)

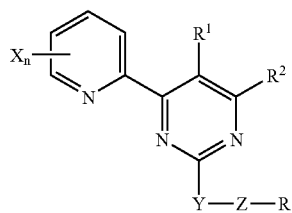

in which
$R^1$ and $R^2$ independently of one another represent hydrogen, halogen, nitro, cyano, alkyl, halogenoalkyl, alkoxy, halogenoalkoxy, alkylthio, halogenoalkylthio, alkenyl, alkinyl, alkenyloxy, halogenoalkenyloxy, alkinyloxy, halogenoalkinyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, cycloalkyl; or represent optionally substituted aryl, arylalkyl, saturated or unsaturated heterocyclyl having 1 to 4 heteroatoms from the group consisting of nitrogen, oxygen and sulphur,
$R^1$ and $R^2$ furthermore together represent alkylene or alkenylene, where the carbon chain may be interrupted by 1 to 3 heteroatoms from the group consisting of nitrogen and oxygen and the resulting ring for its part may optionally be substituted by halogen or alkyl,
X represents halogen, nitro, cyano, hydroxyl, alkyl, halogenoalkyl, alkoxy, halogenoalkoxy, alkylthio, halogenoalkylthio, alkenyl, alkinyl, alkenyloxy, halogenoalkenyloxy, alkinyloxy, halogenoalkinyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, cycloalkyl, aryl, arylalkyl, saturated or unsaturated heterocyclyl having 1 to 4 heteroatoms from the group consisting of nitrogen, oxygen and sulphur;
or, if n represents 2, 3 or 4, two adjacent radicals X furthermore together represent alkylene or alkenylene, where the carbon chain may be interrupted by 1 or 2 heteroatoms from the group consisting of nitrogen and oxygen,
n represents 0, 1, 2, 3 or 4, with X representing identical or different radicals if n represents 2, 3 or 4,
Y represents a direct bond, oxygen, —S(O)$_p$— or —NR$^9$—,
p represents 0, 1 or 2,
z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$— or —(CH$_2$)$_r$—C(R$^{12}$)=C(R$^{13}$)—(CH$_2$)$_w$—,
r represents 1, 2, 3, 4, 5 or 6,
t and w independently of one another represent 0, 1, 2, 3 or 4,
R represents the grouping

or represents a carboxylic acid bioisostere (acid mimetic), in particular from the group consisting of

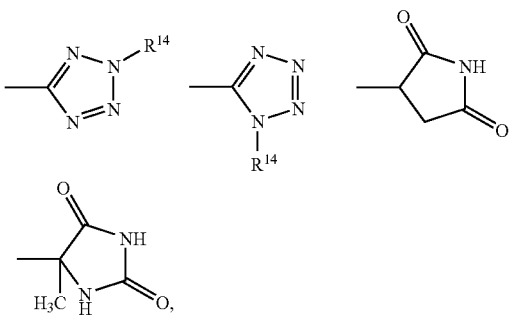

A represents oxygen, sulphur or NR$^{15}$,
E represents —OR$^{16}$, —SR$^{16}$, —O-M, —S-M or —NR$^{17}$R$^{18}$,
M represents ammonium which is optionally substituted by alkyl, aryl or arylalkyl or represents an alkali metal ion,
M furthermore represents an alkaline earth metal ion, where in each case two molecules of a compound form a salt with such an ion,
R$^3$ represents hydrogen, alkyl, halogenoalkyl, cycloalkyl, cycloalkylalkyl; or represents in each case optionally halogen-, alkyl-, halogenoalkyl-, alkoxy-, halogenoalkoxy-, alkylthio-, halogenoalkylthio-substituted aryl, arylalkyl, saturated or unsaturated heterocyclyl or heterocyclylalkyl having 1 to 4 heteroatoms from the group consisting of nitrogen, oxygen and sulphur,
R$^4$ represents hydrogen, alkyl, halogenoalkyl, cycloalkyl or alkylcarbonyl,
R$^5$ represents hydrogen, amino, formyl, alkyl, alkenyl, alkinyl, halogenoalkyl, cycloalkyl, alkoxy, alkoxyalkyl, alkylcarbonyl, alkoxycarbonyl, oxamoyl,
R$^4$ and R$^5$ furthermore together represent alkylidene; or represent optionally halogen-, nitro-, alkyl-, halogenoalkyl-substituted benzylidene;
R$^4$ and R$^5$ furthermore together with the nitrogen atom to which they are attached represent a saturated or unsaturated heterocycle which may optionally contain a further nitrogen, oxygen or sulphur atom and which may optionally be substituted by alkyl,
R$^6$ represents hydrogen, alkyl, halogenoalkyl or arylalkyl,
R$^7$ represents hydrogen, alkyl, halogenoalkyl, cycloalkyl, cycloalkylalkyl, aryl or arylalkyl,
R$^8$ represents alkyl or halogenoalkyl,
R$^9$ represents hydrogen, alkyl, halogenoalkyl, cycloalkyl, cycloalkylalkyl; or represents in each case optionally halogen-, alkyl-, halogenoalkyl-, alkoxy-, halogenoalkoxy-, alkylthio-, halogenoalkylthio-substituted aryl, arylalkyl, saturated or unsaturated heterocyclyl or heterocyclylalkyl having 1 to 4 heteroatoms from the group consisting of nitrogen, oxygen and sulphur, $R^{10}$ represents halogen, alkyl, alkylcarbonyl, alkoxycarbonyl, cycloalkyl, cycloalkylalkyl; or represents aryl or arylalkyl which for their part may be substituted in the aryl moiety by halogen or alkyl, $R^{11}$ represents hydrogen or alkyl, $R^{12}$ and $R^{13}$ independently of one another represent hydrogen, hydroxyl, alkyl or alkoxy, $R^{14}$ represents hydrogen, alkyl or halogenoalkyl, $R^{15}$ represents hydrogen, alkyl, alkoxy, cyano or dialkylamino, $R^{16}$ represents hydrogen; represents in each case optionally halogen-, amino-, hydroxyl-, cyano-, nitro-, alkoxy-, halogenoalkoxy-, alkylthio-, halogenoalkylthio-, alkoxycarbonyl-, alkenyloxycarbonyl-, alkylcarbonyloxy-, alkenylcarbonyloxy-, oxyalkyleneoxy-, oxetanyl-, dioxanyl-, oxazolidinyl-, dioxolanyl-, aryloxy-, halogenoaryloxy-, —CONR$^4$R$^5$—, —NR$^4$R$^5$—, —ONR$^4$R$^5$—, —C(R$^{14}$)=N—OR$^{14}$-substituted alkyl, alkenyl, alkinyl; or represents in each case optionally halogen-, alkyl-, halogenoalkyl-, alkoxy-, halogenoalkoxy-, alkylthio-, halogenoalkylthio-, alkoxycarbonyl-, alkylcarbonyloxy-substituted aryl, arylalkyl, cycloalkyl, cycloalkylalkyl, saturated or unsaturated heterocyclyl or heterocyclylalkyl having 1 to 4 heteroatoms from the group consisting of nitrogen, oxygen and sulphur; or represents —NR$^4$R$^5$ or represents one of the radicals Q, $R^{16}$ furthermore represents in each case optionally substituted aryl, arylalkyl, cycloalkyl, cycloalkylalkyl, saturated or unsaturated heterocyclyl or heterocyclylalkyl having 1 to 4 heteroatoms from the group consisting of nitrogen, oxygen and sulphur, where the substituents may, in addition to those mentioned above, be selected from the group consisting of hydroxyl and nitro, $R^{17}$ represents hydrogen or alkyl, $R^{18}$ represents hydrogen, hydroxyl, amino, alkyl, alkenyl; or represents in each case optionally halogen-, hydroxyl-, alkyl-, halogenoalkyl-, alkoxy-, halogenoalkoxy-, alkylthio-, halogenoalkylthio-, oxyalkyleneoxy-substituted cycloalkyl, cycloalkylalkyl, aryl, arylalkyl, heteroaryl or heteroarylalkyl having 1 to 4 heteroatoms from the group consisting of nitrogen, oxygen and sulphur; or represents —S(O)$_p$R$^3$, —OR$^{14}$ or —NR$^4$R$^5$, $R^{18}$ furthermore represents alkyl or alkenyl, each of which is substituted by identical or different substituents from the group consising of halogen, amino, hydroxyl, cyano, nitro, alkoxy, halogenoalkoxy, alkylthio, halogenoalkylthio, alkoxycarbonyl and alkenyloxycarbonyl, $R^{18}$ furthermore represents in each case optionally substituted cycloalkyl, cycloalkylalkyl, aryl, arylalkyl, heteroaryl or heteroarylalkyl having 1 to 4 heteroatoms from the group consisting of nitrogen, oxygen and sulphur, where the substituents may, in addition to those mentioned above, be selected from the group consisting of nitro and alkoxycarbonyl, $R^{17}$ and $R^{18}$ furthermore together with the nitrogen atom to which they are attached represent a 5- or 6-membered saturated or unsaturated heterocycle which may contain 1 to 2 further heteroatoms from the group consisting of nitrogen, oxygen and sulphur and which may optionally be substituted by alkyl, Q represents one of the groupings below

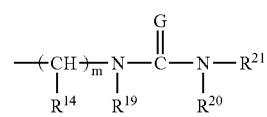
(Q$^1$)

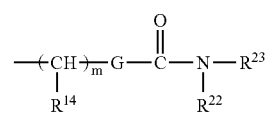
(Q$^2$)

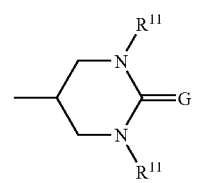
(Q$^3$)

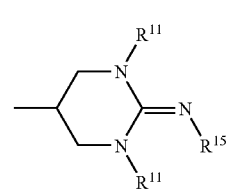
(Q$^4$)

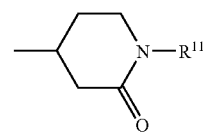
(Q$^5$)

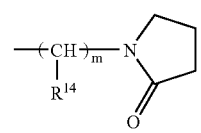
(Q$^6$)

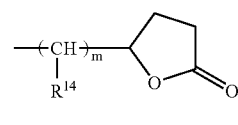
(Q$^7$)

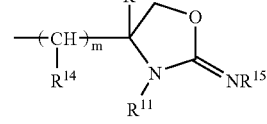
(Q$^8$)

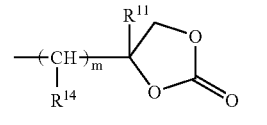
(Q$^9$)

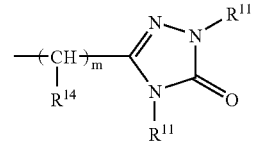
(Q$^{10}$)

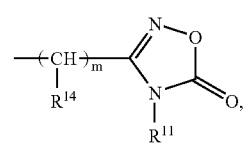
(Q$^{11}$)

where the radicals $R^{11}$ may have identical or different meanings if two or more are present in the same heterocyclic grouping, m represents 0, 1, 2 or 3, where the repeat unit —(CHR$^{14}$)— in the side chain of a heterocyclic grouping may have identical or different meanings if m represents 2 or 3, G represents oxygen or sulphur, $R^{19}$ and $R^{20}$ independently of one another represent hydrogen, alkyl or together represent alkylene, $R^{21}$ represents hydrogen, represents optionally alkylcarbonyloxy- or alkoxy-substituted alkyl; or represents optionally halogen-, cyano-, alkyl-, halogenoalkyl-, alkylcarbonyl-, alkoxycarbonyl-, alkylene-substituted aryl, $R^{22}$ represents hydrogen, alkyl or alkoxyalkyl, $R^{23}$ represents hydrogen, amino, alkyl or alkoxyalkyl Depending on the type and number of substituents, the compounds of the formula (I) may, if appropriate, be present as geometrical and/or optical isomers or regioisomers or isomer mixtures thereof in varying compositions. What is claimed by the invention are both the pure isomers and the isomer mixtures. Furthermore, compounds of the formula (I) can, if appropriate, be present in various tautomeric forms, depending on the type and number of substituents. What is claimed by the invention are all tautomers.

The invention also claims all pyridine and/or pyrimidine N-oxides which can be formed by compounds of the formula (I). Furthermore, the invention claims all salts of compounds of the formula (I), for example with mineral acids such as hydrochloric acid.

Furthermore, it has been found that pyridylpyrimidines of the formula (I-a)

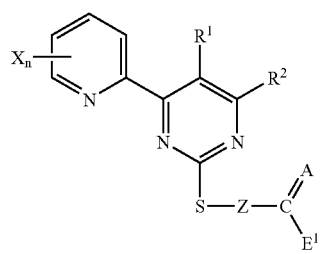

(I-a)

in which $R^1$, $R^2$, X, n, Z and A have the meanings given above and $E^1$ represents —OR$^{16}$, —SR$^{16}$ or —NR$^{17}$R$^{18}$ are obtained by A) reacting thiols of the formula (II)

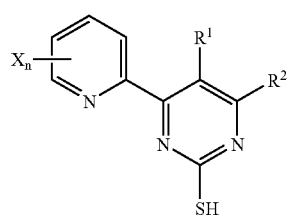

(II)

in which $R^1$, $R^2$, X and n have the meanings given above with halogen compounds of the formula (III)

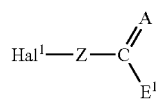

(III)

in which

Z, A and $E^1$ have the meanings given above and

Hal$^1$ represents halogen if appropriate in the presence of a diluent and if appropriate in the presence of an acid binder, or B) reacting halogenopyrimidines of the formula (IV)

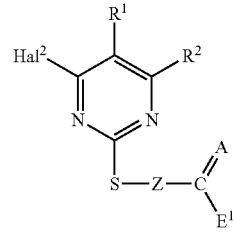

(IV)

in which $R^1$, $R^2$, Z, A and $E^1$ have the meanings given above and Hal$^2$ represents halogen with pyridine compounds of the formula (V)

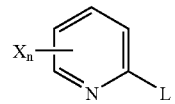

(V)

in which

X and n have the meanings given above and

L represents Sn(alkyl)$_3$, Sn(aryl)$_3$, ZnBr or ZnCl, if appropriate in the presence of a diluent and in the presence of a catalyst, or C) that pyridylpyrimidines of the formula (I-b)

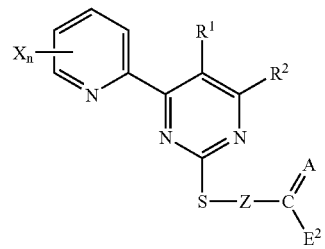

(I-b)

in which $R^1$, $R^2$, X, n, Z and A have the meanings given above and $E^2$ represents —NR$^{17}$R$^{18}$ are obtained by treating pyridylpyrimidines of the formula (I-c)

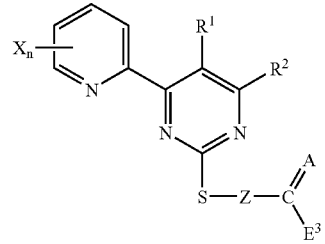

(I-c)

in which $R^1$, $R^2$, X, n, Z and A have the meanings given above and $E^3$ represents —OR$^{16}$, where R$^{16}$ has the meanings given above, in, a first step, if appropriate in the presence of a diluent, with a base and reacting the resulting compound of the formula (I-d)

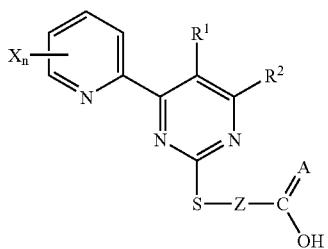

(I-d)

in which
R¹, R², X, n, Z and A have the meanings given above
in a second step with amines of the formula (VI)

HNR¹⁷R¹⁸ (VI)

in which
R¹⁷ and R¹⁸ have the meanings given above,
if appropriate in the presence of a diluent and in the presence of a water-absorbing reagent, or
D) that pyridylpyrimidines of the formula (I-e)

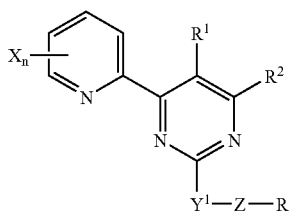

(I-e)

in which
R¹, R², X, n, Z and R have the meanings given above and
Y¹ represents —SO— or —SO₂—
are obtained by
oxidizing pyridylpyrimidines of the formula (I-f)

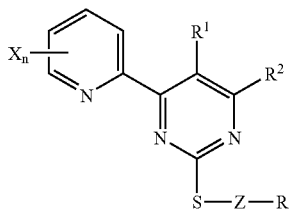

(I-f)

in which
R¹, R², X, n, Z and R have the meanings given above,
with an oxidizing agent, if appropriate in the presence of a diluent, if appropriate in the presence of an acid binder and if appropriate in the presence of a catalyst, or
E) that pyridylpyrimidines of the formula (I-g)

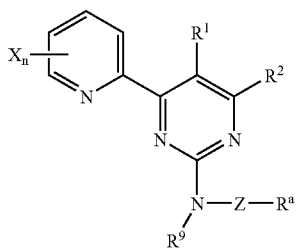

(I-g)

in which
R¹, R², X, n, Z and R⁹ have the meanings given above and
Rᵃ represents one of the groupings below

in which
R¹⁴ has the meanings given above
are obtained by
reacting methylsulphonylpyrimidines of the formula (VII)

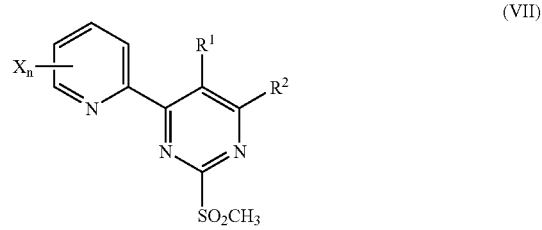

(VII)

in which
R¹, R², X and n have the meanings given above,
with amines of the formula (VIII)

(VIII)

in which
Z, R⁹ and Rᵃ have the meanings given above,
if appropriate in the presence of a diluent and if appropriate in the presence of a base, or
F) that pyridylpyrimidines of the formula (I-h)

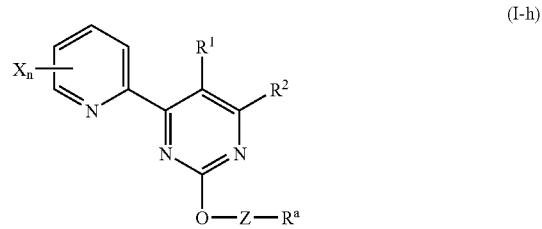

(I-h)

in which
R¹, R², X, n, Z and Rᵃ have the meanings given above,
are obtained by
reacting methylsulphonylpyrimidines of the formula (VII)

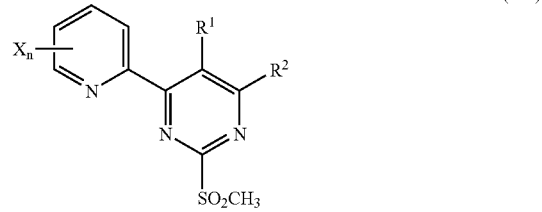

(VII)

in which
R¹, R², X and n have the meanings given above with hydroxyl compounds of the formula (IX)

$$HO-Z-R^a \quad (IX)$$

in which
Z and $R^a$ have the meanings given above,
if appropriate in the presence of a diluent and if appropriate in the presence of a base, or G) that pyridylpyrimidines of the formula (I-i)

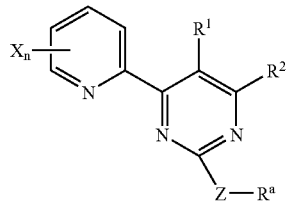

(I-i)

in which
$R^1$, $R^2$, X, n, Z and $R^a$ have the meanings given above
are obtained by
reacting pyridine derivatives of the formula (X)

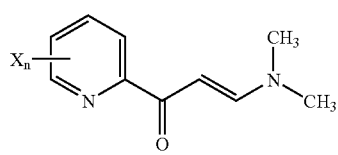

(X)

in which
X and n have the meanings given above,
or pyridine-derivatives of the formula (XI)

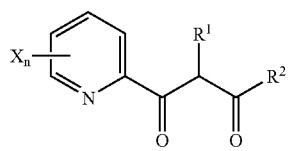

(XI)

in which
$R^1$, $R^2$, X and n have the meanings given above,
with amidines of the formula (XII)

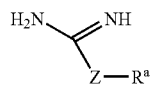

(XII)

in which
Z and $R^a$ have the meanings given above,
if appropriate in the presence of a diluent and if appropriate in the presence of a base, or H) that pyridylpyrimidines of the formula (I-j)

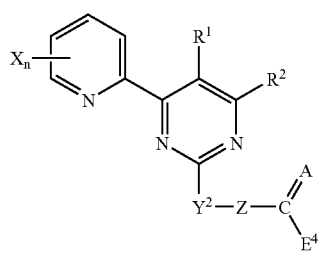

(I-j)

in which
$Y^2$ represents a direct bond, oxygen, sulphur or $-NR^9-$, $E^4$ represents $-O-M$ or $-S-M$ and
$R^1$, $R^2$, X, n, Z, A and M have the meanings given above,
are obtained by
reacting pyridylpyrimidines of the formula (I-k)

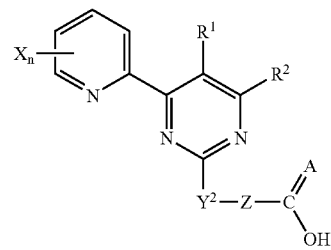

(I-k)

in which
$R^1$, $R^2$, X, n, $Y^2$, Z and A have the meanings given above,
with hydroxides of the formula (XIII)

$$M\ OH- \quad (XIII)$$

in which
M has the meanings given above,
if appropriate in the presence of a diluent, or J) that pyridylpyrimidines of the formula (I-l)

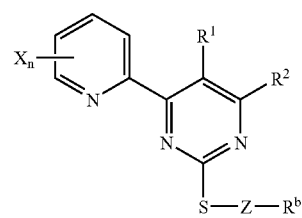

(I-l)

in which
$R^1$, $R^2$, X, n, Y and Z have the meanings given above and
$R^b$ represents one of the groupings below

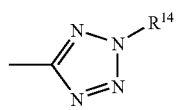 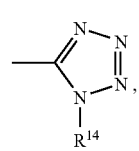

in which $R^{14}$ has the meanings given above
are obtained by
reacting nitrites of the formula (XIV)

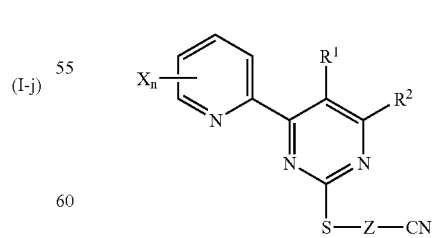

(XIV)

in which
$R^1$, $R^2$, X, n and Z have the meanings given above
with trialkyltin azides, if appropriate in the presence of a diluent, or K) that pyridylpyrimidines of the formula (I-m)

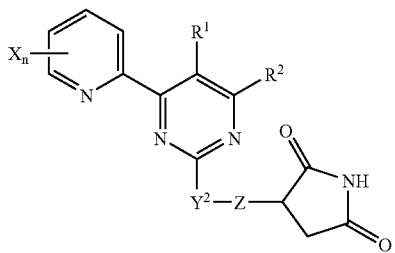

(I-m)

in which
$R^1$, $R^2$, X, n, $Y^2$ and Z have the meanings given above,
are obtained by
hydrogenating pyridylpyrimidines of the formula (I-n)

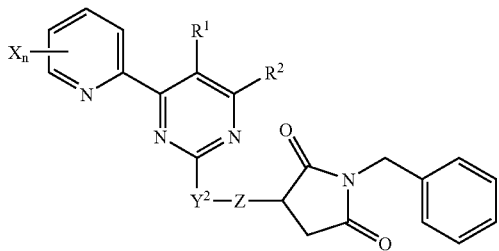

(I-n)

in which
$R^1$, $R^2$, X, n, $Y^2$ and Z have the meanings given above,
if appropriate in the presence of a diluent and in the presence of a catalyst, or L) that pyridylpyrimidines of the formula (I-o)

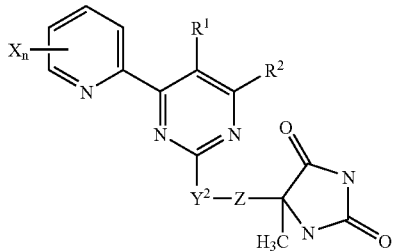

(I-o)

in which
$R^1$, $R^2$, X, n, $Y^2$ and Z have the meanings given above,
are obtained by
reacting keto compounds of the formula (XV)

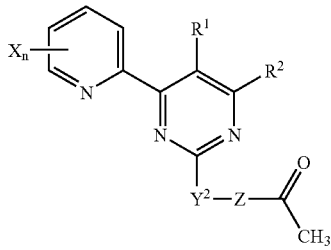

(XV)

in which
$R^1$, $R^2$, X, n, $Y^2$ and Z have the meanings given above, with ammonium carbonate and potassium cyanide, if appropriate in the presence of a diluent.

Finally, it has been found that the compounds of the formula (I) according to the invention have very good insecticidal properties and can be used both in crop protection and in the protection of materials for controlling undesirable pests such as insects. Hitherto, nothing has been disclosed in the prior art about any insecticidal activity of pyridylpyrimidines.

The formula (I) provides a general definition of the pyridylpyrimidines according to the invention.

$R^1$ and $R^2$ independently of one another preferably represent hydrogen, halogen, nitro, cyano, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, $C_1$-$C_6$-halogenoalkylthio, $C_2$-$C_6$-alkenyl, $C_2$-$C_6$-alkinyl, $C_2$-$C_6$-alkenyloxy, $C_2$-$C_6$-halogenoalkenyloxy, $C_2$-$C_6$-alkinyloxy, $C_2$-$C_6$-halogenoalkinyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, $C_3$-$C_7$-cycloalkyl; or represent aryl, aryl-$C_1$-$C_6$-alkyl or 5- or 6-membered saturated or unsaturated heterocyclyl which contains 0 to 3 nitrogen atoms, 0 to 2 nonadjacent oxygen atoms and/or 0 to 2 nonadjacent sulphur atoms, each of which radicals is optionally mono- or polysubstituted by identical or different substituents from the group consisting of halogen, $C_1$-$C_6$-alkyl, $C_1$-$C_6$-halogenoalkyl, $C_1$-$C_6$-alkoxy and $C_1$-$C_6$-halogenoalkoxy.

$R^1$ and $R^2$ furthermnore together preferably represent $C_3$-$C_5$-alkylene or $C_3$-$C_4$-alkenylene, where the carbon chain may be interrupted by 1 or 2 heteroatoms including 0 to 2 nitrogen atoms and/or 0 or 1 oxygen atom, and where the resulting ring for its part may optionally be mono- or polysubstituted by identical or different substituents from the group consisting of halogen and $C_1$-$C_6$-alkyl.

X preferably represents halogen, nitro, cyano, hydroxyl, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, $C_1$-$C_6$-halogenoalkylthio, $C_2$-$C_6$-alkenyl, $C_2$-$C_6$-alkinyl, $C_2$-$C_6$-alkenyloxy, $C_2$-$C_6$-halogenoalkenyloxy, $C_2$-$C_6$-alkinyloxy, $C_2$-$C_6$-halogenoalkinyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, $C_3$-$C_7$-cycloalkyl, aryl, aryl-$C_1$-$C_6$-alkyl, 5- or 6-membered saturated or unsaturated heterocyclyl which contains 0 to 4 nitrogen atoms, 0 to 2 nonadjacent oxygen atoms and/or 0 to 2 nonadjacent sulphur atoms, or, if n represents 2 or 3, two adjacent radicals X furthermore together preferably represent $C_3$-$C_5$-alkylene or $C_3$-$C_4$-alkenylene, where the carbon chain may be interrupted by 1 or 2 heteroatoms including 0 to 2 nitrogen atoms and/or 0 or 1 oxygen atom.

n preferably represents 0, 1, 2 or 3, with X representing identical or different radicals if n reprsents 2 or 3.

Y preferably represents a direct bond, oxygen, —S(O)$_p$— or —NR$^9$—.

p preferably represents 0, 1 or 2.

Z preferably represents —(CH$_2$)$_r$—, —(CH$_2$)$_t$—(CHR$^{10}$)—(CH$_2$)$_w$—, —(CH$_2$)$_t$—C(O)—(CH$_2$)$_t$—, —(CH$_2$)$_r$—O—(CH$_2$)$_t$—, —(CH$_2$)$_t$—S(O)$_p$—(CH$_2$)$_t$—, —(CH$_2$)$_t$—N(R$^{11}$)—(CH$_2$)$_t$— or —(CH$_2$)$_t$—C(R$^{12}$)=C(R$^{13}$)—(CH$_2$)$_w$—.

r preferably represents 1, 2, 3, 4, 5 or 6.

t and w independently of one another preferably represent 0, 1, 2, 3 or 4.

R preferably represents the grouping

or represents a carboxylic acid bioisostere (acid mimetic), in particular from the group consisting of

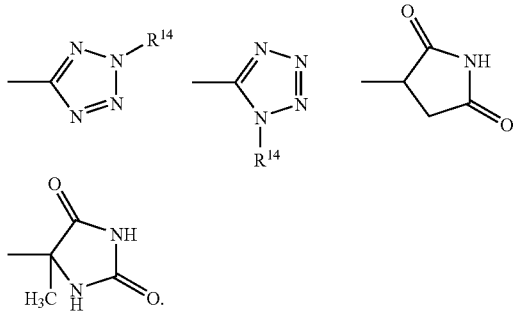

A preferably represents oxygen, sulphur or $NR^{15}$.

E preferably represents $-OR^{16}$, $-SR^{16}$, $-O-M$, $-S-M$ or $-NR^{17}R^{18}$.

M preferably represents ammonium which is optionally mono- to tetrasubstituted by identical or different substituents from the group consisting of $C_1$-$C_6$-alkyl, aryl and aryl-$C_1$-$C_6$-alkyl, or represents a lithium cation ($Li^+$), a sodium cation ($Na^+$) or a potassium cation ($K^+$).

M furthermore preferably represents a magnesium cation ($Mg^{2+}$) or a calcium cation ($Ca^{2+}$), where in each case two molecules of a compound form a salt with such an ion.

$R^3$ preferably represents hydrogen, $C_1$-$C_6$-alkyl, $C_1$-$C_6$-halogenoalkyl, $C_3$-$C_7$-cycloalkyl, $C_3$-$C_7$-cycloalkyl-$C_1$-$C_6$-alkyl; or represents aryl, aryl-$C_1$-$C_6$-alkyl, 5- or 6-membered saturated or unsaturated heterocyclyl or heterocyclyl-$C_1$-$C_6$-alkyl, each of which contains 0 to 4 nitrogen atoms, 0 to 2 nonadjacent oxygen atoms and/or 0 to 2 nonadjacent sulphur atoms, each of which radicals is optionally mono- or polysubstituted by identical or different substituents from the group consisting of halogen, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio and $C_1$-$C_6$-halogenoalkylthio.

$R^4$ preferably represents hydrogen, $C_1$-$C_6$-alkyl, $C_1$-$C_6$-halogenoalkyl, $C_3$-$C_7$-cycloalkyl, $C_1$-$C_6$-alkylcarbonyl.

$R^5$ preferably represents hydrogen, amino, formyl, $C_1$-$C_6$-alkyl, $C_2$-$C_6$-alkenyl, $C_2$-$C_6$-alkinyl, $C_1$-$C_6$-halogenoalkyl, $C_3$-$C_7$-cycloalkyl, $C_1$-$C_6$-alkoxy, $C_1$-$C_6$-alkoxy-$C_1$-$C_6$-alkyl, $C_1$-$C_6$-alkylcarbonyl, $C_1$-$C_6$-alkoxycarbonyl, oxamoyl.

$R^4$ and $R^5$ furthermore together preferably represent $C_1$-$C_6$-alkylidene; or represent benzylidene which is optionally mono- or polysubstituted by identical or different substituents from the group consisting of halogen, nitro, $C_1$-$C_6$-alkyl and $C_1$-$C_6$-halogenoalkyl.

$R^4$ and $R^5$ furthermore together with the nitrogen atom to which they are attached preferably represent a 5- or 6-membered saturated or unsaturated heterocyle which may optionally contain a further nitrogen, oxygen or sulphur atom and which may optionally be mono- or polysubstituted by identical or different $C_1$-$C_6$-alkyl.

$R^6$ preferably represents hydrogen, $C_1$-$C_6$-alkyl, $C_1$-$C_6$-halogenoalkyl or aryl-$C_1$-$C_6$-alkyl.

$R^7$ preferably represents hydrogen, $C_1$-$C_6$-alkyl, $C_1$-$C_6$-halogenoalkyl, $C_3$-$C_7$-cycloalkyl, $C_3$-$C_7$-cycloalkyl-$C_1$-$C_6$-alkyl, aryl or aryl-$C_1$-$C_6$-alkyl.

$R^8$ preferably represents $C_1$-$C_6$-alkyl or $C_1$-$C_6$-halogenoalkyl.

$R^9$ preferably represents hydrogen, $C_1$-$C_6$-alkyl, $C_1$-$C_6$-halogenoalkyl, $C_3$-$C_7$-cycloalkyl, $C_3$-$C_7$-cycloalkyl-$C_1$-$C_6$-alkyl; or represents aryl, aryl-$C_1$-$C_6$-alkyl, 5- or 6-membered saturated or unsaturated heterocyclyl or heterocyclyl-$C_1$-$C_6$-alkyl, each of which contains 0 to 4 nitrogen atoms, 0 to 2 nonadjacent oxygen atoms and/or 0 to 2 nonadjacent sulphur atoms, each of which radicals is optionally mono- or polysubstituted by identical or different substituents from the group consisting of halogen, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio and $C_1$-$C_6$-halogenoalkylthio.

$R^{10}$ preferably represents halogen, $C_1$-$C_6$-alkyl, $C_1$-$C_6$-alkylcarbonyl, $C_1$-$C_6$-alkoxycarbonyl, $C_3$-$C_7$-cycloalkyl, $C_3$-$C_7$-cycloalkyl-$C_1$-$C_6$-alkyl; or represents aryl or aryl-$C_1$-$C_6$-alkyl which for their part may be mono- or polysubstituted in the aryl moiety by identical or different substitutents from the group consisting of halogen and $C_1$-$C_6$-alkyl.

$R^{11}$ preferably represents hydrogen or $C_1$-$C_6$-alkyl.

$R^{12}$ and $R^{13}$ independently of one another preferably represent hydrogen, hydroxyl, $C_1$-$C_6$-alkyl or $C_1$-$C_6$-alkoxy.

$R^{14}$ preferably represents hydrogen, $C_1$-$C_6$-alkyl or $C_1$-$C_6$-halogenoalkyl.

$R^{15}$ preferably represents hydrogen, $C_1$-$C_6$-alkyl, $C_1$-$C_6$-alkoxy, cyano or di($C_1$-$C_6$-alkyl)amino.

$R^{16}$ preferably represents hydrogen; represents $C_1$-$C_{16}$-alkyl, $C_2$-$C_{10}$-alkenyl, $C_2$-$C_6$-alkinyl, each of which is optionally mono- or polysubstituted by identical or different substituents from the group consisting of halogen, amino, hydroxyl, cyano, nitro, $C_1$-$C_6$-alkoxy, $C_1$-$C_6$-halogenoalkoxy, $C_1$-$C_6$-alkylthio, $C_1$-$C_6$-halogenoalkylthio, $C_1$-$C_6$-alkoxycarbonyl, $C_2$-$C_6$-alkenyloxycarbonyl, $C_1$-$C_6$-alkylcarbonyloxy, $C_2$-$C_6$-alkenylcarbonyloxy, oxy($C_1$-$C_6$-alkylene)oxy, oxetanyl, dioxanyl, oxazolidinyl, dioxolanyl, aryloxy, halogenoaryloxy, $-CONR^4R^5$, $-NR^4R^5$, $-ONR^4R^5$ and $-C(R^{14})=N-OR^{14}$; or represents aryl, aryl-$C_1$-$C_6$-alkyl, $C_3$-$C_7$-cycloalkyl, $C_3$-$C_7$-cycloalkyl-$C_1$-$C_6$-alkyl, 4- to 6-membered saturated or unsaturated heterocyclyl or heterocyclyl-$C_1$-$C_6$-alkyl, each of which contains 0 to 4 nitrogen atoms, 0 to 2 nonadjacent oxygen atoms and/or 0 to 2 nonadjacent sulphur atoms, each of which radicals is optionally mono- or polysubstituted by identical or different substituents from the group consisting of halogen, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, $C_1$-$C_6$-halogenoalkylthio, $C_1$-$C_6$-alkoxycarbonyl and $C_1$-$C_6$-alkylcarbonyloxy; or represents $-NR^4R^5$ or represents one of the radicals Q.

$R^{16}$ furthermore preferably represents aryl, aryl-$C_1$-$C_6$-alkyl, $C_3$-$C_7$-cycloalkyl, $C_3$-$C_7$-cycloalkyl-$C_1$-$C_6$-alkyl, 4- to 6-membered saturated or unsaturated heterocyclyl or heterocyclyl-$C_1$-$C_6$-alkyl, each of which contains 0 to 4 nitrogen atoms, 0 to 2 nonadjacent oxygen atoms and/or 0 to 2 nonadjacent sulphur atoms, each of which radicals is optionally mono- or polysubstituted by identical or different substituents, where the substitutents may, in addition to those mentioned above, be selected from the group consisting of hydroxyl and nitro.

$R^{17}$ preferably represents hydrogen or $C_1$-$C_6$-alkyl.

$R^{18}$ preferably represents hydrogen, hydroxyl, amino, $C_1$-$C_6$-alkyl, $C_2$-$C_6$-alkenyl; or represents $C_3$-$C_7$-cycloalkyl, $C_3$-$C_7$-cycloalkyl-$C_1$-$C_6$-alkyl, aryl, aryl-$C_1$-$C_6$-alkyl, heteroaryl or heteroaryl-$C_1$-$C_6$-alkyl, each of which contains 0 to 4 nitrogen atoms, 0 to 2 nonadjacent oxygen atoms and/or 0 to 2 nonadjacent sulphur atoms, each of which radicals is optionally mono- or polysubstituted by identical or different substituents from the group consisting of halogen, hydroxyl, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, $C_1$-$C_6$-halogenoalkylthio and oxy($C_1$-$C_6$-alkylene)oxy; or represents —$S(O)_pR^3$, —$OR^{14}$ or —$NR^4R^5$.

$R^{18}$ furthermore preferably represents $C_1$-$C_6$-alkyl or $C_2$-$C_6$-alkenyl, each of which is optionally mono- or polysubstituted by identical or different substituents from the group consisting of halogen, amino, hydroxyl, cyano, nitro, $C_1$-$C_6$-alkoxy, $C_1$-$C_6$-halogenoalkoxy, $C_1$-$C_6$-alkylthio, $C_1$-$C_6$-halogenoalkylthio, $C_1$-$C_6$-alkoxycarbonyl and $C_2$-$C_6$-alkenyloxycarbonyl.

$R^{18}$ furthermore preferably represents $C_3$-$C_7$-cycloalkyl, $C_3$-$C_7$-cycloalkyl-$C_1$-$C_6$-alkyl, aryl, aryl-$C_1$-$C_6$-alkyl, heteroaryl or heteroaryl-$C_1$-$C_6$-alkyl, each of which contains 0 to 4 nitrogen atoms, 0 to 2 nonadjacent oxygen atoms and/or 0 to 2 nonadjacent sulphur atoms, each of which radicals is optionally mono- or polysubstituted by identical or different substituents where the substituents may, in addition to those mentioned above, be selected from the group consisting of nitro and $C_1$-$C_6$-alkoxycarbonyl.

$R^{17}$ and $R^{18}$ furthermore together with the nitrogen atom to which they are attached preferably represent a 5- or 6-membered saturated or unsaturated heterocycle which may contain 1 or 2 further heteroatoms including 0 to 2 nitrogen atoms, 0 or 1 oxygen atom and/or 0 or 1 sulphur atom, and which may optionally be mono- or polysubstituted by identical or different $C_1$-$C_6$-alkyl.

Q preferably represents one of the groupings below

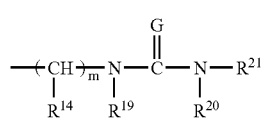
(Q¹)

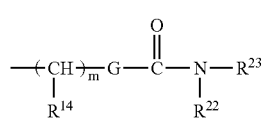
(Q²)

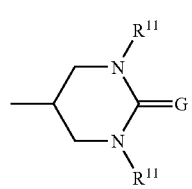
(Q³)

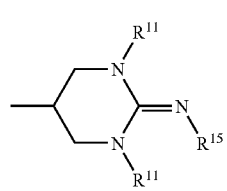
(Q⁴)

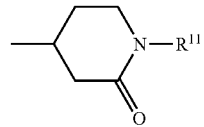
(Q⁵)

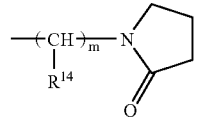
(Q⁶)

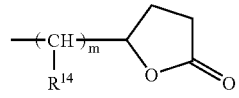
(Q⁷)

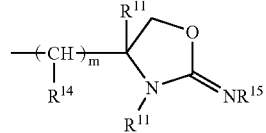
(Q⁸)

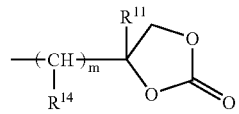
(Q⁹)

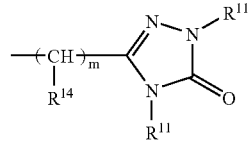
(Q¹⁰)

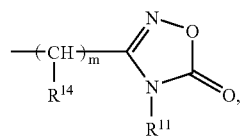
(Q¹¹)

where the radicals $R^{11}$ may have identical or different meanings if two or more are present in the same heterocyclic grouping.

m preferably represents 0, 1, 2 or 3, where the repeat unit —(CHR$^{14}$)— in the side chain of a heterocyclic grouping may have identical or different meanings if m represents 2 or 3.

G preferably represents oxygen or sulphur.

$R^{19}$ and $R^{20}$ independently of one another preferably represent hydrogen, $C_1$-$C_6$-alkyl or together represent $C_2$-$C_4$-alkylene.

$R^{21}$ preferably represents hydrogen, represents $C_1$-$C_6$-alkyl which is optionally mono- or polysubstituted by identical or different substituents from the group consisting of $C_1$-$C_6$-alkylcarbonyloxy and $C_1$-$C_6$-alkoxy; or represents aryl which is optionally mono- or polysubstituted by identical or different substituents from the group consisting of halogen, cyano, $C_1$-$C_6$-alkyl, $C_1$-$C_6$-halogenoalkyl, $C_1$-$C_6$-alkylcarbonyl, $C_1$-$C_{10}$-alkoxycarbonyl and $C_3$-$C_5$-alkylene.

$R^{22}$ preferably represents hydrogen, $C_1$-$C_6$-alkyl or $C_1$-$C_6$-alkoxy-$C_1$-$C_6$-alkyl.

$R^{23}$ preferably represents hydrogen, amino, $C_1$-$C_6$-alkyl or $C_1$-$C_6$-alkoxy-$C_1$-$C_6$-alkyl.

R¹ and R² independently of one another particularly preferably represent hydrogen, fluorine, chlorine, bromine, nitro, cyano, $C_1$-$C_4$-alkyl, $C_1$-$C_4$-halogenoalkyl having 1 to 9 fluorine, chlorine and/or bromine atoms, $C_1$-$C_4$-alkoxy, $C_1$-$C_4$-halogenoalkoxy having 1 to 9 fluorine, chlorine and/or bromine atoms, $C_1$-$C_4$-alkylthio, $C_1$-$C_4$-halogenoalkylthio having 1 to 9 fluorine, chlorine and/or bromine atoms, $C_2$-$C_4$-alkenyl, $C_2$-$C_4$-alkinyl, —S(O)$_p$R³, —NR⁴R⁵, —COR⁶, —CO$_2$R⁷, —CSR⁶, —CONR⁴R⁵, —NHCO$_2$R⁸, $C_3$-$C_6$-cycloalkyl; or represent aryl, aryl-$C_1$-$C_4$-alkyl, 5- or 6-membered saturated or unsaturated heterocyclyl which contains 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents from the group consisting of fluorine, chlorine, bromine, $C_1$-$C_4$-alkyl, $C_1$-$C_4$-halogenoalkyl having 1 to 9 fluorine, chlorine and/or bromine atoms, $C_1$-$C_4$-alkoxy and $C_1$-$C_4$-halogenoalkoxy having 1 to 9 fluorine, chlorine and/or bromine atoms.

R¹ and R² furthermore together particularly preferably represent $C_3$-$C_5$-alkylene or $C_3$-$C_4$-alkenylene, where the carbon chain may be interrupted by 1 or 2 heteroatoms including 0 to 2 nitrogen atoms and/or 0 or 1 oxygen atom and where the resulting ring for its part may optionally be mono- to tetrasubstituted by identical or different substituents from the group consisting of fluorine, chlorine, bromine and $C_1$-$C_4$-alkyl.

X particularly preferably represents fluorine, chlorine, bromine, nitro, cyano, hydroxyl, $C_1$-$C_4$-alkyl, $C_1$-$C_4$-halogenoalkyl having 1 to 9 fluorine, chlorine and/or bromine atoms, $C_1$-$C_4$-alkoxy, $C_1$-$C_4$-halogenoalkoxy having 1 to 9 fluorine, chlorine and/or bromine atoms, $C_1$-$C_4$-alkylthio, $C_1$-$C_4$-halogenoalkylthio having 1 to 9 fluorine, chlorine and/or bromine atoms, $C_2$-$C_4$-alkenyl, $C_2$-$C_4$-alkinyl, —S(O)$_p$R³, —NR⁴R⁵, —COR⁶, —CO$_2$R⁷, —CSR⁶, —CONR⁴R⁵, —NHCO$_2$R⁸, $C_3$-$C_6$-cycloalkyl, aryl, aryl-$C_1$-$C_4$-alkyl, 5- or 6-membered saturated or unsaturated heterocyclyl which contains 0 to 3 nitrogen atoms, 0 to 2 nonadjacent oxygen atoms and/or 0 to 2 nonadjacent sulphur atoms.

or, if n represents 2, two adjacent radicals X furthermore together particularly preferably represent $C_3$-$C_4$-alkylene or $C_3$-$C_4$-alkenylene, where the carbon chain may be interrupted by 1 or 2 heteroatoms including 0 to 2 nitrogen atoms and/or 0 or 1 oxygen atom.

n particularly preferably represents 0, 1 or 2, with X representing identical or different radicals if n represents 2.

Y particularly preferably represents a direct bond, oxygen, —S(O)$_p$— or —NR⁹—.

p particularly preferably represents 0, 1 or 2.

Z particularly preferably represents —(CH$_2$)$_r$—, —(CH$_2$)$_t$—(CHR¹⁰)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R¹¹)—(CH$_2$)$_t$— or —(CH$_2$)$_t$—C(R¹²)=C(R¹³)—(CH$_2$)$_w$—.

r particularly preferably represents 1, 2, 3 or 4.

t and w independently of one another particularly preferably represent 0, 1, 2, 3 or 4.

R particularly preferably represents the grouping

or represents a carboxylic acid bioisostere (acid mimetic), in particular from the group consisting of

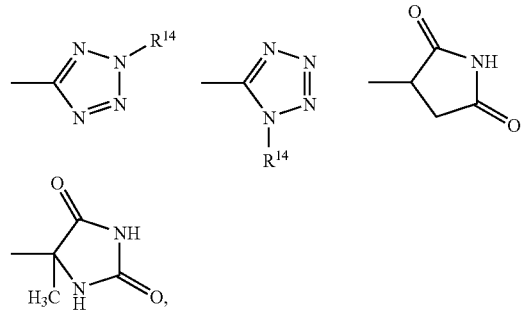

A particularly preferably represents oxygen or sulphur.

E particularly preferably represents —OR¹⁶, —SR¹⁶, —O-M, —S-M or —NR¹⁷R¹⁸.

M particularly preferably represents ammonium which is optionally mono- to tetrasubstituted by identical or different substituents from the group consisting of $C_1$-$C_4$-alkyl, phenyl, benzyl and phenylethyl or represents a sodium cation (Na⁺) or a potassium cation (K⁺).

M furthermore particularly preferably represents a magnesium cation (Mg²⁺) or a calcium cation (Ca²⁺), where in each case two molecules of a compound form a salt with such an ion.

R³ particularly preferably represents hydrogen, $C_1$-$C_4$-alkyl, $C_1$-$C_4$-halogenoalkyl having 1 to 9 fluorine, chlorine and/or bromine atoms, $C_3$-$C_6$-cycloalkyl, $C_3$-$C_6$-cycloalkyl-$C_1$-$C_4$-alkyl; or represents aryl, aryl-$C_1$-$C_4$-alkyl, 5- or 6-membered saturated or unsaturated heterocyclyl or heterocyclyl-$C_1$-$C_4$-alkyl, which contain 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents from the group consisting of fluorine, chlorine, bromine, $C_1$-$C_4$-alkyl, $C_1$-$C_4$-halogenoalkyl having 1 to 9 fluorine, chlorine and/or bromine atoms, $C_1$-$C_4$-alkoxy, $C_1$-$C_4$-halogenoalkoxy having 1 to 9 fluorine, chlorine and/or bromine atoms, $C_1$-$C_4$-alkylthio and $C_1$-$C_4$-halogenoalkylthio having 1 to 9 fluorine, chlorine and/or bromine atoms.

R⁴ particularly preferably represents hydrogen, $C_1$-$C_4$-alkyl, $C_1$-$C_4$-halogenoalkyl having 1 to 9 fluorine, chlorine and/or bromine atoms, $C_3$-$C_6$-cycloalkyl, $C_1$-$C_4$-alkylcarbonyl.

R⁵ particularly preferably represents hydrogen, amino, formyl, $C_1$-$C_4$-alkyl, $C_2$-$C_4$-alkenyl, $C_2$-$C_4$-alkinyl, $C_1$-$C_4$-halogenoalkyl having 1 to 9 fluorine, chlorine and/or bromine atoms, $C_3$-$C_6$-cycloalkyl, $C_1$-$C_4$-alkoxy, $C_1$-$C_4$-alkoxy-$C_1$-$C_4$-alkyl, $C_1$-$C_4$-alkylcarbonyl, $C_1$-$C_4$-alkoxycarbonyl, oxamoyl.

R⁴ and R⁵ furthermore together particularly preferably represent $C_1$-$C_4$-alkylidene; or represent benzylidene which is optionally mono- to tetrasubstituted by identical or different substituents from the group consisting of fluorine, chlorine, bromine, nitro, $C_1$-$C_4$-alkyl and $C_1$-$C_4$-halogenoalkyl having 1 to 9 fluorine, chlorine and/or bromine atoms.

R⁴ and R⁵ furthermore together with the nitrogen atom to which they are attached particularly preferably represent a 5- or 6-membered saturated or unsaturated heterocycle which may optionally contain a further nitrogen, oxygen or sulphur atom and which may optionally be mono- to tetrasubstituted by identical or different $C_1$-$C_4$-alkyl.

$R^6$ particularly preferably represents hydrogen, $C_1$-$C_4$-alkyl, $C_1$-$C_4$-halogenoalkyl having 1 to 9 fluorine, chlorine and/or bromine atoms or aryl-$C_1$-$C_4$-alkyl.

$R^7$ particularly preferably represents hydrogen, $C_1$-$C_4$-alkyl, $C_1$-$C_4$-halogenoalkyl having 1 to 9 fluorine, chlorine and/or bromine atoms, $C_3$-$C_6$-cycloalkyl, $C_3$-$C_6$-cycloalkyl-$C_1$-$C_4$-alkyl, aryl or aryl-$C_1$-$C_4$-alkyl.

$R^8$ particularly preferably represents $C_1$-$C_4$-alkyl or $C_1$-$C_4$-halogenoalkyl having 1 to 9 fluorine, chlorine and/or bromine atoms.

$R^9$ particularly preferably represents hydrogen, $C_1$-$C_4$-alkyl, $C_1$-$C_4$-halogenoalkyl having 1 to 9 fluorine, chlorine and/or bromine atoms, $C_3$-$C_6$-cycloalkyl, $C_3$-$C_6$-cycloalkyl-$C_1$-$C_4$-alkyl; or represents aryl, aryl-$C_1$-$C_4$-alkyl, 5- or 6-membered saturated or unsaturated heterocyclyl or heterocyclyl-$C_1$-$C_4$-alkyl, which contain 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents from the group consisting of fluorine, chlorine, bromine, $C_1$-$C_4$-alkyl, $C_1$-$C_4$-halogenoalkyl having 1 to 9 fluorine, chlorine and/or bromine atoms, $C_1$-$C_4$-alkoxy, $C_1$-$C_4$-halogenoalkoxy having 1 to 9 fluorine, chlorine and/or bromine atoms, $C_1$-$C_4$-alkylthio and $C_1$-$C_4$-halogenoalkylthio having 1 to 9 fluorine, chlorine and/or bromine atoms.

$R^{10}$ particularly preferably represents fluorine, chlorine, bromine, iodine, $C_1$-$C_4$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_4$-alkyl; or represents aryl or aryl-$C_1$-$C_4$-alkyl which for their part may be mono- to tetrasubstituted in the aryl moiety by identical or different substituents from the group consisting of fluorine, chlorine, bromine and $C_1$-$C_4$-alkyl.

$R^{11}$ particularly preferably represents hydrogen or $C_1$-$C_4$-alkyl.

$R^{12}$ and $R^{13}$ independently of one another particularly preferably represent hydrogen, hydroxyl, $C_1$-$C_4$-alkyl or $C_1$-$C_4$-alkoxy.

$R^{14}$ particularly preferably represents hydrogen, $C_1$-$C_4$-alkyl or $C_1$-$C_4$-halogenoalkyl having 1 to 9 fluorine, chlorine and/or bromine atoms.

$R^{15}$ particularly preferably represents hydrogen, $C_1$-$C_4$-alkyl, $C_1$-$C_4$-alkoxy, cyano or di($C_1$-$C_4$-alkyl)amino.

$R^{16}$ particularly preferably represents hydrogen; represents $C_1$-$C_6$-alkyl, decyl, dodecyl, tetradecyl, hexadecyl, $C_2$-$C_6$-alkenyl, decenyl, $C_2$-$C_4$-alkinyl, each of which is optionally mono- to tetrasubstituted by identical or different substituents from the group consisting of fluorine, chlorine, bromine, amino, hydroxyl, cyano, nitro, $C_1$-$C_4$-alkoxy, $C_1$-$C_4$-halogenoalkoxy having 1 to 9 fluorine, chlorine and/or bromine atoms, $C_1$-$C_4$-alkylthio, $C_1$-$C_4$-halogenoalkylthio having 1 to 9 fluorine, chlorine and/or bromine atoms, $C_1$-$C_4$-alkoxycarbonyl, $C_2$-$C_4$-alkenyloxycarbonyl, $C_1$-$C_4$-alkylcarbonyloxy, $C_2$-$C_4$-alkenylcarbonyloxy, oxy($C_1$-$C_4$-alkylene)oxy, oxetanyl, dioxanyl, oxazolidinyl, dioxolanyl, aryloxy, halogenoaryloxy, —CONR$^4$R$^5$, —NR$^4$R$^5$, —ONR$^4$R$^5$ and —C(R$^{14}$)=N—OR$^{14}$; or represents aryl, aryl-$C_1$-$C_4$-alkyl, $C_3$-$C_6$-cycloalkyl, $C_3$-$C_6$-cycloalkyl-$C_1$-$C_4$-alkyl, 4- to 6-membered saturated or unsaturated, heterocyclyl or heterocyclyl-$C_1$-$C_4$-alkyl, each of which contains 0 to 3 nitrogen atoms, 0 to 2 nonadjacent oxygen atoms and/or 0 to 2 nonadjacent sulphur atoms; each of which radicals is optionally mono- to tetrasubstituted by identical or different substituents from the group consisting of fluorine, chlorine, bromine, $C_1$-$C_4$-alkyl, $C_1$-$C_4$-halogenoalkyl having 1 to 9 fluorine, chlorine and/or bromine atoms, $C_1$-$C_4$-alkoxy, $C_1$-$C_4$-halogenoalkoxy having 1 to 9 fluorine, chlorine and/or bromine atoms, $C_1$-$C_4$-alkylthio, $C_1$-$C_4$-halogenoalkylthio having 1 to 9 fluorine, chlorine and/or bromine atoms, $C_1$-$C_4$-alkoxycarbonyl and $C_1$-$C_4$-alkylcarbonyloxy; or represents one of the radicals Q.

$R^{16}$ furthermore particularly preferably represents $C_1$-$C_6$-alkyl, decyl, dodecyl, tetradecyl, hexadecyl, $C_2$-$C_6$-alkenyl, decenyl, $C_2$-$C_4$-alkinyl, each of which is optionally substituted up to the maximum possible number by identical or different substituents from the group consisting of fluorine, chlorine and bromine.

$R^{16}$ furthermore particularly preferably represents aryl, aryl-$C_1$-$C_4$-alkyl, $C_3$-$C_6$-cycloalkyl, $C_3$-$C_6$-cycloalkyl-$C_1$-$C_4$-alkyl, 4- to 6-membered saturated or unsaturated, heterocyclyl or heterocyclyl-$C_1$-$C_4$-alkyl, each of which contains 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents, where the substituents may, in addition to those mentioned above, be selected from the group consisting of hydroxyl and nitro.

$R^{17}$ particularly preferably represents hydrogen or $C_1$-$C_4$-alkyl.

$R^{18}$ particularly preferably represents hydrogen, hydroxyl, amino, $C_1$-$C_4$-alkyl, $C_2$-$C_4$-alkenyl; or represents $C_3$-$C_6$-cycloalkyl, $C_3$-$C_6$-cycloalkyl-$C_1$-$C_4$-alkyl, aryl, aryl-$C_1$-$C_4$-alkyl, heteroaryl or heteroaryl-$C_1$-$C_4$-alkyl, each of which contains 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents from the group consisting of fluorine, chlorine, bromine, hydroxyl, $C_1$-$C_4$-alkyl, $C_1$-$C_4$-halogenoalkyl having 1 to 9 fluorine, chlorine and/or bromine atoms, $C_1$-$C_4$-alkoxy, $C_1$-$C_4$-halogenoalkoxy having 1 to 9 fluorine, chlorine and/or bromine atoms, $C_1$-$C_4$-alkylthio, $C_1$-$C_4$-halogenoalkylthio having 1 to 9 fluorine, chlorine and/or bromine atoms and oxy($C_1$-$C_4$-alkylene)oxy; or represents —S(O)$_p$R$^3$, —OR$^{14}$ or —NR$^4$R$^5$.

$R^{18}$ furthermore particularly preferably represents $C_1$-$C_4$-alkyl or $C_2$-$C_4$-alkenyl, each of which is mono- to tetrasubstituted by identical or different substituents from the group consisting of fluorine, chlorine, bromine, amino, hydroxyl, cyano, nitro, $C_1$-$C_4$-alkoxy, $C_1$-$C_4$-halogenoalkoxy having 1 to 9 fluorine, chlorine and/or bromine atoms, $C_1$-$C_4$-alkylthio, $C_1$-$C_4$-halogenoalkylthio having 1 to 9 fluorine, chlorine and/or bromine atoms, $C_1$-$C_4$-alkoxycarbonyl and $C_2$-$C_4$-alkenyloxycarbonyl; or represents $C_1$-$C_4$-alkyl or $C_2$-$C_4$-alkenyl, each of which is optionally substituted up to the maximum possible number by identical or different substituents from the group consisting of fluorine, chlorine and bromine.

$R^{18}$ furthermore particularly preferably represents $C_3$-$C_6$-cycloalkyl, $C_3$-$C_6$-cycloalkyl-$C_1$-$C_4$-alkyl, aryl, aryl-$C_1$-$C_4$-alkyl, heteroaryl or heteroaryl-$C_1$-$C_4$-alkyl, each of which contains 0 to 3 nitrogen atoms, 0 to 2 nonadjacent oxygen atoms and/or 0 to 2 nonadjacent sulphur atoms, each of which radicals is optionally mono- or tetrasubstituted by identical or different radicals, where the substituents may, in addition to those mentioned, be selected from the group consisting of nitro and $C_1$-$C_6$-alkoxycarbonyl.

$R^{17}$ and $R^{18}$ furthermore together with the nitrogen atom to which they are attached particularly preferably represent a 5- or 6-membered saturated or unsaturated heterocycle which may contain 1 or 2 further heteroatoms including 0 to 2 nitrogen atoms, 0 or 1 oxygen atom and/or 0 or 1 sulphur atom, and which may be optionally mono- to trisubstituted by identical or different $C_1$-$C_4$-alkyl.

Q particularly preferably represents one of the groupings below

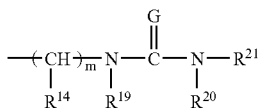
(Q$^1$)

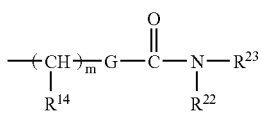
(Q$^2$)

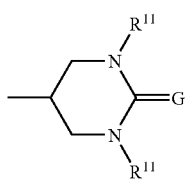
(Q$^3$)

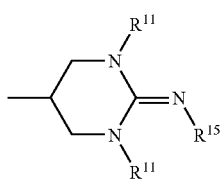
(Q$^4$)

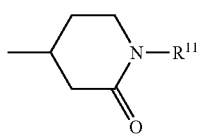
(Q$^5$)

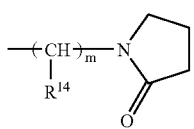
(Q$^6$)

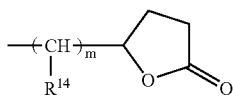
(Q$^7$)

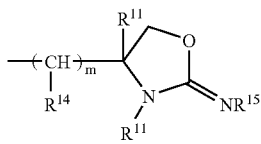
(Q$^8$)

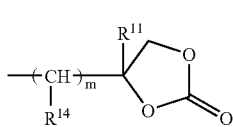
(Q$^9$)

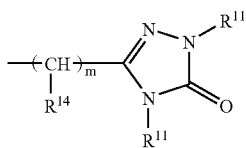
(Q$^{10}$)

(Q$^{11}$)

where the radicals $R^{11}$ may have identical or different meanings if two or more of them are present in the same heterocyclic grouping.

m particularly preferably represents 0, 1, 2 or 3, where the repeat unit —(CHR$^{14}$)— in the side chain of a heterocyclic grouping may have the same or different meanings if m represents 2 or 3.

G particularly preferably represents oxygen or sulphur.

$R^{19}$ and $R^{20}$ independently of one another particularly preferably represent hydrogen, $C_1$-$C_4$-alkyl or together represent $C_2$-$C_3$-alkylene.

$R^{21}$ particularly preferably represents hydrogen, represents $C_1$-$C_4$-alkyl which is optionally mono- or disubstituted by identical or different substituents from the group consisting of $C_1$-$C_4$-alkylcarbonyloxy and $C_1$-$C_4$-alkoxy; or represents aryl which is optionally mono- to tetrasubstituted by identical or different substituents from the group consisting of fluorine, chlorine, bromine, cyano, $C_1$-$C_4$-alkyl, $C_1$-$C_4$-halogenoalkyl having 1 to 9 fluorine, chlorine and/or bromine atoms, $C_1$-$C_4$-alkylcarbonyl, $C_1$-$C_8$-alkoxycarbonyl and $C_3$-$C_5$-alkylene.

$R^{22}$ particularly preferably represents hydrogen, $C_1$-$C_4$-alkyl or $C_1$-$C_4$-alkoxy-$C_1$-$C_4$-alkyl.

$R^{23}$ particularly preferably represents hydrogen, amino, $C_1$-$C_4$-alkyl or $C_1$-$C_4$-alkoxy-$C_1$-$C_4$-alkyl.

$R^1$ and $R^2$ independently of one another very particularly preferably represent hydrogen, fluorine, chlorine, bromine, nitro, cyano, methyl, ethyl, n-propyl, isopropyl, n-butyl, sec-butyl, isobutyl, tert-butyl, —CF$_3$, —CCl$_3$, —CHF$_2$, —CClF$_2$, —CHCl$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, methoxy, ethoxy, n-propoxy, isopropoxy, n-butoxy, trifluoromethoxy, trichloromethoxy, —OCH$_2$CF$_3$, —SCF$_3$, —SCHF$_2$, —SO$_2$Me, —SO$_2$CHF$_2$, —SO$_2$CF$_3$, —SOCHF$_2$, —SOCF$_3$, —COMe, —CO$_2$Me, —CO$_2$Et, amino, cyclopentyl, cyclohexyl; represent phenyl, benzyl, pyridinyl, furyl, furfuryl, each of which is optionally substituted by chlorine, bromine, methyl; ethyl, methoxy, ethoxy, trifluoromethyl, trifluoromethoxy.

$R^1$ and $R^2$ furthermore together very particularly preferably represent propylene, butylene, propenylene or butadienylene, —(CH$_2$)$_2$—O—CH$_2$—, —(CH$_2$)$_2$—NH—CH$_2$—, —CH═CH—N═CH—, —CH═CCl—CH═CH—.

X very particularly preferably represents fluorine, chlorine, bromine, nitro, cyano, hydroxyl, methyl, ethyl, n-propyl, isopropyl, n-butyl, sec-butyl, isobutyl, tert-butyl, —CF$_3$, —CCl$_3$, —CHF$_2$, —CClF$_2$, —CHCl$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, methoxy, ethoxy, n-propoxy, isopropoxy, n-butoxy, trifluoromethoxy, trichloromethoxy, —OCH$_2$CF$_3$, —SCF$_3$, —SCHF$_2$, —SO$_2$Me, —SO$_2$CHF$_2$, —SO$_2$CF$_3$, —SOCHF$_2$, —SOCF$_3$, —CH═CH$_2$, —C≡CH, amino, —NHMe, —NMe$_2$, —CHO, —COMe, —CO$_2$Me, —CO$_2$Et, —NHCOMe, cyclopentyl, cyclohexyl, phenyl, benzyl, furyl, thienyl, pyrrolyl, oxazolyl, isoxazyl, imidazyl, pyrazyl, thiazolyl, pyridyl, pyrimidinyl, pyridazyl, triazinyl, triazyl; or, if n represents 2, two adjacent radicals X furthermore together very particularly preferably represent propylene, butylene, propenylene or butadienylene, —(CH$_2$)$_2$—O—CH$_2$—, —(CH$_2$)$_2$—NH—CH$_2$—, —CH=CH—N=CH—.

X furthermore very particularly preferably represents methylthio, ethylthio, n-propylthio, isopropylthio.

n very particularly preferably represents 0, 1 or 2, with X representing identical or different radicals if n represents 2.

Y very particularly preferably represents a direct bond, oxygen, —S(O)$_p$— or —NR$^9$—.

p very particularly preferably represents 0, 1 or 2.

Z very particularly preferably represents —CH$_2$—, —(CH$_2$)$_2$—, —(CH$_2$)$_3$—, —(CH$_2$)$_4$—, —(CHR$^{10}$)—, —CH$_2$—C(O)—CH$_2$—, —CH$_2$—NH—, —CH=CH—, —CH$_2$—CH=CH—, —CH=C(OH)—, —CH=C(OMe)—, —CH$_2$—C(OMe)=CH—.

Z furthermore very particularly preferably represents —CH$_2$—C(OEt)=CH—.

R very particularly preferably represents the grouping

or represents a carboxylic acid bioisostere (acid mimetic), in particular from the group consisting of

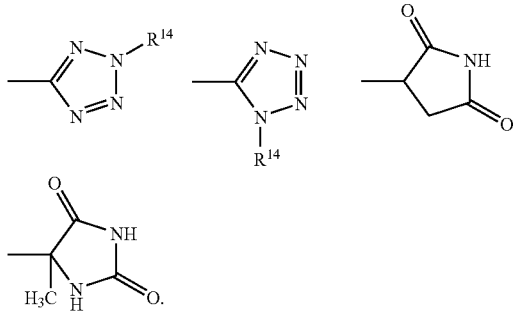

A very particularly preferably represents oxygen or sulphur.

E very particularly preferably represents —OR$^{16}$, —SR$^{16}$, —O-M or —NR$^{17}$R$^{18}$.

M very particularly preferably represents tetrabutylammonium, trimethylbenzylammonium or represents a sodium cation (Na$^+$) or a potassium cation (K$^+$).

M furthermore very particularly preferably represents a magnesium cation (Mg$^{2+}$) or a calcium cation (Ca$^{2+}$), where in each case two molecules of a compound form a salt with such an ion.

R$^4$ very particularly preferably represents hydrogen, methyl, ethyl, n-propyl, isopropyl, n-butyl, sec-butyl, isobutyl, tert-butyl, —COMe.

R$^5$ very particularly preferably represents hydrogen, amino, formyl, methyl, ethyl, n-propyl, isopropyl, n-butyl, sec-butyl, isobutyl, tert-butyl, vinyl, propargyl, methoxy, methoxymethyl, —COMe, —COEt, tert-butoxycarbonyl, oxamoyl.

R$^4$ and R$^5$ furthermore together very particularly preferably represent ethylidene, isopropylidene, sec-butylidene, nitrobenzylidene.

R$^4$ and R$^5$ furthermore together with the nitrogen atom to which they are attached very particularly preferably represent a 5- or 6-membered saturated or unsaturated heterocycle from the group consisting of morpholine, piperidine, thiomorpholine, pyrrolidine, tetrahydropyridine, which may optionally be mono- or disubstituted by methyl, ethyl, n-propyl, isopropyl, n-butyl, sec-butyl, isobutyl, tert-butyl.

R$^8$ very particularly preferably represents methyl, ethyl, n-propyl, isopropyl, n-butyl, sec-butyl, isobutyl, tert-butyl, —CF$_3$, —CCl$_3$, —CHF$_2$, —CClF$_2$, —CHCl$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H or represents —CF$_2$CHFCF$_3$.

R$^9$ very particularly preferably represents hydrogen, methyl, ethyl, n-propyl, isopropyl, n-butyl, sec-butyl, isobutyl, tert-butyl, —CH$_2$CF$_3$, —CH$_2$CF$_2$H, —CH$_2$CF$_2$CF$_3$, cyclopropyl, cyclopentyl or cyclohexyl.

R$^{10}$ very particularly preferably represents fluorine, chlorine, bromine, methyl, ethyl, n-propyl, isopropyl, n-butyl, sec-butyl, isobutyl, tert-butyl, —COMe, —COEt, —CO$_2$Me, —CO$_2$Et, cyclohexyl; phenyl or benzyl, which for their part may be mono- to tetrasubstituted in the aryl moiety by identical or different substituents from the group consisting of fluorine, chlorine, bromine and methyl.

R$^{11}$ very particularly preferably represents hydrogen, methyl, ethyl, n-propyl, isopropyl, n-butyl, sec-butyl, isobutyl, tert-butyl.

R$^{14}$ very particularly preferably represents hydrogen, methyl, ethyl, n-propyl, isopropyl, n-butyl, sec-butyl, isobutyl or tert-butyl.

R$^{15}$ very particularly preferably represents hydrogen, methyl, ethyl, n-propyl, isopropyl, n-butyl, sec-butyl, isobutyl, tert-butyl or cyano.

R$^{16}$ very particularly preferably represents hydrogen; represents methyl, ethyl, n-propyl, isopropyl, n-butyl, sec-butyl, isobutyl, tert-butyl, n-pentyl, isopentyl, siamyl, hexyl, n-decyl, n-dodecyl, n-tetradecyl, n-hexadecyl, vinyl, allyl, butenyl, 2-isopentenyl, hexenyl, n-decenyl, ethinyl, propinyl, butinyl, each of which is optionally mono- to trisubstituted by identical or different substituents from the group consisting of fluorine, chlorine, bromine, amino, hydroxyl, cyano, nitro, methoxy, ethoxy, isopropoxy, trifluoromethoxy, —OCH$_2$CF$_3$, trichloromethoxy, difluoromethoxy, methylthio, trifluoromethylthio, methoxycarbonyl, ethoxycarbonyl, isopropoxycarbonyl, tert-butoxycarbonyl, methylcarbonyloxy, vinylcarbonyloxy, —O—(CH$_2$)$_2$—O—, oxetanyl, dioxanyl, oxazolidinyl, dioxolanyl, phenoxy, fluorophenoxy, —CONR$^4$R$^5$, —NR$^4$R$^5$, —ONR$^4$R$^5$ and —CH=N—OCH$_3$; or represents phenyl, benzyl, phenylethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, oxetanyl, oxazolanyl, dioxanyl, dioxolanyl, furyl, thienyl, pyrrolyl, oxazolyl, isoxazyl, imidazolyl, pyrazyl, thiazolyl, pyridinyl, pyrimidinyl, pyridazyl, triazinyl, triazolyl, tetrahydropyranyl, thietanyl, thietane dioxide, oxetanylmethyl, oxazolanylmethyl, dioxanylmethyl, dioxolanylmethyl, furylmethyl, thienylmethyl, pyrrolylmethyl, oxazolylmethyl, isoxazylmethyl, imidazolylmethyl, pyrazylmethyl, thiazolylmethyl, pyridinylmethyl, pyrimidinylmethyl, pyridazylmethyl, triazinylmethyl, triazolylmethyl, tetrahydropyranylmethyl, thietanylmethyl, thietane dioxide methyl, oxetanylethyl, oxazolanylethyl, dioxanylethyl, dioxolanylethyl, furylethyl, thienylethyl, pyrrolylethyl, oxazolylethyl, isoxazylethyl, imidazolylethyl, pyrazylethyl, thiazolylethyl, pyridinylethyl, pyrimidinylethyl, pyridazylethyl, triazinylethyl, triazolylethyl, tetrahydropyranylethyl, thietanylethyl, thietane dioxide ethyl; each of which is optionally mono- to trisubstituted by identical or different substituents from the group consisting of fluorine, chlorine, bromine, methyl, ethyl, n-propyl, isopropyl, n-butyl, sec-butyl, isobutyl, tert-butyl, —CF$_3$, —CCl$_3$, —CHF$_2$, —CClF$_2$, —CHCl$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, methoxy, ethoxy, n-propoxy, n-butoxy, trifluoromethoxy, trichloromethoxy, methylthio, trifluoromethylthio, —CO$_2$Me, —CO$_2$Et, methylcarbonyloxy and ethylcarbonyloxy; or represents one of the radicals Q.

$R^{16}$ furthermore very particularly preferably represents methyl, ethyl, n-propyl, isopropyl, n-butyl, sec-butyl, isobutyl, tert-butyl, n-pentyl, isopentyl, siamyl, hexyl, n-decyl, n-dodecyl, n-tetradecyl, n-hexadecyl, vinyl, allyl, butenyl, 2-isopentenyl, hexenyl, n-decenyl, ethinyl, propinyl, butinyl, each of which is optionally substituted up to the maximum possible number by identical or different radicals from the group consisting of fluorine, chlorine and bromine.

$R^{16}$ furthermore very particularly preferably represents phenyl, benzyl, phenylethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, oxetanyl, oxazolanyl, dioxanyl, dioxolanyl, furyl, thienyl, pyrrolyl, oxazolyl, isoxazyl, imidazolyl, pyrazyl, thiazolyl, pyridinyl, pyrimidinyl, pyridazyl, triazinyl, triazolyl, tetrahydropyranyl, thietanyl, thietane dioxide, oxetanylmethyl, oxazolanylmethyl, dioxanylmethyl, dioxolanylmethyl, furylmethyl, thienylmethyl, pyrrolylmethyl, oxazolylmethyl, isoxazylmethyl, imidazolylmethyl, pyrazylmethyl, thiazolylmethyl, pyridinylmethyl, pyrimidinylmethyl, pyridazylmethyl, triazinylmethyl, triazolylmethyl, tetrahydropyranylmethyl, thietanylmethyl, thietane dioxide methyl, oxetanylethyl, oxazolanylethyl, dioxanylethyl, dioxolanylethyl, furylethyl, thienylethyl, pyrrolylethyl, oxazolylethyl, isoxazylethyl, imidazolylethyl, pyrazylethyl, thiazolylethyl, pyridinylethyl, pyrimidinylethyl, pyridazylethyl, triazinylethyl, triazolylethyl, tetrahydropyranylethyl, thietanylethyl, thietane dioxide ethyl, each of which is optionally mono- to tetrasubstituted by identical or different substituents, where the substituents may, in addition to those mentioned above, also be selected from the group consisting of hydroxyl and nitro.

$R^{17}$ very particularly preferably represents hydrogen, methyl or ethyl.

$R^{18}$ very particularly preferably represents hydrogen, hydroxyl, amino, methyl, ethyl, n-propyl, isopropyl, n-butyl, sec-butyl, isobutyl, tert-butyl, vinyl, allyl; or represents cyclopropyl, cyclopropylmethyl, cyclohexyl, phenyl, benzyl, phenylethyl, pyridinyl, pyridinylmethyl, pyridinylethyl, furyl, furfuryl, each of which is optionally mono- to trisubstituted by identical or different substituents from the group consisting of fluorine, chlorine, hydroxyl, methyl, ethyl, n-propyl, isopropyl, n-butyl, sec-butyl, isobutyl, tert-butyl, trifluoromethyl, trichloromethyl, methoxy, ethoxy, trifluoromethoxy, methylthio, trifluoromethylthio and —O—CH$_2$—O—; or represents —SO$_2$Me, —SO$_2$Et or —NR$^4$R$^5$.

$R^{18}$ furthermore very particularly preferably represents methyl, ethyl, n-propyl, isopropyl, n-butyl, sec-butyl, isobutyl, tert-butyl, vinyl, allyl, each of which is optionally mono- to trisubstituted by identical or different substituents from the group consisting of fluorine, chlorine, bromine, amino, hydroxyl, cyano, nitro, methoxy, ethoxy, isopropoxy, trifluoromethoxy, —OCH$_2$CF$_3$, trichloromethoxy, difluoromethoxy, methylthio, trifluoromethylthio, methoxycarbonyl, ethoxycarbonyl, isopropoxycarbonyl and tert-butoxycarbonyl; or represents methyl, ethyl, n-propyl, isopropyl, n-butyl, sec-butyl, isobutyl, tert-butyl, vinyl, allyl, each of which is optionally substituted up to the maximum possible number by identical or different substituents from the group consisting of fluorine, chlorine and bromine.

$R^{18}$ furthermore very particularly preferably represents cyclopropyl, cyclopropylmethyl, cyclohexyl, phenyl, benzyl, phenylethyl, pyridinyl, pyridinylmethyl, pyridinylethyl, furyl, furfuryl, each of which is optionally mono- to trisubstituted by identical or different substituents, where the substituents may, in addition to those mentioned above, also be selected from the group consisting of nitro, methoxycarbonyl and ethoxycarbonyl.

$R^{17}$ and $R^{18}$ furthermore together with the nitrogen atom to which they are attached very particularly preferably represent a 5- or 6-membered saturated heterocycle from the group consisting of piperazine, morpholine, piperidine, pyrrolidine, which may optionally be mono- to trisubstituted by identical or different substituents from the group consisting of methyl, ethyl, n-propyl and isopropyl.

Q very particularly preferably represents one of the groupings below

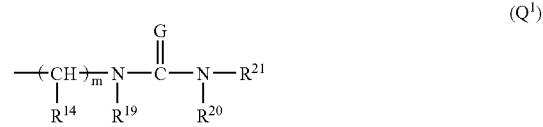

(Q$^1$)

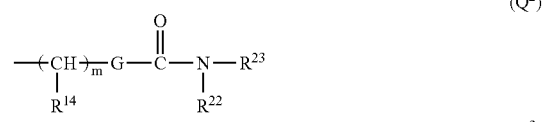

(Q$^2$)

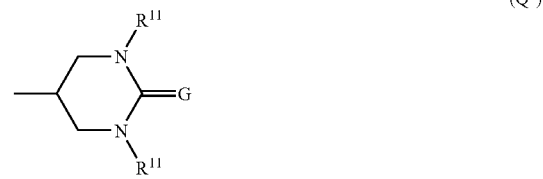

(Q$^3$)

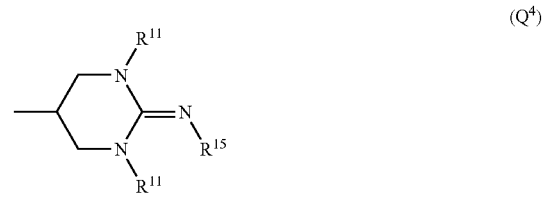

(Q$^4$)

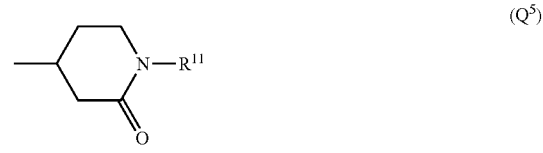

(Q$^5$)

-continued

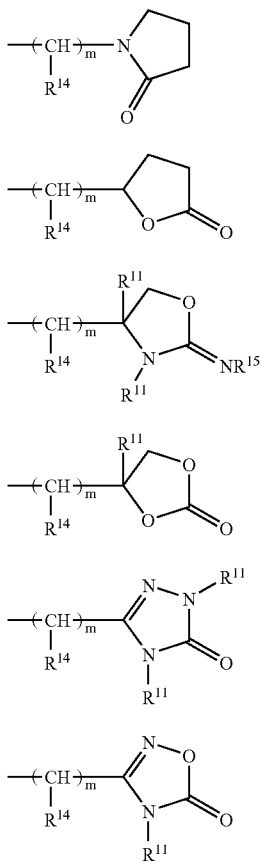

where the radicals R¹¹ may have identical or different meanings if two or more of them are present in the same heterocyclic grouping.

m very particularly preferably represents 0, 1, 2 or 3, where the repeat unit —(CHR¹⁴)— in the side chain of a heterocyclic grouping may have the same or different meanings if m represents 2 or 3.

G very particularly preferably represents oxygen or sulphur.

$R^{19}$ and $R^{20}$ independently of one another very particularly preferably represent hydrogen, methyl, ethyl, n-propyl, isopropyl, n-butyl, sec-butyl, isobutyl, tert-butyl, or together represent —(CH₂)₂— or —(CH₂)₃—.

$R^{21}$ very particularly preferably represents hydrogen, represents methyl, ethyl, n-propyl, isopropyl, n-butyl, sec-butyl, isobutyl, tert-butyl, each of which is optionally monosubstituted by tert-butylcarbonyloxy or methoxy; or represents phenyl which is optionally mono- or disubstituted by identical or different substituents from the group consisting of chlorine, cyano, methyl, ethyl, tert-butyl, trifluoromethyl, sec-butyloxycarbonyl, tert-butyloxycarbonyl, n-octyloxycarbonyl and —(CH₂)₄—.

$R^{22}$ very particularly preferably represents hydrogen, methyl, ethyl or methoxymethyl.

$R^{23}$ very particularly preferably represents hydrogen, amino, methyl, ethyl, n-propyl, isopropyl or methoxymethyl.

Especially very particularly preferred are pyridylpyrimidines of the formula (I-p)

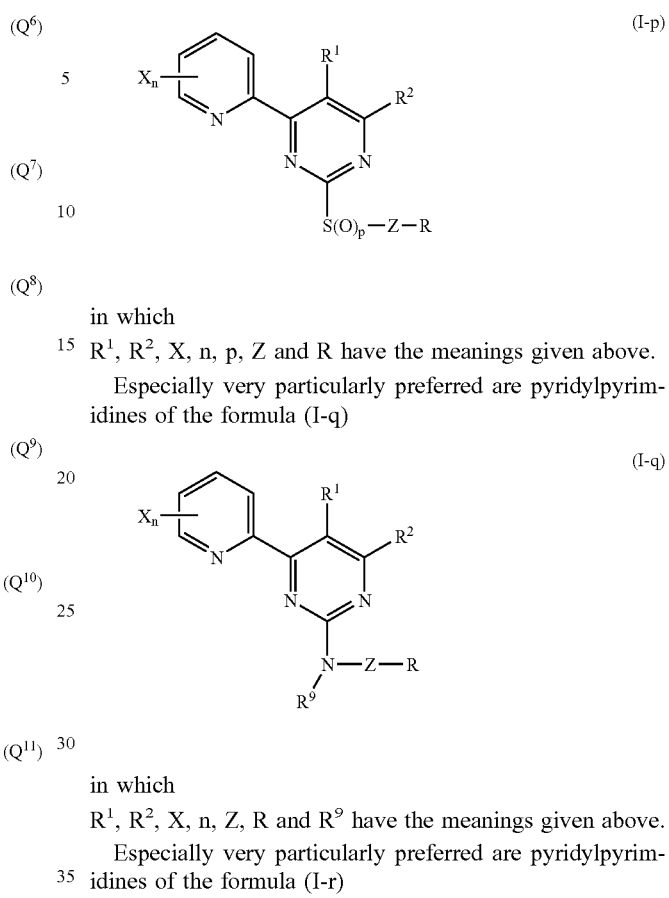

in which
R¹, R², X, n, p, Z and R have the meanings given above.

Especially very particularly preferred are pyridylpyrimidines of the formula (I-q)

in which
R¹, R², X, n, Z, R and R⁹ have the meanings given above.

Especially very particularly preferred are pyridylpyrimidines of the formula (I-r)

in which
R¹, R², X, n, Z and R have the meanings given above.

Especially very particularly preferred are pyridylpyrimidines of the formula (I-s)

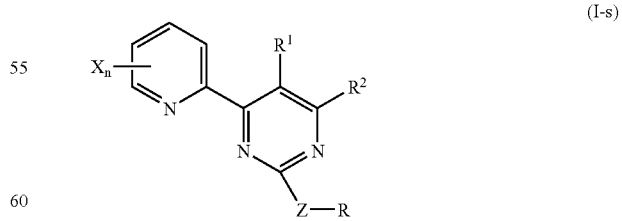

in which
R¹, R², X, n, Z and R have the meanings given above.

Especially very particularly preferred are pyridylpyrimidines of the formula (I-t)

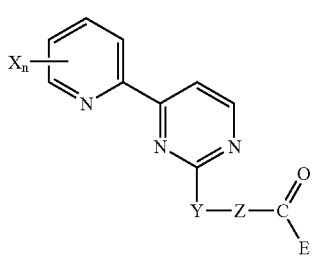
(I-t)

in which

X represents methyl, ethyl, chlorine, bromine, —CF$_3$, methoxy or trifluoromethoxy, n represents 0, 1 or 2, with X representing identical or different radicals if n represents 2, Y represents —S— or —NR$^9$—, Z represents —CH$_2$— or —(CH$_2$)$_2$—, E represents hydroxyl, methoxy, ethoxy, n-propoxy, isopropoxy, n-butoxy, isobutoxy, sec-butoxy, tert-butoxy, —NH—SO$_2$Me or —NH—SO$_2$Et, R$^9$ represents hydrogen, methyl or ethyl.

Saturated hydrocarbon radicals such as alkyl can in each case be straight-chain or branched as far as this is possible, including in combination with heteroatoms, such as, for example, in alkoxy.

However, it is also possible to combine the abovementioned general or preferred radical definitions or illustrations with one another as desired, i.e. between the respective ranges and preferred ranges. The definitions apply both to the end products and, correspondingly, to the precursors and intermediates.

Using 4-(2-pyridinyl)-2-pyrimidinylthiol and isopropyl 2-chloroacetate as starting materials, the course of process (A) according to the invention can be illustrated by the equation below.

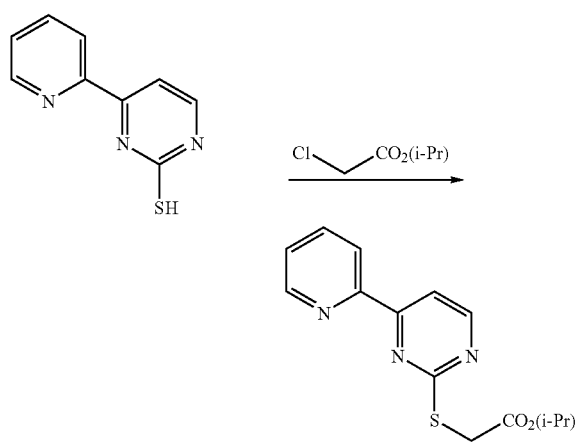

Using ethyl [(4-bromo-6-methyl-2-pyrimidinyl)thio]acetate, 2-(tributylstannyl)-pyridine and a palladium catalyst as starting materials, the course of process (B) according to the invention can be illustrated by the equation below.

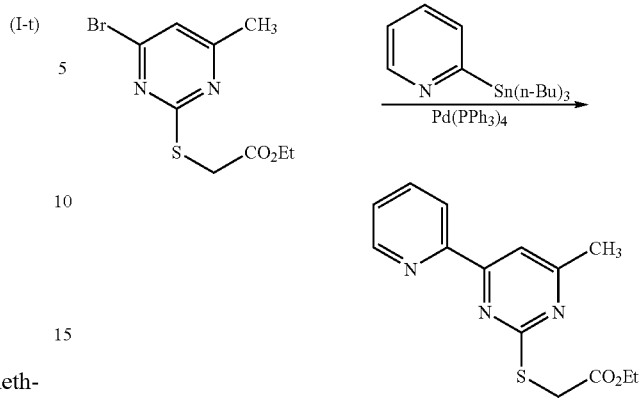

Using isopropyl {[4-(2-pyridinyl)-2-pyrimidinyl]thio}acetate as starting material and aqueous sodium hydroxide solution and triethylamine as reaction auxiliaries, the course of the process (C) according to the invention can be illustrated by the equation below.

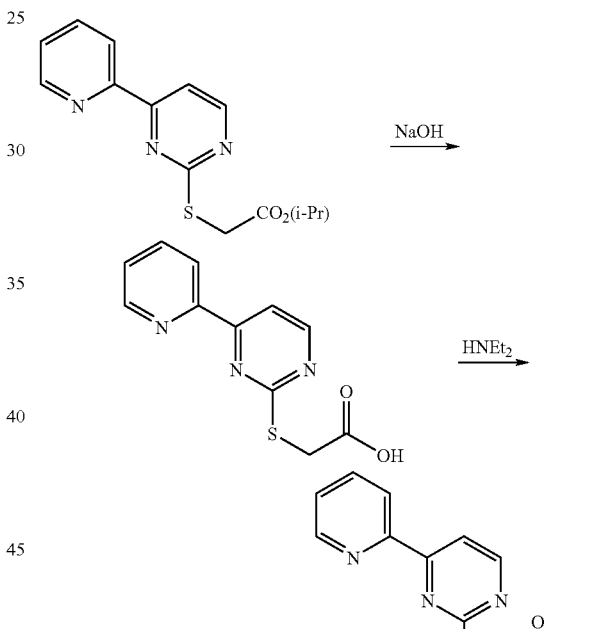

Using methyl {[4-(2-pyridinyl)-2-pyrimidinyl]thio}acetate as starting material and meta-chloroperbenzoic acid (m-CPBA) as oxidizing agent, the course of process (D) according to the invention can be illustrated by the equation below.

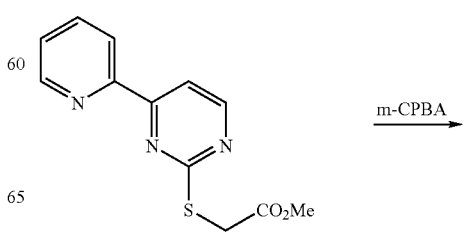

-continued

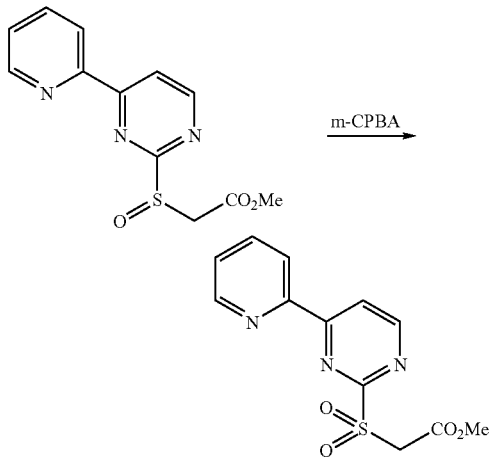

Using 2-(methylsulphonyl)-4-(2-pyridinyl)pyrimidine and ethyl glycinate as starting materials, the course of the process (E) according to the invention can be illustrated by the equation below.

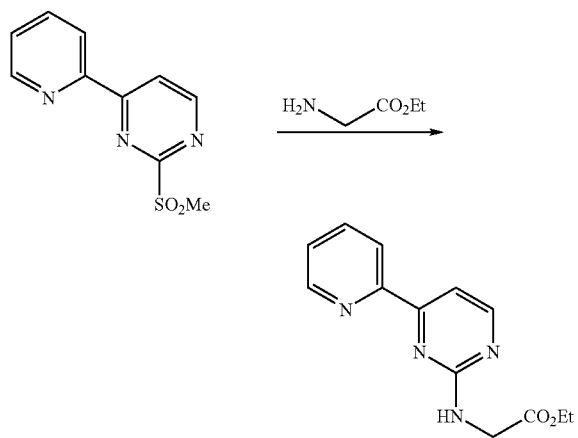

Using 2-(methylsulphonyl)-4-(2-pyridinyl)pyrimidine and ethyl glycolate as starting materials, the course of process (F) according to the invention can be illustrated by the equation below.

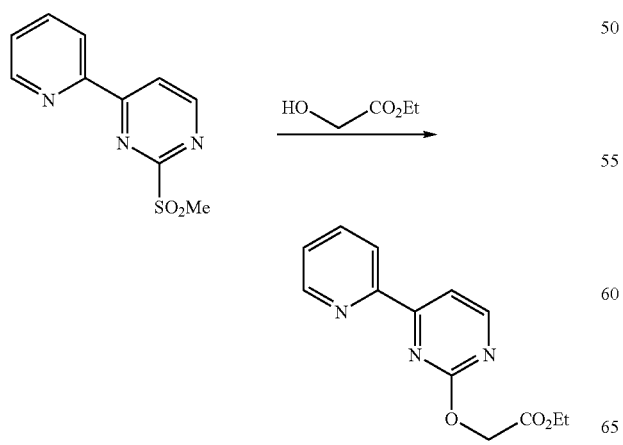

Using 3-(dimethylamino)-1-(2-pyridinyl)-2-propen-1-one and methyl 2-amino-2-iminoethylcarbamate as starting materials, the course of the process (G) according to the invention can be illustrated by the equation below.

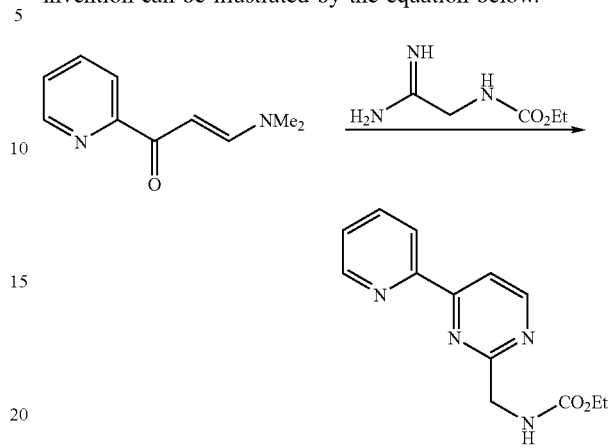

Using {[4-(2-pyridinyl)-2-pyrimidinyl]thio}acetic acid and tetrabutylammonium hydroxide as starting materials, the course of the process (H) according to the invention can be illustrated by the equation below.

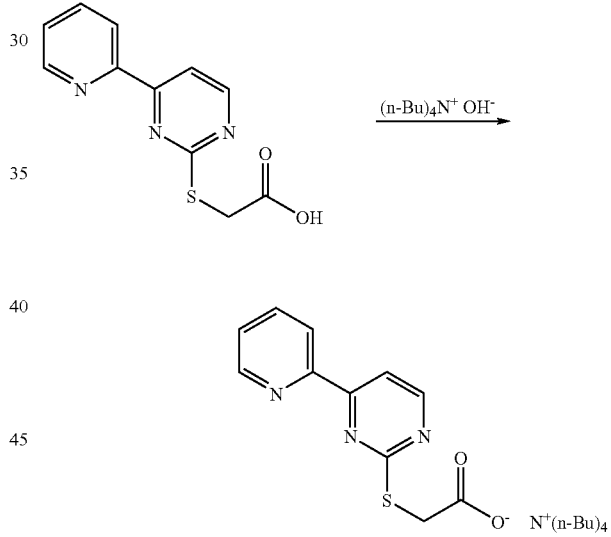

Using {[4-(2-pyridinyl)-2-pyrimidinyl]thio}acetonitrile and trimethyltin azide as starting materials, the course of process (J) according to the invention can be illustrated by the equation below.

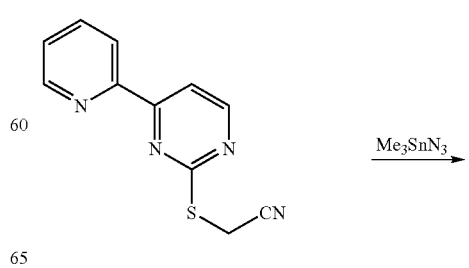

-continued

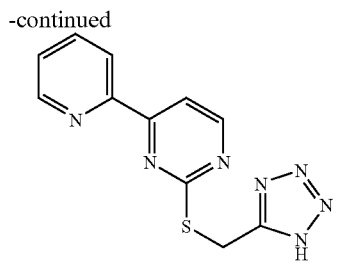

Using 1-benzyl-3-({[4-(2-pyridinyl)-2-pyrimidinyl]thio}methyl)-2,5-pyrrolidinedione and hydrogen as starting materials and palladium/activated carbon as catalyst, the course of the process (K) according to the invention can be illustrated by the equation below.

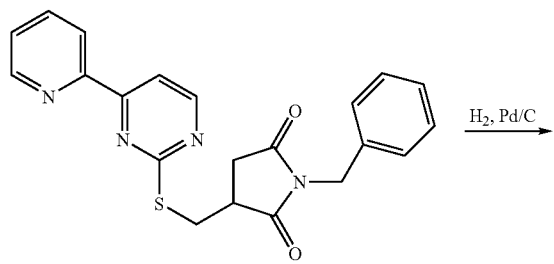

Using 1-{[4-(2-pyridinyl)-2-pyrimidinyl]thio}acetone, potassium cyanide and ammonium carbonate as starting materials, the course of the process (L) according to the invention can be illustrated by the formula scheme below.

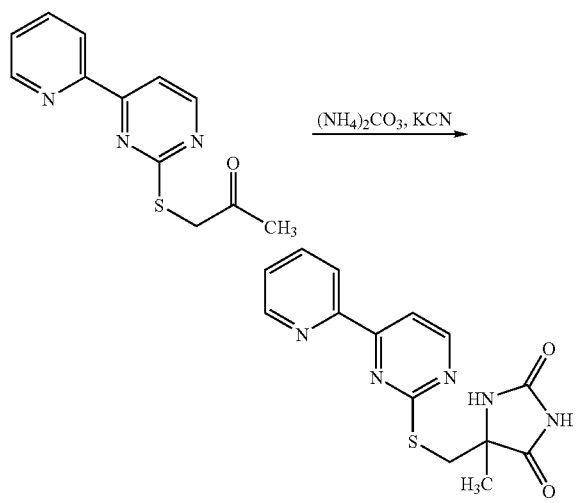

Explanation of the Processes and Intermediates

Process (A)

The formula (II) provides a general definition of the thiols required as starting materials for carrying out the process (A) according to the invention. In this formula, $R^1$, $R^2$, X and n preferably, particularly preferably and very particularly preferably have those meanings which have already been mentioned in connection with the description of the compounds of the formula (I) as being preferred, particularly preferred, etc., for these radicals.

The thiols of the formula (II-a)

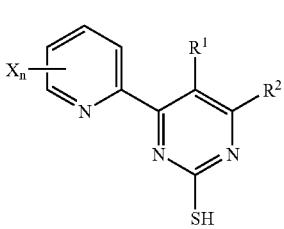
(II-a)

in which $R^1$, $R^2$, X and n have the meanings given above, with the proviso that at least one of the radicals $R^1$, $R^2$ and X does not represent hydrogen, are novel. They can be prepared by a) reacting pyridine derivatives of the formula (X)

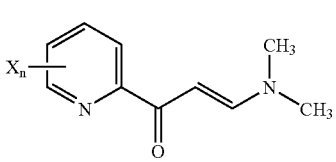
(X)

in which

X and n have the meanings given above with thiourea, if appropriate in the presence of a diluent (for example methanol, water) and if appropriate in the presence of a base (for example sodium hydroxide, sodium ethoxide), or b) reacting pyridine derivatives of the formula (XI)

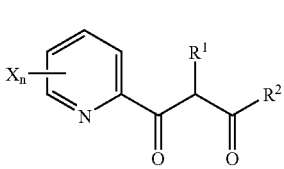
(XI)

in which $R^1$, $R^2$, X and n have the meanings given above with thiourea, if appropriate in the presence of a diluent (for example methanol, water) and if appropriate in the presence of a base (for example sodium hydroxide, sodium ethoxide) or an acid (for example hydrochloric acid or trifluoroacetic acid).

The formulae (X) and (XI) provide general definitions of the pyridine derivatives required as starting materials for carrying out the processes (a) and (b). In these formulae, $R^1$, $R^2$, X and n preferably, particularly preferably and very particularly preferably have those meanings which have already been mentioned in connection with the description of the compounds of the formula (I), according to the invention as being preferred, particularly preferred, etc., for these radicals.

Pyridine derivatives of the formulae (X) and (XI) are known and/or can be prepared by known processes (cf. J. Chem. Soc., Dalton Trans. 1999, 3095, J. Amer. Chem. Soc. 1951, 73, 5614).

The formula (III) provides a general definition of the halogen compounds required as starting materials for carrying out the process (A) according to the invention. In this formula, Z and A preferably, particularly preferably and very particularly preferably have those meanings which have already been mentioned in connection with the description of the compounds of the formula (I) according to the invention as being preferred, particularly preferred, etc., for these radicals. $E^1$ preferably represents —$OR^{16}$, —$SR^{16}$ or —$NR^{17}R^{18}$, particularly preferably —$OR^{16}$ or —$SR^{16}$, where $R^{16}$, $R^{17}$ and $R^{18}$ each preferably, particularly preferably and very particularly preferably have those meanings which have already been mentioned in connection with the description of the compounds of the formula (I) according to the invention as being preferred, particularly preferred, etc., for these radicals. $Hal^1$ preferably represents chlorine, bromine or iodine, particularly preferably chlorine or bromine.

Halogen compounds of the formula (III) are known and can be prepared by known processes.

Suitable diluents for carrying out the process (A) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl tert-butyl ether, ethyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; or sulphones, such as sulpholane. Particular preference is given to using acetonitrile or dimethylformamide.

Suitable acid binders for carrying out the process (A) according to the invention are in each case all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal hydrides, such as sodium hydride, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). Particular preference is given to using alkali metal carbonates or hydrides, very particularly preferably potassium carbonate.

When carrying out the process (A) according to the invention, the reaction temperatures can in each case be varied within a relatively wide range. In general, the process is carried out at temperatures between −20° C. and 200° C., preferably between 0° C. and 150° C., very particularly preferably between 20° C. and 100° C.

When carrying out the process (A) according to the invention, in general 1 mol or a slight excess of the compound of the formula (III) and 1-10 mol of acid binder are employed per mole of the compound of the formula (II). However, it is also possible to employ the reaction components in other ratios. Work-up is carried out by customary methods. In general, the reaction mixture is concentrated and extracted and the organic phase is washed, dried, filtered and concentrated. The residue is, if required, freed from any impurities that may still be present using customary methods, such as chromatography or recrystallization.

Process (B)

The formula (IV) provides a general definition of the halogenopyrimidines required as starting materials for carrying out the process (B) according to the invention In this formula, $R^1$, $R^2$, Z and A preferably, particularly preferably and very particularly preferably have those meanings which have already been mentioned in connection with the description of the compounds of the formula (I) according to the invention as being preferred, particularly preferred,. etc. for these radicals. $E^1$ preferably represents —$OR^{16}$, —$SR^{16}$ or —$NR^{17}R^{18}$, particularly preferably —$OR^{16}$ or —$SR^{16}$, where $R^{16}$, $R^{17}$ and $R^{18}$ each preferably, particularly preferably and very particularly preferably have those meanings which have already been mentioned in connection with the description of the compounds of the formula (I) according to the invention as being preferred, particularly preferred, etc., for these radicals. $Hal^2$ preferably represents fluorine, chlorine, bromine or iodine, particularly preferably chlorine, bromine or iodine, very particularly preferably chlorine or bromine.

Some of the halogenopyrimidines of the formula (IV) are known, and/or can be prepared by known processes (cf. U.S. Pat. No. 3,910,910).

Halogenopyrimidines of the formula (IV-a)

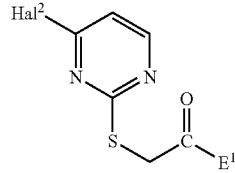

(IV-a)

in which
a) $E^1$ represents methoxy or ethoxy and
 $Hal^2$ represents bromine, or
b) $E^1$ represents methoxy and
 $Hal^2$ represents chlorine, are novel.

The formula (V) provides a general definition of the pyridine compounds required as starting materials for carrying out the process (B) according to the invention. In this formula, X and n preferably, particularly preferably and very particularly preferably have those meanings which have already been mentioned in connection with the description of the compounds of the formula (I) according to the invention as being preferred, particularly preferred, etc., for these radicals. L preferably represents $Sn(n-Bu)_3$, $Sn(Me)_3$, $Sn(phenyl)_3$, ZnBr or ZnCl, particularly preferably $Sn(n-Bu)_3$, $Sn(Me)_3$, $Sn(phenyl)_3$ or ZnBr, very particularly preferably $Sn(n-Bu)_3$, $Sn(Me)_3$ or ZnBr.

Pyridine compounds of the formula (V) are known and/or can be prepared by known processes.

Suitable diluents for carrying out the process (B) according to the invention are in each case all customary inert organic solvents. Preference is given using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide. Particular preference is given to using aromatic hydrocarbons, very particularly preferably benzene, toluene or xylene.

When carrying out the process (B) according to the invention, in general a palladium catalyst is employed which for its part can be used with or without addition of further ligands. The catalyst used is preferably $PdCl_2(dppf)$ [dppf=1,1'-bis(diphenylphosphino)ferrocene], $Pd(PPh_3)_4$, $PdCl_2(PPh_3)_2$, $PdCl_2(CH_3CN)_2$, $Pd_2(dba)_3$ [dba=dibenzylideneacetone] or $Pd(OAc)_2$, particularly preferably $PdCl_2(dppf)$, $Pd(PPh_3)_4$, $PdCl_2(PPh_3)_2$, or $Pd(OAc)_2$, very particularly preferably $PdCl_2(dppf)$ or $Pd(PPh_3)_4$.

Suitable ligands are triarylphosphines, trialkylphosphines or arsines. Preference is given to using dppf, $PPh_3$, $P(t-Bu)_3$, $Pcy_3$ or $AsPh_3$, particularly preferably dppf.

When carrying out the process (B) according to the invention, the reaction temperatures can be varied within a relatively wide range. In general, the process is carried out at temperatures between $-20°$ C. and $200°$ C., preferably between $0°$ C. and $150°$ C.

When carrying out the process (B) according to the invention, in general 1 mol or a slight excess of the compound of the formula (V) and 1-5 mol % of catalyst are employed per mole of the compound of the formula (IV). However, it is also possible to employ the reaction components in other ratios. Work-up is carried out by customary methods. In general, the reaction mixture is concentrated and the crude product is freed from any impurities that may be present using customary methods such as chromatography or recrystallization.

Process (C)

The formula (I-c) provides a general definition of the pyridylpyrimidines required as starting materials for carrying out the process (C) according to the invention. In this formula, $R^1$, $R^2$, X, n, Z and A preferably, particularly preferably and very particularly preferably have those meanings which have already been mentioned in connection with the description of the compounds of the formula (I) according to the invention as being preferred, particularly preferred, etc., for these radicals. $E^3$ preferably represents $-OR^{16}$, where $R^{16}$ preferably, particularly preferably and very particularly preferably have those meanings which have already been mentioned in connection with the description of the compounds of the formula (I) according to the invention as being preferred, particularly preferred, etc., for these radicals.

The pyridylpyrimidines of the formula (I-c) fall under the definition of the compounds of the formula (I) according to the invention and are prepared by one of the processes (A) or (B).

The formula (I-d) provides a general definition of the pyridylpyrimidines formed as intermediates when carrying out the process (C) according to the invention. In this formula, $R^1$, $R^2$, X, n, Z and A preferably, particularly preferably and very particularly preferably have those meanings which have already been mentioned in connection with the description of the compounds of the formula (I) according to the invention as being preferred, particularly preferred, etc., for these radicals.

The formula (VI) provides a general definition of the amines required as starting materials for carrying out the process (C) according to the invention. In this formula, $R^{17}$ and $R^{18}$ preferably, particularly preferably and very particularly preferably have those meanings which have already been mentioned in connection with the description of the compounds of the formula (I) according to the invention as being preferred, particularly preferred etc., for these radicals.

Amines of the formula (VI) are known and/or can be prepared by known processes.

Suitable diluents for carrying out the process (C) according to the invention are in each case all customary protic solvents. Preference is given to using water or alcohols, such as methanol, ethanol; nitriles, such as acetonitrile, propionitrile, n- or isobutyronitrile or benzonitrile; esters, such as methyl acetate or ethyl acetate. Particular preference is given to using water or alcohols, very particularly preferably methanol or ethanol.

Suitable water-absorbing reagents for carrying out the process (C) according to the invention are in each case all customary dehydrating agents. Preference is given to using carbodiimides. Particular preference is given to using dicyclohexylcarbodiimide (DCC) or N-(3-dimethylaminopropyl)-N'-ethyl-carbodiimide (EDC).

Suitable bases for carrying out the process (C) according to the invention are all inorganic and organic bases which are customary for such reactions. Preference is given to alkaline earth metal or alkali metal hydroxides, such as sodium hydroxide, calcium hydroxide, potassium hydroxide, or else ammonium hydroxide.

When carrying out the process (C) according to the invention, the reaction temperatures can in each case be varied within a relatively wide range. In general, the process is carried out at temperatures between $-20°$ C. and $200°$ C., preferably between $0°$ C. and $150°$ C., very particularly preferably between $20°$ C. and $100°$ C.

When carrying out the process (C) according to the invention, in general 1 mol of the compound of the formula (I-c) is, in the first step, initially treated with a base and, in the second step, treated with 1 mol or a slight excess of the compound of the formula (VI) and 1-1.5 mol % of a water-absorbing reagent. However, it is also possible to employ the reaction components in other ratios. Work-up is carried out by customary methods. In general, the reaction mixture is concentrated and the crude product is freed from any impurities that may be present using customary methods, such as chromatography or recrystallization.

Process (D)

The formula (I-f) provides a general definition of the pyridylpyrimidines required as starting materials for carrying out the process (D) according to the invention. In this formula, $R^1$, $R^2$, X, n, Z and R preferably, particularly preferably and very particularly preferably have those meanings which have already been mentioned in connection with the description of the compounds of the formula (I) according to the invention as being preferred, particularly preferred, etc., for these radicals.

The pyridylpyrimidines of the formula (I-f) fall under the definition of the compounds of the formula (I) according to the invention and are prepared, for example, by one of the processes (A) or (B).

Suitable oxidizing agents for carrying out the process (D) according to the invention are all cusotmary oxidizing agents which can be used for oxidizing sulphur. Hydrogen peroxide, organic peracids, such as, for example, peracetic acid, m-chloroperbenzoic acid, p-nitroperbenzoic acid or atmospheric oxygen are particularly suitable.

Suitable diluents for carrying out the process (D) according to the invention are likewise inert organic solvents. Preference is given to using hydrocarbons, such as benzine, benzene, toluene, hexane or petroleum ether; chlorinated hydrocarbons, such as dichloromethane, 1,2-dichloroethane, chloroform, carbon tetrachloride or chlorobenzene; ethers, such as diethyl ether, dioxane or tetrahydrofuran; carboxylic acids, such as acetiacicid or propionic acid; or dipolar aprotic solvents, such as acetonitrile, acetone, ethyl acetate or dimethylformamide.

If appropriate, the process (D) according to the invention can be carried out in the presence of an acid binder. Suitable acid binders are all organic and inorganic acid binders which are customarily used. Preference is given to using alkaline earth metal or alkali metal hydroxides, acetates or carbonates, such as, for example, calcium hydroxide, sodium hydroxide, sodium acetate or sodium carbonate.

If appropriate, the process (D) according to the invention can be carried out in the presence of a suitable catalyst. Suitable catalysts are all metal salt catalysts which are customarily used for such oxidations of sulphur. In this context, ammonium molybdate and sodium tungstate may be mentioned by way of example.

When carrying out the process (D) according to the invention, the reaction temperatures can be varied within a relatively wide range. In general, the process is carried out at temperatures between −20° C. and +70° C., preferably at temperatures between 0° C. and +50° C.

For carrying out the process (D) according to the invention, in general from 0.8 to 1.2 mol preferably equimolar amounts, of oxidizing agent are used per mole of the compound of the formula (I-f) if the oxidation of the sulphur is to be stopped at the suilphoxide stage. For the oxidation to the sulphone, in general from 1.8 to 3.0 mol, preferably twice the molar amount, of oxidizing agent is used per mole of the compound of the formula (I-f). The practice of the reaction, work-up and isolation of the end product are carried out by customary processes.

Process (E)

The formula (VII) provides a general definition of the methylsulphonylpyrimidines required as starting materials for carrying out the process (E) according to the invention. In this formula,;R¹, R², X and n preferably, particularly preferably and very particularly preferably have those meanings which have already been mentioned in connection with the description of the compounds of the formula (I) according to the invention as being preferred, particularly preferred etc. for these radicals.

The methylsulphonylpyrimidines of the formula (VI) are novel. They can be prepared by
c) reacting methylthio derivatives of the formula (XVI)

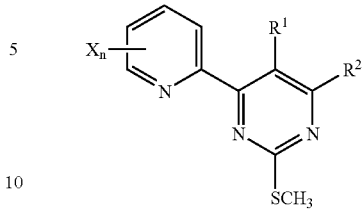

(XVI)

in which
R¹, R², X and n have the meanings given above
with an oxidizing agent (for example m-chloroperbenzoic acid), if appropriate in the presence of a diluent (for example dichloromethane).

The formula (XVI) provides a general definition of the methylthio derivatives required as starting materials for carrying out the process (c). In this formula, R¹, R², X and n preferably, particularly preferably and very particularly preferably have those meanings which have already been mentioned in connection with the description of the compounds of the formula (I) according to the invention as being preferred, particularly preferred, etc., for these radicals.

Methylthio derivatives of the formula (XVI) are novel. They can be prepared by
d) reacting thiols of the formula (II)

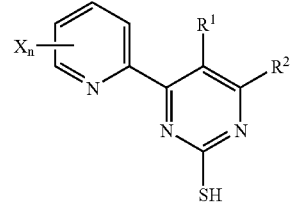

(II)

in which
R¹, R², X and n have the meanings given above
with a methylating agent (for example iodomethane), if appropriate in the presence of a diluent (for example acetonitrile) and if appropriate in the presence of an acid binder (for example potassium carbonate).

Thiols of the formula (II) have already been described in connection with the description of the process (A) according to the invention.

The formula (VIII) provides a general definition of the amines required as starting materials for carrying out the process (E) according to the invention. In this formula, Z and R⁹ preferably, particularly preferably and very particularly preferably have those meanings which have already been mentioned in connection with the description of the compounds of the formula (I) according to the invention as being preferred, particularly preferred etc., for these radicals.

Amines of the formula (VIII) are known and/or can be prepared by known processes.

Suitable diluents for carrying out the process (E) according to the invention are in each case all customary inert organic solvents. Preference is given to using nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; ethers, such as diethyl ether, diisopropyl ether, methyl tert-butyl ether, methyl tert-amyl ether, dioxane, tetrahydrofuran, 1,2- dimethoxyethane, 1,2-diethoxyethane or anisole; esters, such as methyl acetate or ethyl acetate; sulphoxides, such as dimethyl sulphoxide; or sulphones, such as sulpholane. Particular preference is given to using nitriles, amides or sulphoxides, very particularly preferably acetonitrile, dimethylformamide, tetrahydrofuran or dimethyl sulphoxide.

Suitable bases for carrying out the process (E) according to the invention are in each case all inorganic and organic bases customary for such reactions. Preference is given to using alkaline earth metal or alkali metal hydroxides, such as sodium hydroxide, calcium hydroxide, potassium hydroxide, or else ammonium hydroxide, alkali metal hydrides, such as sodium hydride, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). Particular preference is given to using alkali metal carbonates or hydrides, very particularly preferably potassium carbonate or sodium hydride.

When carrying out the process (E) according to the invention, the reaction temperatures can in each case be varied within a relatively wide range. In general, the process is carried out at temperatures between −20° C. and 200° C., preferably between 0° C. and 150° C., very particularly preferably between 20° C. and 100° C.

When carrying out the process (E) according to the invention, in general 1 mol or a slight excess of the compound of the formula (VIII) and 0.1-5 mol of acid binder are employed per mole of the compound of the formula (VII). However, it is also possible to employ the reaction components in other ratios. Work-up is carried out by customary methods. In general, the reaction mixture is concentrated and extracted and the organic phase is washed, dried, filtered and concentrated. The residue is, if required, freed from any impurities that may still be present, using customary methods such as chromatography or recrystallization.

Process (F)

The methylsulphonylpyrimidines of the formula (VII) required as starting materials for carrying out the process (F) according to the invention have already been described in connection with the explanation of process (E).

The formula (IX) provides a general definition of the hydroxyl compounds required as starting materials for carrying out the process (F) according to the invention. In this formula, Z preferably, particularly preferably and very particularly preferably has those meanings which have already been mentioned in connection with the description of the compounds of the formula (I) according to the invention as being preferred, particularly preferred etc. for these radicals.

Hydroxyl compounds of the formula (IX) are known and/or can be prepared by known processes.

Suitable diluents for carrying out the process (F) according to the invention are in each case all customary inert organic solvents. Preference is given to using nitriles, such as acetonitrile, propionitrile, n- or isobutyronitrile or benzonitrile; amides, such as N,N-dimethylformamide, N,N-dimethylacetamide, N-methylfomanilide, N-methylpyrrolidone or hexamethylphosphoric triamide; esters, such as methyl acetate or ethyl acetate; sulphoxides, such as dimethyl sulphoxide; or sulphones, such as sulpholane. Particular preference is given to using nitriles, amides or sulphoxides, very particularly preferably acetonitrile, dimethylformamide or dimethyl sulphoxide.

Suitable bases for carrying out the process (F) according to the invention are in each case all inorganic and organic bases which are customary for such reactions. Preference is given to using alkaline earth metal or alkali metal hydroxides, such as sodium hydroxide, calcium hydroxide, potassium hydroxide, or else ammonium hydroxide, alkali metal hydrides, such as sodium hydride, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, and also tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU). Particular preference is given to using alkali metal carbonates or hydrides, very particularly preferably potassium carbonate or sodium hydride.

When carrying out the process (F) according to the invention, the reaction temperatures can in each case be varied within a relatively wide range. In general, the process is carried out at temperatures between −20° C. and 200° C., preferably between 0° C. and 150° C., very particularly preferably between 20° C. and 100° C.

When carrying out the process (F) according to the invention, in general 1 mol or a slight excess of the compound of the formula (IX) and 0.1-5 mol of acid binder are employed per mole of the compound of the formula (VII). However, it is also possible to employ the reaction components in other reactions. Work-up is carried out by customary methods. In general, the reaction mixture is concentrated and extracted and the organic phase is washed, dried, filtered and concentrated. The residue is, as required, freed from any impurities that may still be present using customary methods, such as chromatography or recrystallization.

Process (G)

The pyridine derivatives of the formulae (X) and (XI) required as starting materials for carrying out the process (G) according to the invention have already been described in connection with the explanation of process (A).

The formula (XII) provides a general definition of the amidines required as starting materials for carrying out the process (G) according to the invention. In this formula, Z preferably, particularly preferably and very particularly preferably has those meanings which have already been mentioned in connection with the description of the compounds of the formula (I) according to the invention as being preferred, particularly preferred etc., for these radicals.

Amidines of the formula (XII) are known and/or can be prepared by known processes.

Suitable diluents for carrying out the process (G) according to the invention are in each case all customary protic solvents. Preference is given to using water or alcohols, such as methanol, ethanol; nitriles, such as acetonitrile, propionitrile, n- or isobutyronitrile or benzonitrile; esters, such as methyl acetate or ethyl acetate.

Particular preference is given to using water or alcohols, very particularly preferably methanol or ethanol.

Suitable bases for carrying out the process (G) according to the invention are in each case all inorganic and organic bases which are customary for such reactions. Preference is given to using alkaline earth metal or alkali metal hydroxides, such as sodium hydroxide, calcium hydroxide, potassium hydroxide, or ammonium hydroxide, alkali metal hydrides, such as sodium hydride, alkali metal carbonates, such as sodium carbonate, potassium carbonate, potassium bicarbonate, sodium bicarbonate, alkali metal or alkaline earth metal acetates, such as sodium acetate, potassium acetate, calcium acetate, alkali metal alkoxides, such as sodium methoxide, sodium ethoxide. Particular preference is given to using alkali metal alkoxides, very particularly preferably sodium methoxide.

When carrying out the process (G) according to the invention, the reaction temperatures can in each case be varied within a relatively wide range. In general, the process is carried out at temperatures between −20° C. and 200° C., preferably between 0° C. and 150° C., very particularly preferably between 20° C. and 100° C.

When carrying out the process (G) according to the invention, in general 1 mol or a slight excess of the compound the formula (XII) and 0.1-5 mol of acid binder are employed per mole of the compound of the formula (X) or (XI). However, it is also possible to employ the reaction components in other ratios. Work-up is carried out by customary methods. In general, the reaction mixture is concentrated and extracted and the organic phase is washed, dried, filtered and concentrated. The residue is, if required, freed from any impurities that may still be present using customary methods, such as chromatography recrystallization.

Process (H)

The formula (I-k) provides a general definition of the pyridylpyrimidines required as starting materials for carrying out the process (H) according to the invention. In this formula, $R^1$, $R^2$, X, n, Z and A preferably, particularly preferably and very particularly preferably have those meanings which have already been mentioned in connection with the description of the compounds of the formula (I) as being preferred, particularly preferred etc., for these radicals. $Y^2$ preferably represents a direct bond, sulphur, oxygen or $NR^9$.

Pyridylpyrimidines of the formula (I-k) are likewise compounds according to the invention; they can be prepared, for example, by e) treating esters of the formula (I-u)

(I-u)

in which $R^1$, $R^2$, X, n, $Y^2$, A and $E^3$ have the meanings given above with a base (for example sodium hydroxide), if appropriate in the presence of a diluent (for example methanol).

Pyridylpyrimidines of the formula (I-u) also form part of the subject-matter of the present invention and can be prepared by process (A) or (B).

The formula (XIII) provides a general definition of the hydroxides required as starting materials for carrying out the process (H) according to the invention. In this formula, M preferably, particularly preferably and very particularly preferably has those meanings which have already been mentioned in connection with the description of the compounds of the formula (I) according to the invention as being preferred, particularly preferred etc., for these radicals.

Hydroxides of the formula (XIII) are known and/or can be prepared by known processes.

Suitable diluents for carrying out the process (H) according to the invention are in each case all customary protic solvents. Preference is given to using water or alcohols, such as methanol, ethanol; nitriles, such as acetonitrile, propionitrile, n- or isobutyronitrile or benzonitrile. Particular preference is given to using water or alcohols.

When carrying out the process (H) according to the invention, the reaction temperatures can in each case be varied within a relatively wide range. In general, the process is carried out at temperatures between 0° C. and 200° C., preferably between 0° C. and 150° C., very particularly preferably between 20° C. and 100° C.

When carrying out the process (H) according to the invention, in general 1 mol or a slight excess of the compound of the formula (XIII) is employed per mole of the compound of the formula (I-k). However, it is also possible to employ the reaction components in other ratios. Work-up is carried out by customary methods. In general, the reaction mixture is concentrated and extracted and the organic phase is washed, dried, filtered and concentrated. The residue is, if required, freed from any impurities that may still be present using customary methods, such as chromatography or recrystallization.

Process (J)

The formula (XIV) provides a general definition of the nitrites required as starting materials for carrying out the process (J) according to the invention. In this formula, $R^1$, $R^2$, X, n, Y and Z preferably, particularly preferably and very particularly preferably have those meanings which have already been mentioned in connection with the description of the compounds of the formula (I) according to the invention as being preferred, particularly preferred, etc., for these radicals.

Nitriles of the formula (XIV) are novel. They can be prepared by f) reacting thiols of the formula (II)

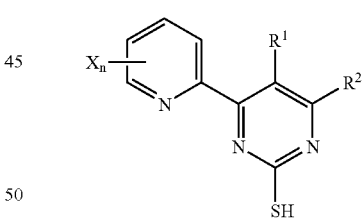

(II)

in which $R^1$, $R^2$, X and n have the meanings given above with chorinated nitriles of the formula (XVII)

Cl-Z-CN                                    (XVII)

in which

Z has the meanings given above, if appropriate in the presence of a diluent (for example toluene) and if appropriate in the presence of an acid binder (for example sodium hydroxide).

The compounds of the formula (II) required as starting materials for carrying out the process (f) have already been described in connection with the description of the process (A) according to the invention.

The formula (XVII) provides a general definition of the chlorinated nitriles required as starting materials for carrying out the process (f). In this formula, Z preferably, particularly preferably and very particularly preferably has those meanings which have already been mentioned in connection with the description of the compounds of the formula (I) according to the invention as being preferred, particularly preferred, etc., for these radicals.

Chlorinated nitriles of the formula (XVII) are known.

The trialkyltin azides required for carrying out the process (J) according to the invention are known. Preference is given to using trimethyltin azide or tri(n-butyl)tin azide.

Suitable diluents for carrying out the process (J) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylfdrmanilide, N-methylpyrrolidone or hexamethylphosphoric triamide; esters, such as methyl acetate or ethyl acetate; sulphoxides, such as dimethyl sulphoxide; or sulphones, such as sulpholane. Particular preference is given to using toluene.

When carrying out the process (J) according to the invention, in general 1 mol or a slight excess of the trialkyltin azide is employed per mole of the compound of the formula (XIV). However, it is also possible to employ the reaction components in other ratios. Work-up is carried out by customary methods. In general, the reaction mixture is concentrated and extracted and the organic phase is washed, dried, filtered and concentrated. The residue is, if required, freed from any impurities that may still be present using customary methods, such as chromatography or recrystallization.

Process (K)

The formula (I-n) provides a general definition of the pyridylpyrimidines required as starting materials for carrying out the process (K) according to the invention. In this formula, $R^1$, $R^2$, X, n and Z preferably, particularly preferably and very particularly preferably have those meanings which have already been mentioned in connection with the description of the compounds of the formula (I) according to the invention as being preferred, particularly preferred, etc., for these radicals. $Y^2$ preferably represents a direct bond, sulphur, oxygen or $NR^9$.

Pyridylpyrimidines of the formula (I-n) are novel. They can be prepared by g) reacting compounds of the formula (XVIII)

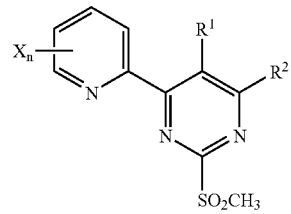

(XVIII)

in which

Z has the meanings given above,
$Y^3$ represents oxygen, sulphur or —$NR^9$—, where $R^9$ has the meanings given above, or Grignard reagents of the formula (XIX)

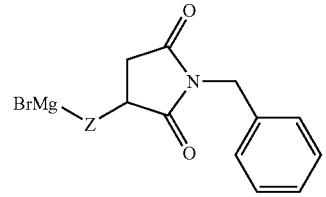

(XIX)

in which

Z has the meanings given above, with methylsulphonylpyrimidines of the formula (VII)

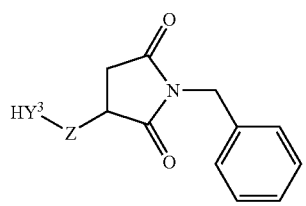

(VII)

in which $R^1$, $R^2$, X and n have the meanings given above, if appropriate in the presence of a diluent (for example tetrahydrofuran) and if appropriate in the presence of an acid binder (for example triethylamine).

The formulae (XVIII) and (XIX) provide general definitions of the compounds required as starting materials for carrying out the process (g). In these formulae, Z preferably, particularly preferably and very particularly preferably has those meanings which have already been mentioned in connection with the description of the compounds of the formula (I) according to the invention as being preferred, particularly preferred, etc., for these radicals.

Compounds of the formula (XVIII) and Grignard reagents of the formula (XIX) can be prepared by known processes.

Compounds of the formula (VII) have already been described above in connection with the description of the process (E).

Suitable diluents for carrying out the process (K) according to the invention are in each case all customary inert organic solvents. Preference is given to using nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; esters, such as methyl acetate or ethyl acetate; sulphoxides, such as dimethyl sulphoxide; or sulphones, such as sulpholane. Particular preference is given to using nitriles, amides or sulphoxides, very particularly preferably acetonitrile, dimethylformamide, tetrahydrofuran or dimethylsulphoxide.

Suitable catalysts for carrying out the process (K) according to the invention are all catalysts suitable for hydrogenation reactions. Preference is given to using palladium or platinum catalysts, particularly preferably palladium/activated carbon.

When carrying out the process (K) according to the invention, the reaction temperatures can in each case be varied within a relatively wide range. In general, the process is carried out at temperatures between −20° C. and 200° C., preferably between 0° C. and 150° C.

When carrying out the process (K) according to the invention, in general 1-10 mol % of a catalyst are employed per mole of the compound of the formula (I-n). However, it is also possible to employ the reaction components in other ratios. Work-up is carried out by customary methods. In general, the reaction mixture is concentrated and extracted and the organic phase is washed, dried, filtered and concentrated. The residue is, if required, freed from any impurities that may still be present using customary methods, such as chromatography or recrystallization.

Process (L)

The formula (XV) provides a general definition of the keto compounds required as starting materials for carrying out the process (L) according to the invention. In this formula, $R^1$, $R^2$, X, n and Z preferably, particularly preferably and very particularly preferably have those meanings which have already been mentioned in connection with the description of the compounds of the formula (I) according to the invention as being preferred, particularly preferred, etc., for these radicals. $Y^2$ preferably represents a direct bond, sulphur, oxygen or $NR^9$.

Keto compounds of the formula (XV) are novel. They can be prepared by h) reacting compounds of the formula (XX)

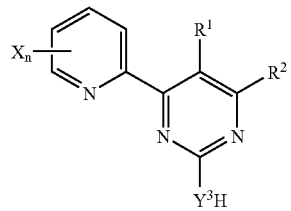

(XX)

in which
$R^1$, $R^2$, X, n and $Y^3$ have the meanings given above
with methyl ketones of the formula (XXI)

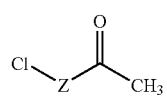

(XXI)

in which
Z has the meanings given above
if appropriate in the presence of a diluent (for example tetrahydrofuran) and if appropriate in the presence of an acid binder (for example triethylamine) or i) reacting methylsulphonylpyrimidines of the formula (VII)

(VII)

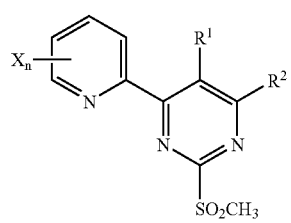

in which
$R^1$, $R^2$, X and n have the meanings given above
with Grignard reagents of the formula (XXII)

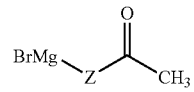

(XXII)

in which
Z has the meanings given above,
if appropriate in the presence of a diluent (for example tetrahydrofuran) and if appropriate in the presence of an acid binder (for example triethylamine).

The formula (XX) provides a general definition of the compounds required as starting materials for carrying out the process (h). In this formula, $R^1$, $R^2$, X and n preferably, particularly preferably and very particularly preferably have those meanings which have already been mentioned in connection with the description of the compounds of the formula (I) according to the invention as being preferred, particularly preferred, etc., for these radicals. $Y^3$ preferably represents sulphur, oxygen or $NR^9$.

Some of the compounds of the formula (XX) are known and/or can be prepared by known processes.

The formula (XXI) provides a general definition of the methyl ketones required as starting materials for carrying out the process (h). In this formula, Z preferably, particularly preferably and very particularly preferably has those meanings which have already been mentioned in connection with the description of the compounds of the formula (I) according to the invention as being preferred, particularly preferred, etc., for these radicals.

Methyl ketones of the formula (XXI) are known.

The methylsulphonylpyrimidines of the formula (VII) required as starting materials for carrying out the process (i) have already been described in connection with the explanation of process (E).

The formula (XXII) provides a general definition of the Grignard reagents required as starting materials for carrying out the process (i). In this formula, Z preferably, particularly preferably and very particularly preferably has those meanings which have already been mentioned in connection with the description of the compounds of the formula (I) according to the invention as being preferred, particularly preferred, etc., for these radicals.

Grignard reagents of the formula (XXII) are known.

Suitable diluents for carrying out the process (L) according to the invention are in each case all customary inert organic solvents. Preference is given to using optionally halogenated aliphatic, alicyclic or aromatic hydrocarbons, such as petroleum ether, hexane, heptane, cyclohexane, methylcyclohexane, benzene, toluene, xylene or decalin; chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide; esters, such as methyl acetate or ethyl acetate; sulphoxides, such as dimethyl sulphoxide; or sulphones, such as sulpholane.

When carrying out the process (L) according to the invention, in general 1 mol or a slight excess of ammonium carbonate and 1 mol or a slight excess of potassium cyanide are employed per mole of the compound of the formula (XV). However, it is also possible to employ the reaction components in other ratios. Work-up is carried out by customary methods. In general, the reaction mixture is concentrated and extracted and the organic phase is washed, dried, filtered and concentrated. The residue is, if appropriate, freed from any impurities that may still be present using customary methods, such as chromatography or recrystallization.

All processes according to the invention are generally carried out under atmospheric pressure. However, in each case it is also possible to operate under elevated or reduced pressure.

The active compounds according to the invention are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may preferably be employed as plant protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae* and *Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliiiella accidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyarni, Ceratitis capitata, Dacus oleae, Tipula paludosa, Hylemyla* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Omithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp. and *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

In particular, the compounds of the formula (I) according to the invention have excellent activity against caterpillars, beetle larvae, spider mites, aphids and leaf-mining flies.

If appropriate, the compounds according to the invention can, at certain concentrations or application rates, also be used as herbicides or microbicides, for example as fungicides, antimycotics and bactericides. If appropriate, they can also be employed as intermediates or precursors for the synthesis of other active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and including the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offsets and seeds.

The treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on and, in the case of propagation material, in particular in the case of seeds, also by applying one or more coats.

The active compounds according to the invention can be converted into the customary formulations, such as solutions, emulsions, wettable powders, suspensions, powders, dusts, pastes, soluble powders, granules, suspension-emulsion concentrates, natural and synthetic materials impregnated with active compound and microencapsulations in, polymeric substances.

These formulations are produced in a known manner, for example by mixing the active compounds according to the invention with extenders, that is to say liquid solvents and/or solid carriers, optionally with the use of surfactants, that is to say emulsifiers and/or dispersants and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are:
for example ammonium salts and ground natural minerals such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks;
suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates;
suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compounds according to the invention can be present in commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly suitable co-components are, for example, the following compounds:

Fungicides:
aldimorph, ampropylfos, ampropylfos-potassium, andoprim, anilazine, azaconazole, azoxystrobin,
benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram,
debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon,
edifenphos, epoxiconazole, etaconazole, ethirimol, etridiazole,
famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole,
imazalil, imibenconazole, iminoctadine, iminoctadine albesilate, iminoctadine triacetate, iodocarb, ipconazole, iprobenfos (IBP), iprodione, irumamycin, isoprothiolane, isovaledione,
kasugamycin, kresoxim-methyl, copper preparations, such as: copper hydroxide, copper naphthenate, copper oxychloride, copper sulphate, copper oxide, oxine-copper and Bordeaux mixture,
mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin,
nickel dimethyldithiocarbamate, nitrothal-isopropyl, nuarimol,
ofurace, oxadixyl, oxamocarb, oxolinic acid, oxycarboxim, oxyfenthiin,
paclobutrazole, pefurazoate, penconazole, pencycuron, phosdiphen, pimaricin, piperalin, polyoxin, polyoxbrim, probenazole, prochioraz, procymidone, propamocarb, propanosine-sodium, propiconazole, propineb, pyrazophos, pyrifenox, pyrimethanil, pyroquilon, pyroxyfur,
quinconazole, quintozene (PCNB),
sulphur and sulphur preparations,
tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflurnizole, triforine, triticonazole,
uniconazole,
validamycin A, vinclozolin, viniconazole,
zarilamide, zineb, ziram and also
Dagger G, OK-8705, OK-8801,
α-(1,1-dimethylethyl)-β-(2-phenoxyethyl)-1H-1,2,4-triazole-1-ethanol,
α-(2,4-dichlorophenyl)-β-fluoro-β-propyl-1H-1,2,4-triazole-1-ethanol,
α-(2,4-dichlorophenyl)-β-methoxy-α-methyl-1H-1,2,4-triazole-1-ethanol,
α-(5-methyl-1,3-dioxan-5-yl)-β-[[4-(trifluoromethyl)-phenyl]-methylene]-1H-1,2,4-triazole-1-ethanol,
(5RS,6RS)-6-hydroxy-2,2,7,7-tetramethyl-5-(1H-1,2,4-triazol-1-yl)-3-octanone,
(E)-α-(methoxyimino)-N-methyl-2-phenoxy-phenylacetamide,
1-isopropyl{2-methyl-1-[[[1-(4-methylphenyl)-ethyl]-amino]-carbonyl]-propyl}-carbamate,
1-(2,4-dichlorophenyl)-2-(1H-1,2,4-triazol-1-yl)-ethanone-O-(phenylmethyl)-oxime,
1-(2-methyl-1-naphthalenyl)-1H-pyrrole-2,5-dione,
1-(3,5-dichlorophenyl)-3-(2-propenyl)-2,5-pyrrolidinedione,
1-[(diiodomethyl)-sulphonyl]-4-methyl-benzene,
1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl -2-propynyl)-oxy]-methyl]-benzamide,
3-(1,1-dimethylpropyl)-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl[(4-chlorophenyl)-azo]-cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide,
N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidineamine,
N-(4-hexylphenyl)-1,4,5,6-tetrahydro-2-pyrimidineamine,
N-(5-chloro-2-methylphenyl)-2-methoxy-N-(2-oxo-3-oxazolidinyl)-acetamide,
N-(6-methoxy-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methaneimidamide,
N-formyl-N-hydroxy-DL-alanine-sodium salt,
O,O-diethyl[2-(dipropylamino)-2-oxoethyl]-ethylphosphoramindothioate,
O-methyl S-phenyl phenylpropylphosphoramidothioate,
S-methyl 1,2,3-benzothiadiazole-7-carbothioate,
spiro[2H]-1-benzopyran-2,1'(3'H)-isobenzofuran]-3'-one.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alphacypermethrin, alphamethrin, amitraz, averrmectin, AZ 60541, azadirachtin, azamethiphos, azinphos A, azinphos M, azocyclotin,

*Bacillus popilliae, Bacillus sphaericus, Bacillus subtilis, Bacillus thuringiensis,* baculoviruses, *Beauveria bassiana, Beauveria tenella,* bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpynifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypernethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, Entomopfthora spp., eprinomectin, esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses, halofenozide, HCH, heptenophos, hexaflumuron, hexythiazox, hydroprene, imidacloprid, isazofos, isofenphos, isoxathibn, ivermectin, nuclear polyhedrosis viruses, lambda-cyhalothrin, lufenuron, malathion, mecarbam, metaldehyde, methamidophos, *Metharhizium anisopliae,* Metharhizium flavoviride, methidathion, methiocarb, methomyl, methoxyfenozide, metolcarb, metoxadiozone, mevinphos, milbemectin, monocrotophos, naled, nitenpyram, nithiazine, novaluron, omethoate, oxamyl, oxydemethon M,

*Paecilamyces fumosoroseus,* parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, phraclofos, pyresmethrin, pyrethrum, pyridaben, pyridathion, pyrimidifen, pyrinproxyfen, quinalphos, ribavirin, salithion, sebufos, selamectin, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, thetacypermethrin, thiamethoxam, thiapronil, thiatriphos, thiocyclam hydrogen oxalate, thiodicarb, thiofanox, thuringiensin, tralocythrin, tralomethrin, triarathene, triazamate, thiazophos, thrazuron, trichlophenidine, trichlorfon, triflumuron, trimethacarb, vamidothion, vaniliprole, *Verticillium lecanii,*

YI 5302, zeta-cypermethrin, zolaprofos, (1R-cis)-[5-(phenylmethyl)-3-furanyl]-methyl-3-[(dihydro-2-oxo-3(2H)-furanyliden)-methyl]-2,2-dimethylcyclopropanecarboxylate, (3-phenoxyphenyl)-methyl-2,2,3,3-tetramethylcyclopropanecarboxylate, 1-[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl)phenyl]-4,5-dihydro-oxazole, 2-(acetyloxy)-3-dodecyl-1,4-naphthalenedione, 2-chloro-N-[[[4-)1-phenylethoxy)-phenyl]-amino]-carbonyl]-benzamide, 2-chlor-N-[[[4-(2,2-dichloro-1,1-difluoroethoxy)-phenyl]-amino]-carbonyl]-benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro [4.5] dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl[2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N''-nitroguanidine, N-methyl-N'-(1-methyl-2-propenyl)-1,2-hydrazinedicarbothioamide, N-methyl-N'-2-propenyl-1,2-hydrazinedicarbothioamide, O,O-diethyl[2-(dipropylamino)-2-oxoethyl]-ethylphosphoramidothioate.

It is also possible to admix other known active compounds, such as herbicides, fertilizers and growth regulators.

When used as insecticides, the active compounds according to the invention can furthermore be present in their commercially available formulations and in the use forms, prepared from these formulations, as a mixture with synergistic agents. Synergistic agents are compounds which increase the action of the active compounds according to the invention, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound is distinguished by an excellent residual action on wood and clay as well as a good stability to alkali on limed substrates.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above.

Particularly preferably, plants of the plant cultivars which are in each case commercially available or in use are treated according to the invention. Plant cultivars are to be understood as meaning plants having specific properties ("traits") which have been obtained by conventional breeding, by mutagenesis or by recombinant DNA techniques. This can be varieties, bio- and genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions to be used according to the invention, better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products are possible which extend beyond the effects which were actually to be expected.

The preferred transgenic plants or plant cultivars (i.e. those obtained by genetic engineering) which are to be treated according to the invention include all plants which, in the genetic modification, received genetic material which impaired particularly advantageous useful properties ("traits") to these plants. Examples of such properties are better plant growth, increased tolerance to high or low temperatures, increased tolerance to drought or to water or soil salt content, increased flowering performance, easier harvesting, accelerated maturation, higher harvest yields, better quality and/or a higher nutritional value of the harvested products, better storage stability and/or processability of the harvested products. Further and particularly emphasized examples of such properties are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, cotton, oilseed rape and also fruit plants (with the fruits apples, pears, citrus fruits and grapevines), and particular emphasis is given to maize, soya beans, potatoes, cotton and oilseed rape. Traits that are emphasized are in particular increased defence of the plants against insects by toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof) (hereinbelow referred to as "Bt plants"). Traits that are also particularly emphasized are the increased defence of plants to fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combinations with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya bean), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these or still to be developed genetic traits, which plants will be developed and/or marketed in the future.

The plants listed can be treated according to the invention in a particularly advantageous manner with the compounds of the general formula (I) or the active compound mixtures according to the invention. The preferred ranges stated above for the active compounds or mixtures also apply to the treatment of these plants. Particular emphasis is given to the treatment of plants with the compounds or the mixtures specifically mentioned in the present text.

The active compounds according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon,* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyla* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example, *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example, *Blatta orientalis, Periplaneta americana, Blattella germanica* and *Supella* spp.

From the subclass of the Acaria (Acarida) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

They have, for example, excellent activity against the development stages of ticks, against flies and against fleas.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) according to the invention can be used as formulations (for example powders, emulsions, free-flowing compositions), which comprise the active compounds according to the invention in an amount of 1 to 80% by weight, directly or after 100 to 10 000-fold dilution, or they can be used as a chemical bath.

It has furthermore been found that the compounds according to the invention have a strong insecticidal action against insects which destroy industrial materials.

The following insects may be mentioned as examples and as preferred—but without a limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec.*, Tryptodendron* spec.*, Apate monachus, Bostrychus capucins, Heterobostrychus brunneus, Sinoxylon* spec. and *Dinoderus minutus.*

Hymenopterons, such as

*Sirex juvencus, Urocerus gigas, Urocerus gigas taignus* and *Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus.*

Bristletails, such as *Lepisma saccharina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising it are to be understood as meaning, for example:
building timber, wooden beams, railway sleepers, bridge components, boat jetties, wooden vehicles, boxes, pallets, containers, telegraph poles, wood panelling, wooden window frames and doors, plywood, chipboard, joinery or wooden products which are used quite generally in housebuilding or in building joinery.

The active compounds according to the invention can be used as such, in the form of concentrates or in generally customary formulations, such as, powders, granules, solutions, suspensions, emulsions or pastes.

The formulations mentioned can be prepared in a manner known per se, for example by mixing the active compounds according to the invention with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, provided that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or. polyaddition resin, polyurethane resin, alkyd resin or modified alkyd resin, phenolic resin, hydrocarbon resin, such as indene-coumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or a drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

Possible additional mixing partners are, preferably, the insecticides and fungicides mentioned in WO 94/29 268. The compounds mentioned in this document are an explicit constituent of the present application.

Very particularly preferred mixing partners which may be mentioned are insecticides, such as chlorpyriphos, phoxim, silafluofin, alphamethrin, cyfluthrin, cypermethrin, deltamethrin, permethrin, imidacloprid, NI-25, flufenoxuron, hexaflumuron, transfluthrin, thiacloprid, methoxyfenozide and triflumuron, and also fungicides, such as epoxyconazole, hexaconazole, azaconazole, propiconazole, tebuconazole, cyproconazole, metconazole, imazalil, dichlorfluanid, tolylfluanid, 3-iodo-2-propinyl-butyl carbamate, N-octyl-isothiazolin-3-one and 4,5-dichloro-N-octylisothiazolin-3-one.

The compounds according to the invention can at the same time be employed for protecting objects, which come into contact with salt water or brackish water, in particular-hulls, screens, nets, buildings, moorings and signalling systems, against fouling.

Fouling by sessile Oligochaeta, such as Serpulidae, and by shells and species from the Ledamorpha group (goose barnacles), such as various Lepas and Scalpellum species, or by species from the Balanomorpha group (acorn barnacles), such as Balanus or Pollicipes species, increases the frictional drag of ships and, as a consequence, leads to a marked increase in operation costs owing to higher energy consumption and additionally frequent residence in the dry dock.

Apart from fouling by algae, for example Ectocarpus sp. and Ceramium sp., fouling by sessile Entomostraka groups, which come under the generic term Cirripedia (*cirriped crustaceans*), is of particular importance.

Surprisingly, it has now been found that the compounds according to the invention, alone or in combination with other active compounds, have an outstanding antifouling action.

Using the compounds according to the invention, alone or in combination with other active compounds, allows the use of heavy metals such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl-(bispyridine)-bismuth chloride, tri-n-butyltin fluoride, manganese ethylenebisthio-carbamate, zinc dimethyldithio-carbamate, zinc ethylenebisthiocarbamate, zinc salts and copper salts of 2-pyridinethiol 1-oxide, bisdimethyldithio-carbamoylzinc ethylene-bisthiocarbamate, zinc oxide, copper(I) ethylene-bisdithiocarbamate, copper thiocyanate, copper naphthenate and tributyltin halides to be dispensed with, or the concentration of these compounds to be substantially reduced.

If appropriate, the ready-to-use antifouling paints can additionally comprise other active compounds, preferably algicides, fungicides, herbicides, molluscicides, or other antifouling active compounds.

Preferably suitable components in combinations with the antifouling compositions according to the invention are:

algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as benzo[b]thiophenecarboxylic acid cyclohexylamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as fentin acetate, metaldehyde, methiocarb, niclosamid, thiodicarb and trimethacarb;

or conventional antifouling active compounds such as 4,5-dichloro-2-octyl-4-isothiazolin-3-one, diiodomethylparatryl sulphone, 2-(N,N-dimethylthiocarbamoylthio)-5-nitrothiazyl, potassium, copper, sodium and zinc salts of 2-pyridinethiol 1-oxide, pyridine-triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound according to the invention of the compounds according to the invention in a concentration of 0.001 to 50% by weight, in particular 0.01 to 20% by weight.

Moreover, the antifouling compositions according to the invention comprise the customary components such as, for example, those described in Ungerer, *Chem. Ind.* 1985, 37, 730-732 and Williams, Antifouling Marine Coatings, Noyes, Park Ridge, 1973.

Besides the algicidal, fungicidal, molluscicidal active compounds and insecticidal active compounds according to the invention, antifouling paints comprise, in particular, binders.

Examples of recognized binders are polyvinyl chloride in a solvent system, chlorinated rubber in a solvent system, acrylic resins in a solvent system, in particular in an aqueous system, vinyl chloride/vinyl acetate copolymer systems in the form of aqueous dispersions or in the form of organic solvent systems, butadiene/-styrene/acrylonitrile rubbers, drying oils such as linseed oil, resin esters or modified hardened resins in combination with tar or bitumens, asphalt and-epoxy compounds, small amounts of chlorine rubber, chlorinated polypropylene and vinyl resins.

If appropriate, paints also comprise inorganic pigments, organic pigments or colorants which are preferably insoluble in salt water. Paints may furthermore comprise materials such as colophonium to allow controlled release of the active compounds. Furthermore, the paints may comprise plasticizers, modifiers which affect the Theological properties and other conventional constituents. The compounds according to the invention or the abovementioned mixtures may also be incorporated into self-polishing antifouling systems.

The active compounds according to the invention are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all development stages. These pests include:

From the order of the Scorpionidea, for example, *Buthus occitanus.*

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus* and *Dermatophagoides forinae.*

From the order of the Araneae, for example, *Aviculariidae* and *Araneidae.*

From the order of the Opiliones, for example, *Pseudoscorpiones chelifer, Pseudoscorpiones cheiridium* and *Opiliones phalangium.*

From the order of the Isopoda, for example, *Oniscus asellus* and *Porcellio scaber.*

From the order of the Diplopoda, for example, *Blaniulus guttulatus* and *Polydesmus* spp.

From the order of the Chilopoda, for example, *Geophilus* spp.

From the order of the Zygentoma, for example, *Ctenolepisma* spp., *Lepisma saccharina* and *Lepismodes inquilinus.*

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa* and *Supella longipalpa.*

From the order of the Saltatoria, for example, *Acheta domesticus.*

From the order of the Dermaptera, for example, *Forficula auricularia.*

From the order of the Isoptera, for example, *Kalotermes* spp. and *Reticulitermes* spp.

From the order of the Psocoptera, for example, *Lepinatus* spp. and *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais* and *Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans* and *Tipula paludosa.*

From the order of the Lepidoptera, for example, *Achroia grisella, Galleria mellonella, Plodia interpunctella, Tinea cloacella, Tinea pellionella* and *Tineola bisselliella.*

From the order of the Siphonaptera, for example, *Ctenocephalides canis, Ctenocephalides felis, Pulex irritans, Tunga penetrans* and *Xenopsylla cheopis.*

From the order of the Hymenoptera, for example, *Camponotus herculeanus, Lasius fuliginosus, Lasius niger, Lasius umbratus, Monomorium pharaonis, Paravespula* spp. and *Tetramorium caespitum.*

From the order of the Anoplura, for example, *Pediculus humanus capitis, Pediculus humanus corporis* and *Phthirus pubis.*

From the order of the Heteroptera, for example, *Cimex hemipterus, Cimex lectularius, Rhodinus prolixus* and *Triatoma infestans.*

In the field of household insecticides, they are used alone or in combination with other suitable active compounds, such as phosphoric acid esters, carbamates, pyrethroids, growth regulators or active compounds from other known classes of insecticides.

They are used as aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive evaporation systems, moth papers, moth bags and moth gels, as granules or dusts, in baits for spreading or in bait stations.

The preparation and use of the substances according to the invention is shown in the examples below.

PREPARATION EXAMPLES

Example 1

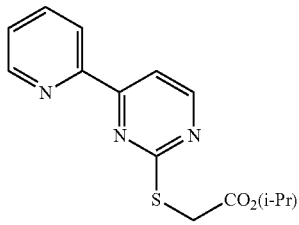

0.57 g (3 mmol) of 4-(2-pyridinyl)-2-pyrimidinethiol and 1.66 g (12 mmol) of potassium carbonate are initially charged in 30 ml of acetonitrile. 0.41 g (3 mmol) of isopropyl 2-chloroacetate are added, and the mixture is then stirred at 60° C. for 16 h. For work-up, the reaction mixture is concentrated under reduced pressure and partitioned between water and methylene chloride and the organic phase is dried and concentrated under reduced pressure.

This gives 0.72 g (79% of theory) of isopropyl {[4-(2-pyridinyl)-2-pyrimidinyl]thio}-acetate as an oil.

HPLC: log P (pH 2.3)=2.56.

Example 2

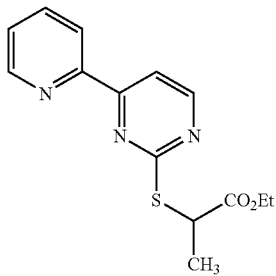

35.6 mg (0.188 mmol) of 4-(2-pyridinyl)-2-pyrimidinethiol and 104 mg (0.752 mmol) of potassium carbonate are initially charged in 5 ml of tetrahydrofuran. 34.0 mg (0.188 mmol) of ethyl 2-bromopropionate are added and the mixture is then stirred at 60° C. for 16 h. For work-up, 0.5 ml of water and 2 ml of ethyl acetate are added and the reaction mixture is stirred for 30 min, passed through an Extrelut silica gel cartridge and then concentrated under reduced pressure.

This gives 41 mg (70% of theory) of ethyl-2-{[4-(2-pyridinyl)-2-pyrimidinyl]thio}-propanoate.

HPLC: log P (pH 2.3)=2.74.

Example 3

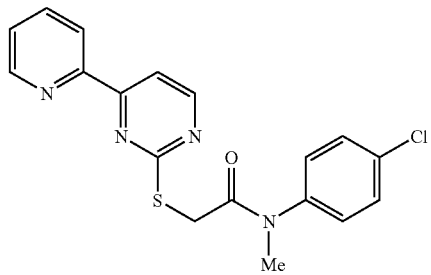

0.57 g (3 mmol) of 4-(2-pyridinyl)-2-pyrimidinethiol and 1.66 g (12 mmol) of potassium carbonate are initially charged in 30 ml of acetonitrile. 0.65 g (3 mmol) of N-(4-chlorophenyl)-N-methyl-2-chloroacetamide is added, and the mixture is then stirred at 60° C. for 16 h. For work-up, the mixture is concentrated under reduced pressure and partitioned between water and methylene chloride and the organic phase is dried and concentrated under reduced pressure.

This gives 1.09 g (81% of theory) of N-(4-chlorophenyl)-N-methyl-2-{[4-(2-pyridinyl)-2-pyrimidinyl]thio}acetamide.

HPLC: log P (pH 2.3)=2.73.

m.p. 142° C.

Example 4

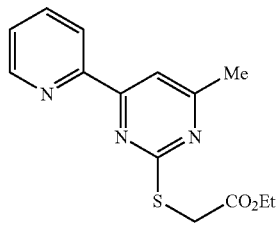

0.30 g (1.04 mmol) of ethyl [(4-bromo-6-methyl-2-pyrimidinyl)thio]acetate, 0.38 g (1.04 mmol) of 2-(tributylstannyl)pyridine and 0.06 g (0.05 mmol) of tetrakis(triphenylphosphine)palladium are initially charged under argon in 10 ml of xylene and refluxed for 16 h. For work-up, the mixture is concentrated under reduced pressure and the crude product is chromatographed on silica gel (mobile phase: dichloromethane).

This gives 0.215 g (70% of theory) of ethyl {[4-methyl-6-(2-pyridinyl)-2-pyrimidinyl]thio}acetate.

HPLC: log P (pH 2.3)=2.45.

Example 5

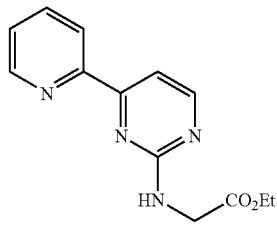

0.71 g (3 mmol) of 2-(methylsulphonyl)-4-(2-pyridinyl)pyrimidine and 0.33 g (3 mmol) of triethylamine are initially charged in 30 ml of ethanol, 0.46 g (3.3 mmol) of ethyl glycinate hydrochloride are added and the mixture is heated at reflux for 16 h. For work-up, the reaction mixture is concentrated under reduced pressure, taken up in dichloromethane, washed with sodium bicarbonate solution and citric acid solution, dried and concentrated under reduced pressure. The crude product is chromatographed on silica gel (mobile phase: dichloromethane/acetone 95:5).

This gives 0.12 g (13% of theory) of ethyl N-(4-(2-pyridinyl)-2-pyrimidinyl]glycinate.

HPLC log P (pH 2.3)=1.14.

m.p. 85° C.

Example 6

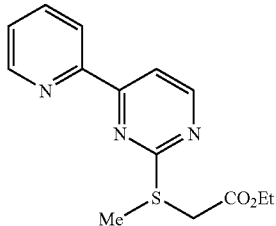

0.41 g (1.74 mmol) of 2-(methylsulphonyl)-4-(2-pyridinyl)pyrimidine and 0.48 g (3.49 mmol) of potassium carbonate are initially charged in 20 ml of DMF, 0.29 g (1.92 mmol) of ethyl N-methyl-glycinate hydrochloride are added and the mixture is stirred at 80° C. for 16 h. For work-up, the mixture is concentrated under reduced pressure, the residue is taken up in dichloromethane and the mixture is washed with sodium bicarbonate solution and citric acid solution, dried and concentrated under reduced pressure. The crude product is chromatographed on silica gel (mobile phase: dichloromethane/acetone 95:5).

This gives 0.14 g (30% of theory) of ethyl N-methyl-N-[4-(2-pyridinyl)-2-pyrimidinyl]glycinate as an oil.

HPLC: log P (pH 2.3)=1.66.

Example 7

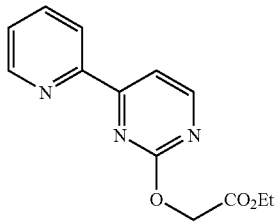

0.71 g (3 mmol) of 2-(methylsulphonyl)-4-(2-pyridinyl)pyrimidine is initially charged in 3 ml of ethyl glycolate. At a temperature of below 35° C., 0.18 g (4.5 mmol) of sodium hydride (60%) is then added a little at a time. The mixture is stirred at room temperature for another 30 min, after which water is added, and the mixture is extracted with dichloromethane. The crude product is chromatographed on silica gel (mobile phase: dichloromethane/acetone 95:5).

This gives 0.39 g (46% of theory) of ethyl {[4-(2-pyridinyl)-2-pyrimidinyl]oxy}acetate.

HPLC: log P (pH 2.3)=1.73 m.p. 48-53° C.

Example 8

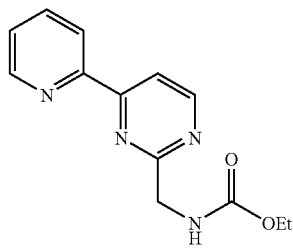

0.88 g (5 mmol) of 3-(dimethyl-amino)-1-(2-pyridinyl)-2-propen-1-one, 0.91 g (5 mmol) of methyl 2-amino-2-iminoethylcarbamate hydrochloride and 0.68 g (10 mmol) of sodium ethoxide are initially charged in 20 ml of ethanol and refluxed for 16 h. For work-up, the mixture is concentrated under reduced pressure, the residue is taken up in dichloromethane and the mixture is washed with a citric acid solution, dried and concentrated under reduced pressure.

This gives 0.35 g (25% of theory) of ethyl [4-(2-pyridinyl)-2-pyrimidinyl]methylcarbamate.

HPLC: log P (pH 2.3)=1.14.

Example 9

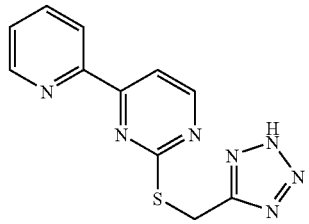

0.6 g (2.6 mmol) of 4-(2-pyridinyl)-pyrimidine-2-thioacetonitrile and 0.54 g (2.6 mmol) of trimethyltin azide in 30 ml of toluene are heated under reflux for 16 h. For work-up, the mixture is concentrated, the residue is dissolved in sodium hydroxide solution (10% strength in water) and the mixture is filtered to remove undissolved components. The filtrate is adjusted to pH 4 using hydrochloric acid (10% strength in water) and extracted with ethyl acetate. The organic phase is dried and concentrated under reduced pressure. To remove the last remaining traces of tin derivatives, the crude product is dissolved in dichloromethane and stirred with a saturated potassium fluoride solution for 5 hours. The organic phase is dried once more and concentrated under reduced pressure.

This gives 0.4 g (57% of theory) of 4-(2-pyridinyl)-pyrimidine-2-thiomethyl-tetrazole.

m.p. 162° C.

Preparation of Starting Materials

Nitriles of the Formula (XIV)

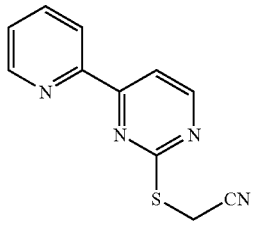

0.95 g (5 mmol) of 4-(2-pyridinyl)-2-pyrimidinethiol, 0.75 g (10 mmol) of chloroacetonitrile and 2.46 g (30 mmol) of sodium acetate in 30 ml of ethanol are boiled under reflux for 6 hours and then concentrated. The mixture is partitioned between dichloromethane and water and the organic phase is then separated off, dried and concentrated.

This gives 0.95 g (75% of theory) of 4-(2-pyridinyl)-pyrimidine-2-thioacetonitrile.

HPLC: log P (pH 2.3)=1.68.

Methylthio Derivatives of the Formula

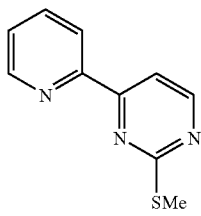

4.73 g (25 mmol) of 4-(2-pyridinyl)-2-pyrimidinethiol and 5.18 g (37.5 mmol) of potassium carbonate are initially charged in 50 ml of acetonitrile. 3.55 g (25 mmol) of iodomethane are added dropwise, and the mixture is stirred at 40° C. for 16 h. For work-up, the mixture is concentrated under reduced pressure, the residue is partitioned between water and methylene chloride and the organic phase is dried and concentrated under reduced pressure.

This gives 4.45 g (81% of theory) of 2-(methylthio)-4-(2-pyridinyl)pyrimidine.

HPLC: log P (pH 2.3)=1.93.

Methylsulphonylpyrimidines of the Formula (VII)

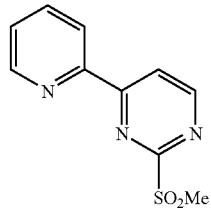

4.07 g (20 mmol) of 2-(methylthio)-4-(2-pyridinyl)pyrimidine are dissolved in 100 ml of dichloromethane. With ice-cooling, 10.85 g (44 mmol) of m-chloroperbenzoic acid (70% strength) are added a little at a time, and the mixture is stirred at room temperature for 16 h. The organic phase is washed successively with saturated sodium bicarbonate solution and sodium bisulphite solution, dried and concentrated under reduced pressure.

This gives 3.6 g (53% of theory) of 2-(methylsulphonyl)-4-(2-pyridinyl)pyrimidine.

HPLC: log P (pH 2.3)=0.99.

The compounds listed in the table below can be prepared according to one of the processes according to the invention described above.

| No. | Structure | log P (pH 2.3) | m.p./° C. |
|---|---|---|---|
| 10 | 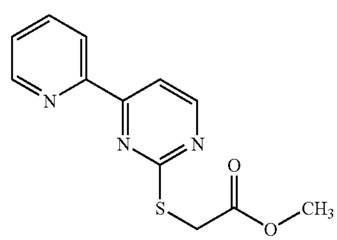 | 1.81 | 95 |
| 11 | 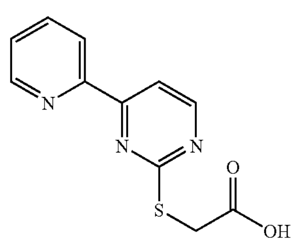 | 1.14 | 181 |

-continued

| No. | Structure | log P (pH 2.3) | m.p./ °C. |
|---|---|---|---|
| 12 | 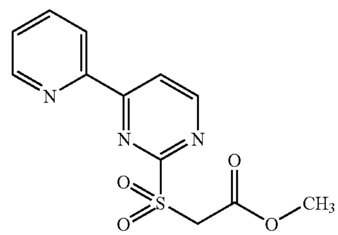 | 1.37 | 125 |
| 13 | 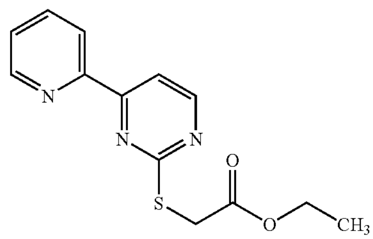 | 2.17 | 78-80 |
| 14 | 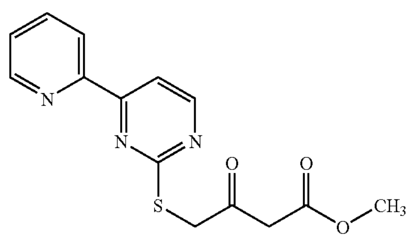 | 1.76 | |
| 15 | 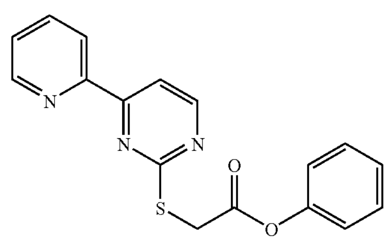 | 2.88 | |
| 16 | 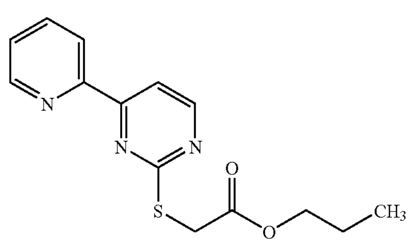 | 2.76 | |
| 17 | 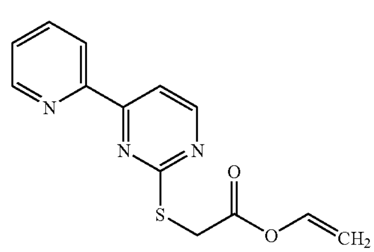 | 2.37 | 108 |

-continued

| No. | Structure | log P (pH 2.3) | m.p./ °C |
|---|---|---|---|
| 18 | 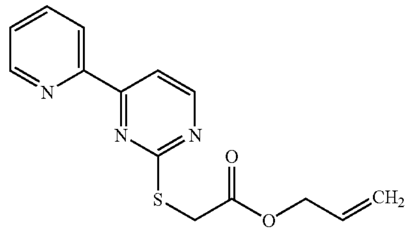 | 2.40 | 68 |
| 19 | 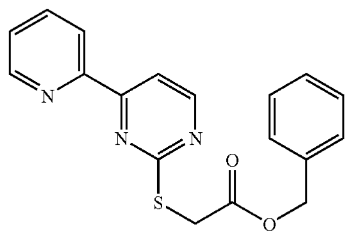 | 2.99 | 88 |
| 20 | 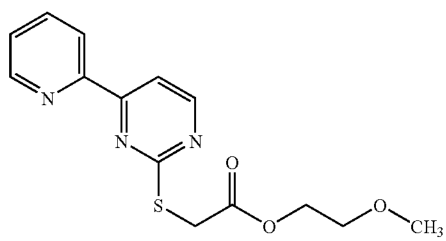 | 1.97 | |
| 21 | 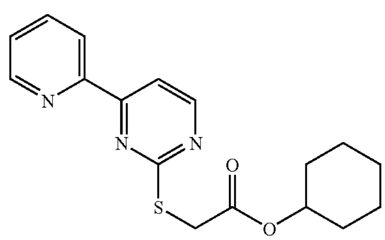 | 3.53 | |
| 22 | 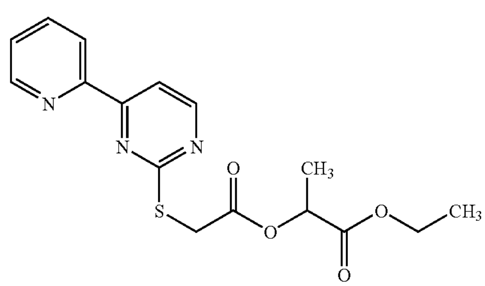 | 2.58 | |
| 23 | 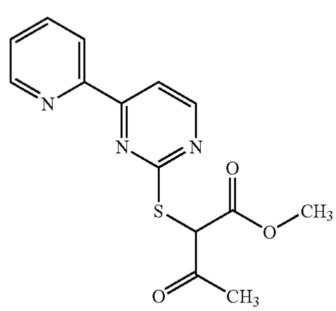 | 2.34 | 95 |

-continued

| No. | Structure | log P (pH 2.3) | m.p./ °C. |
|---|---|---|---|
| 24 | 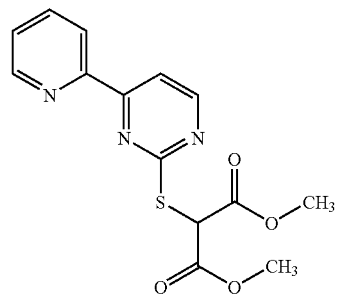 | 2.16 | |
| 25 | 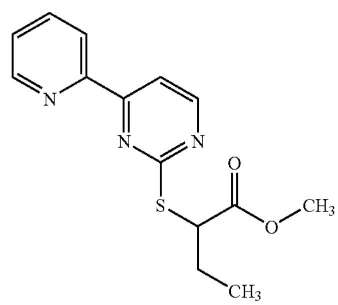 | 2.68 | |
| 26 | 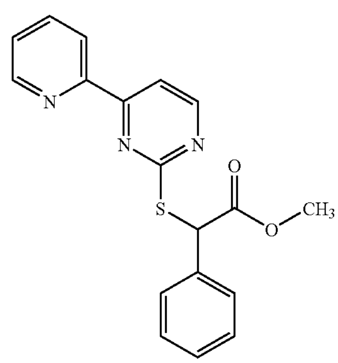 | 3.50 | 118 |
| 27 | 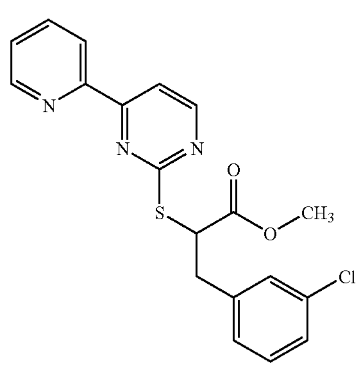 | 3.84 | |

-continued

| No. | Structure | log P (pH 2.3) | m.p./ °C |
|---|---|---|---|
| 28 | 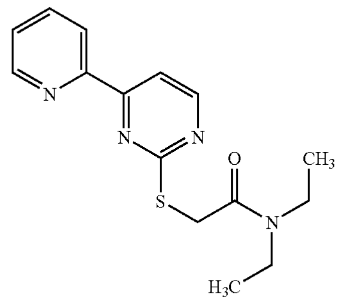 | 1.80 | 120 |
| 29 | 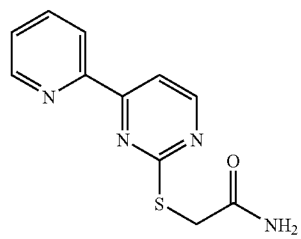 | 0.69 | 172 |
| 30 | 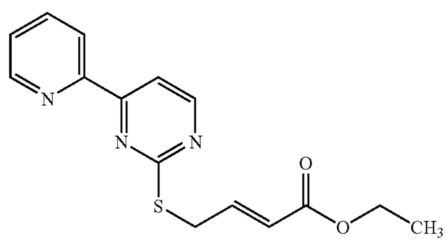 | 2.92 | |
| 31 | 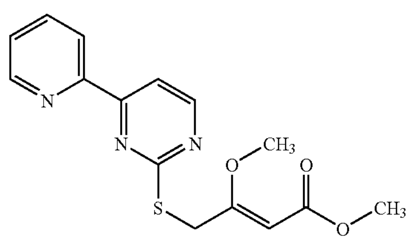 | 2.70 | |
| 32 | 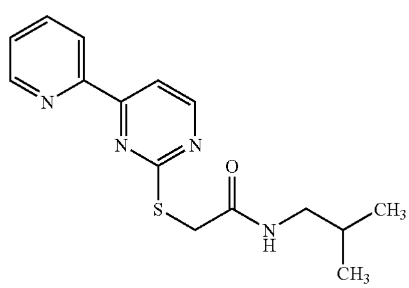 | 1.81 | |
| 33 | 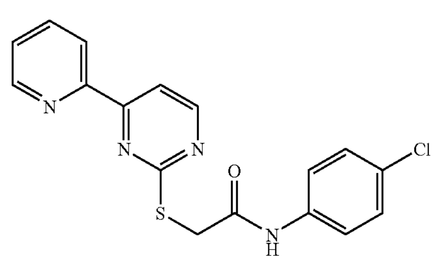 | 2.58 | |

-continued

| No. | Structure | log P (pH 2.3) | m.p./ °C. |
|---|---|---|---|
| 34 | 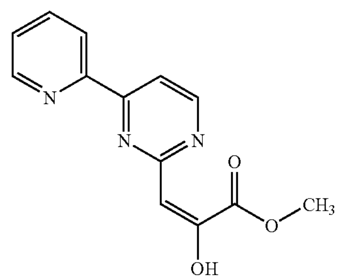 | 1.89 | 183 |
| 35 | 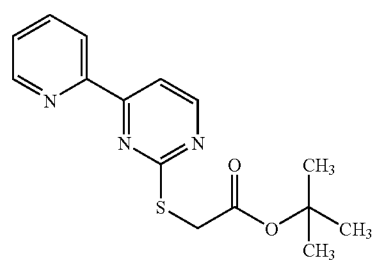 | 2.96 | 86 |
| 36 | 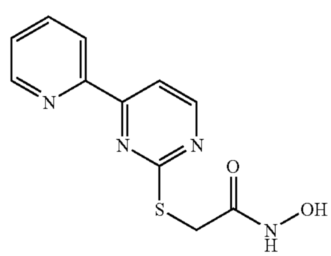 | 0.55 | 157 |
| 37 | 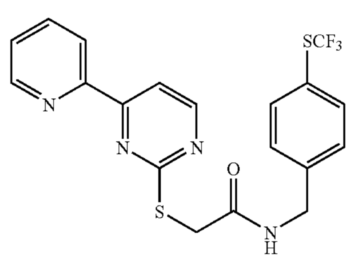 | 2.93 | |
| 38 | 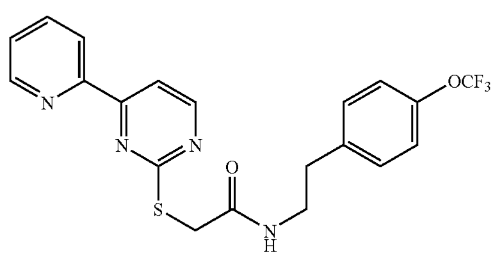 | 2.96 | |

-continued

| No. | Structure | log P (pH 2.3) | m.p./ °C. |
|---|---|---|---|
| 39 | 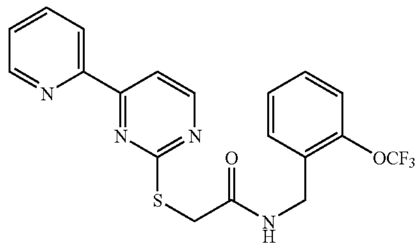 | 2.72 | |
| 40 | 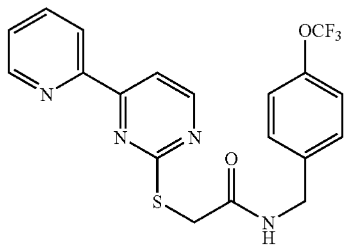 | 2.76 | |
| 41 | 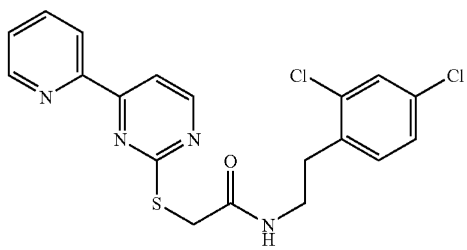 | 2.83 | |
| 42 | 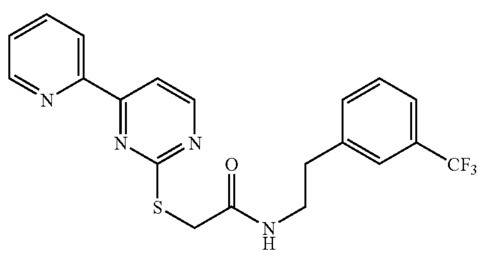 | 2.82 | |
| 43 | 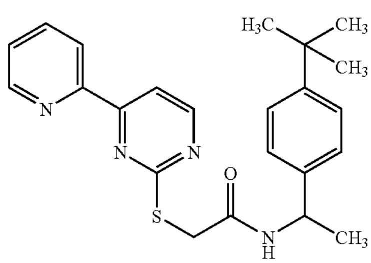 | 3.40 | |
| 44 | 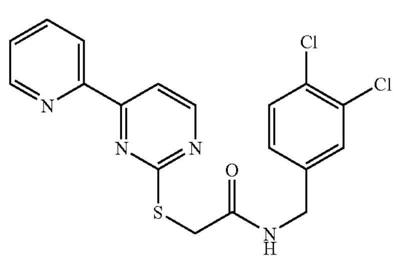 | 2.64 | |

-continued
| No. | Structure | log P (pH 2.3) | m.p./ °C. |
|---|---|---|---|
| 45 | 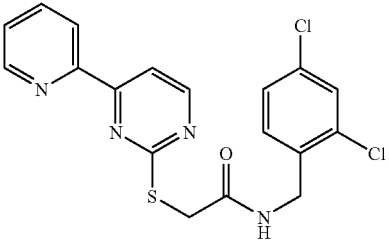 | 2.69 | |
| 46 | 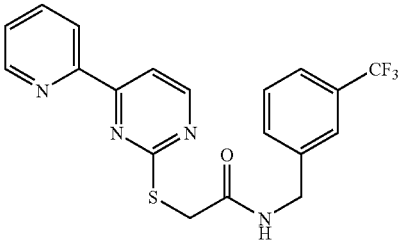 | 2.62 | |
| 47 | 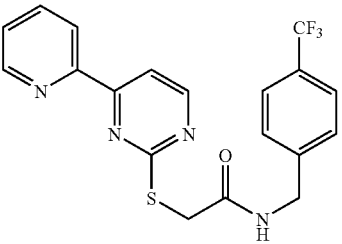 | 2.64 | |
| 48 | 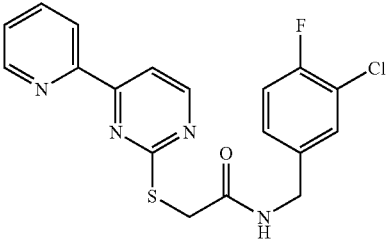 | 2.42 | |
| 49 | 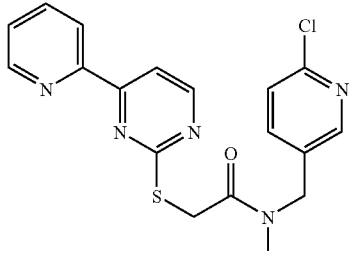 | 2.01 | |
| 50 | 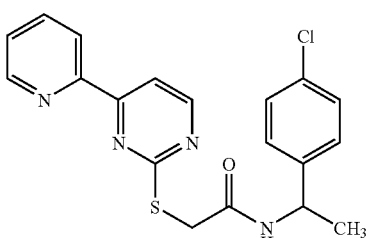 | 2.58 | |

-continued

| No. | Structure | log P (pH 2.3) | m.p./ °C |
|---|---|---|---|
| 51 | 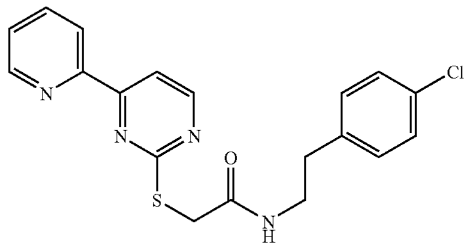 | 2.58 | |
| 52 | 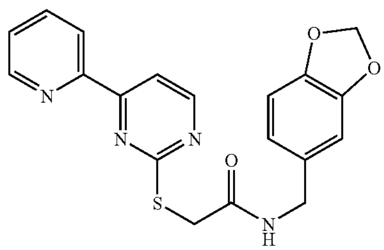 | 1.94 | |
| 53 | 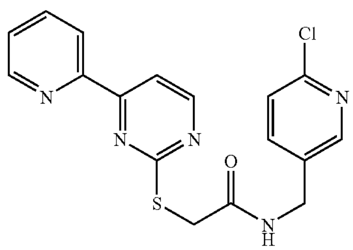 | 1.71 | |
| 54 | 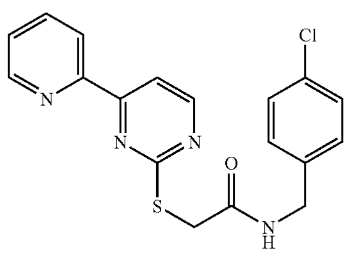 | 2.38 | |
| 55 | 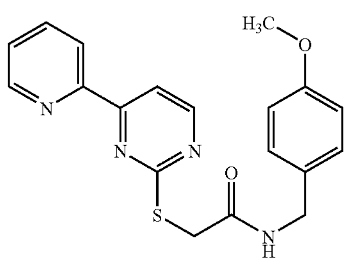 | 2.00 | |
| 56 | 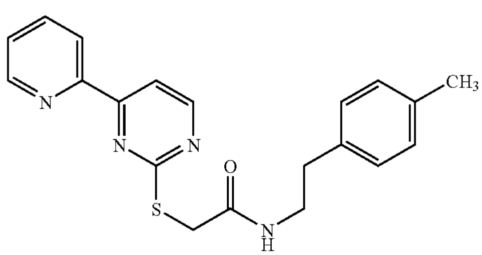 | 2.56 | |

-continued

| No. | Structure | log P (pH 2.3) | m.p./ °C. |
|---|---|---|---|
| 57 | 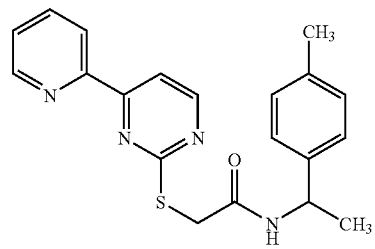 | 2.48 | |
| 58 | 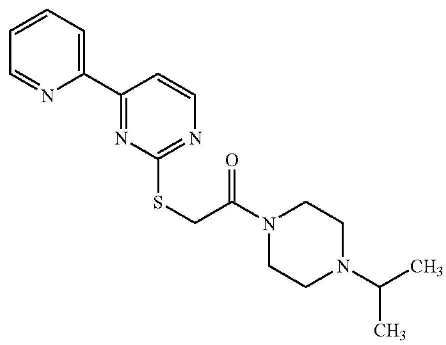 | 0.95 | |
| 59 | 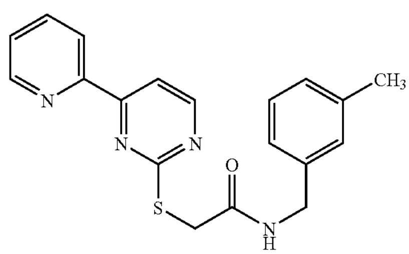 | 2.29 | |
| 60 | 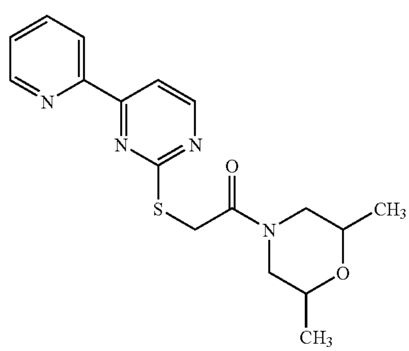 | 1.94 | |
| 61 | 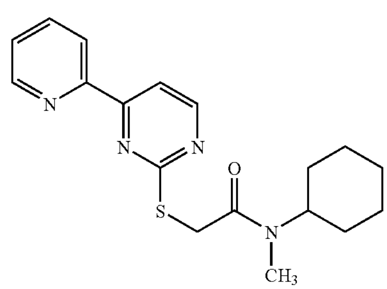 | 2.67 | |

-continued

| No. | Structure | log P (pH 2.3) | m.p./ °C. |
|---|---|---|---|
| 62 | 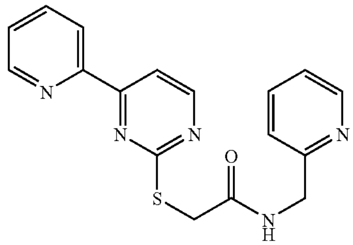 | 1.14 | |
| 63 | 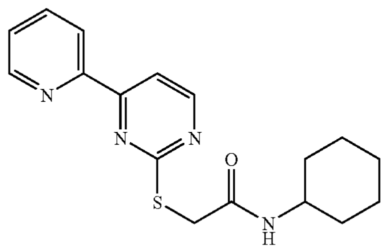 | 2.31 | |
| 64 | 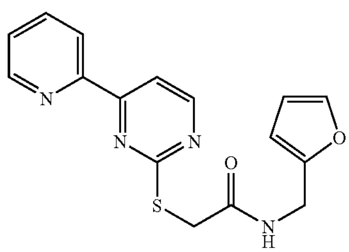 | 1.82 | |
| 65 | 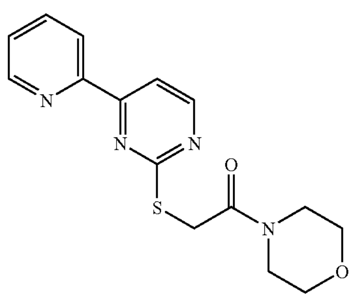 | 1.55 | |
| 66 | 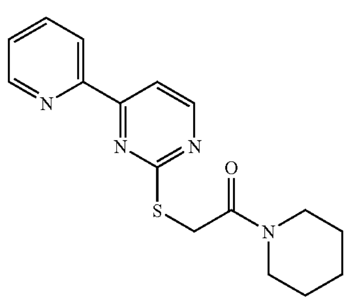 | 2.09 | |

-continued

| No. | Structure | log P (pH 2.3) | m.p./ °C |
|---|---|---|---|
| 67 | 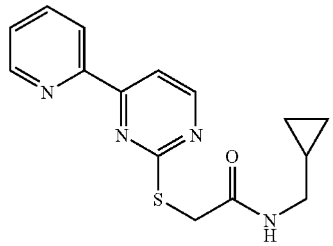 | 1.83 | |
| 68 | 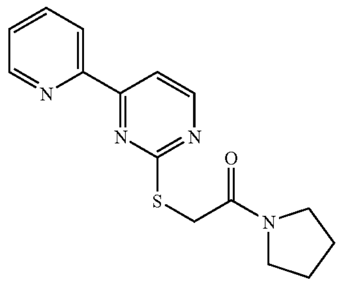 | 1.75 | |
| 69 | 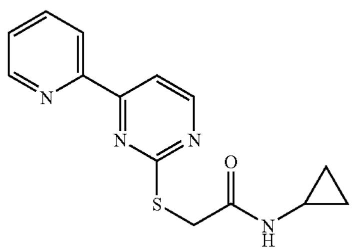 | 1.56 | |
| 70 | 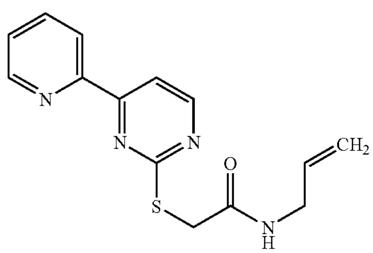 | 1.65 | |
| 71 | 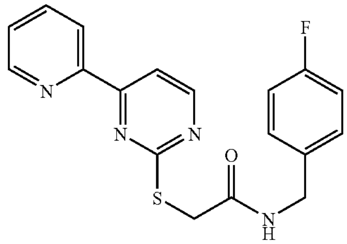 | | |
| 72 | 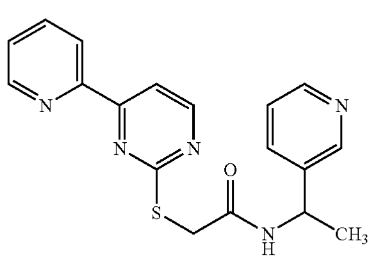 | | |

-continued

| No. | Structure | log P (pH 2.3) | m.p./ °C. |
|---|---|---|---|
| 73 | 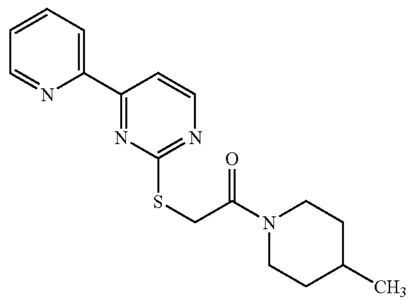 | | |
| 74 | 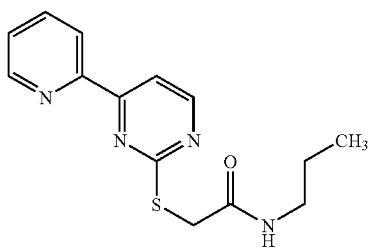 | | |
| 75 | 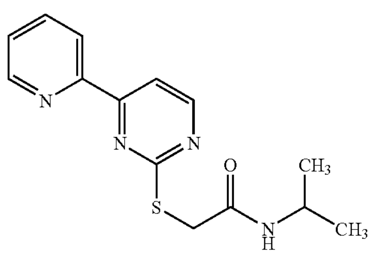 | | |
| 76 | 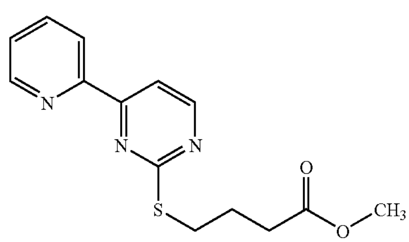 | 2.35 | |
| 77 | 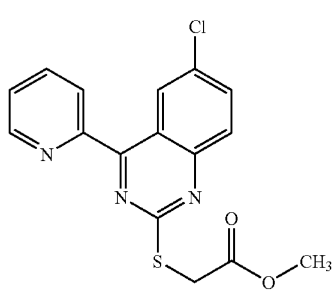 | 3.46 | 136 |

-continued

| No. | Structure | log P (pH 2.3) | m.p./ °C. |
|---|---|---|---|
| 78 | 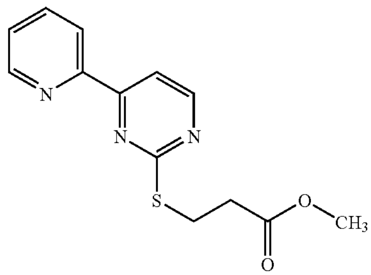 | 2.13 | 87-95 |
| 79 | 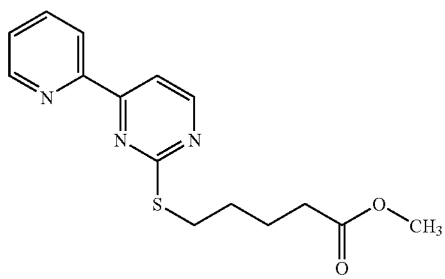 | 2.68 | |
| 80 | 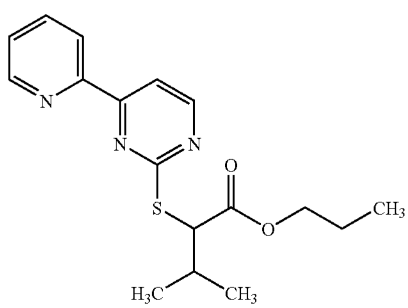 | 3.96 | |
| 81 | 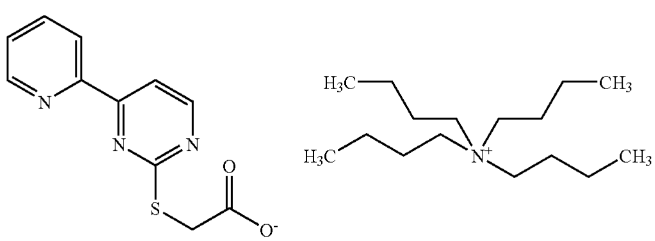 | | |
| 82 | 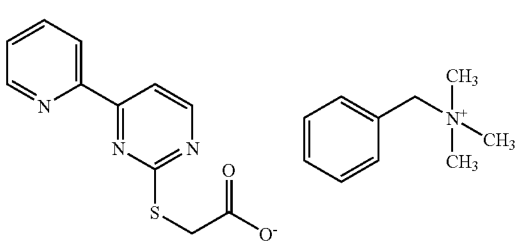 | | |

-continued

| No. | Structure | log P (pH 2.3) | m.p./ °C. |
|---|---|---|---|
| 83 | 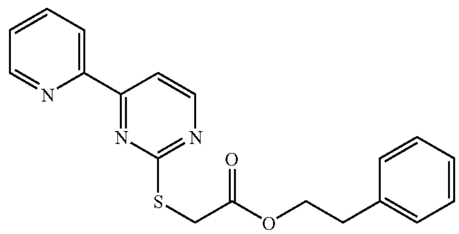 | 3.37 | |
| 84 | 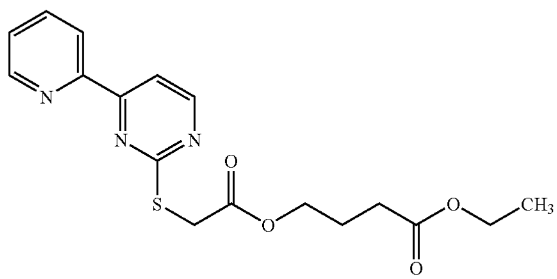 | 2.72 | |
| 85 | 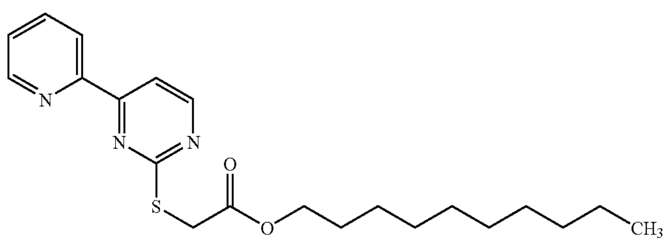 | 6.15 | |
| 86 | 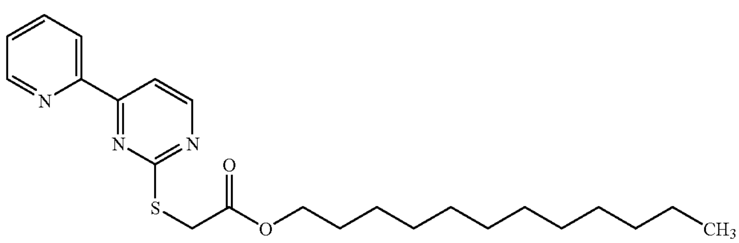 | 7.22 | |
| 87 | 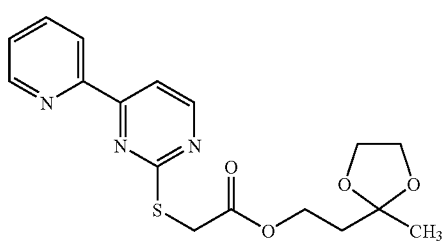 | | |
| 88 | 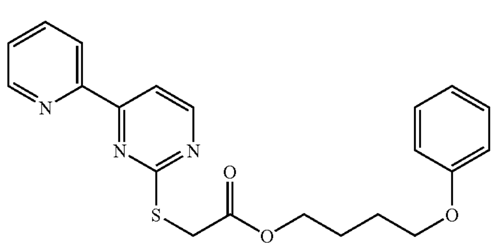 | 3.86 | |

| No. | Structure | log P (pH 2.3) | m.p./ °C. |
|---|---|---|---|
| 89 | 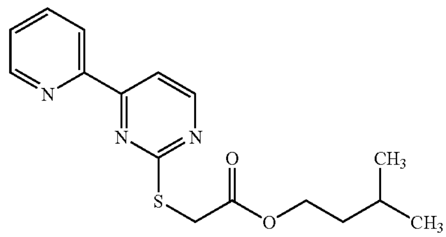 | 3.56 | |
| 90 | 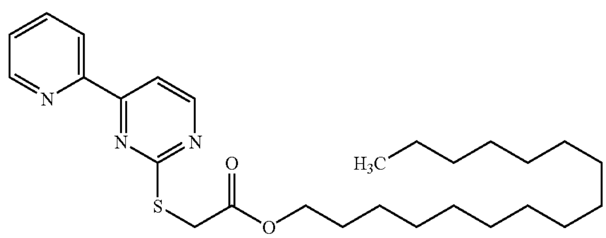 | | |
| 91 | 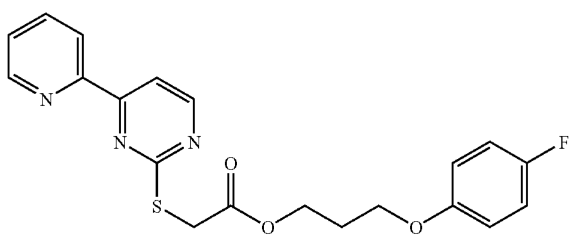 | 3.59 | |
| 92 | 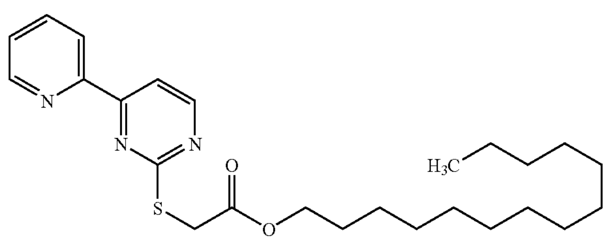 | | |
| 93 | 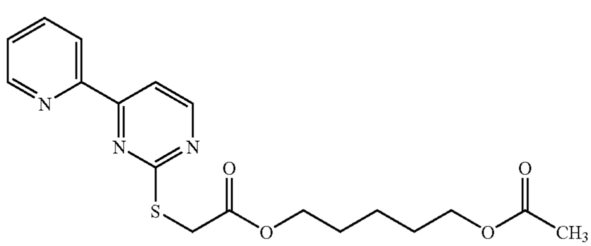 | 2.82 | |
| 94 | 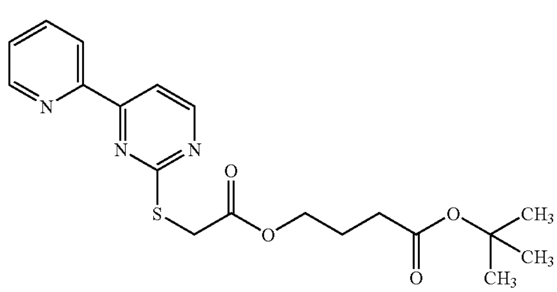 | 3.48 | |

| No. | Structure | log P (pH 2.3) | m.p./ °C |
|---|---|---|---|
| 95 | 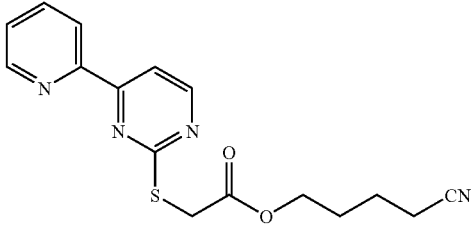 | 2.29 | |
| 96 | 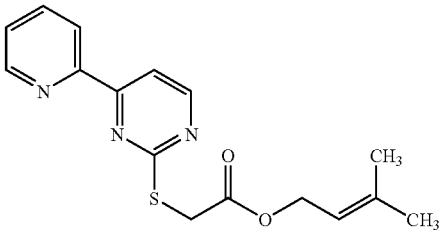 | 3.18 | |
| 97 | 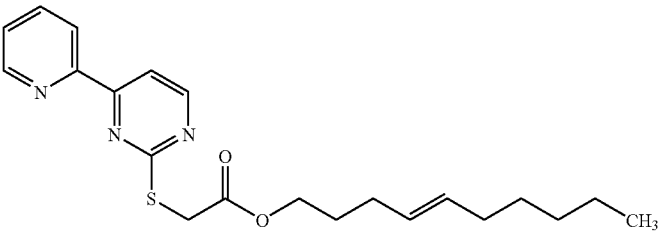 | | |
| 98 | 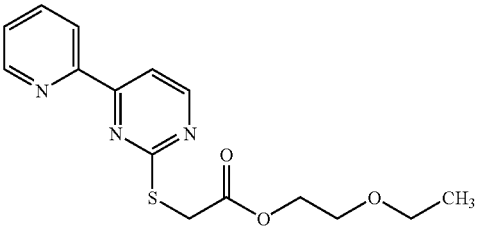 | 2.34 | |
| 99 | 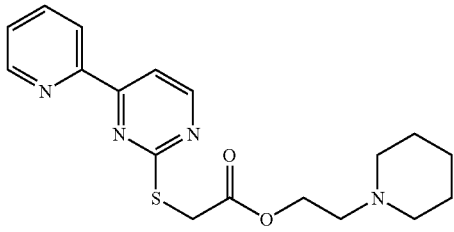 | 1.04 | |
| 100 | 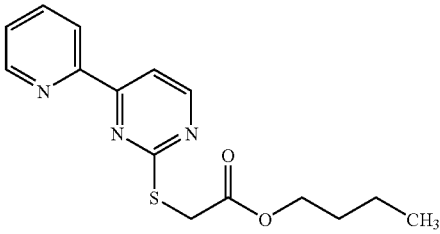 | 3.07 | |

-continued
| No. | Structure | log P (pH 2.3) | m.p./ °C |
|---|---|---|---|
| 101 | 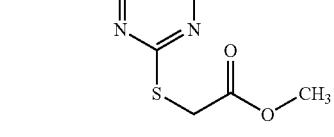 | 2.81 | 117 |
| 102 | 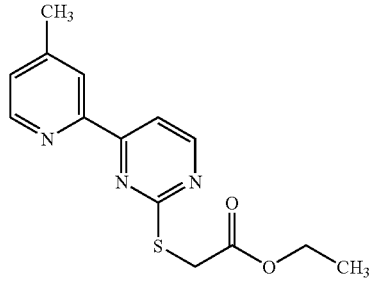 | 2.20 | 60 |
| 103 | 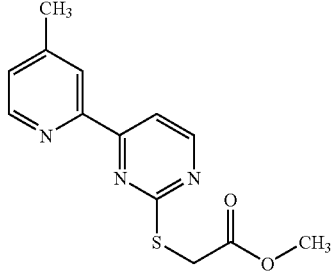 | 1.80 | 105 |
| 104 | 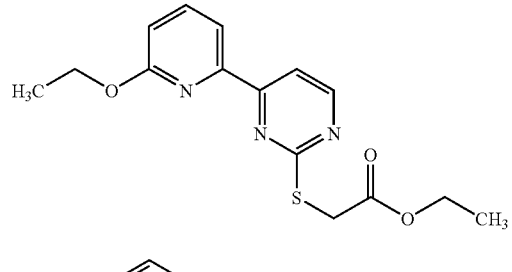 | 3.67 | |
| 105 | 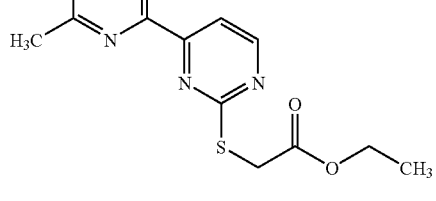 | 2.46 | |
| 106 | 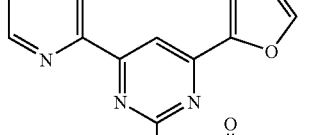 | 3.01 | |

| No. | Structure | log P (pH 2.3) | m.p./ °C. |
|---|---|---|---|
| 107 | 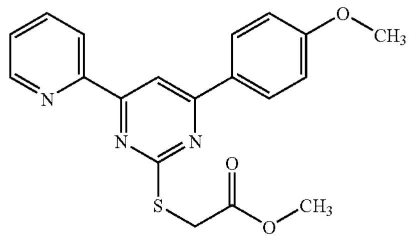 | 3.50 | |
| 108 | 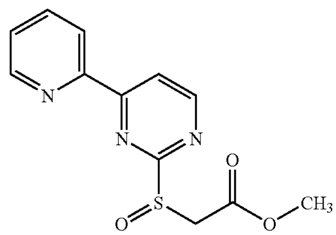 | 0.89 | |
| 109 | 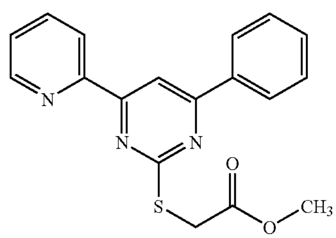 | 3.57 | |
| 110 | 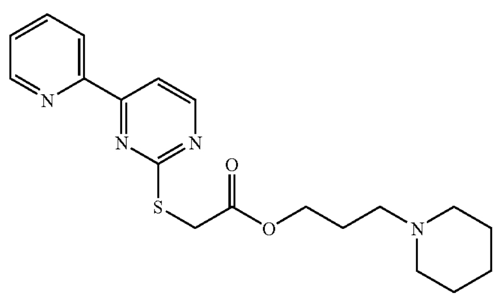 | 1.13 | |
| 111 | 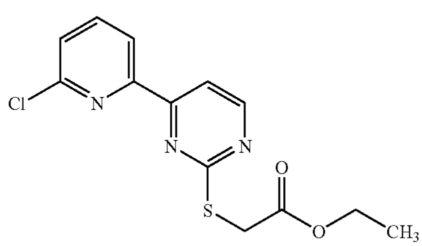 | 3.19 | |
| 112 | 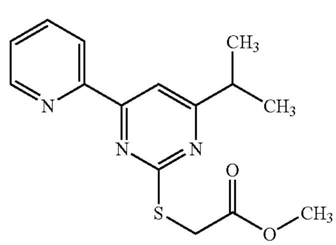 | 3.11 | |

-continued

| No. | Structure | log P (pH 2.3) | m.p./ ° C. |
|---|---|---|---|
| 113 | 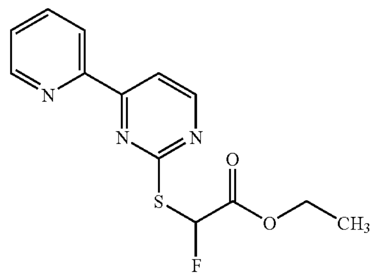 | 2.55 | |
| 114 | 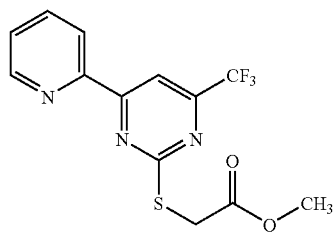 | 3.34 | |
| 115 | 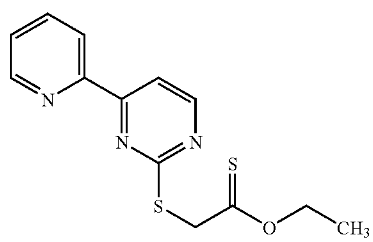 | 3.30 | |
| 116 | 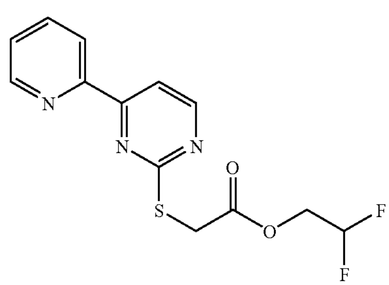 | 2.25 | |
| 117 | 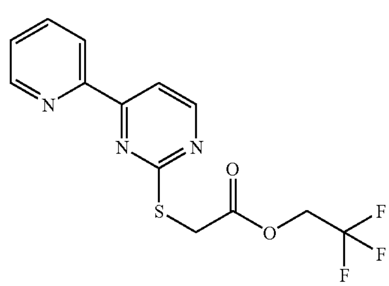 | 2.69 | |

-continued

| No. | Structure | log P (pH 2.3) | m.p./ °C |
|---|---|---|---|
| 118 | 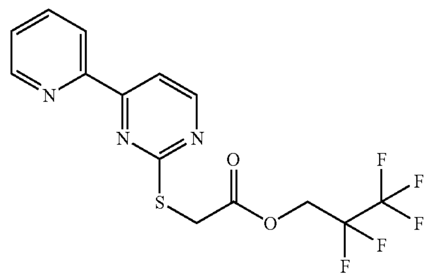 | 3.24 | |
| 119 | 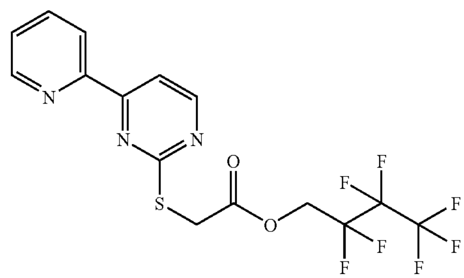 | 3.37 | |
| 120 | 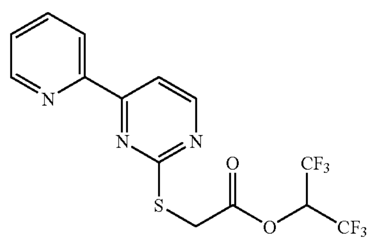 | 3.59 | |
| 121 | 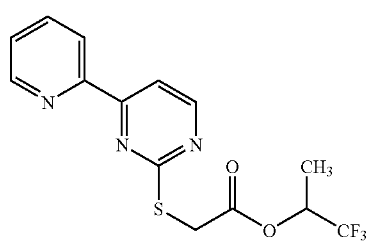 | 3.06 | |
| 122 | 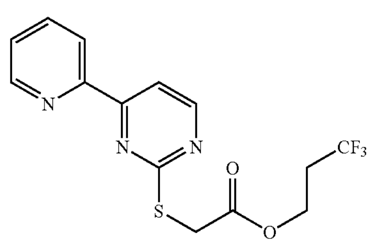 | 2.26 | |
| 123 | 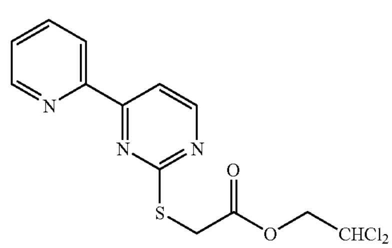 | 2.78 | |

| No. | Structure | log P (pH 2.3) | m.p./ °C. |
|---|---|---|---|
| 124 | 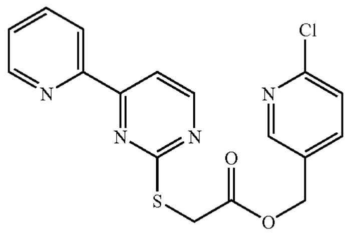 | 2.31 | |
| 125 | 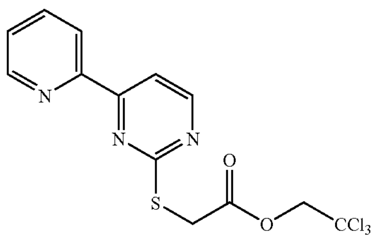 | 3.31 | |
| 126 | 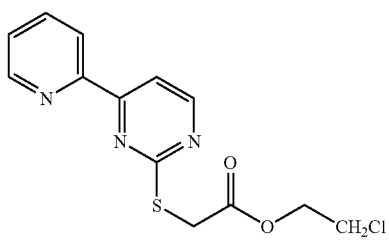 | 2.29 | |
| 127 | 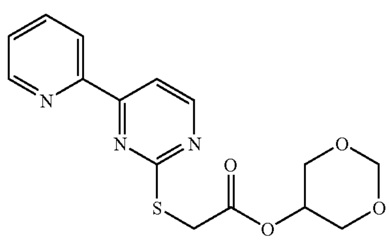 | 1.76 | |
| 128 | 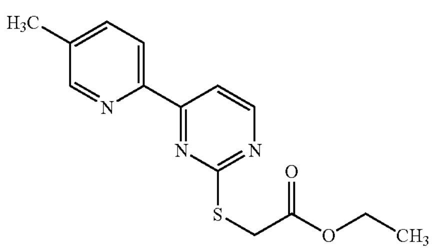 | 2.50 | |
| 129 | 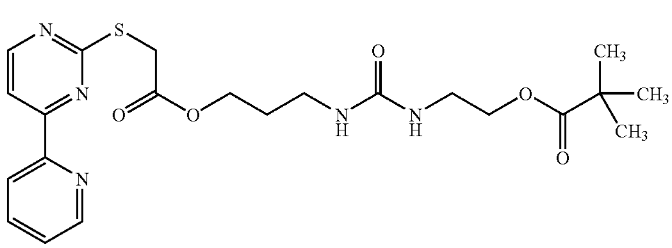 | 2.51 | |

-continued

| No. | Structure | log P (pH 2.3) | m.p./ °C. |
|---|---|---|---|
| 130 | 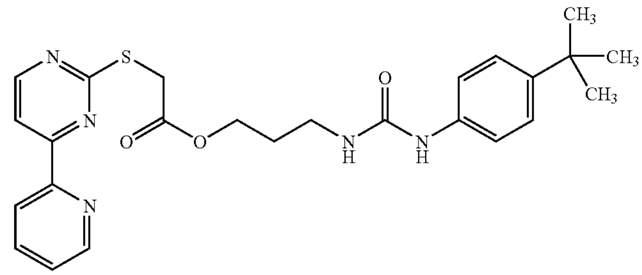 | 3.51 | |
| 131 | 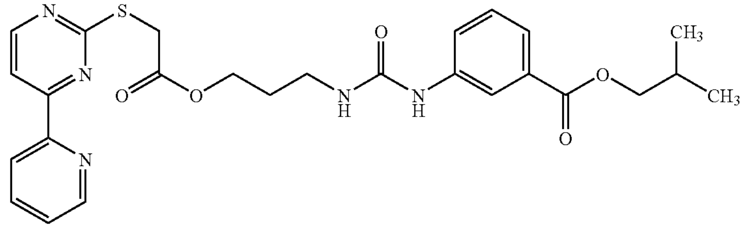 | 3.45 | |
| 132 | 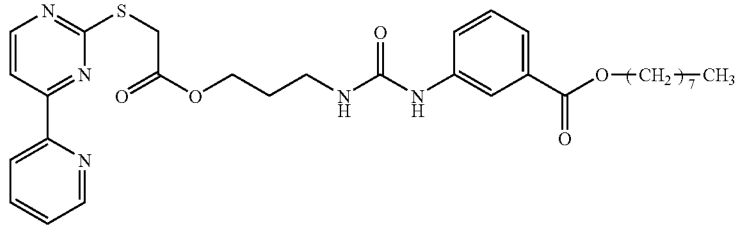 | | |
| 133 | 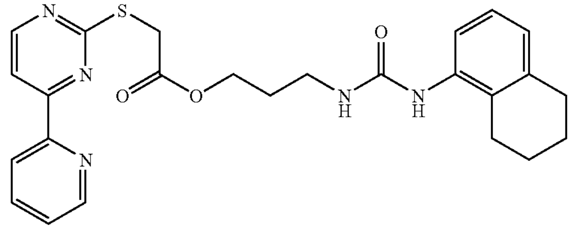 | 3.06 | |
| 134 | 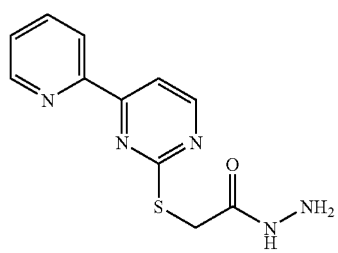 | 0.43 | 184 |
| 135 | 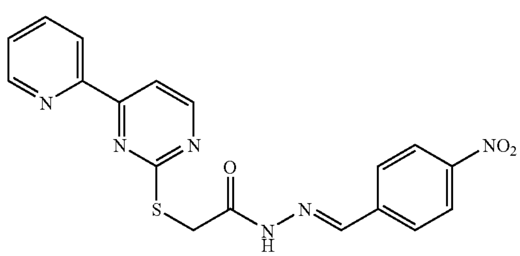 | 2.23 | 220 |

| No. | Structure | log P (pH 2.3) | m.p./ °C |
|---|---|---|---|
| 136 | 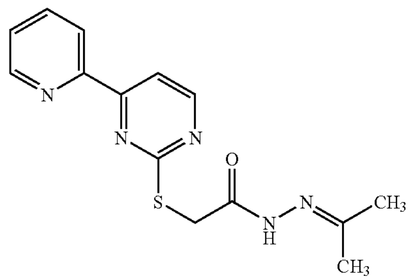 | 0.44 | 195 |
| 137 | 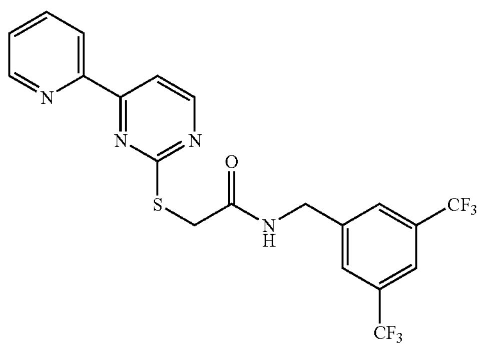 | 3.22 | |
| 138 | 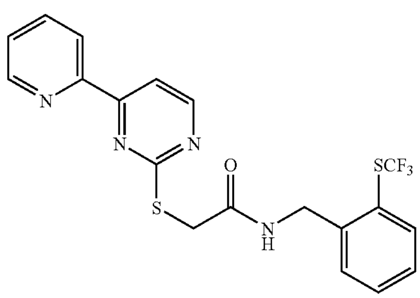 | 2.92 | |
| 139 | 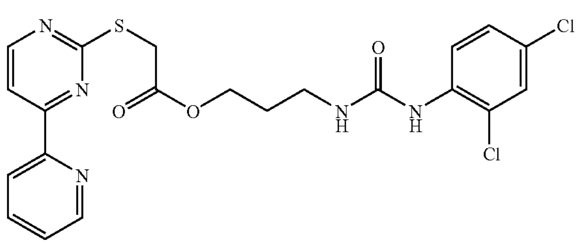 | 3.20 | |
| 140 | 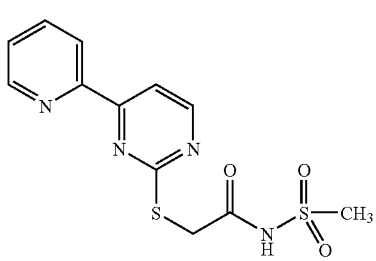 | 1.13 | |

-continued

| No. | Structure | log P (pH 2.3) | m.p./ °C. |
|---|---|---|---|
| 141 | 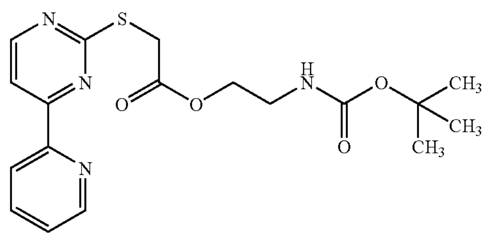 | 2.63 | |
| 142 | 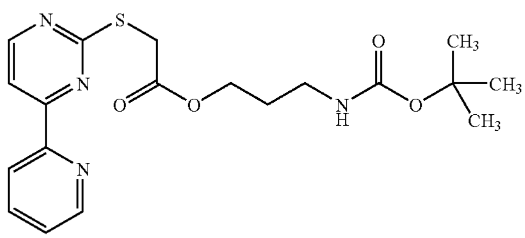 | 2.79 | |
| 143 | 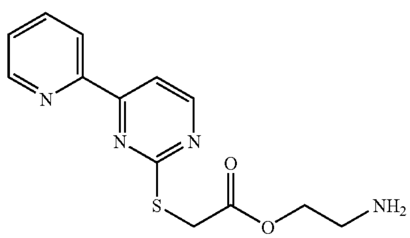 | | |
| 144 | 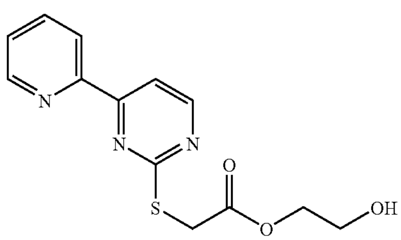 | | |
| 145 | 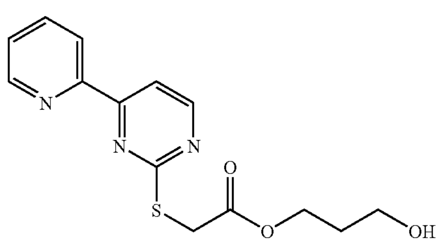 | | |
| 146 | 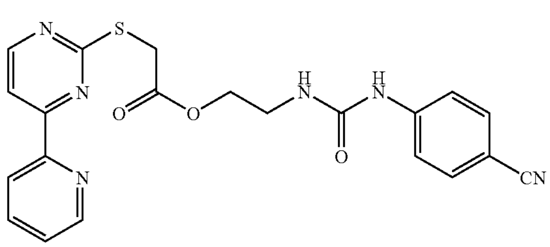 | 2.3 | |

-continued

| No. | Structure | log P (pH 2.3) | m.p./ °C. |
|---|---|---|---|
| 147 | 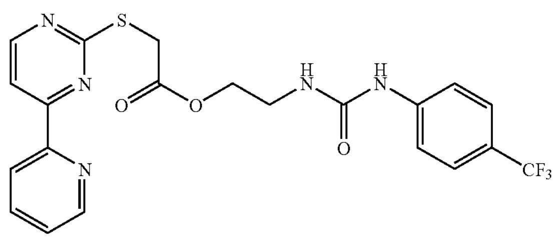 | 3.04 | |
| 148 | 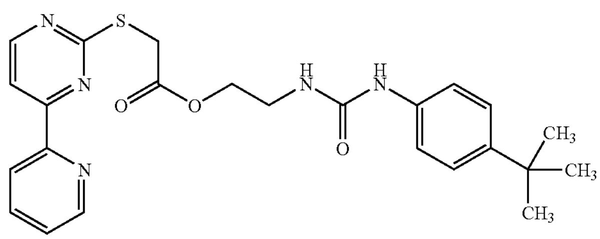 | 3.35 | |
| 149 | 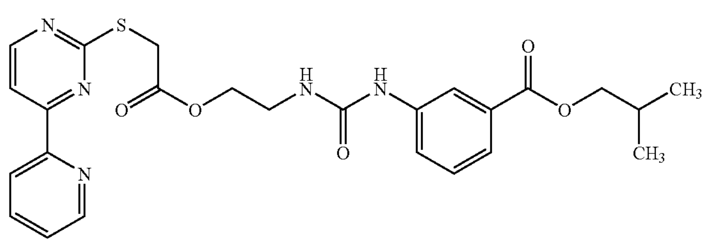 | 3.01 | |
| 150 | 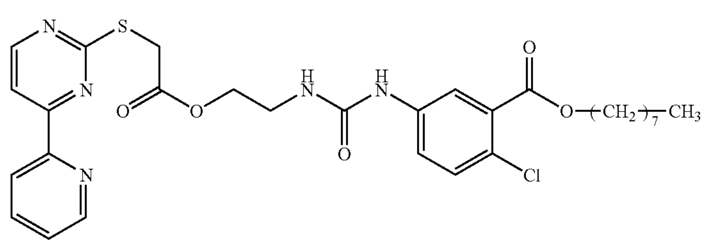 | 4.95 | |
| 151 | 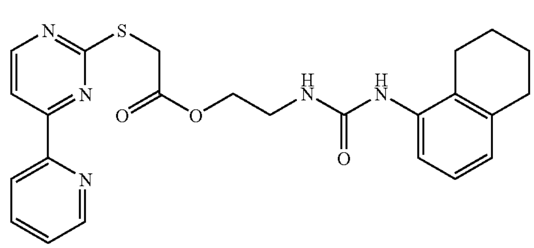 | 2.94 | |
| 152 | 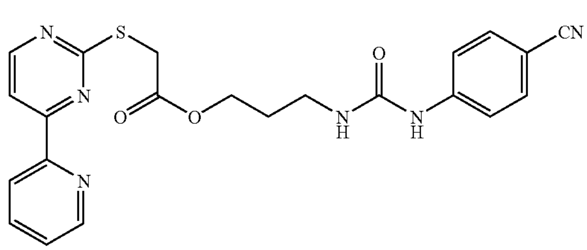 | 2.45 | |

-continued

| No. | Structure | log P (pH 2.3) | m.p./ ° C. |
|---|---|---|---|
| 153 | 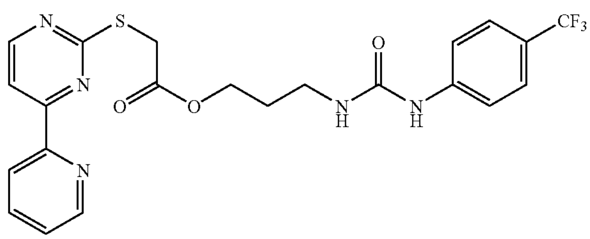 | 3.2 | |
| 154 | 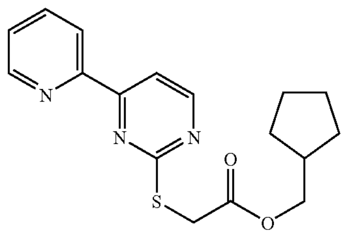 | 3.60 | |
| 155 | 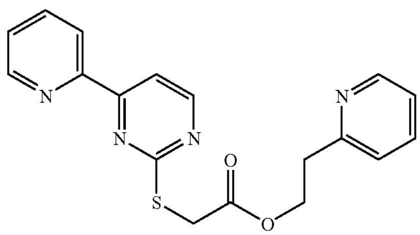 | | |
| 156 | 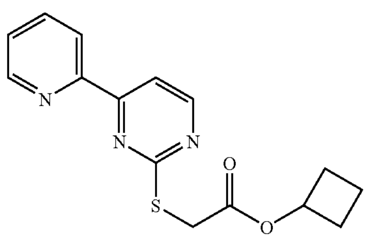 | | |
| 157 | 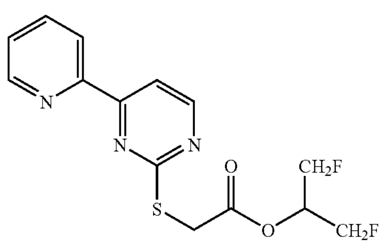 | | |
| 158 | 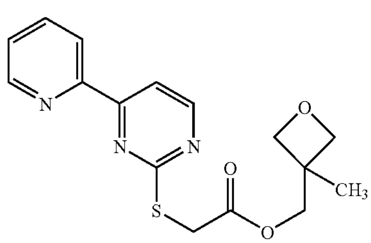 | 1.98 | |

-continued

| No. | Structure | log P (pH 2.3) | m.p./ °C. |
|---|---|---|---|
| 159 | 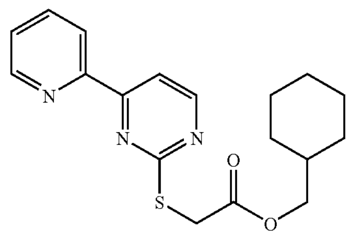 | 4.00 | |
| 160 | 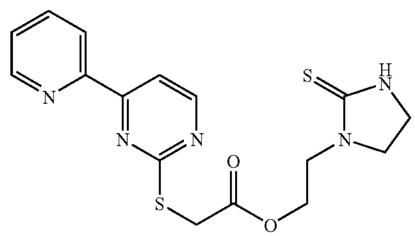 | 1.59 | |
| 161 | 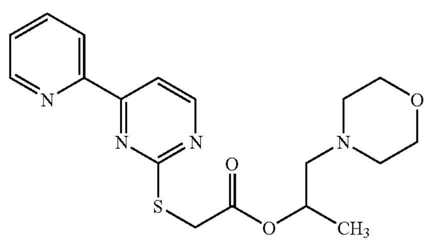 | 1.16 | |
| 162 | 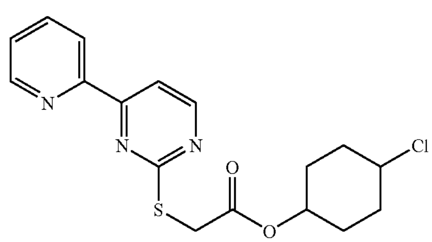 | | |
| 163 | 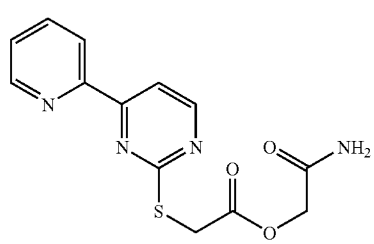 | 1.11 | |
| 164 | 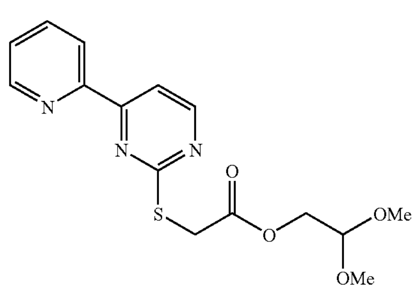 | 2.05 | |

| No. | Structure | log P (pH 2.3) | m.p./ °C |
|---|---|---|---|
| 165 | 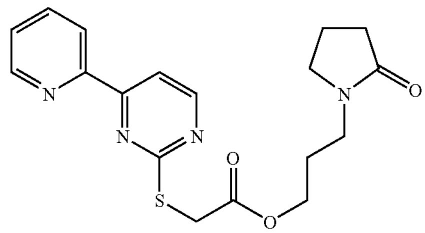 | 1.64 | |
| 166 | 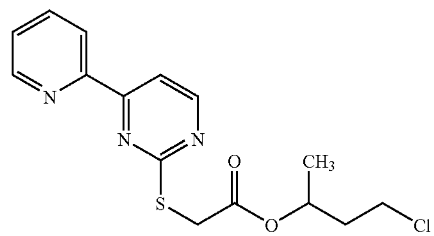 | | |
| 167 | 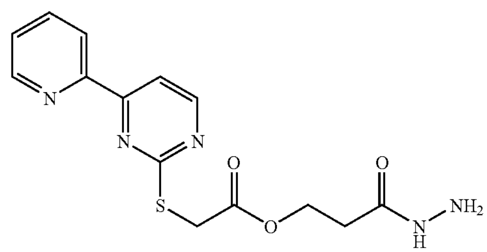 | | |
| 168 | 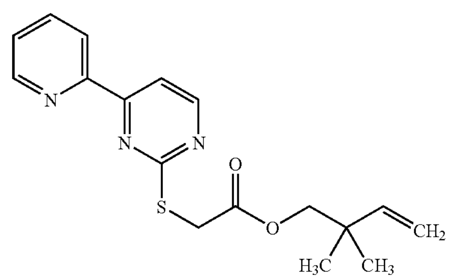 | 3.48 | |
| 169 | 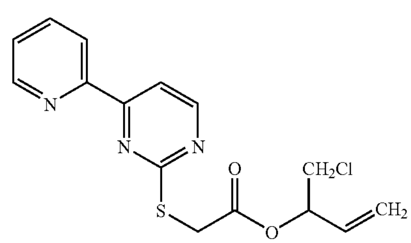 | | |
| 170 | 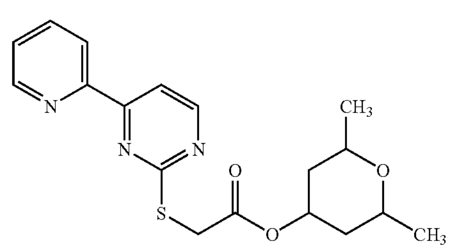 | | |

-continued

| No. | Structure | log P (pH 2.3) | m.p./ °C |
|---|---|---|---|
| 171 | 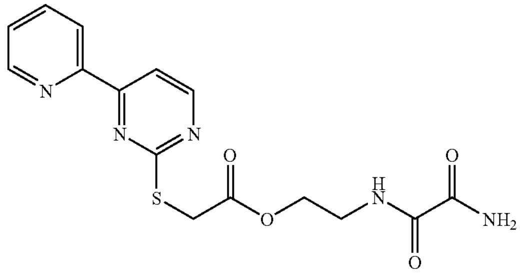 | | |
| 172 | 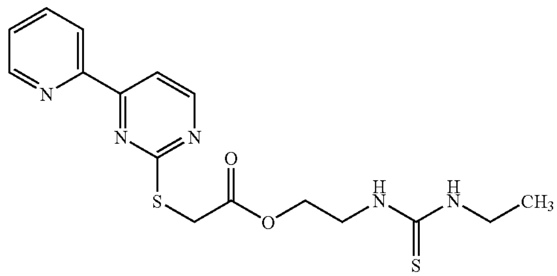 | 1.79 | |
| 173 | 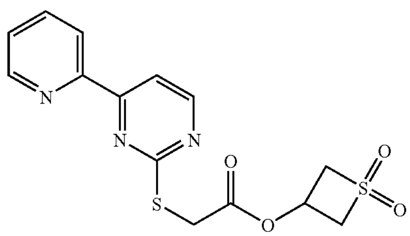 | 1.67 | |
| 174 | 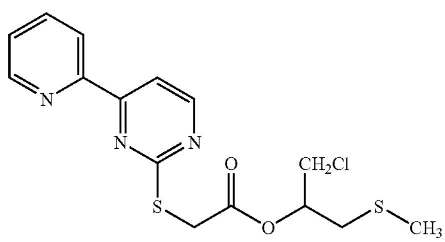 | | |
| 175 | 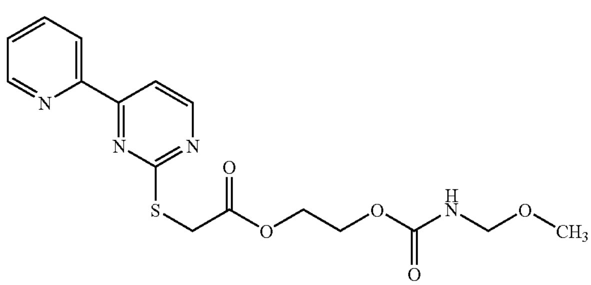 | 1.64 | |
| 176 | 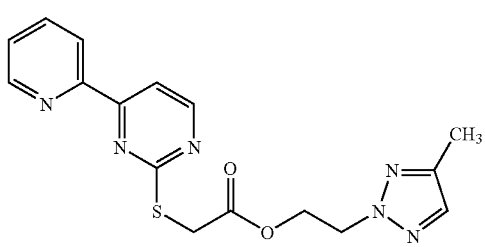 | 1.93 | |

-continued

| No. | Structure | log P (pH 2.3) | m.p./ °C. |
|---|---|---|---|
| 177 | 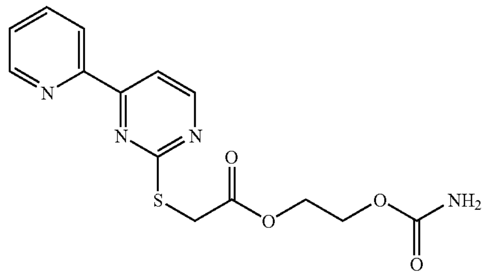 | 1.41 | |
| 178 | 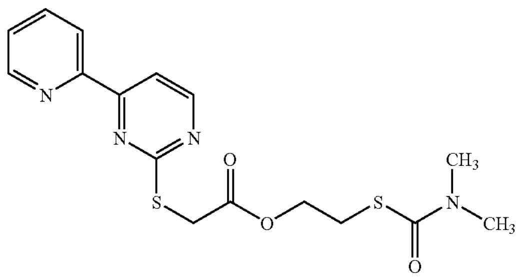 | 2.20 | |
| 179 | 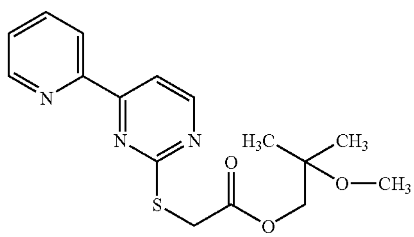 | 2.29 | |
| 180 | 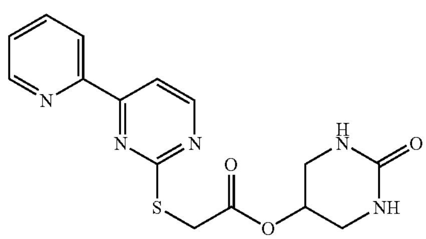 | | |
| 181 | 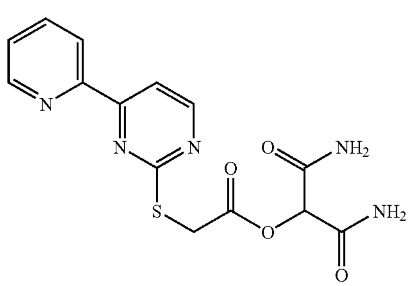 | | |

-continued

| No. | Structure | log P (pH 2.3) | m.p./ °C. |
|---|---|---|---|
| 182 | 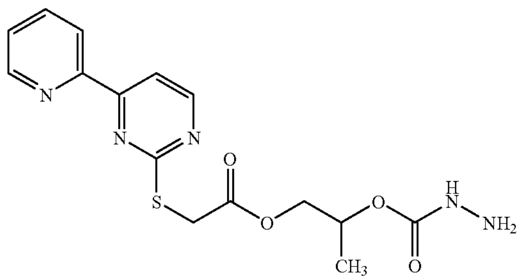 | | |
| 183 | 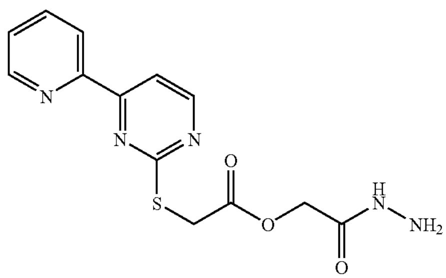 | | |
| 184 | 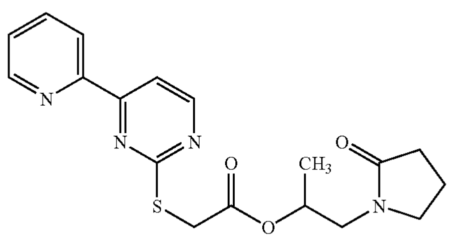 | | |
| 185 | 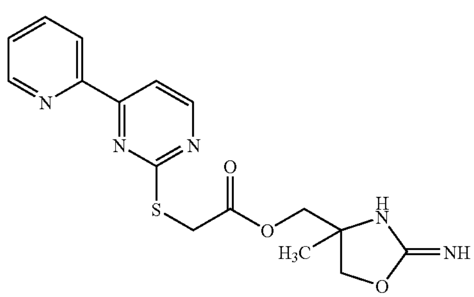 | | |
| 186 | 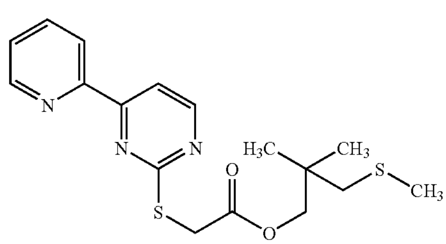 | 3.46 | |

-continued

| No. | Structure | log P (pH 2.3) | m.p./ °C. |
|---|---|---|---|
| 187 | 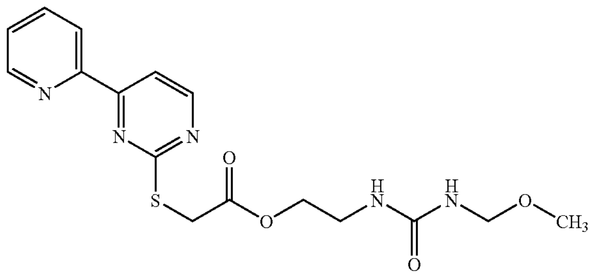 | | |
| 188 | 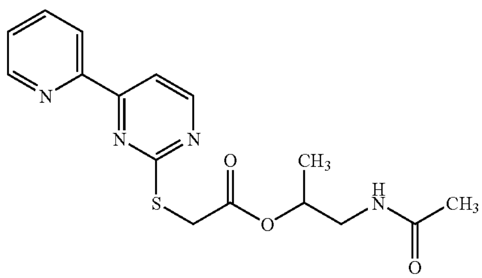 | 1.97 | |
| 189 | 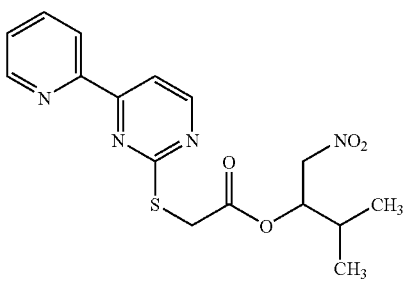 | | |
| 190 | 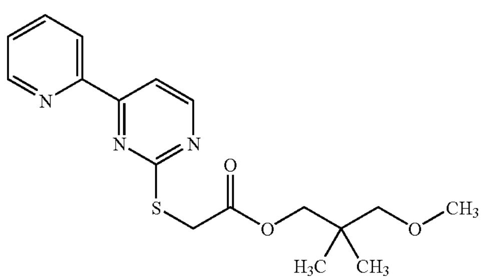 | 3.05 | |
| 191 | 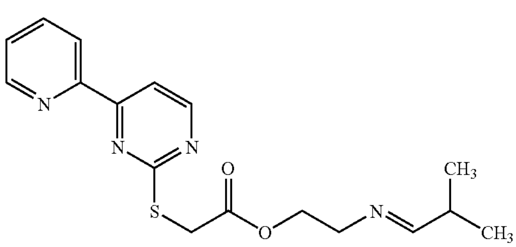 | 2.02 | |

|      |           | log P   | m.p./ |
|------|-----------|---------|-------|
| No.  | Structure | (pH 2.3)| ° C.  |
| 192  |           | 1.63    |       |
| 193  |           | 2.46    |       |
| 194  |           | 2.95    |       |
| 195  |           | 2.72    |       |
| 196  |           | 2.66    |       |

-continued

| No. | Structure | log P (pH 2.3) | m.p./ °C. |
|-----|-----------|----------------|-----------|
| 197 | 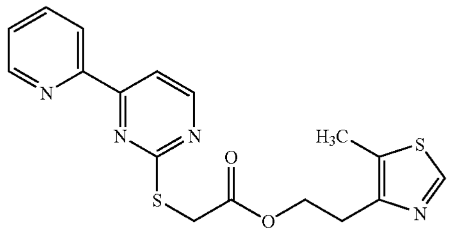 | 1.79 | |
| 198 | 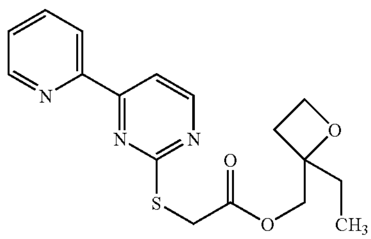 | 2.20 | |
| 199 | 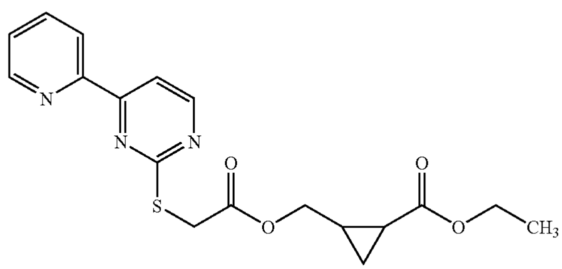 | 2.64 | |
| 200 | 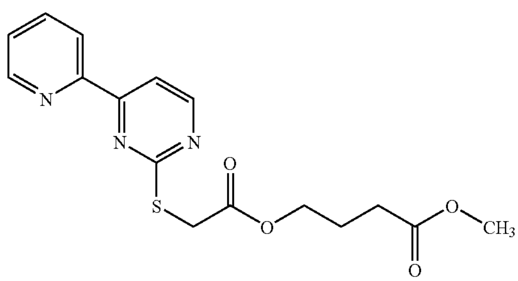 | 2.21 | |
| 201 | 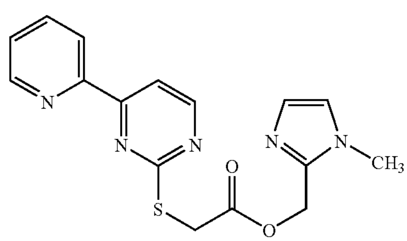 | 1.02 | |
| 202 | 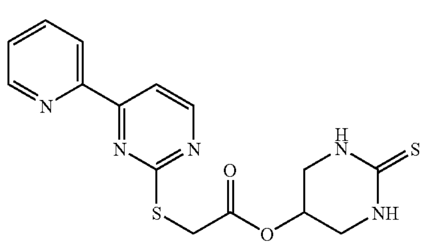 | | |

-continued

| No. | Structure | log P (pH 2.3) | m.p./ ° C. |
|---|---|---|---|
| 203 | 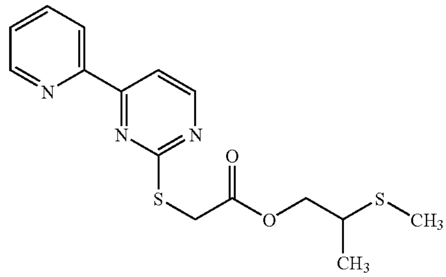 | 2.78 | |
| 204 | 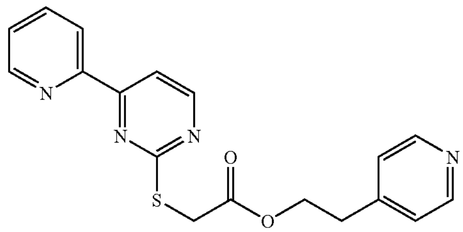 | 1.20 | |
| 205 | 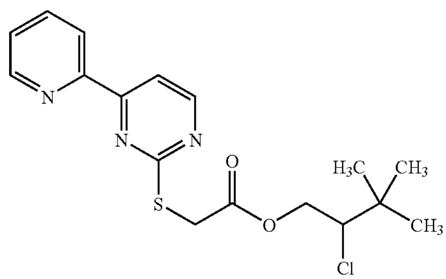 | 3.81 | |
| 206 | 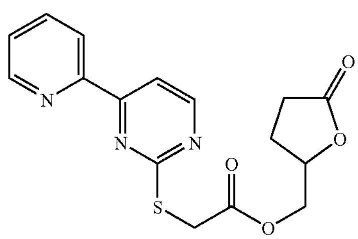 | 1.64 | |
| 207 | 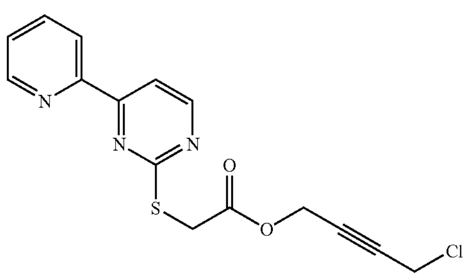 | 2.61 | |
| 208 | 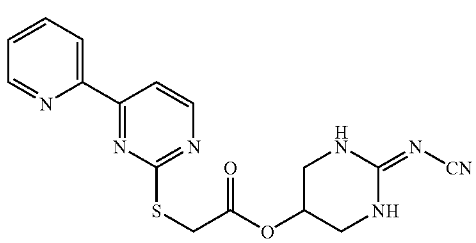 | | |

-continued
| No. | Structure | log P (pH 2.3) | m.p./ °C. |
|---|---|---|---|
| 209 | 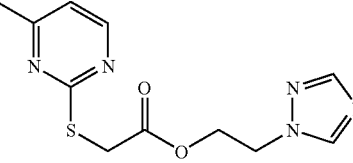 | 1.32 | |
| 210 | 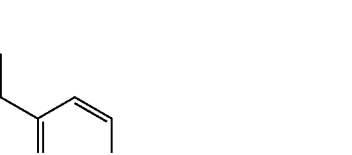 | 1.42 | |
| 211 | 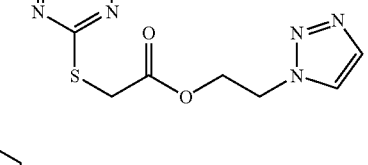 | 2.75 | |
| 212 | 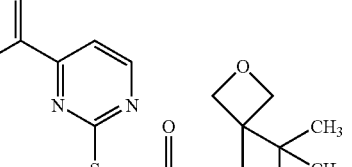 | 2.13 | |
| 213 | 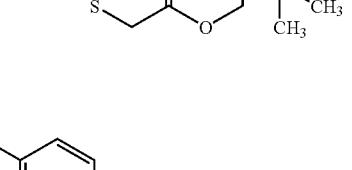 | 1.42 | |
| 214 | 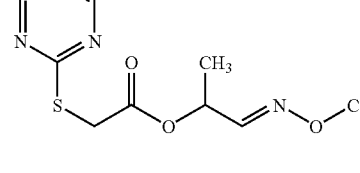 | 2.13 | |

-continued

| No. | Structure | log P (pH 2.3) | m.p./ °C. |
|---|---|---|---|
| 215 | 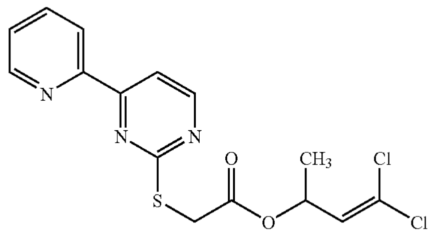 | 3.48 | |
| 216 | 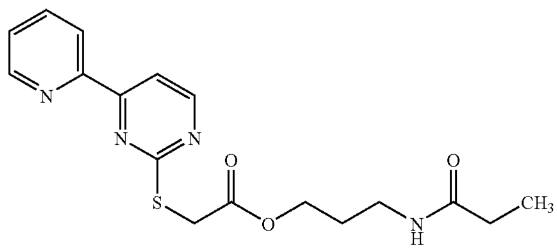 | 2.04 | |
| 217 | 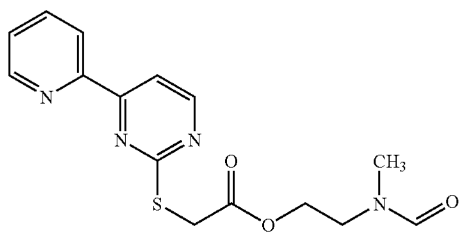 | 1.40 | |
| 218 | 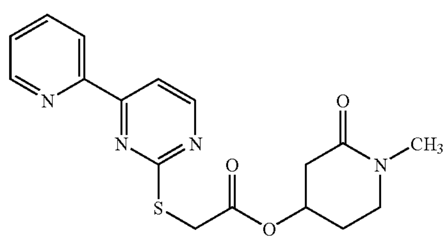 | | |
| 219 | 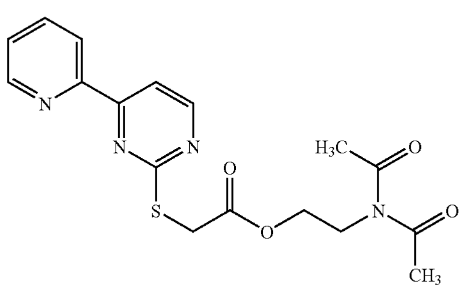 | | |
| 220 | 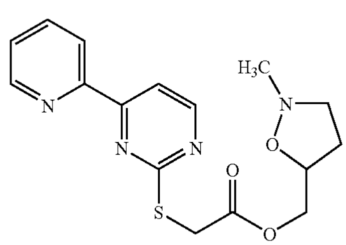 | 1.12 | |

-continued

| No. | Structure | log P (pH 2.3) | m.p./ ° C. |
|---|---|---|---|
| 221 | 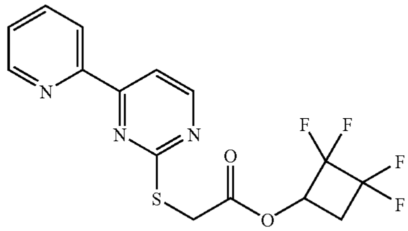 | 3.00 | |
| 222 | 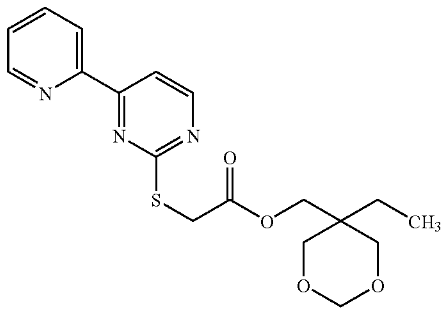 | 2.51 | |
| 223 | 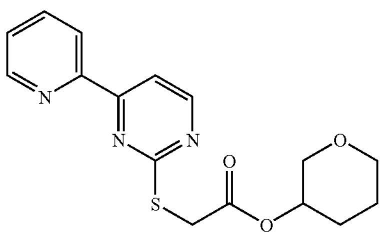 | | |
| 224 | 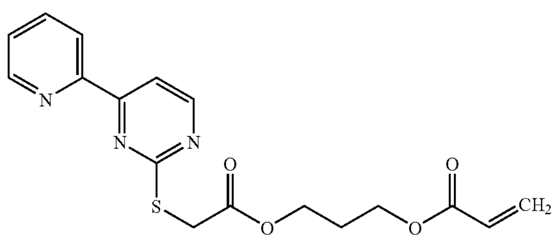 | 2.49 | |
| 225 | 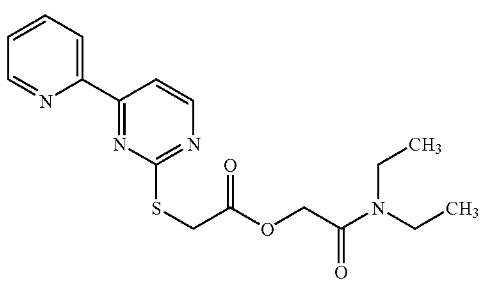 | | |
| 226 | 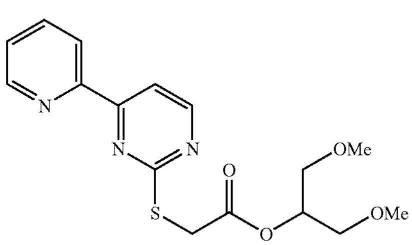 | | |

| No. | Structure | log P (pH 2.3) | m.p./ °C |
|---|---|---|---|
| 227 | 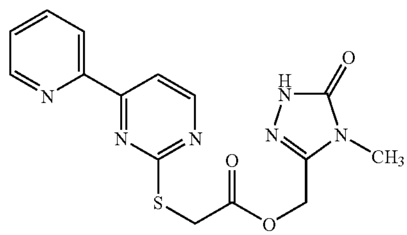 | | |
| 228 | 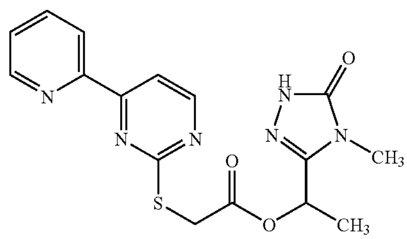 | | |
| 229 | 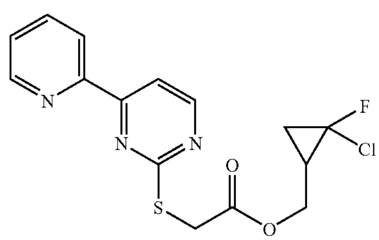 | | |
| 230 | 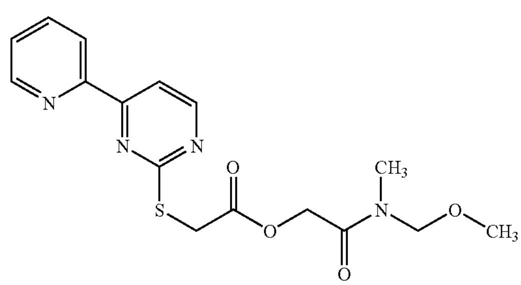 | 1.96 | |
| 231 | 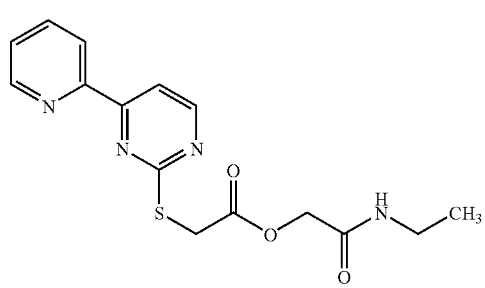 | 1.97 | |

-continued

| No. | Structure | log P (pH 2.3) | m.p./ °C |
|---|---|---|---|
| 232 | 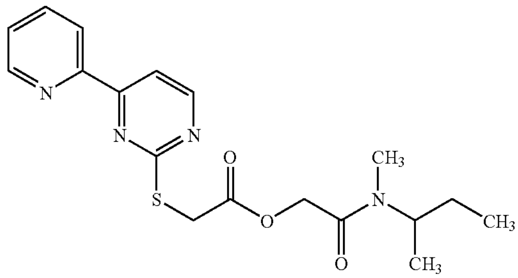 | | |
| 233 | 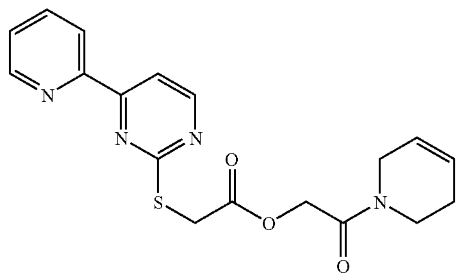 | | |
| 234 | 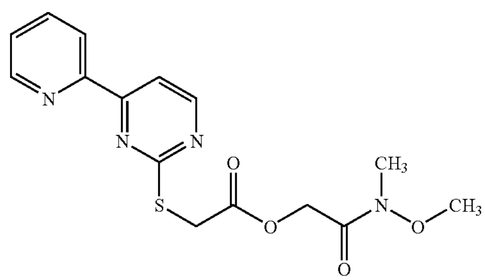 | 1.97 | |
| 235 | 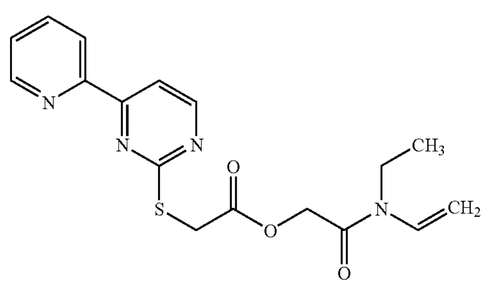 | | |
| 236 | 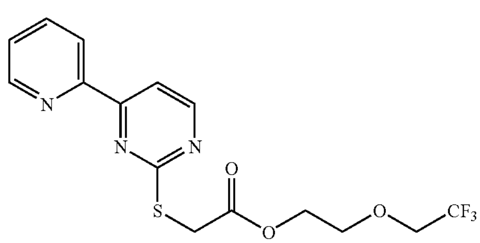 | 2.70 | |

| No. | Structure | log P (pH 2.3) | m.p./ °C |
|-----|-----------|----------------|----------|
| 237 | 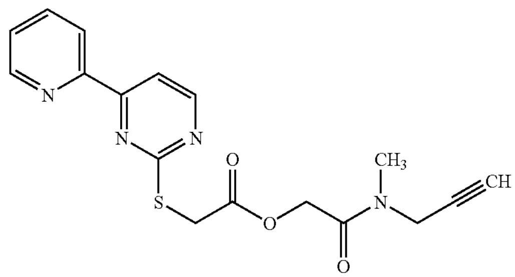 | | |
| 238 | 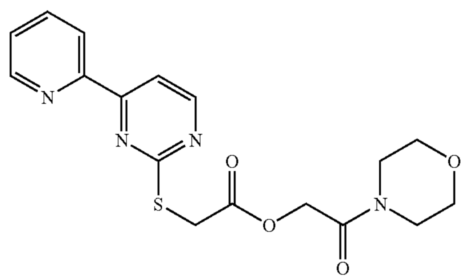 | | |
| 239 | 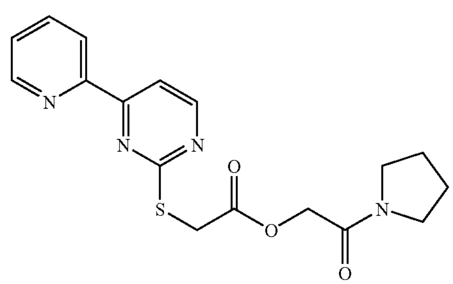 | | |
| 240 | 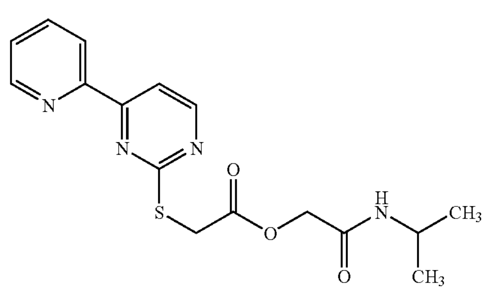 | | |
| 241 | 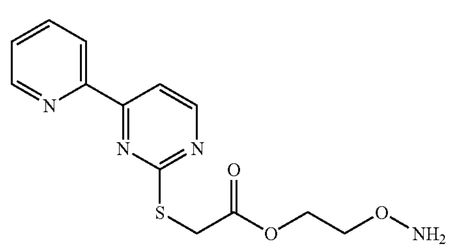 | | |

-continued

| No. | Structure | log P (pH 2.3) | m.p./ ° C. |
|---|---|---|---|
| 242 | 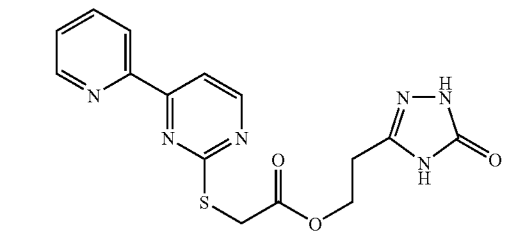 | | |
| 243 | 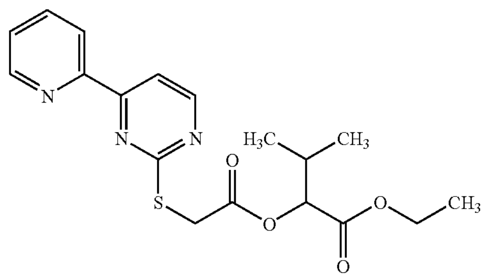 | 3.20 | |
| 244 | 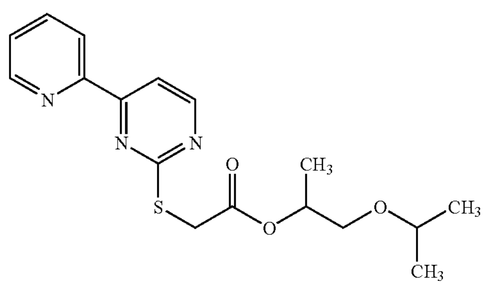 | | |
| 245 | 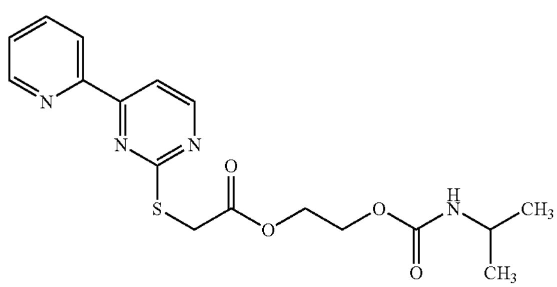 | 2.19 | |
| 246 | 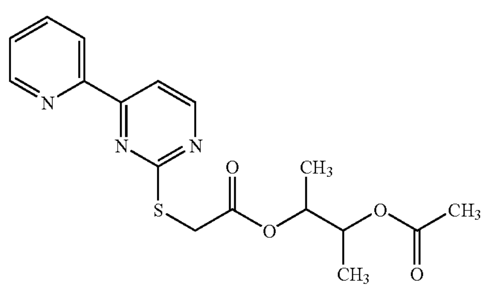 | 2.54 | |

| No. | Structure | log P (pH 2.3) | m.p./ °C |
|---|---|---|---|
| 247 | 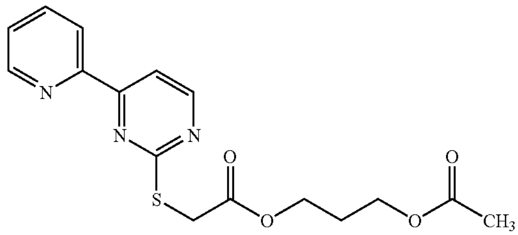 | | |
| 248 | 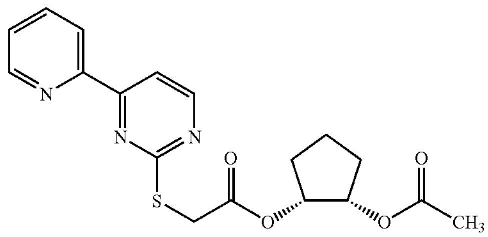 | 2.65 | |
| 249 | 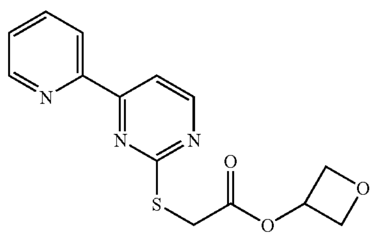 | 1.69 | |
| 250 | 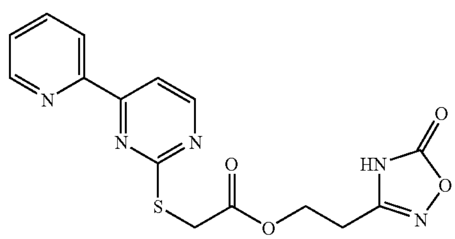 | 1.97 | |
| 251 | 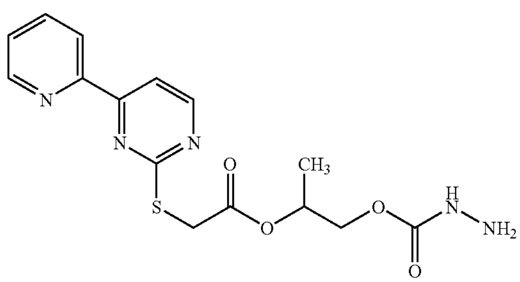 | | |
| 252 | 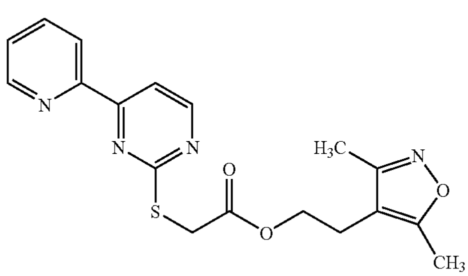 | 2.25 | |

-continued

| No. | Structure | log P (pH 2.3) | m.p./ °C. |
|---|---|---|---|
| 253 | 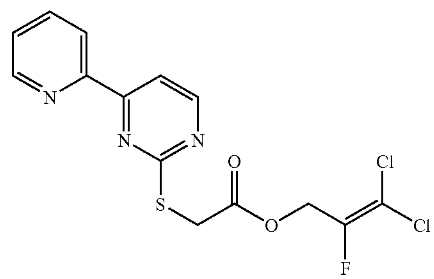 | 3.19 | |
| 254 | 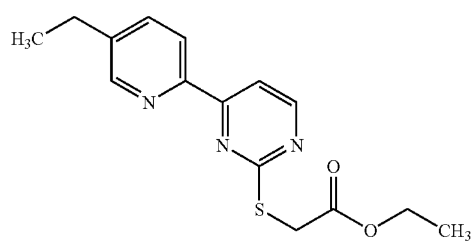 | 2.98 | |
| 255 | 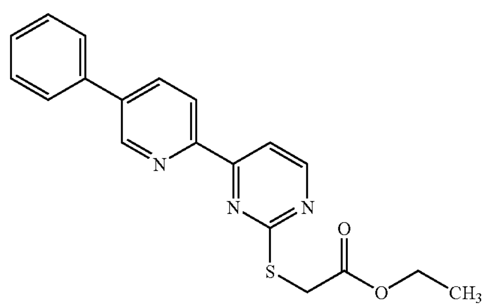 | | |
| 256 | 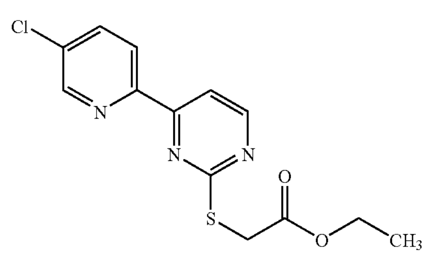 | 3.23 | |
| 257 | 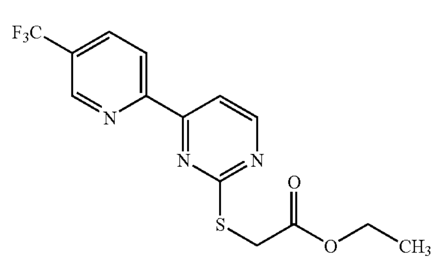 | 3.48 | |

| No. | Structure | log P (pH 2.3) | m.p./ °C |
|-----|-----------|----------------|----------|
| 258 | 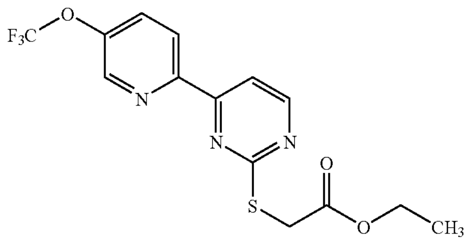 | | |
| 259 | 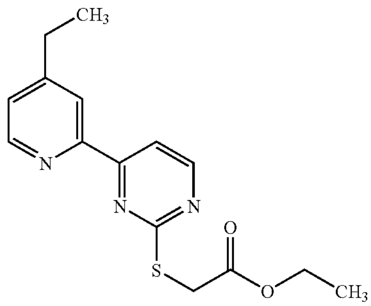 | 2.69 | |
| 260 | 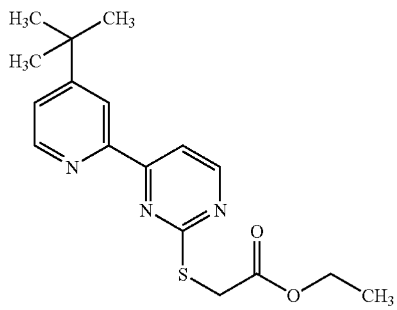 | | |
| 261 | 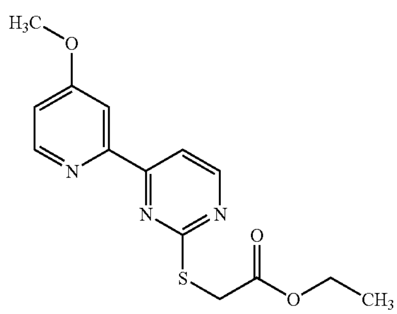 | 1.62 | |
| 262 | 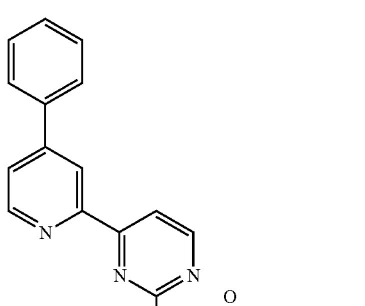 | 3.54 | |

-continued

| No. | Structure | log P (pH 2.3) | m.p./ °C. |
|---|---|---|---|
| 263 | 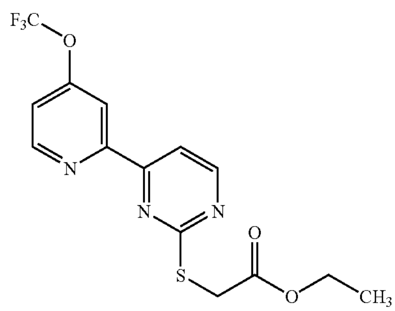 | | |
| 264 | 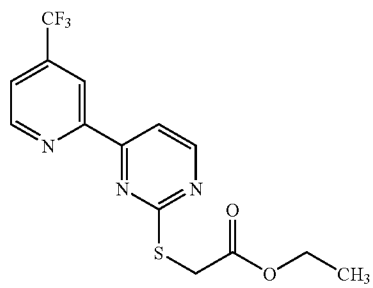 | | |
| 265 | 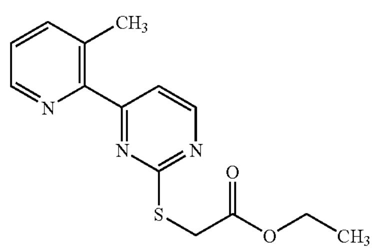 | 1.85 | |
| 266 | 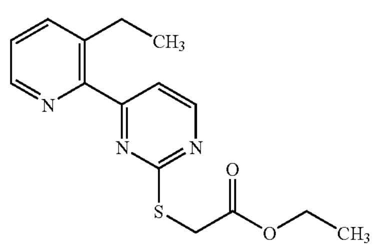 | 2.22 | |
| 267 | 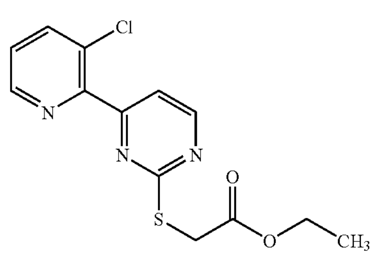 | | |

-continued

| No. | Structure | log P (pH 2.3) | m.p./ °C. |
|---|---|---|---|
| 268 | 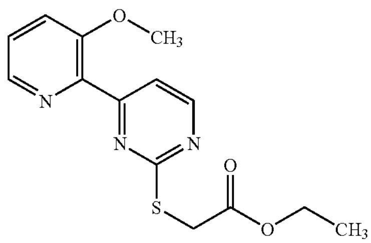 | 1.34 | |
| 269 | 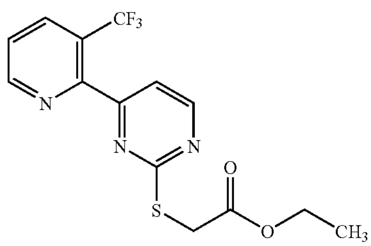 | 2.53 | |
| 270 | 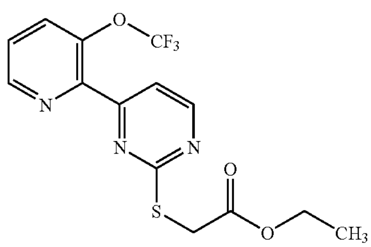 | | |
| 271 | 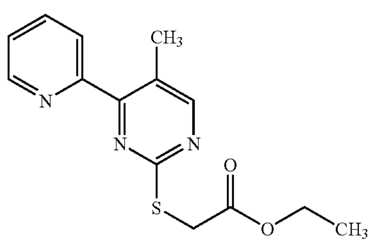 | 2.18 | 64-65 |
| 272 | 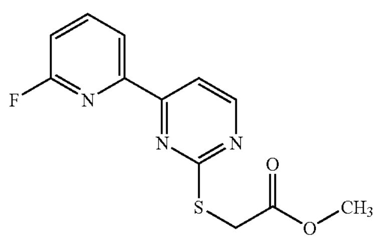 | | |
| 273 | 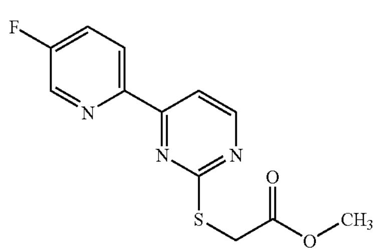 | | |

|No.|Structure|log P (pH 2.3)|m.p./ °C.|
|---|---|---|---|
|274|4-fluoropyridin-2-yl pyrimidin-2-yl-S-CH₂-C(=O)-O-CH₃|||
|275|3-fluoropyridin-2-yl pyrimidin-2-yl-S-CH₂-C(=O)-O-CH₃|||
|276|pyridin-2-yl 5-fluoropyrimidin-2-yl-S-CH₂-C(=O)-O-CH₃|||
|277|pyridin-2-yl 6-fluoropyrimidin-2-yl-S-CH₂-C(=O)-O-CH₃|||
|278|6-fluoropyridin-2-yl pyrimidin-2-yl-S-CH₂-C(=O)-O-C₂H₅|||
|279|5-fluoropyridin-2-yl pyrimidin-2-yl-S-CH₂-C(=O)-O-C₂H₅|||

| No. | Structure | log P (pH 2.3) | m.p./ °C |
|---|---|---|---|
| 280 | 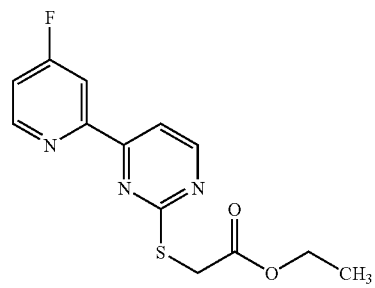 | | |
| 281 | 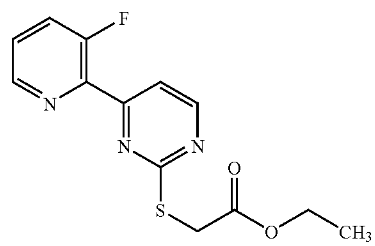 | 2.04 | |
| 282 | 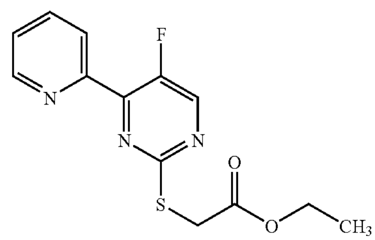 | | |
| 283 | 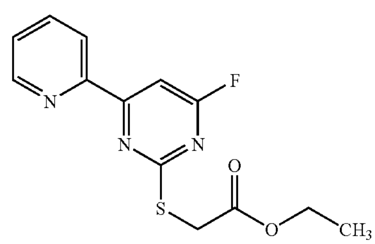 | | |
| 284 | 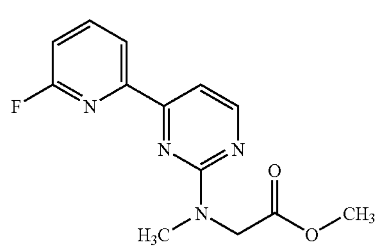 | | |
| 285 | 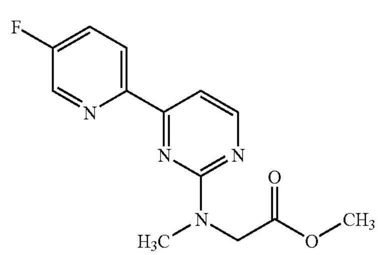 | | |

-continued

| No. | Structure | log P (pH 2.3) | m.p./ °C |
|---|---|---|---|
| 286 | 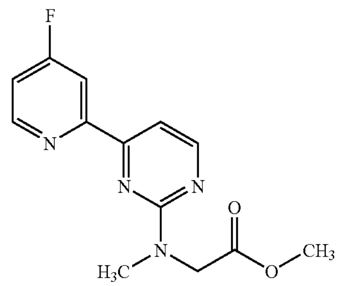 | | |
| 287 | 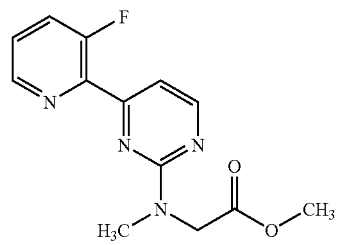 | | |
| 288 | 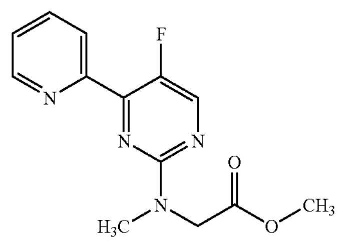 | | |
| 289 | 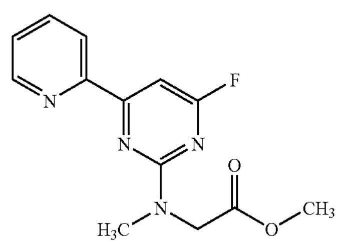 | | |
| 290 | 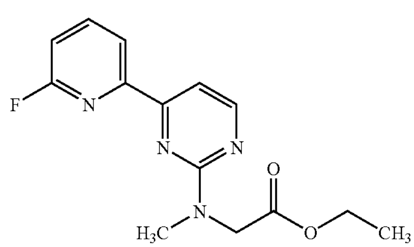 | | |
| 291 | 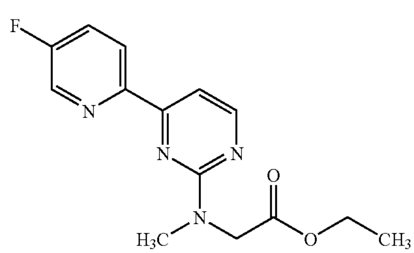 | | |

-continued

| No. | Structure | log P (pH 2.3) | m.p./ °C. |
|-----|-----------|----------------|-----------|
| 292 | 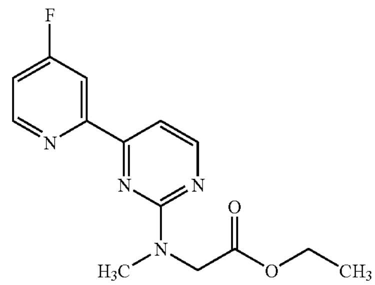 | | |
| 293 | 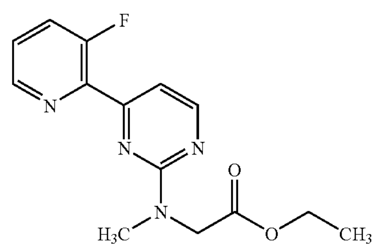 | | |
| 294 | 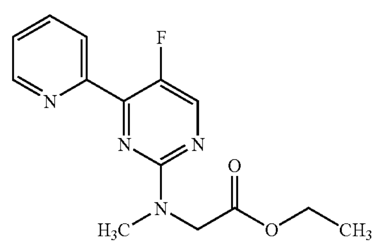 | | |
| 295 | 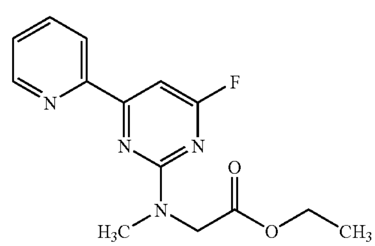 | | |
| 296 | 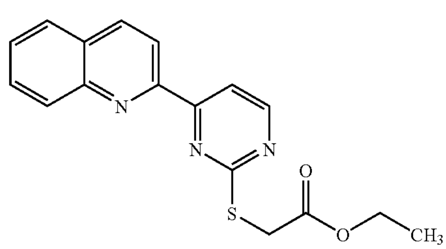 | 3.49 | |

-continued

| No. | Structure | log P (pH 2.3) | m.p./ °C. |
|---|---|---|---|
| 297 | 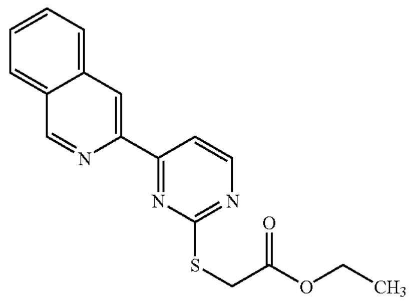 | | |
| 298 | 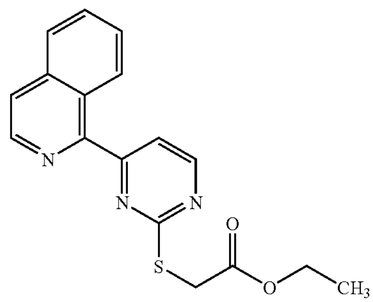 | 2.51 | |
| 299 | 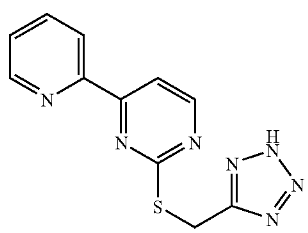 | 1.17 | 162 |
| 300 | 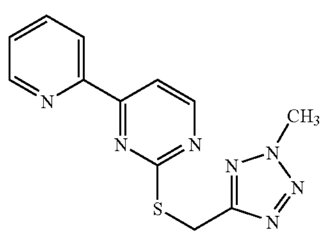 | 1.59 | |
| 301 | 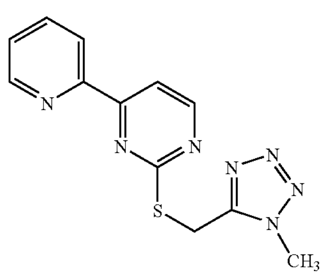 | 1.24 | |

-continued

| No. | Structure | log P (pH 2.3) | m.p./ °C. |
|---|---|---|---|
| 302 | 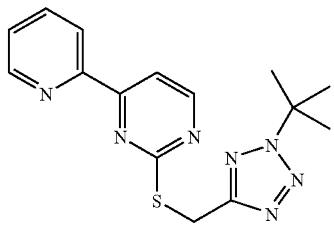 | 2.69 | |
| 303 | 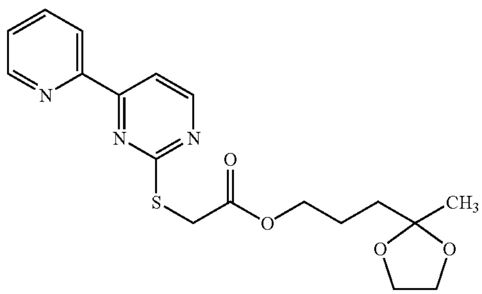 | 2.57 | |
| 304 | 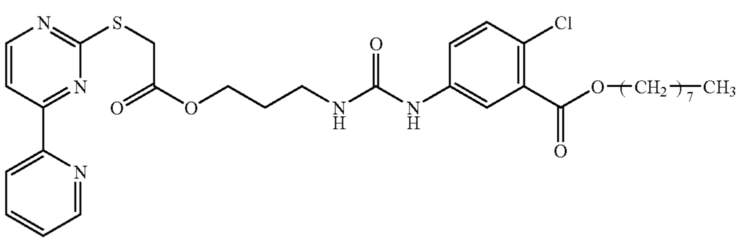 | 5.37 | |
| 305 | 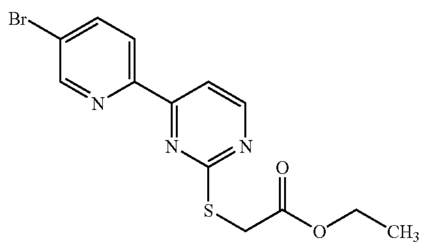 | 3.39 | |
| 306 | 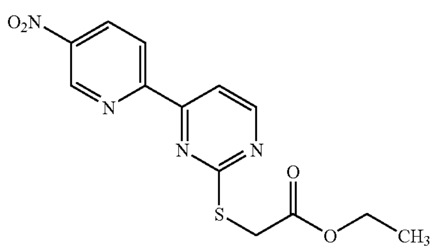 | 2.77 | |
| 307 | 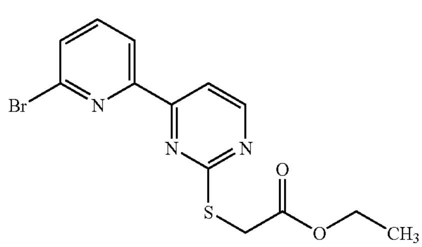 | 3.31 | |

-continued

| No. | Structure | log P (pH 2.3) | m.p./ °C. |
|---|---|---|---|
| 308 | 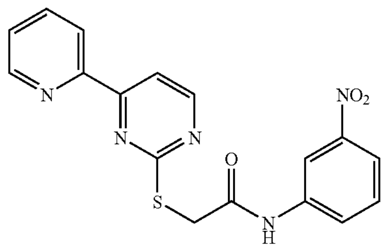 | 2.25 | |
| 309 | 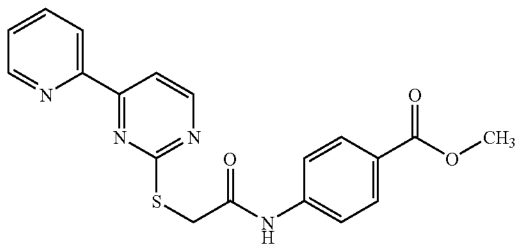 | 2.16 | |
| 310 | 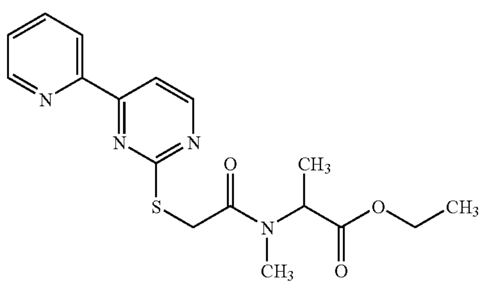 | 1.93 | |
| 311 | 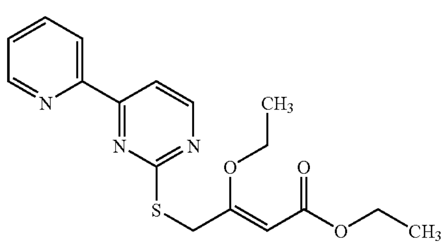 | 3.39 | |
| 312 | 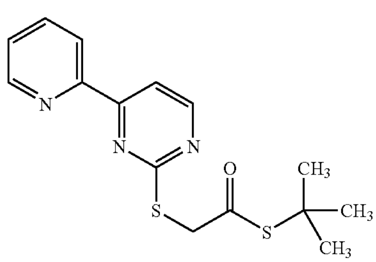 | 3.61 | |

-continued
| No. | Structure | log P (pH 2.3) | m.p./ ° C. |
|---|---|---|---|
| 313 | 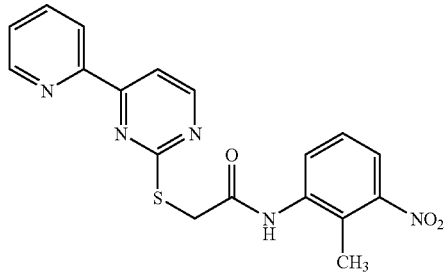 | 2.28 | |
| 314 | 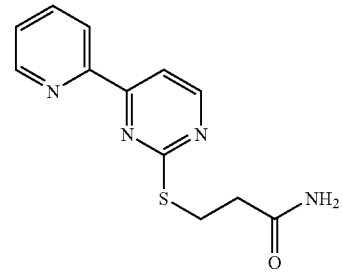 | 0.96 | |
| 315 | 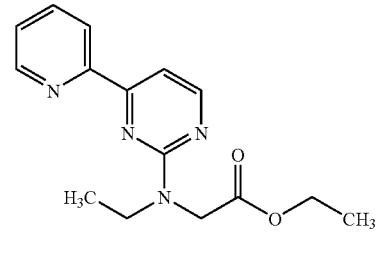 | 2.13 | |
| 316 | 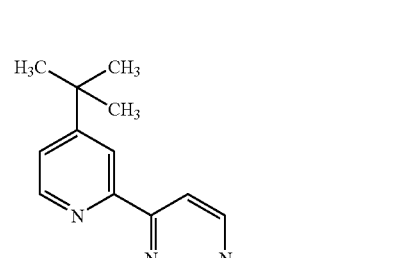 | 3.55 | |

| No. | Structure | log P (pH 2.3) | m.p./ °C |
|---|---|---|---|
| 317 | H₃C-S-pyridine-pyrimidine-S-CH₂-C(O)-O-CH₂CH₃ | 1.68 | |
| 318 | H₃C-O-pyridine-pyrimidine-S-CH₂-C(O)-O-CH₂CH₃ | | |
| 319 | (H₃C)(CH₃)N-pyridine-pyrimidine-S-CH₂-C(O)-O-CH₂CH₃ | | |
| 320 | H₃C-C(O)-NH-pyridine-pyrimidine-S-CH₂-C(O)-O-CH₂CH₃ | | |

The stated log P values were determined in accordance with EEC Directive 79/831 Annex V.A8 by HPLC (High Performance Liquid Chromatography) using a reversed-phase column, (C 18). Temperature: 43° C.

Mobile phases for the determination in the acidic range: 0.1% aqueous phosphoric acid, acetonitrile; linear gradient from 10% acetonitrile to 90% acetonitrile.

Calibration was carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

Use Examples

Example A

*Aphis gossypii* Test

| Solvent: | 30 parts by weight of dimethylformamide |
|---|---|
| Emulsifier: | 1 part by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*) which are heavily infested by the cotton aphid (*Aphis gossypii*) are treated by being dipped into the preparation of active compound of the desired concentration.

After the desired period of time, the kill in % is determined. 100% means that all aphids have been killed; 0% means that none of the aphids have been killed.

Active compounds, active compound concentration and test results are shown in the table below.

TABLE A

Plant-damaging insects
*Aphis gossypii* test

| Active compounds | Concentration of active compound in ppm | Kill rate in % after 6ᵈ |
|---|---|---|
| 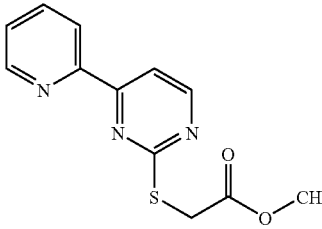 | 200 | 85 |
| 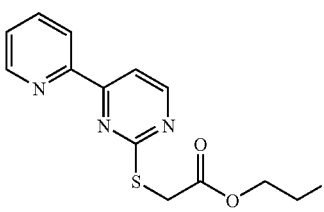 | 200 | 85 |
| 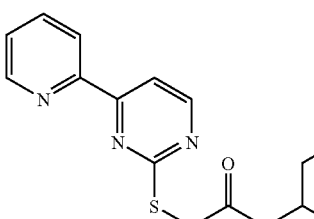 | 200 | 90 |

Example B

Franklinella Test

| Solvent: | 3 parts by weight of dimethylformamide |
| Emulsifier: | 1 part by weight of alkylaryl polyglycol ether |

To product a suitable preparation of active compound, 1 part by weight of active compound is mixed with the stated amounts of solvent and emulsifier, and the concentrate is diluted to the desired concentration.

Cucumber plants (*Cucumis sativus*) which are heavily infested by all stages of thrips (*Franklinella occidentalis*) are sprayed with a preparation of active compound of the desired concentration.

After the desired period of time, the effect in % is determined. 100% means that all thrips have been killed; 0% means that none of the thrips have been killed.

Active compounds, active compound concentration and test results are shown in the table below.

TABLE B

Plant-damaging insects
Franklinella test

| Active compounds | Concentration of active compound in ppm | Kill rate in % after 7ᵈ |
|---|---|---|
| 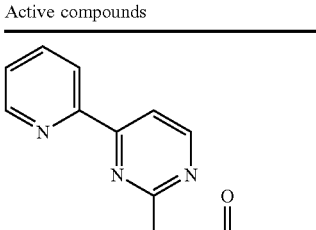 | 1000 | 99 |

Example C

Meloidogyne Test

To produce a suitable preparation of active compound, 1 part by weight of active compound is mixed with the stated amounts of solvent and emulsifier, and the concentrate is diluted with water to the desired concentration.

Vessels are filled with sand, solution of active compound, *Meloidogyne incognita* egg/larvae suspension and lettuce seeds. The lettuce seeds germinate and the plants develop. On the roots, galls are formed.

After the desired period of time, the nematicidal action is determined in % by the gall formation. 100% means that no galls were found; 0% means that the number of galls on the treated plants corresponds to that of the untreated control.

The amount of solvent, amount of emulsifier, active compounds, active compound concentration and test results are shown in the tables below.

TABLE C-1

Plant-damaging nematodes
Meloidogyne test
Solvent: 30 parts by weight of dimethylformamide
Emulsifier: 1 part by weight of alkylaryl polyglycol ether

| Active compounds | Concentration of active compound in ppm | Kill rate in % after 14$^d$ |
|---|---|---|
| (pyridin-2-yl)-pyrimidin-2-yl-S-CH₂-C(O)-O-CH₂CH₃ | 20 | 90 |
| (pyridin-2-yl)-pyrimidin-2-yl-S-CH₂-C(O)-O-CH₂CH₂-O-CH₃ | 20 | 90 |
| (pyridin-2-yl)-pyrimidin-2-yl-S-CH₂-C(O)-NH-N=C(CH₃)₂ | 20 | 98 |
| (pyridin-2-yl)-pyrimidin-2-yl-S-CH₂CH₂CH₂-C(O)-O-CH₃ | 20 | 90 |
| 6-chloro-4-(pyridin-2-yl)-quinazolin-2-yl-S-CH₂-C(O)-O-CH₃ | 20 | 98 |

TABLE C-1-continued

Plant-damaging nematodes
Meloidogyne test
Solvent: 30 parts by weight of dimethylformamide
Emulsifier: 1 part by weight of alkylaryl polyglycol ether

| Active compounds | Concentration of active compound in ppm | Kill rate in % after 14$^d$ |
|---|---|---|
| 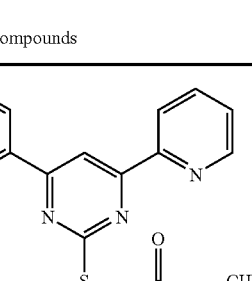 | 20 | 95 |
| | 20 | 100 |

TABLE C-2

Plant-damaging nematodes
Meloidogyne test
Solvent: 7 parts by weight of dimethylformamide
Emulsifier: 2 parts by weight of alkylaryl polyglycol ether

| Active compounds | Concentration of active compound in ppm | Kill rate in % after 14$^d$ |
|---|---|---|
| 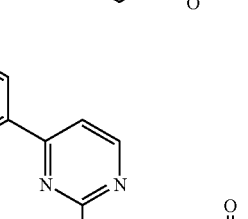 | 20 | 80 |
| | 20 | 100 |

TABLE C-2-continued

Plant-damaging nematodes
Meloidogyne test
Solvent: 7 parts by weight of dimethylformamide
Emulsifier: 2 parts by weight of alkylaryl polyglycol ether

| Active compounds | Concentration of active compound in ppm | Kill rate in % after 14$^d$ |
|---|---|---|
| (structure) | 20 | 90 |
| (structure) | 20 | 90 |
| (structure) | 20 | 100 |
| (structure) | 20 | 90 |

Example D

Myzus Test

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) which are heavily infested by peach aphids (*Myzus persicae*) are treated by being dipped into the preparation of the active compound of the desired concentration.

After the desired period of time, the kill in % is determined. 100% means that all aphids have been killed; 0% means that none of the aphids has been killed.

The amount of solvent, amount of emulsifier, active compounds, active compound concentration and test results are shown in the tables below.

TABLE D-1
Plant-damaging insects
Myzus test
Solvent: 30 parts by weight of dimethylformamide
Emulsifier: 1 part by weight of alkylaryl polyglycol ether
| Active compounds | Concentration of active compound in ppm | Kill rate in % after 6$^d$ |
|---|---|---|
| 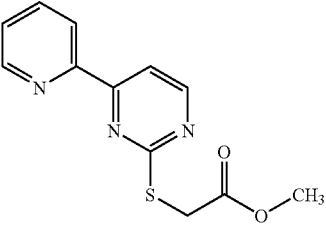 | 100 | 100 |
| 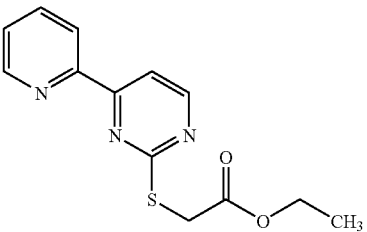 | 1000 | 100 |
| 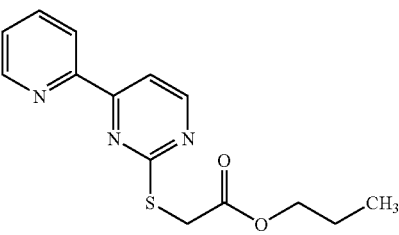 | 1000 | 95 |
| 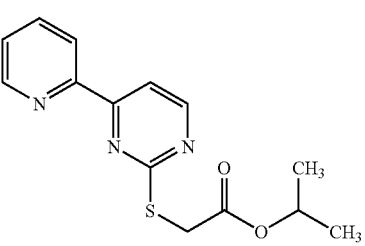 | 1000 | 100 |
| 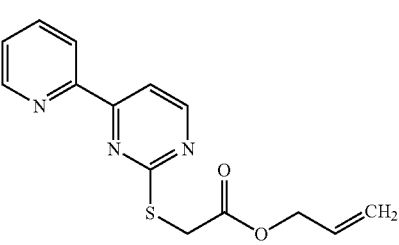 | 1000 | 95 |

TABLE D-1-continued

Plant-damaging insects
Myzus test
Solvent: 30 parts by weight of dimethylformamide
Emulsifier: 1 part by weight of alkylaryl polyglycol ether

| Active compounds | Concentration of active compound in ppm | Kill rate in % after 6$^d$ |
|---|---|---|
| [structure: 4-(pyridin-2-yl)pyrimidin-2-yl-S-CH$_2$-C(=O)-O-cyclohexyl] | 1000 | 100 |
| [structure: 4-(pyridin-2-yl)pyrimidin-2-yl-S-CH(C(=O)OCH$_3$)$_2$] | 100 | 95 |
| [structure: 4-(pyridin-2-yl)pyrimidin-2-yl-S-CH$_2$-C(=O)-NH$_2$] | 1000 | 95 |
| [structure: 4-(pyridin-2-yl)pyrimidin-2-yl-S-(CH$_2$)$_3$-C(=O)-OCH$_3$] | 1000 | 100 |
| [structure: 4-(pyridin-2-yl)pyrimidin-2-yl-S-CH$_2$-C(=O)-O$^-$ · benzyltrimethylammonium$^+$] | 1000 | 100 |

TABLE D-1-continued

Plant-damaging insects
Myzus test
Solvent: 30 parts by weight of dimethylformamide
Emulsifier: 1 part by weight of alkylaryl polyglycol ether

| Active compounds | Concentration of active compound in ppm | Kill rate in % after 6$^d$ |
|---|---|---|
| 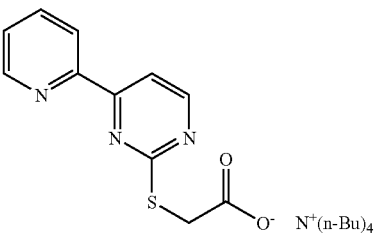 | 1000 | 100 |
| 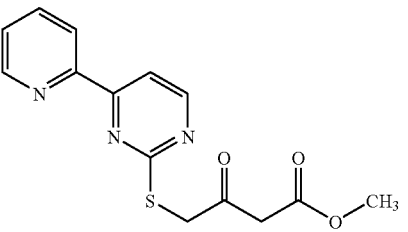 | 200 | 95 |

TABLE D-2

Plant-damaging insects
Myzus test
Solvent: 7 parts by weight of dimethylformamide
Emulsifier: 2 parts by weight of alkylaryl polyglycol ether

| Active compounds | Concentration of active compound in ppm | Kill rate in % after 6$^d$ |
|---|---|---|
| 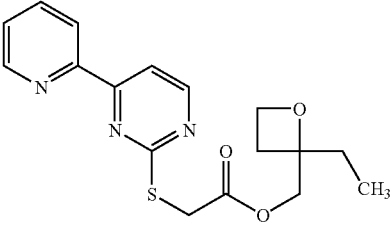 | 500 | 98 |
| 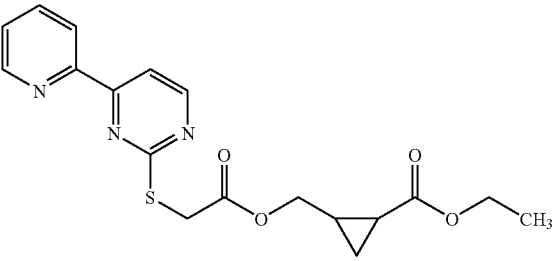 | 500 | 98 |

TABLE D-2-continued

Plant-damaging insects
Myzus test
Solvent: 7 parts by weight of dimethylformamide
Emulsifier: 2 parts by weight of alkylaryl polyglycol ether

| Active compounds | Concentration of active compound in ppm | Kill rate in % after 6$^d$ |
|---|---|---|
| | 500 | 98 |
| | 500 | 100 |
| | 500 | 100 |
| | 500 | 95 |

TABLE D-2-continued

Plant-damaging insects
Myzus test
Solvent: 7 parts by weight of dimethylformamide
Emulsifier: 2 parts by weight of alkylaryl polyglycol ether

| Active compounds | Concentration of active compound in ppm | Kill rate in % after 6$^d$ |
|---|---|---|
| (pyridin-2-yl-pyrimidin-2-yl-S-CH₂-C(O)-O-CH(CH₃)-C(O)-O-CH(CH₃)₂) | 500 | 95 |
| (pyridin-2-yl-pyrimidin-2-yl-S-CH₂-C(O)-O-(2,2,3,3-tetrafluorocyclobutyl)) | 500 | 100 |
| (pyridin-2-yl-pyrimidin-2-yl-S-CH₂-C(O)-O-(oxetan-3-yl)) | 500 | 95 |
| (pyridin-2-yl-pyrimidin-2-yl-S-CH₂-CH₂-C(O)-NH₂) | 500 | 80 |
| (pyridin-2-yl-pyrimidin-2-yl-S-CH₂-C(O)-S-C(CH₃)₃) | 500 | 95 |

TABLE D-2-continued

Plant-damaging insects
Myzus test
Solvent: 7 parts by weight of dimethylformamide
Emulsifier: 2 parts by weight of alkylaryl polyglycol ether

| Active compounds | Concentration of active compound in ppm | Kill rate in % after 6$^d$ |
|---|---|---|
| 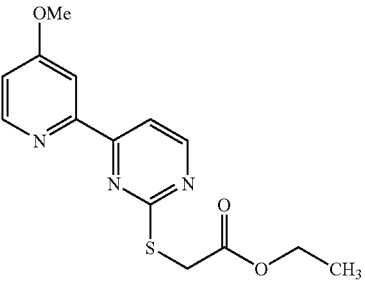 | 500 | 90 |
| 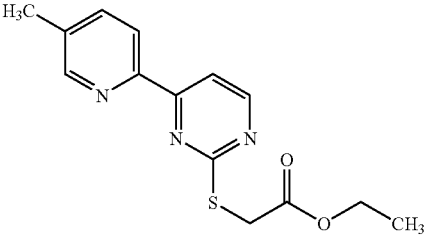 | 500 | 98 |

Example E

*Phaedon larvae* Test

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed.

The amount of solvent, amount of emulsifier, active compounds, active compound concentration and test results are shown in the tables below.

TABLE E-1

Plant-damaging insects
Phaedon larvae test
Solvent: 30 parts by weight of dimethylformamide
Emulsifier: 1 part by weight of alkylaryl polyglycol ether

| Active compounds | Concentration of active compound in ppm | Kill rate in % after 7$^d$ |
|---|---|---|
| 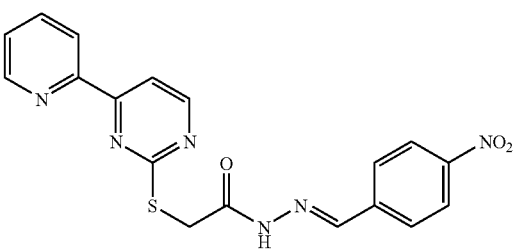 | 1000 | 100 |

TABLE E-2

Plant-damaging insects
Phaedon larvae test
Solvent: 7 parts by weight of dimethylformamide
Emulsifier: 2 parts by weight of alkylaryl polyglycol ether

| Active compounds | Concentration of active compound in ppm | Kill rate in % after 7$^d$ |
|---|---|---|
| 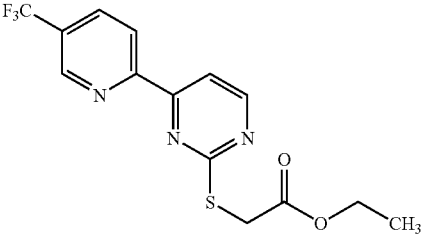 | 500 | 100 |
| 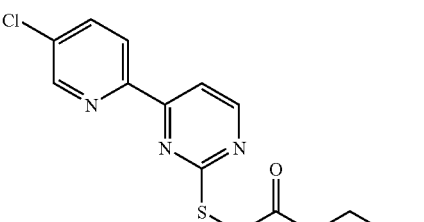 | 500 | 100 |
| 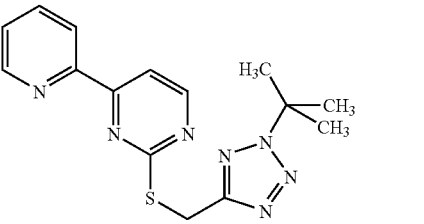 | 500 | 100 |

Example F

*Spodoptera frugiperda* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentrated and are populated with caterpillars of the army worm (*Spodoptera frugiperda*) while the leaves are still moist.

After the desired period of time, the kill in % is determined. 100% means that all caterpillars have been killed; 0% means that none of the caterpillars has been killed.

Active compounds, active compound concentrations and test results are shown in the table below.

TABLE F

Plant-damaging insects
*Spodoptera frugiperda* test

| Active compounds | Concentration of active compound in ppm | Kill rate in % after 7$^d$ |
|---|---|---|
| [structure: 2-pyridyl-methylpyrimidine-S-CH2-C(O)-O-CH2CH3] | 500 | 100 |
| [structure: 5-CF3-pyridyl-pyrimidine-S-CH2-C(O)-O-CH2CH3] | 500 | 100 |
| [structure: 2-pyridyl-pyrimidine-S-CH2-tetrazole-C(CH3)3] | 500 | 100 |

Example G

*Diabrotica balteata* Test (Larvae in Soil)

Critical concentration test/soil insects—treatment of transgenic plants

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

The preparation of active compound is poured onto the soil. Here, the concentration of active compound in the preparation is virtually immaterial, only the amount by weight of active compound per volume unit of soil, which is stated in ppm (mg/l), matters. The soil is filled into 0.25 l pots, and these are allowed to stand at 20° C.

Immediately after the preparation, 5 pregerminated maize corns of the cultivar YIELD GUARD (trade mark of Monsanto Comp., USA) are placed into each pot. After 2 days, the corresponding test insects are placed into the treated soil. After a further 7 days, the efficacy of the active compound is determined by counting the number of maize plants that have emerged (1 plant=20% activity).

Example H

*Heliothis virescens* Test (Treatment of Transgenic Plants)

| Solvent: | 7 parts by weight of dimethylformamide |
|---|---|
| Emulsifier: | 1 part by weight of alkylaryl polyglycol ether |

To produce a suitable preparation of active compound, 1 part by weight of active compound is mixed with the stated amount of solvent and the stated amount of emulsifier, and the concentrate is diluted with water to the desired concentration.

Soya bean shoots (*Glycine max*) of the cultivar Roundup Ready (trade mark of Monsanto Comp., USA) are treated by being dipped into the preparation of active compound of the desired concentration and populated with the tobacco bud worm caterpillar Heliothis virescens while the leaves are still moist.

After the desired period of time, the kill in % is determined. 100% means that all caterpillars have been killed; 0% means that none of the caterpillars have been killed.

What is claimed is:

1. A pyridylpyrimidine of formula (I)

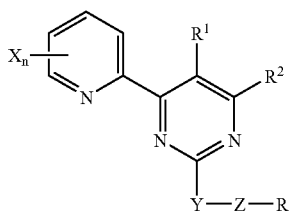

in which
R$^1$ and R$^2$ independently of one another represent hydrogen, halogen, nitro, cyano, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, or cycloalkyl; or represent optionally substituted aryl, or arylalkyl, saturated or unsaturated heterocyclyl having 1 to 4 heteroatoms from the group consisting of nitrogen, oxygen and sulphur, or R$^1$ and R$^2$ together represent alkylene or alkenylene, where the carbon chain is optionally interrupted by 1 to 3 heteroatoms selected from the group consisting of nitrogen and oxygen and the resulting ring is optionally substituted by halogen or alkyl, X represents halogen, nitro, cyano, hydroxyl, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, cycloalkyl, aryl, arylalkyl, or saturated or unsaturated heterocyclyl having 1 to 4 heteroatoms selected from the group consisting of nitrogen, oxygen and sulphur; or, when n represents 2, 3 or 4, two adjacent X together optionally represent alkylene or alkenylene, where the carbon chain is optionally interrupted by 1 or 2 heteroatoms selected from the group consisting of nitrogen and oxygen, n represents 0, 1, 2, 3 or 4, with X representing identical or different radicals when n represents 2, 3 or 4, Y represents a direct bond, oxygen, —S(O)$_p$—, or —NR$^9$—, p represents 0, 1 or 2, Z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$—, or —(CH$_2$)$_t$—C(R$^{12}$)=C(R$^{13}$)—(CH$_2$)$_w$—, r represents 1, 2, 3, 4, 5 or 6, t and w independently of one another represent 0, 1, 2, 3 or 4, R represents the group

where A represents oxygen, sulphur, or NR$^{15}$ and E represents —SR$^{16}$ or —S-M, or where A represents sulphur or NR$^{15}$ and E represents —OR$^{16}$, —SR$^{16}$, —O-M, or —S-M, or represents a carboxylic acid bioisostere (acid mimic) selected from the group consisting of

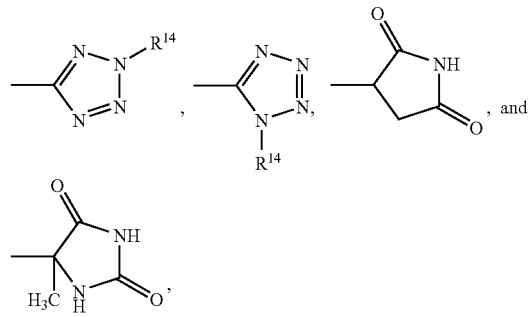

M represents ammonium that is optionally substituted by alkyl, aryl or arylalkyl; or represents an alkali metal ion, or represents an alkaline earth metal ion forming a salt with two molecules of a compound of formula (I), R$^3$ represents hydrogen, alkyl, halogenoalkyl, cycloalkyl, cycloalkylalkyl; or represents optionally halogen-, alkyl-, halogenoalkyl-, alkoxy-, halogenoalkoxy-, alkylthio-, halogenoalkylthio-substituted aryl, arylalkyl, saturated or unsaturated heterocyclyl or heterocyclylalkyl having 1 to 4 heteroatoms selected from the group consisting of nitrogen, oxygen and sulphur, R$^4$ represents hydrogen, alkyl, halogenoalkyl, cycloalkyl or alkylcarbonyl, R$^5$ represents hydrogen, amino, formyl, alkyl, alkenyl, alkynyl, halogenoalkyl, cycloalkyl, alkoxy, alkoxyalkyl, alkylcarbonyl, alkoxycarbonyl, or oxamoyl, or R$^4$ and R$^5$ together represent alkylidene; or represent optionally halogen-, nitro-, alkyl-, or halogenoalkyl-substituted benzylidene; or R$^4$ and R$^5$ together with the nitrogen atom to which they are attached represent a saturated or unsaturated heterocycle that optionally contains a further nitrogen, oxygen or sulphur atom and is optionally be substituted by alkyl, R$^6$ represents hydrogen, alkyl, halogenoalkyl or arylalkyl, R$^7$ represents hydrogen, alkyl, halogenoalkyl, cycloalkyl, cycloalkylalkyl, aryl or arylalkyl, R$^8$ represents alkyl or halogenoalkyl, R$^9$ represents hydrogen, alkyl, halogenoalkyl, cycloalkyl, cycloalkylalkyl; or represents optionally halogen-, alkyl-, halogenoalkyl-, alkoxy-, halogenoalkoxy-, alkylthio-, halogenoalkylthio-substituted aryl, arylalkyl, or saturated or unsaturated heterocyclyl or heterocyclylalkyl having 1 to 4 heteroatoms selected from the group consisting of nitrogen, oxygen and sulphur, R$^{10}$ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, R$^{11}$ represents hydrogen or alkyl, R$^{12}$ and R$^{13}$ independently of one another represent hydrogen, hydroxyl, alkyl or alkoxy, R$^{14}$ represents hydrogen, alkyl or halogenoalkyl, R$^{15}$ represents hydrogen, alkyl, alkoxy, cyano or dialkylamino, R$^{16}$ represents hydrogen; represents optionally halogen-, amino-, hydroxyl-, cyano-, nitro-, alkoxy-, halogenoalkoxy-, alkylthio-, halogenoalkylthio-, alkoxycarbonyl-, alkenyloxy-carbonyl-, alkylcarbonyloxy-, alkenylcarbonyloxy-, oxyalkyleneoxy-, oxetanyl-, dioxanyl-, oxazolidinyl-, dioxolanyl-, aryloxy-, halogenoaryloxy-, —CONR⁴R⁵—, —NR⁴R⁵—, —ONR⁴R⁵—, or —C(R¹⁴)=N—OR¹⁴-substituted alkyl, alkenyl, or alkynyl; represents optionally halogen-, alkyl-, halogenoalkyl-, alkoxy-, halogenoalkoxy-, alkylthio-, halogenoalkylthio-, alkoxycarbonyl-, alkylcarbonyloxy-substituted aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen and sulphur; or represents —NR⁴R⁵; represents Q; or represents optionally substituted aryl, arylalkyl, cycloalkyl, cycloalkylalkyl, or saturated or unsaturated heterocyclyl or heterocyclylalkyl having 1 to 4 heteroatoms from the group consisting of nitrogen, oxygen and sulphur, where the substituents are those mentioned above or are hydroxyl or nitro, and Q represents one of the groups

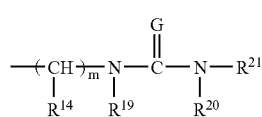 (Q¹)

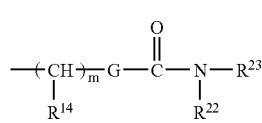 (Q²)

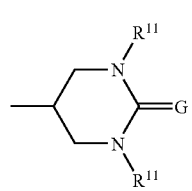 (Q³)

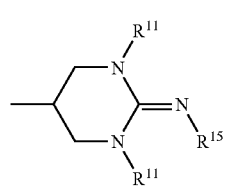 (Q⁴)

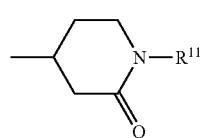 (Q⁵)

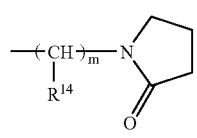 (Q⁶)

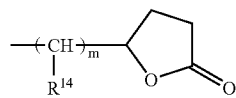 (Q⁷)

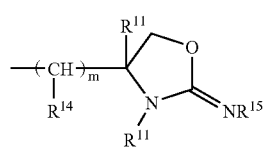 (Q⁸)

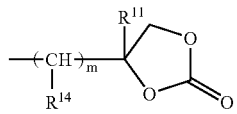 (Q⁹)

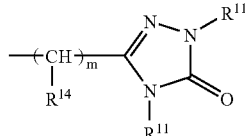 (Q¹⁰)

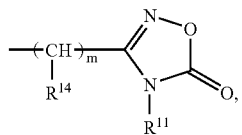 (Q¹¹)

where
each R¹¹ may have identical or different meanings when two or more R¹¹ are present in the same heterocyclic group,
m represents 0, 1, 2 or 3, where each repeat unit —(CHR¹⁴)— in the side chain of a heterocyclic grouping optionally has identical or different meanings when m represents 2 or 3,
G represents oxygen or sulphur,
R¹⁹ and R²⁰ independently of one another represent hydrogen, alkyl or R¹⁹ and R²⁰ together represent alkylene,
R²¹ represents hydrogen, represents optionally alkylcarbonyloxy- or alkoxy-substituted alkyl; or represents optionally halogen-, cyano-, alkyl-, halogenoalkyl-, alkylcarbonyl-, alkoxycarbonyl-, or alkylene-substituted aryl,
R²² represents hydrogen, alkyl or alkoxyalkyl, and
R²³ represents hydrogen, amino, alkyl or alkoxyalkyl.

2. A pyridylpyrimidine of the formula (I) according to claim 1 wherein R represents a carboxylic acid bioisostere selected from the group consisting of

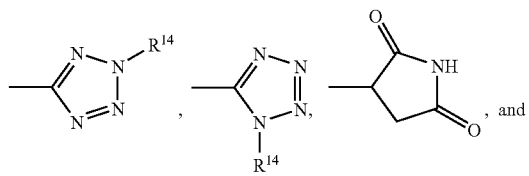

where R¹⁴ represents hydrogen, alkyl or halogenoalkyl.

3. A pyridylpyrimidine of the formula (I) according to claim 1 wherein
R¹⁶ represents hydrogen, represents optionally halogen-, amino-, hydroxyl-, cyano-, nitro-, alkoxy-, halogenoalkoxy-, alkylthio-, halogenoalkylthio-, alkoxycarbonyl-, alkenyloxycarbonyl-, alkylcarbonyloxy-, alkenylcarbonyloxy-, oxyalkyleneoxy-, oxetanyl-, dioxanyl-, oxazolidinyl-, dioxolanyl-, aryloxy-, halogenoaryloxy-, —CONR⁴R⁵—, —NR⁴R⁵—, —ONR⁴R⁵—, or —C(R¹⁴)═N—OR¹⁴-substituted alkyl, alkenyl, alkynyl; represents optionally halogen-, alkyl-, halogenoalkyl-, alkoxy-, halogenoalkoxy-, alkylthio-, halogenoalkylthio-, alkoxycarbonyl-, or alkylcarbonyloxy-substituted aryl, arylalkyl, cycloalkyl, cycloalkylalkyl, saturated or unsaturated heterocyclyl or heterocyclylalkyl having 1 to 4 heteroatoms selected from the group consisting of nitrogen, oxygen and sulphur; represents —NR⁴R⁵; or represents Q.

4. A pyridylpyrimidines of the formula (I) according to claim 1 wherein

R¹ and R² independently of one another represent hydrogen, halogen, nitro, cyano, C₁-C₆-alkyl, C₁-C₆-halogenoalkyl, C₁-C₆-alkoxy, C₁-C₆-halogenoalkoxy, C₁-C₆-alkylthio, C₁-C₆-halogenoalkylthio, C₂-C₆-alkenyl, C₂-C₆-alkynyl, C₂-C₆-alkenyloxy, C₂-C₆-halogenoalkenyloxy, C₂-C₆-alkynyloxy, C₂-C₆-halogenoalkynyloxy, —S(O)ₚR³, —NR⁴R⁵, —COR⁶, —CO₂R⁷, —CSR⁶, —CONR⁴R⁵, —NHCO₂R⁸, or C₃-C₇-cycloalkyl; or represent aryl, aryl-C₁-C₆-alkyl or 5- or 6-membered saturated or unsaturated heterocyclyl which contains 0 to 3 nitrogen atoms, 0 to 2 nonadjacent oxygen atoms and/or 0 to 2 nonadjacent sulphur atoms, each of which radicals is optionally mono- or polysubstituted by identical or different substituents selected from the group consisting of halogen, C₁-C₆-alkyl, C₁-C₆-halogenoalkyl, C₁-C₆-alkoxy, and C₁-C₆-halogenoalkoxy, or R¹ and R² together represent C₃-C₅-alkylene or C₃-C₄-alkenylene, where the carbon chain is optionally interrupted by 1 or 2 heteroatoms that are 0 to 2 nitrogen atoms and/or 0 or 1 oxygen atom, and where the resulting ring is optionally mono- or polysubstituted by identical or different substituents selected from the group consisting of halogen and C₁-C₆-alkyl, X represents halogen, nitro, cyano, hydroxyl, C₁-C₆-alkyl, C₁-C₆-halogenoalkyl, C₁-C₆-alkoxy, C₁-C₆-halogenoalkoxy, C₁-C₆-alkylthio, C₁-C₆-halogenoalkylthio, C₂-C₆-alkenyl, C₂-C₆-alkynyl, C₂-C₆-alkenyloxy, C₂-C₆-halogenoalkenyloxy, C₂-C₆-alkynyloxy, C₂-C₆-halogenoalkynyloxy, —S(O)ₚR³, —NR⁴R⁵, —COR⁶, —CO₂R⁷, —CSR⁶, —CONR⁴R⁵, —NHCO₂R⁸, C₃-C₇-cycloalkyl, aryl, aryl-C₁-C₆-alkyl, 5- or 6-membered saturated or unsaturated heterocyclyl that contains 0 to 4 nitrogen atoms, 0 to 2 nonadjacent oxygen atoms and/or 0 to 2 nonadjacent sulphur atoms; or, when n represents 2 or 3, two adjacent radicals X together optionally represent C₃-C₅-alkylene or C₃-C₄-alkenylene, where the carbon chain s optionally interrupted by 1 or 2 heteroatoms that are 0 to 2 nitrogen atoms and/or 0 or 1 oxygen atom, n represents 0, 1, 2 or 3, with X representing identical or different radicals when n represents 2 or 3, Y represents a direct bond, oxygen, —S(O)ₚ—, or —NR⁹—, p represents 0, 1 or 2, Z represents —(CH₂)ᵣ—, —(CH₂)ₜ—(CHR¹⁰)—(CH₂)_w—, —(CH₂)ᵣ—C(O)—(CH₂)ₜ—, —(CH₂)ᵣ—O—(CH₂)ₜ—, —(CH₂)ᵣ—S(O)ₚ—(CH₂)ₜ—, —(CH₂)ᵣ—N(R¹¹)—(CH₂)ₜ—, or —(CH₂)ₜ—C(R¹²)═C(R¹³)—(CH₂)_w—, r represents 1, 2, 3, 4, 5 or 6, t and w independently of one another represent 0, 1, 2, 3 or 4, R represents the group

where A represents oxygen, sulphur, or NR¹⁵ and E represents —SR¹⁶ or —S-M, or where A represents sulphur or NR¹⁵ and E represents —OR¹⁶, —SR¹⁶, —O-M, or —S-M, or represents a carboxylic acid bioisostere (acid mimetic), selected from the group consisting of

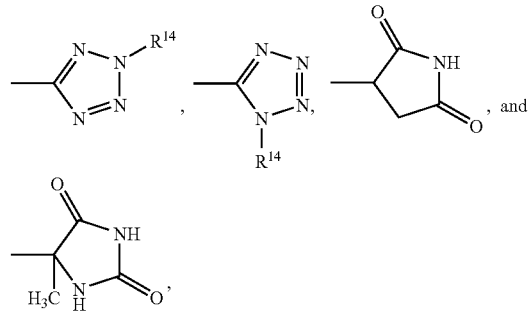

M represents ammonium which is optionally mono- to tetrasubstituted by identical or different substituents selected from the group consisting of C₁-C₆-alkyl, aryl, and aryl-C₁-C₆-alkyl, or represents a lithium cation (Li⁺), a sodium cation (Na⁺) or a potassium cation (K⁺), or represents a magnesium cation (Mg²⁺) or a calcium cation (Ca²⁺) forming a salt with two molecules of a compound of formula (I), R³ represents hydrogen, C₁-C₆-alkyl, C₁-C₆-halogenoalkyl, C₃-C₇-cycloalkyl, or C₃-C₇-cycloalkyl-C₁-C₆-alkyl; or represents aryl, aryl-C₁-C₆-alkyl, or 5- or 6-membered saturated or unsaturated heterocyclyl or heterocyclyl-C₁-C₆-alkyl, each of which contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, C₁-C₆-alkyl, C₁-C₆-halogenoalkyl, C₁-C₆-alkoxy, C₁-C₆-halogenoalkoxy, C₁-C₆-alkylthio, and C₁-C₆-halogenoalkylthio, R⁴ represents hydrogen, C₁-C₆-alkyl, C₁-C₆-halogenoalkyl, C₃-C₇-cycloalkyl, or C₁-C₆-alkylcarbonyl, R⁵ represents hydrogen, amino, formyl, C₁-C₆-alkyl, C₂-C₆-alkenyl, C₂-C₆-alkynyl, C₁-C₆-halogenoalkyl, C₃-C₇-cycloalkyl, C₁-C₆-alkoxy, C₁-C₆-alkoxy-C₁-C₆-alkyl, C₁-C₆-alkylcarbonyl, C₁-C₆-alkoxycarbonyl, or oxamoyl, or R⁴ and R⁵ together represent C₁-C₆-alkylidene; or represent benzylidene that is optionally mono- or polysubstituted by identical or different substituents selected from the group consisting of halogen, nitro, C₁-C₆-alkyl, and C₁-C₆-halogenoalkyl; or R⁴ and R⁵ together with the nitrogen atom to which they are attached represent a 5- or 6-membered saturated or unsaturated heterocyle that optionally contain a further nitrogen, oxygen or sulphur atom and that is optionally be mono- or polysubstituted by identical or different C₁-C₆-alkyl, R⁶ represents hydrogen, C₁-C₆-alkyl, C₁-C₆-halogenoalkyl or aryl-C₁-C₆-alkyl, R⁷ represents hydrogen, $C_1$-$C_6$-alkyl, $C_1$-$C_6$-halogenoalkyl, $C_3$-$C_7$-cycloalkyl, $C_3$-$C_7$-cycloalkyl-$C_1$-$C_6$-alkyl, aryl or aryl-$C_1$-$C_6$-alkyl, R⁸ represents $C_1$-$C_6$-alkyl or $C_1$-$C_6$-halogenoalkyl, R⁹ represents hydrogen, $C_1$-$C_6$-alkyl, $C_1$-$C_6$-halogenoalkyl, $C_3$-$C_7$-cycloalkyl, or $C_3$-$C_7$-cycloalkyl-$C_1$-$C_6$-alkyl; or represents aryl, aryl-$C_1$-$C_6$-alkyl, or 5- or 6-membered saturated or unsaturated heterocyclyl or heterocyclyl-$C_1$-$C_6$-alkyl, each of which contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, and $C_1$-$C_6$-halogenoalkylthio, R¹⁰ represents halogen, $C_1$-$C_6$-alkyl, $C_1$-$C_6$-alkylcarbonyl, $C_1$-$C_6$-alkoxycarbonyl, $C_3$-$C_7$-cycloalkyl, or $C_3$-$C_7$-cycloalkyl-$C_1$-$C_6$-alkyl; or represents aryl or aryl-$C_1$-$C_6$-alkyl that is optionally mono- or polysubstituted in the aryl moiety by identical or different substituents selected from the group consisting of halogen and $C_1$-$C_6$-alkyl, R¹¹ represents hydrogen or $C_1$-$C_6$-alkyl, R¹² and R¹³ independently of one another represent hydrogen, hydroxyl, $C_1$-$C_6$-alkyl, or $C_1$-$C_6$-alkoxy, R¹⁴ represents hydrogen, $C_1$-$C_6$-alkyl or $C_1$-$C_6$-halogenoalkyl, R¹⁵ represents hydrogen, $C_1$-$C_6$-alkyl, $C_1$-$C_6$-alkoxy, cyano, or di($C_1$-$C_6$-alkyl)-amino, R¹⁶ represents hydrogen; represents $C_1$-$C_{16}$-alkyl, $C_2$-$C_{10}$-alkenyl, $C_2$-$C_6$-alkynyl, each of which is optionally mono- or polysubstituted by identical or different substituents selected from the group consisting of halogen, amino, hydroxyl, cyano, nitro, $C_1$-$C_6$-alkoxy, $C_1$-$C_6$-halogenoalkoxy, $C_1$-$C_6$-alkylthio, $C_1$-$C_6$-halogenoalkylthio, $C_1$-$C_6$-alkoxycarbonyl, $C_2$-$C_6$-alkenyloxycarbonyl, $C_1$-$C_6$-alkylcarbonyloxy, $C_2$-$C_6$-alkenylcarbonyloxy, oxy($C_1$-$C_6$-alkylene)oxy, oxetanyl, dioxanyl, oxazolidinyl, dioxolanyl, aryloxy, halogenoaryloxy, —CONR⁴R⁵, —NR⁴R⁵, —ONR⁴R⁵ and —C(R¹⁴)=N—OR¹⁴; or represents aryl, aryl-$C_1$-$C_6$-alkyl, $C_3$-$C_7$-cycloalkyl, $C_3$-$C_7$-cycloalkyl-$C_1$-$C_6$-alkyl, 4- to 6-membered saturated or unsaturated heterocyclyl or heterocyclyl-$C_1$-$C_6$-alkyl, each of which contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, $C_1$-$C_6$-halogenoalkylthio, $C_1$-$C_6$-alkoxycarbonyl and $C_1$-$C_6$-alkylcarbonyloxy; represents —NR⁴R⁵; represents Q; or represents aryl, aryl-$C_1$-$C_6$-alkyl, $C_3$-$C_7$-cycloalkyl, $C_3$-$C_7$-cycloalkyl-$C_1$-$C_6$-alkyl, 4- to 6-membered saturated or unsaturated heterocyclyl or heterocyclyl-$C_1$-$C_6$-alkyl, each of which contains 0 to 4 nitrogen atoms, 0 to 2 nonadjacent oxygen atoms and/or 0 to 2 nonadjacent sulphur atoms, each of which radicals is optionally mono- or polysubstituted by identical or different substituents, where the substituents are those mentioned above or are hydroxyl or nitro, and Q represents one of the groups

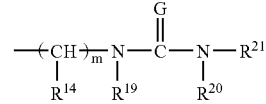 (Q¹)

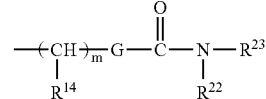 (Q²)

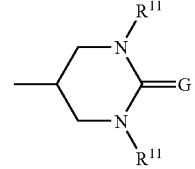 (Q³)

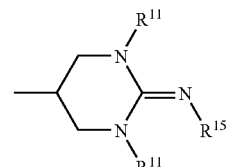 (Q⁴)

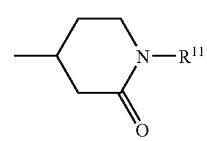 (Q⁵)

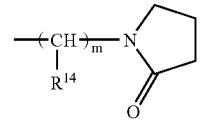 (Q⁶)

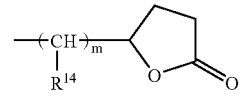 (Q⁷)

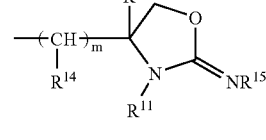 (Q⁸)

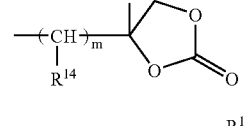 (Q⁹)

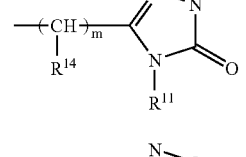 (Q¹⁰)

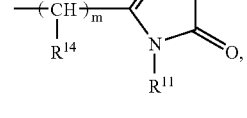 (Q¹¹)

where
each $R^{11}$ may have identical or different meanings when two or more are present in the same heterocyclic group,
m represents 0, 1, 2 or 3, where the repeat unit —(CHR$^{14}$)— in the side chain of a heterocyclic grouping may has identical or different meanings when m represents 2 or 3,
G represents oxygen or sulphur,
$R^{19}$ and $R^{20}$ independently of one another represent hydrogen, $C_1$-$C_6$-alkyl or $R^{19}$ and $R^{20}$ together represent $C_2$-$C_4$-alkylene,
$R^{21}$ represents hydrogen, represents $C_1$-$C_6$-alkyl that is optionally mono- or polysubstituted by identical or different substituents selected from the group consisting of $C_1$-$C_6$-alkylcarbonyloxy, and $C_1$-$C_6$-alkoxy; or represents aryl which is optionally mono- or polysubstituted by identical or different substituents selected from the group consisting of halogen, cyano, $C_1$-$C_6$-alkyl, $C_1$-$C_6$-halogenoalkyl, $C_1$-$C_6$-alkylcarbonyl, $C_1$-$C_{10}$-alkoxycarbonyl, and $C_3$-$C_5$-alkylene,
$R^{22}$ represents hydrogen, $C_1$-$C_6$-alkyl, or $C_1$-$C_6$-alkoxy-$C_1$-$C_6$-alkyl, and
$R^{23}$ represents hydrogen, amino, $C_1$-$C_6$-alkyl, or $C_1$-$C_6$-alkoxy-$C_1$-$C_6$-alkyl.

5. A pyridylpyrimidine of the formula (I) according to claim 4 wherein R represents a carboxylic acid bioisostere selected from the group consisting of

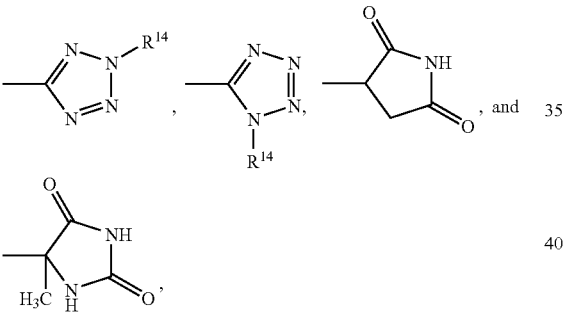

$R^{14}$ represents hydrogen, $C_1$-$C_6$-alkyl or $C_1$-$C_4$-halogenoalkyl.

6. A pyridylpyrimidine of the formula (I) according to claim 4 wherein
$R^{16}$ represents hydrogen; represents $C_1$-$C_{16}$-alkyl, $C_2$-$C_{10}$-alkenyl, $C_2$-$C_6$-alkynyl, each of which is optionally mono- or polysubstituted by identical or different substituents selected from the group consisting of halogen, amino, hydroxyl, cyano, nitro, $C_1$-$C_6$-alkoxy, $C_1$-$C_6$-halogenoalkoxy, $C_1$-$C_6$-alkylthio, $C_1$-$C_6$-halogenoalkylthio, $C_1$-$C_6$-alkoxycarbonyl, $C_2$-$C_6$-alkenyloxycarbonyl, $C_1$-$C_6$-alkylcarbonyloxy, $C_2$-$C_6$-alkenylcarbonyloxy, oxy($C_1$-$C_6$-alkylene)oxy, oxetanyl, dioxanyl, oxazolidinyl, dioxolanyl, aryloxy, halogenoaryloxy, —CONR$^4$R$^5$, —NR$^4$R$^5$, —ONR$^4$R$^5$, and —C(R$^{14}$)=N—OR$^{14}$; or represents aryl, aryl-$C_1$-$C_6$-alkyl, $C_3$-$C_7$-cycloalkyl, $C_3$-$C_7$-cycloalkyl-$C_1$-$C_6$-alkyl, or 4- to 6-membered saturated or unsaturated heterocyclyl or heterocyclyl-$C_1$-$C_6$-alkyl, each of which contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, $C_1$-$C_6$-halogenoalkylthio, $C_1$-$C_6$-alkoxycarbonyl and $C_1$-$C_6$-alkylcarbonyloxy; represents —NR$^4$R$^5$; or represents Q.

7. A pyridylpyrimidine of the formula (I) according to claim 1 wherein
$R^1$ and $R^2$ independently of one another represent hydrogen, fluorine, chlorine, bromine, nitro, cyano, $C_1$-$C_4$-alkyl, $C_1$-$C_4$-halogenoalkyl having 1 to 9 fluorine, chlorine and/or bromine atoms, $C_1$-$C_4$-alkoxy, $C_1$-$C_4$-halogenoalkoxy having 1 to 9 fluorine, chlorine and/or bromine atoms, $C_1$-$C_4$-alkylthio, $C_1$-$C_4$-halogenoalkylthio having 1 to 9 fluorine, chlorine, and/or bromine atoms, $C_2$-$C_4$-alkenyl, $C_2$-$C_4$-alkynyl, —S(O)$_p$R$^3$, —NR$^4$R$^5$, —COR$^6$, —CO$_2$R$^7$, —CSR$^6$, —CONR$^4$R$^5$, —NHCO$_2$R$^8$, or $C_3$-$C_6$-cycloalkyl; or represent aryl, aryl-$C_1$-$C_4$-alkyl, or 5- or 6-membered saturated or unsaturated heterocyclyl that contains 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents selected from the group consisting of fluorine, chlorine, bromine, $C_1$-$C_4$-alkyl, $C_1$-$C_4$-halogenoalkyl having 1 to 9 fluorine, chlorine, and/or bromine atoms, $C_1$-$C_4$-alkoxy, and $C_1$-$C_4$-halogenoalkoxy having 1 to 9 fluorine, chlorine, and/or bromine atoms, or
$R^1$ and $R^2$ together represent $C_3$-$C_5$-alkylene or $C_3$-$C_4$-alkenylene, where the carbon chain are optionally interrupted by 1 or 2 heteroatoms that are 0 to 2 nitrogen atoms and/or 0 or 1 oxygen atom and where the resulting ring is optionally mono- to tetrasubstituted by identical or different substituents from the group consisting of fluorine, chlorine, bromine and $C_1$-$C_4$-alkyl,
X represents fluorine, chlorine, bromine, nitro, cyano, hydroxyl, $C_1$-$C_4$-alkyl, $C_1$-$C_4$-halogenoalkyl having 1 to 9 fluorine, chlorine, and/or bromine atoms, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine, and/or bromine atoms, $C_2$-$C_4$-alkenyl, $C_2$-$C_4$-alkynyl, —S(O)$_p$R$^3$, —NR$^4$R$^5$, —COR$^6$, —CO$_2$R$^7$, —CSR$^6$, —CONR$^4$R$^5$, —NHCO$_2$R$^8$, $C_3$-$C_6$-cycloalkyl, aryl, aryl-$C_1$-$C_4$-alkyl, 5- or 6-membered saturated or unsaturated heterocyclyl which contains 0 to 3 nitrogen atoms, 0 to 2 nonadjacent oxygen atoms, and/or 0 to 2 nonadjacent sulphur atoms, or when n represents 2, two adjacent radicals X together optionally represent $C_3$-$C_4$-alkylene or $C_3$-$C_4$-alkenylene, where the carbon chain may be interrupted by 1 or 2 heteroatoms that are 0 to 2 nitrogen atoms and/or 0 or 1 oxygen atom,
n represents 0, 1 or 2, with X representing identical or different radicals when n represents 2,
Y represents a direct bond, oxygen, —S(O)$_p$—, or —NR$^9$—,
p represents 0, 1 or 2,
Z represents —(CH$_2$)$_r$—, —(CH$_2$)$_r$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$—, or —(CH$_2$)$_t$—C(R$^{12}$)=C(R$^{13}$)—(CH$_2$)$_w$—,
r represents 1, 2, 3 or 4,
t and w independently of one another represent 0, 1, 2, 3 or 4, R represents the group

where A represents oxygen, sulphur, and E represents —SR$^{16}$ or —S-M, or where A represents sulphur and E represents —OR$^{16}$, —SR$^{16}$, —O-M, or —S-M, or represents a carboxylic acid bioisostere (acid mimic) selected from the group consisting of

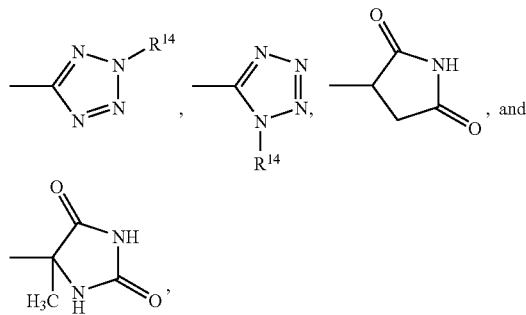

M represents ammonium which is optionally mono- to tetrasubstituted by identical or different substituents selected from the group consisting of $C_1$-$C_4$-alkyl, phenyl, benzyl and phenylethyl; or represents a sodium cation (Na$^+$) or a potassium cation (K$^+$), or represents a magnesium cation (Mg$^{2+}$) or a calcium cation (Ca$^{2+}$) forming a salt with two molecules of a compound of formula (I), $R^3$ represents hydrogen, $C_1$-$C_4$-alkyl, $C_1$-$C_4$-halogenoalkyl having 1 to 9 fluorine, chlorine, and/or bromine atoms, $C_3$-$C_6$-cycloalkyl, or $C_3$-$C_6$-cycloalkyl-$C_1$-$C_4$-alkyl; represents aryl, aryl-$C_1$-$C_4$-alkyl, 5- or 6-membered saturated or unsaturated heterocyclyl or heterocyclyl-$C_1$-$C_4$-alkyl, each of which contain 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents selected from the group consisting of fluorine, chlorine, bromine, $C_1$-$C_4$-alkyl, $C_1$-$C_4$-halogenoalkyl having 1 to 9 fluorine, chlorine, and/or bromine atoms, $C_1$-$C_4$-alkoxy, $C_1$-$C_4$-halogenoalkoxy having 1 to 9 fluorine, chlorine, and/or bromine atoms, $C_1$-$C_4$-alkylthio, and $C_1$-$C_4$-halogenoalkylthio having 1 to 9 fluorine, chlorine, and/or bromine atoms, $R^4$ represents hydrogen, $C_1$-$C_4$-alkyl, $C_1$-$C_4$-halogenoalkyl having 1 to 9 fluorine, chlorine, and/or bromine atoms, $C_3$-$C_6$-cycloalkyl, $C_1$-$C_4$-alkylcarbonyl, $R^5$ represents hydrogen, amino, formyl, $C_1$-$C_4$-alkyl, $C_2$-$C_4$-alkenyl, $C_2$-$C_4$-alkynyl, $C_1$-$C_4$-halogenoalkyl having 1 to 9 fluorine, chlorine, and/or bromine atoms, $C_3$-$C_6$-cycloalkyl, $C_1$-$C_4$-alkoxy, $C_1$-$C_4$-alkoxy-$C_1$-$C_4$-alkyl, $C_1$-$C_4$-alkylcarbonyl, $C_1$-$C_4$alkoxycarbonyl, or oxamoyl, or $R^4$ and $R^5$ together represent $C_1$-$C_4$-alkylidene; or represent benzylidene that is optionally mono- to tetrasubstituted by identical or different substituents selected from the group consisting of fluorine, chlorine, bromine, nitro, $C_1$-$C_4$-alkyl, and $C_1$-$C_4$-halogenoalkyl having 1 to 9 fluorine, chlorine, and/or bromine atoms;

or $R^4$ and $R^5$ together with the nitrogen atom to which they are attached represent a 5- or 6-membered saturated or unsaturated heterocycle that optionally contains a further nitrogen, oxygen, or sulphur atom and is optionally mono- to tetrasubstituted by identical or different $C_1$-$C_4$-alkyl, $R^6$ represents hydrogen, $C_1$-$C_4$-alkyl, $C_1$-$C_4$-halogenoalkyl having 1 to 9 fluorine, chlorine, and/or bromine atoms, or aryl-$C_1$-$C_4$-alkyl, $R^7$ represents hydrogen, $C_1$-$C_4$-alkyl, $C_1$-$C_4$-halogenoalkyl having 1 to 9 fluorine, chlorine, and/or bromine atoms, $C_3$-$C_6$-cycloalkyl, $C_3$-$C_6$-cycloalkyl-$C_1$-$C_4$-alkyl, aryl, or aryl-$C_1$-$C_4$-alkyl, $R^8$ represents $C_1$-$C_4$-alkyl or $C_1$-$C_4$-halogenoalkyl having 1 to 9 fluorine, chlorine, and/or bromine atoms, $R^9$ represents hydrogen, $C_1$-$C_4$-alkyl, $C_1$-$C_4$-halogenoalkyl having 1 to 9 fluorine, chlorine, and/or bromine atoms, $C_3$-$C_6$-cycloalkyl, $C_3$-$C_6$-cycloalkyl-$C_1$-$C_4$-alkyl; or represents aryl, aryl-$C_1$-$C_4$-alkyl, 5- or 6-membered saturated or unsaturated heterocyclyl or heterocyclyl-$C_1$-$C_4$-alkyl, each of which contains 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents selected from the group consisting of fluorine, chlorine, bromine, $C_1$-$C_4$-alkyl, $C_1$-$C_4$-halogenoalkyl having 1 to 9 fluorine, chlorine, and/or bromine atoms, $C_1$-$C_4$-alkoxy, $C_1$-$C_4$-halogenoalkoxy having 1 to 9 fluorine, chlorine, and/or bromine atoms, $C_1$-$C_4$-alkylthio, and $C_1$-$C_4$-halogenoalkylthio having 1 to 9 fluorine, chlorine and/or bromine atoms, $R^{10}$ represents fluorine, chlorine, bromine, iodine, $C_1$-$C_4$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_4$-alkyl; or represents aryl or aryl-$C_1$-$C_4$-alkyl that are optionally mono- to tetrasubstituted in the aryl moiety by identical or different substituents selected from the group consisting of fluorine, chlorine, bromine, and $C_1$-$C_4$-alkyl, $R^{11}$ represents hydrogen or $C_1$-$C_4$-alkyl, $R^{12}$ and $R^{13}$ independently of one another represent hydrogen, hydroxyl, $C_1$-$C_4$-alkyl, or $C_1$-$C_4$-alkoxy, $R^{14}$ represents hydrogen, $C_1$-$C_4$-alkyl or $C_1$-$C_4$-halogenoalkyl having 1 to 9 fluorine, chlorine, and/or bromine atoms, $R^{15}$ represents hydrogen, $C_1$-$C_4$-alkyl, $C_1$-$C_4$-alkoxy, cyano or di($C_1$-$C_4$-alkyl)amino, $R^{16}$ represents hydrogen; represents $C_1$-$C_6$-alkyl, decyl, dodecyl, tetradecyl, hexadecyl, $C_2$-$C_6$-alkenyl, decenyl, $C_2$-$C_4$-alkynyl, each of which is optionally mono- to tetrasubstituted by identical or different substituents selected from the group consisting of fluorine, chlorine, bromine, amino, hydroxyl, cyano, nitro, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine, and/or bromine atoms, $C_1$-$C_4$-alkoxycarbonyl, $C_2$-$C_4$-alkenyloxycarbonyl, $C_1$-$C_4$-alkylcarbonyloxy, $C_2$-$C_4$-alkenylcarbonyloxy, oxy($C_1$-$C_4$-alkylene)oxy, oxetanyl, dioxanyl, oxazolidinyl, dioxolanyl, aryloxy, halogenoaryloxy, —CONR$^4$R$^5$, —NR$^4$R$^5$, —ONR$^4$R$^5$, and —C(R$^{14}$)=N—OR$^{14}$; represents aryl, aryl-$C_1$-$C_4$-alkyl, $C_3$-$C_6$-cycloalkyl, $C_3$-$C_6$-cycloalkyl-$C_1$-$C_4$-alkyl, or 4- to 6-membered saturated or unsaturated, heterocyclyl or heterocyclyl-$C_1$-$C_4$-alkyl, each of which contains 0 to 3 nitrogen atoms, 0 to 2 nonadjacent oxygen atoms, and/or 0 to 2 nonadjacent sulphur atoms, each of which radicals is optionally mono- to tetrasubstitutred by identical or different substitutents selected from the group consisting of fluorine, chlorine, bromine, $C_1$-$C_4$-alkyl, $C_1$-$C_4$-halogenoalkyl having 1 to 9 fluorine, chlorine, and/or bromine atoms, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine and/or bromine atoms, $C_1$-$C_4$-alkoxycarbonyl, and $C_1$-$C_4$-alkylcarbonyloxy; represents Q; represents $C_1$-$C_6$-alkyl, decyl, dodecyl, tetradecyl, hexadecyl, $C_2$-$C_6$-alkenyl, decenyl, or $C_2$-$C_4$-alkynyl, each of which is optionally substituted up to the maximum possible number by identical or different substituents from the group consisting of fluorine, chlorine and bromine; or represents aryl, aryl-$C_1$-$C_4$-alkyl, $C_3$-$C_6$-cycloalkyl, $C_3$-$C_6$-cycloalkyl-$C_1$-$C_4$-alkyl, 4- to 6-membered saturated or unsaturated heterocyclyl or heterocyclyl-$C_1$-$C_4$-alkyl, each of which contains 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents, where the substituents are those mentioned above or are hydroxyl or nitro, and Q represents one of the groups

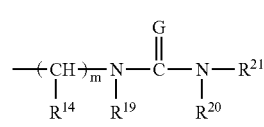

(Q¹)

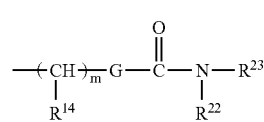

(Q²)

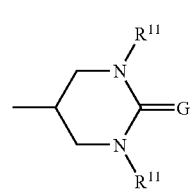

(Q³)

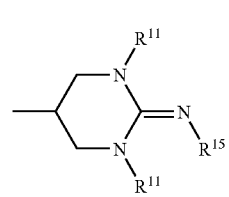

(Q⁴)

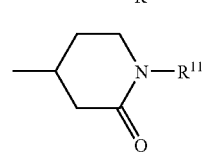

(Q⁵)

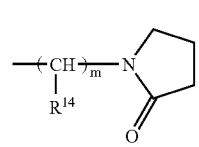

(Q⁶)

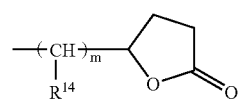

(Q⁷)

-continued

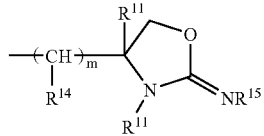

(Q⁸)

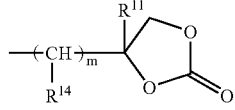

(Q⁹)

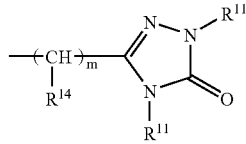

(Q¹⁰)

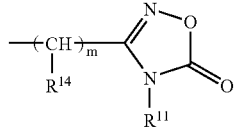

(Q¹¹)

where each $R^{11}$ may have identical or different meanings when two or more $R^{11}$ are present in the same heterocyclic group, m represents 0, 1, 2 or 3, where the repeat unit —(CHR¹⁴)— in the side chain of a heterocyclic grouping optionally has identical or different meanings when m represents 2 or 3, G represents oxygen or sulphur, $R^{19}$ and $R^{20}$ independently of one another represent hydrogen $C_1$-$C_4$-alkyl or $R^{19}$ and $R^{20}$ together represent $C_2$-$C_3$-alkylene, $R^{21}$ represents hydrogen; represents $C_1$-$C_4$-alkyl which is optionally mono- or disubstituted by identical or different substituents selected from the group consisting of $C_1$-$C_4$-alkylcarbonyloxy and $C_1$-$C_4$-alkoxy; or represents aryl which that is optionally mono- to tetrasubstituted by identical or different substituents selected from the group consisting of fluorine, chlorine, bromine, cyano, $C_1$-$C_4$-alkyl, $C_1$-$C_4$-halogenoalkyl having 1 to 9 fluorine, chlorine and/or bromine atoms, $C_1$-$C_4$-alkylcarbonyl, $C_1$-$C_8$-alkoxycarbonyl, and $C_3$-$C_5$-alkylene, $R^{22}$ represents hydrogen, $C_1$-$C_4$-alkyl or $C_1$-$C_4$-alkoxy-$C_1$-$C_4$-alkyl, and $R^{23}$ represents hydrogen, amino, $C_1$-$C_4$-alkyl or $C_1$-$C_4$-alkoxy-$C_1$-$C_4$-alkyl.

8. A pyridylpyrimidine of the formula (I) according to claim 7 wherein R represents a carboxylic acid bioisostere selected from the group consisting of

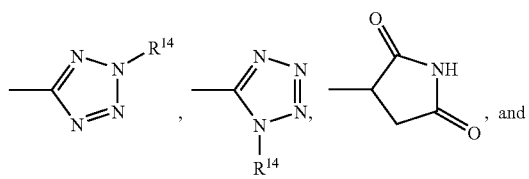

-continued

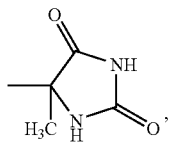

where $R^{14}$ represents hydrogen, $C_1$-$C_4$-alkyl, or $C_1$-$C_4$-halogenoalkyl having 1 to 9 fluorine, chlorine, and/or bromine atoms.

9. A pyridylpyrimidine of the formula (I) according to claim 7 wherein $R^{16}$ represents hydrogen; represents $C_1$-$C_6$-alkyl, decyl, dodecyl, tetradecyl, hexadecyl, $C_2$-$C_6$-alkenyl, decenyl, $C_2$-$C_4$-alkynyl, each of which is optionally mono- to tetrasubstituted by identical or different substituents selected from the group consisting of fluorine, chlorine, bromine, amino, hydroxyl, cyano, nitro, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine, and/or bromine atoms, $C_1$-$C_4$-alkoxycarbonyl, $C_2$-$C_4$-alkenyloxycarbonyl, $C_1$-$C_4$-alkylcarbonyloxy, $C_2$-$C_4$-alkenylcarbonyloxy, oxy($C_1$-$C_4$-alkylene)oxy, oxetanyl, dioxanyl, oxazolidinyl, dioxolanyl, aryloxy, halogenoaryloxy, —$CONR^4R^5$, —$NR^4R^5$, —$ONR^4R^5$, and —$C(R^{14})$=N—$OR^{14}$; represents aryl, aryl-$C_1$-$C_4$-alkyl, $C_3$-$C_6$-cycloalkyl, $C_3$-$C_6$-cycloalkyl-$C_1$-$C_4$-alkyl, 4- to 6-membered saturated or unsaturated, heterocyclyl or heterocyclyl-$C_1$-$C_4$-alkyl, each of which contains 0 to 3 nitrogen atoms, 0 to 2 nonadjacent oxygen atoms and/or 0 to 2 nonadjacent sulphur atoms, each of which radicals is optionally mono- to tetrasubstitutred by identical or different substituents selected from the group consisting of fluorine, chlorine, bromine, $C_1$-$C_4$-alkyl, $C_1$-$C_4$-halogenoalkyl having 1 to 9 fluorine, chlorine, and/or bromine atoms, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine, and/or bromine atoms, $C_1$-$C_4$-alkoxycarbonyl, and $C_1$-$C_4$-alkylcarbonyloxy; or represents Q.

10. A pyridylpyrimidine of the formula (I) according to claim 1 wherein $R^1$ and $R^2$ independently of one another represent hydrogen, fluorine, chlorine, bromine, nitro, cyano, methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, —$CF_2CHFCF_3$, methoxy, ethoxy, n-propoxy, isopropoxy, n-butoxy, trifluoromethoxy, trichloromethoxy, —$OCH_2CF_3$, —$SCF_3$, —$SCHF_2$, —$SO_2Me$, —$SO_2CHF_2$, —$SO_2CF_3$, —$SOCHF_2$, —$SOCF_3$, —$COMe$, —$CO_2Me$, —$CO_2Et$, amino, cyclopentyl, or cyclohexyl; or represent phenyl, benzyl, pyridinyl, furyl, or furfuryl, each of which is optionally substituted by chlorine, bromine, methyl, ethyl, methoxy, ethoxy, trifluoromethyl, or trifluoromethoxy, or $R^1$ and $R^2$ together represent propylene, butylene, propenylene butadienylene, —$(CH_2)_2$—O—$CH_2$—, —$(CH_2)_2$—NH—$CH_2$—, —CH=CH—N=CH—, —CH=CCl—CH=CH—, X represents fluorine, chlorine, bromine, nitro, cyano, hydroxyl, methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, —$CF_2CHFCF_3$, methoxy, ethoxy, n-propoxy, isopropoxy, n-butoxy, trifluoromethoxy, trichloromethoxy, —$OCH_2CF_3$, —$SCF_3$, —$SCHF_2$, —$SO_2Me$, —$SO_2CHF_2$, —$SO_2CF_3$, —$SOCHF_2$, —$SOCF_3$, —CH=$CH_2$, —C≡CH, amino, —NHMe, —$NMe_2$, —CHO, —COMe, —$CO_2Me$, —$CO_2Et$, —NHCOMe, cyclopentyl, cyclohexyl, phenyl, benzyl, furyl, thienyl, pyrrolyl, oxazolyl, isoxazyl, imidazyl, pyrazyl, thiazolyl, pyridyl, pyrimidinyl, pyridazyl, triazinyl, triazyl; or represents methylthio, ethylthio, n-propylthio, or isopropylthio; or when n represents 2, two adjacent radicals X together optionally represent propylene, butylene, propenylene or butadienylene, —$(CH_2)_2$—O—$CH_2$—, —$(CH_2)_2$—NH—$CH_2$—, or —CH=CH—N=CH—, n represents 0, 1 or 2, with X representing identical or different radicals when n represents 2, Y represents a direct bond, oxygen, —S(O)$_p$—, or —$NR^9$—, p represents 0, 1 or 2, Z represents —$CH_2$—, —$(CH_2)_2$—, —$(CH_2)_3$—, —$(CH_2)_4$—, —$(CHR^{10})$—, —$CH_2$—C(O)—$CH_2$—, —$CH_2$—NH—, —CH=CH—, —$CH_2$—CH=CH—, —CH=C(OH)—, —CH=C(OMe)—, or —$CH_2$—C(OMe)=CH—; or represents —$CH_2$—C(OEt)=CH—, R represents the group

where A represents oxygen or sulphur and E represents —$SR^{16}$ or —S-M, or where A represents sulphur E represents —$OR^{16}$, —$SR^{16}$, —O-M, or —S-M, M represents tetrabutylammonium, trimethylbenzylammonium; or represents a sodium cation ($Na^+$) or a potassium cation ($K^+$), or represents a magnesium cation ($Mg^{2+}$) or a calcium cation ($Ca^{2+}$), forming a salt with two molecules of a compound of formula (I), $R^4$ represents hydrogen, methyl, ethyl, n-propyl, isopropyl, n-butyl, sec-butyl, isobutyl, tert-butyl, or —COMe, $R^5$ represents hydrogen, amino, formyl, methyl, ethyl, n-propyl, isopropyl, n-butyl, sec-butyl, isobutyl, tert-butyl, vinyl, propargyl, methoxy, methoxymethyl, —COMe, —COEt, tert-butoxycarbonyl, oxamoyl, or $R^4$ and $R^5$ together represent ethylidene, isopropylidene, sec-butylidene, or nitrobenzylidene; or $R^4$ and $R^5$ together with the nitrogen atom to which they are attached represent a 5- or 6-membered saturated or unsaturated heterocycle selected from the group consisting of morpholine, piperidine, thiomorpholine, pyrrolidine, tetrahydropyridine, which is optionally mono- or disubstituted by methyl, ethyl, n-propyl, isopropyl, n-butyl, sec-butyl, isobutyl, tert-butyl, $R^8$ represents methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H or —CF$_2$CHFCF$_3$, $R^9$ represents hydrogen, methyl, ethyl, n-propyl, isopropyl, n-butyl, sec-butyl, isobutyl, tert-butyl, —CH$_2$CF$_3$, —CH$_2$CF$_2$H, —CH$_2$CF$_2$CF$_3$, cyclopropyl, cyclopentyl, or cyclohexyl;

$R^{10}$ represents fluorine, chlorine, bromine, methyl, ethyl, n-propyl, isopropyl, n-butyl, sec-butyl, isobutyl, tert-butyl, —COMe, —COEt, —CO$_2$Me, —CO$_2$Et, or cyclohexyl; represents phenyl or benzyl, that are opitonally mono- to tetrasubstituted in the aryl moiety by identical or different substituents selected from the group consisting of fluorine, chlorine, bromine and methyl, $R^{11}$ represents hydrogen, methyl, ethyl, n-propyl, isopropyl, n-butyl, sec-butyl, isobutyl, tert-butyl, $R^{14}$ represents hydrogen, methyl, ethyl, n-propyl, isopropyl, n-butyl, sec-butyl, isobutyl, or tert-butyl, $R^{15}$ represents hydrogen, methyl, ethyl, n-propyl, isopropyl, n-butyl, sec-butyl, isobutyl, tert-butyl or cyano, $R^{16}$ represents hydrogen; represents methyl, ethyl, n-propyl, isopropyl, n-butyl, sec-butyl, isobutyl, tert-butyl, n-pentyl, isopentyl, siamyl, hexyl, n-decyl, n-dodecyl, n-tetradecyl, n-hexadecyl, vinyl, allyl, butenyl, 2-isopentenyl, hexenyl, n-decenyl, ethynyl, propynyl, butynyl, each of which is optionally mono- to trisubstituted by identical or different substituents selected from the group consisting of fluorine, chlorine, bromine, amino, hydroxyl, cyano, nitro, methoxy, ethoxy, isopropoxy, trifluoromethoxy, —OCH$_2$CF$_3$, trichloromethoxy, difluoromethoxy, methylthio, trifluoromethylthio, methoxycarbonyl, ethoxycarbonyl, isopropoxycarbonyl, tert-butoxycarbonyl, methylcarbonyloxy, vinylcarbonyloxy, —O—(CH$_2$)$_2$—O—, oxetanyl, dioxanyl, oxazolidinyl, dioxolanyl, phenoxy, fluorophenoxy, —CONR$^4$R$^5$, —NR$^4$R$^5$, —ONR$^4$R$^5$, and —CH=N—OCH$_3$; represents phenyl, benzyl, phenylethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, oxetanyl, oxazolanyl, dioxanyl, dioxolanyl, furyl, thienyl, pyrrolyl, oxazolyl, isoxazyl, imidazolyl, pyrazyl, thiazolyl, pyridinyl, pyrimidinyl, pyridazyl, triazinyl, triazolyl, tetrahydropyranyl, thietanyl, thietane dioxide, oxetanylmethyl, oxazolanylmethyl, dioxanylmethyl, dioxolanylmethyl, furylmethyl, thienylmethyl, pyrrolylmethyl, oxazolylmethyl, isoxazylmethyl, imidazolylmethyl, pyrazylmethyl, thiazolylmethyl, pyridinylmethyl, pyrimidinylmethyl, pyridazylmethyl, triazinylmethyl, triazolylmethyl, tetrahydropyranylmethyl, thietanylmethyl, thietane dioxide methyl, oxetanylethyl, oxazolanylethyl, dioxanylethyl, dioxolanylethyl, furylethyl, thienylethyl, pyrrolylethyl, oxazolylethyl, isoxazylethyl, imidazolylethyl, pyrazylethyl, thiazolylethyl, pyridinylethyl, pyrimidinylethyl, pyridazylethyl, triazinylethyl, triazolylethyl, tetrahydropyranylethyl, thietanylethyl, thietane dioxide ethyl, each of which is optionally mono- to trisubstituted by identical or different substituents selected from the group consisting of fluorine, chlorine, bromine, methyl, ethyl, n-propyl, isopropyl, n-butyl, sec-butyl, isobutyl, tert-butyl, —CF$_3$, —CCl$_3$, —CHF$_2$, —CClF$_2$, —CHCl$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, methoxy, ethoxy, n-propoxy, n-butoxy, trifluoromethoxy, trichloromethoxy, methylthio, trifluoromethylthio, —CO$_2$Me, —CO$_2$Et, methylcarbonyloxy and ethylcarbonyloxy; represents Q; represents methyl, ethyl, n-propyl, isopropyl, n-butyl, sec-butyl, isobutyl, tert-butyl, n-pentyl, isopentyl, siamyl, hexyl, n-decyl, n-dodecyl, n-tetradecyl, n-hexadecyl, vinyl, allyl, butenyl, 2-isopentenyl, hexenyl, n-decenyl, ethynyl, propynyl, or butynyl, each of which is optionally substituted up to the maximum possible number by identical or different radicals selected from the group consisting of fluorine, chlorine and bromine; or represents phenyl, benzyl, phenylethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, oxetanyl, oxazolanyl, dioxanyl, dioxolanyl, furyl, thienyl, pyrrolyl, oxazolyl, isoxazyl, imidazolyl, pyrazyl, thiazolyl, pyridinyl, pyrimidinyl, pyridazyl, triazinyl, triazolyl, tetrahydropyranyl, thietanyl, thietane dioxide, oxetanylmethyl, oxazolanylmethyl, dioxanylmethyl, dioxolanylmethyl, furylmethyl, thienylmethyl, pyrrolylmethyl, oxazolylmethyl, isoxazylmethyl, imidazolylmethyl, pyrazylmethyl, thiazolylmethyl, pyridinylmethyl, pyrimidinylmethyl, pyridazylmethyl, triazinylmethyl, triazolylmethyl, tetrahydropyranylmethyl, thietanylmethyl, thietane dioxide methyl, oxetanylethyl, oxazolanylethyl, dioxanylethyl, dioxolanylethyl, furylethyl, thienylethyl, pyrrolylethyl, oxazolylethyl, isoxazylethyl, imidazolylethyl, pyrazylethyl, thiazolylethyl, pyridinylethyl, pyrimidinylethyl, pyridazylethyl, triazinylethyl, triazolylethyl, tetrahydropyranylethyl, thietanylethyl, or thietane dioxide ethyl, each of which is optionally mono- to tetrasubstituted by identical or different substituents, where the substituents are those mentioned above or are hydroxyl and nitro, and Q represents one of the groups

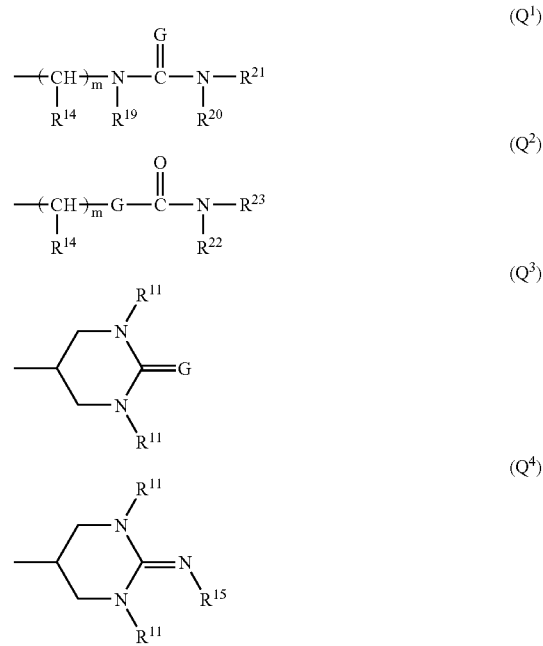

-continued

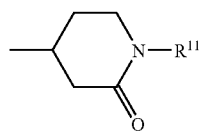
(Q⁵)

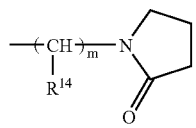
(Q⁶)

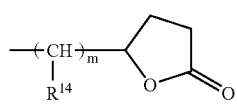
(Q⁷)

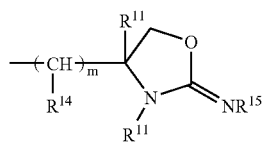
(Q⁸)

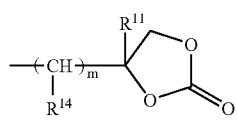
(Q⁹)

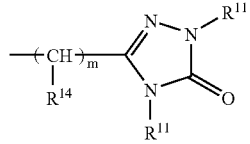
(Q¹⁰)

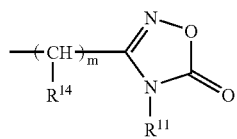
(Q¹¹)

where
each $R^{11}$ may have identical or differente meanings when two or more $R^{11}$ are present in the same heterocyclic group, m represents 0, 1, 2 or 3, where the repeat unit —(CHR¹⁴)— in the side chain of a heterocyclic grouping has the same or different meanings when m represents 2 or 3, G represents oxygen or sulphur, $R^{19}$ and $R^{20}$ independently of one another represent hydrogen, methyl, ethyl, n-propyl, isopropyl, n-butyl, sec-butyl, isobutyl, tert-butyl, or $R^{19}$ and $R^{20}$ together represent —(CH₂)₂— or —(CH₂)₃—, $R^{21}$ represents hydrogen, represents methyl, ethyl, n-propyl, isopropyl, n-butyl, sec-butyl, isobutyl, or tert-butyl, each of which is optionally monosubstituted by tert-butylcarbonyloxy or methoxy; or represents phenyl that is optionally mono- or disubstituted by identical or different substituents selected from the group consisting of chlorine, cyano, methyl, ethyl, tert-butyl, trifluoromethyl, sec-butyloxycarbonyl, tert-butyloxycarbonyl, n-octyloxycarbonyl and —(CH₂)₄—, $R^{22}$ represents hydrogen, methyl, ethyl or methoxymethyl, and $R^{23}$ represents hydrogen, amino, methyl, ethyl, n-propyl, isopropyl or methoxymethyl.

11. A pyridylpyrimidine of the formula (I) according to claim 10 wherein

X represents fluorine, chlorine, bromine, nitro, cyano, hydroxyl, methyl, ethyl, n-propyl, isopropyl, n-butyl, sec-butyl, isobutyl, tert-butyl, —CF₃, —CCl₃, —CHF₂, —CClF₂, —CHCl₂, —CF₂CHFCl, —CF₂CH₂F, —CF₂CCl₃, —CH₂CF₃, —CF₂CHFCF₃, —CH₂CF₂H, —CH₂CF₂CF₃, —CF₂CF₂H, —CF₂CHFCF₃, methoxy, ethoxy, n-propoxy, isopropoxy, n-butoxy, trifluoromethoxy, trichloromethoxy, —OCH₂CF₃, —SCF₃, —SCHF₂, —SO₂Me, —SO₂CHF₂, —SO₂CF₃, —SOCHF₂, —SOCF₃, —CH=CH₂, —C≡CH, amino, —NHMe, —NMe₂, —CHO, —COMe, —CO₂Me, —CO₂Et, —NHCOMe, cyclopentyl, cyclohexyl, phenyl, benzyl, furyl, thienyl, pyrrolyl, oxazolyl, isoxazyl, imidazyl, pyrazyl, thiazolyl, pyridyl, pyrimidinyl, pyridazyl, triazinyl, or triazyl; or when n represents 2, two adjacent radicals X together represent propylene, butylene, propenylene, butadienylene, —(CH₂)₂—O—CH₂—, —(CH₂)₂—NH—CH₂—, or —CH=CH—N=CH—;

Z represents —CH₂—, —(CH₂)₂—, —(CH₂)₃—, —(CH₂)₄—, —(CHR¹⁰)—, —CH₂—C(O)—CH₂—, —CH₂—NH—, —CH=CH—, —CH₂—CH=CH—, —CH=C(OH)—, —CH=C(OMe)—, or —CH₂—C(OMe)=CH—, $R^{16}$ represents hydrogen; represents methyl, ethyl, n-propyl, isopropyl, n-butyl, sec-butyl, isobutyl, tert-butyl, n-pentyl, isopentyl, siamyl, hexyl, n-decyl, n-dodecyl, n-tetradecyl, n-hexadecyl, vinyl, allyl, butenyl, 2-isopentenyl, hexenyl, n-decenyl, ethynyl, propynyl, or butinyl, each of which is optionally mono- to trisubstituted by identical or different substituents selected from the group consisting of fluorine, chlorine, bromine, amino, hydroxyl, cyano, nitro, methoxy, ethoxy, isopropoxy, trifluoromethoxy, —OCH₂CF₃, trichloromethoxy, difluoromethoxy, methylthio, trifluoromethylthio, methoxycarbonyl, ethoxycarbonyl, isopropoxycarbonyl, tert-butoxycarbonyl, methylcarbonyloxy, vinylcarbonyloxy, —O—(CH₂)₂—O—, oxetanyl, dioxanyl, oxazolidinyl, dioxolanyl, phenoxy, fluorophenoxy, —CONR⁴R⁵, —NR⁴R⁵, —ONR⁴R⁵ and —CH=N—OCH₃; represents phenyl, benzyl, phenylethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, oxetanyl, oxazolanyl, dioxanyl, dioxolanyl, furyl, thienyl, pyrrolyl, oxazolyl, isoxazyl, imidazolyl, pyrazyl, thiazolyl, pyridinyl, pyrimidinyl, pyridazyl, triazinyl, triazolyl, tetrahydropyranyl, thietanyl, thietane dioxide, oxetanylmethyl, oxazolanylmethyl, dioxanylmethyl, dioxolanylmethyl, furylmethyl, thienylmethyl, pyrrolylmethyl oxazolylmethyl, isoxazylmethyl, imidazolylmethyl, pyrazylmethyl, thiazolylmethyl, pyridinylmethyl, pyrimidinylmethyl, pyridazylmethyl, triazinylmethyl, triazolylmethyl, tetrahydropyranylmethyl, thietanylmethyl, thietane dioxide methyl, oxetanylethyl, oxazolanylethyl, dioxanylethyl, dioxolanylethyl, furylethyl, thienylethyl, pyrrolylethyl, oxazolylethyl, isoxazylethyl, imidazolylethyl, pyrazylethyl, thiazolylethyl, pyridinylethyl, pyrimidinylethyl, pyridazylethyl, triazinylethyl, triazolylethyl, tetrahydropyranylethyl, thietanylethyl, or thietane dioxide ethyl, each of which is optionally mono- to trisubstituted by identical or different substituents selected from the group consisting of fluorine, chlorine, bromine, methyl, ethyl, n-propyl, isopropyl, n-butyl, sec-butyl, isobutyl, tert-butyl, —CF$_3$, —CCl$_3$, —CHF$_2$, —CClF$_2$, —CHCl$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, methoxy, ethoxy, n-propoxy, n-butoxy, trifluoromethoxy, trichloromethoxy, methylthio, trifluoromethylthio, —CO$_2$Me, —CO$_2$Et, methylcarbonyloxy, and ethylcarbonyloxy; or represents Q.

12. A pyridylpyrimidine of the formula (I-p)

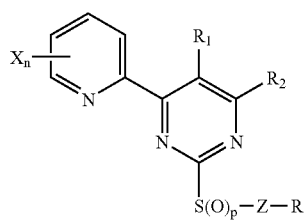

(I-p)

in which
R$^1$ and R$^2$ independently of one another represent hydrogen, halogen, nitro, cyano, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, or cycloalkyl; or represent optionally substituted aryl, arylalkyl, saturated or unsaturated heterocyclyl having 1 to 4 heteroatoms from the group consisting of nitrogen, oxygen and sulphur, or R$^1$ and R$^2$ together represent alkylene or alkenylene, where the carbon chain is optionally interrupted by 1 to 3 heteroatoms selected from the group consisting of nitrogen and oxygen and the resulting ring is optionally substituted by halogen or alkyl, X represents halogen, nitro, cyano, hydroxyl, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, cycloalkyl, aryl, arylalkyl, or saturated or unsaturated heterocyclyl having 1 to 4 heteroatoms from the group consisting of nitrogen, oxygen and sulphur; or, when n represents 2, 3 or 4, two adjacent X together optionally represent alkylene or alkenylene, where the carbon chain is optionally interrupted by 1 or 2 heteroatoms selected from the group consisting of nitrogen and oxygen, n represents 0, 1, 2, 3 or 4, with X representing identical or different radicals when n represents 2, 3 or 4, p represents 0, 1 or 2, Z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$—, or —(CH$_2$)$_t$—C(R$^{12}$)=C(R$^{13}$)—(CH$_2$)$_w$—, r represents 1, 2, 3, 4, 5 or 6, t and w independently of one another represent 0, 1, 2, 3 or 4, R represents the group

where A represents oxygen, sulphur, or NR$^{15}$, and E represents —OR$^{16}$, or —SR$^{16}$, —O-M, or —S-M, or represents a carboxylic acid bioisostere (acid mimic) selected from the group consisting of

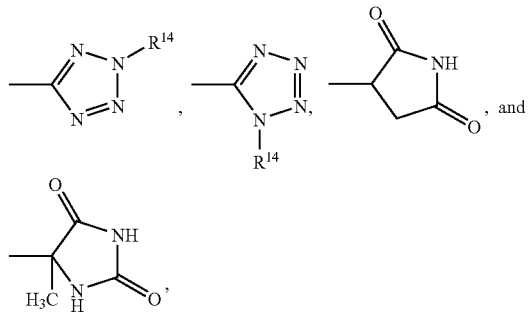

M represents ammonium which is optionally substituted by alkyl, aryl or arylalkyl; or represents an alkali metal ion, or represents an alkaline earth metal ion forming a salt with two molecules of a compound of formula (I), R$^3$ represents hydrogen, alkyl, halogenoalkyl, cycloalkyl, cycloalkylalkyl; or represents optionally halogen-, alkyl-, halogenoalkyl-, alkoxy-, halogenoalkoxy-, alkylthio-, halogenoalkylthio-substituted aryl, arylalkyl, or saturated or unsaturated heterocyclyl or heterocyclylalkyl having 1 to 4 heteroatoms selected from the group consisting of nitrogen, oxygen and sulphur, R$^4$ represents hydrogen, alkyl, halogenoalkyl, cycloalkyl or alkylcarbonyl, R$^5$ represents hydrogen, amino, formyl, alkyl, alkenyl, alkynyl, halogenoalkyl, cycloalkyl, alkoxy, alkoxyalkyl, alkylcarbonyl, alkoxycarbonyl, or oxamoyl, or R$^4$ and R$^5$ together represent alkylidene; or represent optionally halogen-, nitro-, alkyl-, halogenoalkyl-substituted benzylidene; or R$^4$ and R$^5$ together with the nitrogen atom to which they are attached represent a saturated or unsaturated heterocycle that optionally contains a further nitrogen, oxygen or sulphur atom and is optionally be substituted by alkyl, R$^6$ represents hydrogen, alkyl, halogenoalkyl or arylalkyl, R$^7$ represents hydrogen, alkyl, halogenoalkyl, cycloalkyl, cycloalkylalkyl, aryl, or arylalkyl, R$^8$ represents alkyl or halogenoalkyl, R$^{10}$ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, R$^{11}$ represents hydrogen or alkyl, R$^{12}$ and R$^{13}$ independently of one another represent hydrogen, hydroxyl, alkyl or alkoxy, R$^{14}$ represents hydrogen, alkyl, or halogenoalkyl, R$^{15}$ represents hydrogen, alkyl, alkoxy, cyano, or dialkylamino, R$^{16}$ represents hydrogen; represents optionally halogen-, amino-, hydroxyl-, cyano-, nitro-, alkoxy-, halogenoalkoxy-, alkylthio-, halogenoalkylthio-, alkoxycarbonyl-, alkenyloxy-carbonyl-, alkylcarbonyloxy-, alkenylcarbonyloxy-, oxyalkyleneoxy-, oxetanyl-, dioxanyl-, oxazolidinyl-, dioxolanyl-, aryloxy-, halogenoaryloxy-, —CONR⁴R⁵—, —NR⁴R⁵—, —ONR⁴R⁵—, or —C(R¹⁴)=N—OR¹⁴-substituted alkyl, alkenyl, or alkynyl; represents optionally halogen-, alkyl-, halogenoalkyl-, alkoxy-, halogenoalkoxy-, alkylthio-, halogenoalkylthio-, alkoxycarbonyl-, alkylcarbonyloxy-substituted aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen, and sulphur; or represents —NR⁴R⁵; represents Q; or represents optionally substituted aryl, arylalkyl, cycloalkyl, cycloalkylalkyl, or saturated or unsaturated heterocyclyl or heterocyclylalkyl having 1 to 4 heteroatoms from the group consisting of nitrogen, oxygen and sulphur, where the substituents are those mentioned above or are hydroxyl or nitro, and Q represents one of the groups

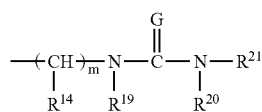
(Q¹)

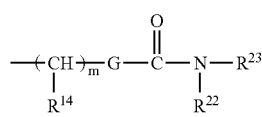
(Q²)

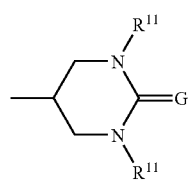
(Q³)

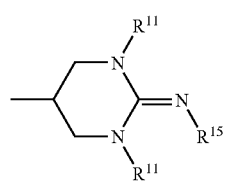
(Q⁴)

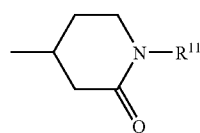
(Q⁵)

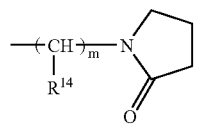
(Q⁶)

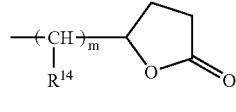
(Q⁷)

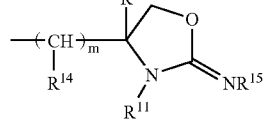
(Q⁸)

-continued

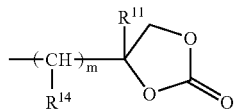
(Q⁹)

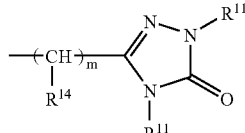
(Q¹⁰)

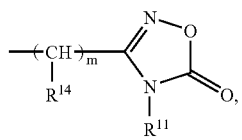
(Q¹¹)

where
each R¹¹ may have identical or different meanings when two or more R¹¹ are present in the same heterocyclic group,
m represents 0, 1, 2 or 3, where the repeat unit —(CHR¹⁴)— in the side chain of a heterocyclic grouping may have identical or different meanings when m represents 2 or 3,
G represents oxygen or sulphur,
R¹⁹ and R²⁰ independently of one another represent hydrogen, alkyl or R¹⁹ and R²⁰ together represent alkylene,
R²¹ represents hydrogen, represents optionally alkylcarbonyloxy- or alkoxy-substituted alkyl; or represents optionally halogen-, cyano-, alkyl-, halogenoalkyl-, alkylcarbonyl-, alkoxycarbonyl-, or alkylene-substituted aryl,
R²² represents hydrogen, alkyl or alkoxyalkyl, and
R²³ represents hydrogen, amino, alkyl or alkoxyalkyl.

13. A pyridylpyrimidine of the formula (I-q)

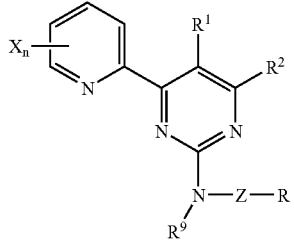
(I-q)

in which
R¹ and R² independently of one another represent hydrogen, halogen, nitro, cyano, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)$_p$R³, —NR⁴R⁵, —COR⁶, —CO₂R⁷, —CSR⁶, —CONR⁴R⁵, —NHCO₂R⁸, or cycloalkyl; or represent optionally substituted aryl, or arylalkyl, saturated or unsaturated heterocyclyl having 1 to 4 heteroatoms selected from the group consisting of nitrogen, oxygen and sulphur, or
R¹ and R² together represent alkylene or alkenylene, where the carbon chain is optionally interrupted by 1 to 3 heteroatoms selected from the group consisting of nitrogen and oxygen and the resulting ring is optionally substituted by halogen or alkyl, X represents halogen, nitro, cyano, hydroxyl, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, cycloalkyl, aryl, arylalkyl, or saturated or unsaturated heterocyclyl having 1 to 4 heteroatoms from the group consisting of nitrogen, oxygen and sulphur; or, when n represents 2, 3 or 4, two adjacent X together optionally represent alkylene or alkenylene, where the carbon chain is optionally interrupted by 1 or 2 heteroatoms selected from the group consisting of nitrogen and oxygen, n represents 0, 1, 2, 3 or 4, with X representing identical or different radicals when n represents 2, 3 or 4, Z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$—, or —(CH$_2$)$_t$—C(R$^{12}$)=C(R$^{13}$)—(CH$_2$)$_w$—, r represents 1, 2, 3, 4, 5 or 6, t and w independently of one another represent 0, 1, 2, 3 or 4, R represents the group

where A represents oxygen, sulphur, or NR$^{15}$ and E represents —SR$^{16}$ or —S-M, or where A represents sulphur or NR$^{15}$ and E represents —OR$^{16}$, —SR$^{16}$, —O-M, or —S-M, or represents a carboxylic acid bioisostere (acid mimic) selected from the group consisting of

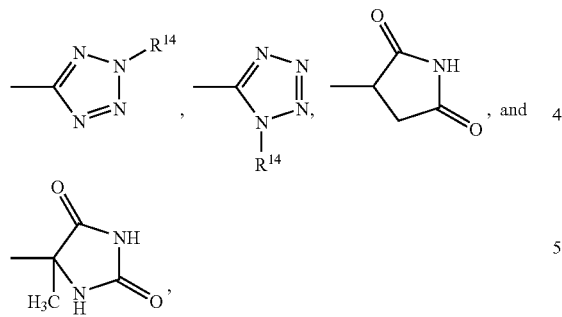

M represents ammonium which is optionally substituted by alkyl, aryl or arylalkyl; or represents an alkali metal ion, or represents an alkaline earth metal ion forming a salt with two molecules of a compound of formula (I), R$^3$ represents hydrogen, alkyl, halogenoalkyl, cycloalkyl, cycloalkylalkyl; or represents optionally halogen-, alkyl-, halogenoalkyl-, alkoxy-, halogenoalkoxy-, alkylthio-, halogenoalkylthio-substituted aryl, arylalkyl, saturated or unsaturated heterocyclyl or heterocyclylalkyl having 1 to 4 heteroatoms selected from the group consisting of nitrogen, oxygen and sulphur, R$^4$ represents hydrogen, alkyl, halogenoalkyl, cycloalkyl or alkylcarbonyl, R$^5$ represents hydrogen, amino, formyl, alkyl, alkenyl, alkynyl, halogenoalkyl, cycloalkyl, alkoxy, alkoxyalkyl, alkylcarbonyl, alkoxycarbonyl, or oxamoyl, or R$^4$ and R$^5$ together represent alkylidene; or represent optionally halogen-, nitro-, alkyl-, or halogenoalkyl-substituted benzylidene; or R$^4$ and R$^5$ together with the nitrogen atom to which they are attached represent a saturated or unsaturated heterocycle that optionally contains a further nitrogen, oxygen or sulphur atom and is optionally be substituted by alkyl, R$^6$ represents hydrogen, alkyl, halogenoalkyl or arylalkyl, R$^7$ represents hydrogen, alkyl, halogenoalkyl, cycloalkyl, cycloalkylalkyl, aryl or arylalkyl, R$^8$ represents alkyl or halogenoalkyl, R$^{10}$ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, R$^{11}$ represents hydrogen or alkyl, R$^{12}$ and R$^{13}$ independently of one another represent hydrogen, hydroxyl, alkyl or alkoxy, R$^{14}$ represents hydrogen, alkyl or halogenoalkyl, R$^{15}$ represents hydrogen, alkyl, alkoxy, cyano or dialkylamino, R$^{16}$ represents hydrogen; represents optionally halogen-, amino-, hydroxyl-, cyano-, nitro-, alkoxy-, halogenoalkoxy-, alkylthio-, halogenoalkylthio-, alkoxycarbonyl-, alkenyloxy-carbonyl-, alkylcarbonyloxy-, alkenylcarbonyloxy-, oxyalkyleneoxy-, oxetanyl-, dioxanyl-, oxazolidinyl-, dioxolanyl-, aryloxy-, halogenoaryloxy-, —CONR$^4$R$^5$—, —NR$^4$R$^5$—, —ONR$^4$R$^5$—, or —C(R$^{14}$)=N—OR$^{14}$-substituted alkyl, alkenyl, or alkynyl; represents optionally halogen-, alkyl-, halogenoalkyl-, alkoxy-, halogenoalkoxy-, alkylthio-, halogenoalkylthio-, alkoxycarbonyl-, alkylcarbonyloxy-substituted aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen, and sulphur; or represents —NR$^4$R$^5$; represents Q; or represents optionally substituted aryl, arylalkyl, cycloalkyl, cycloalkylalkyl, or saturated or unsaturated heterocyclyl or heterocyclylalkyl having 1 to 4 heteroatoms from the group consisting of nitrogen, oxygen and sulphur, where the substituents are those mentioned above or are hydroxyl or nitro, and Q represents one of the groups

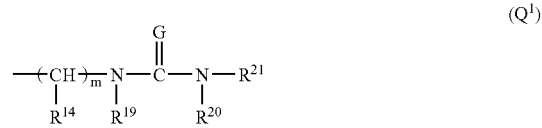 (Q$^1$)

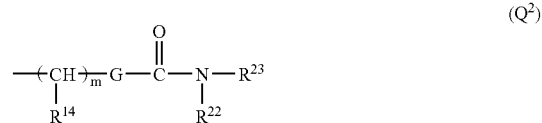 (Q$^2$)

 (Q$^3$)

-continued

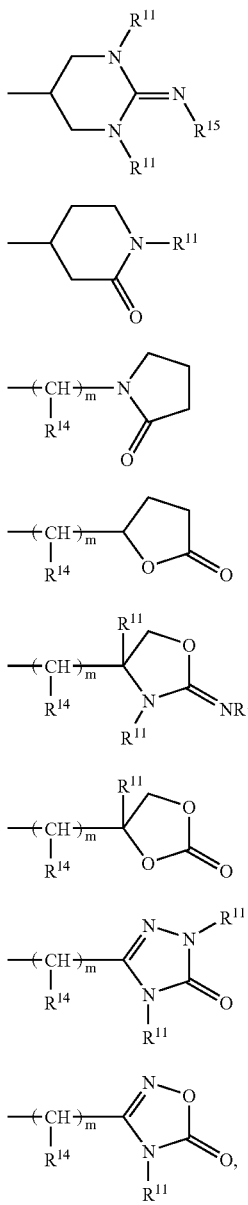

where
each $R^{11}$ may have identical or different meanings when two or more $R^{11}$ are present in the same heterocyclic group, m represents 0, 1, 2 or 3, where the repeat unit —(CHR$^{14}$)— in the side chain of a heterocyclic grouping may have identical or different meanings when m represents 2 or 3, G represents oxygen or sulphur, $R^{19}$ and $R^{20}$ independently of one another represent hydrogen, alkyl or $R^{19}$ and $R^{20}$ together represent alkylene, $R^{21}$ represents hydrogen, represents optionally alkylcarbonyloxy- or alkoxy-substituted alkyl; or represents optionally halogen-, cyano-, alkyl-, halogenoalkyl-, alkylcarbonyl-, alkoxycarbonyl-, or alkylene-substituted aryl, $R^{22}$ represents hydrogen, alkyl or alkoxyalkyl, and
$R^{23}$ represents hydrogen, amino, alkyl or alkoxyalkyl.

14. A pyridylpyrimidine of the formula (I-r)

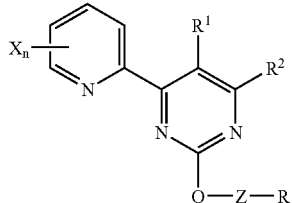

(I-r)

in which
$R^1$ and $R^2$ independently of one another represent hydrogen, halogen, nitro, cyano, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, or cycloalkyl; or represent optionally substituted aryl, or arylalkyl, saturated or unsaturated heterocyclyl having 1 to 4 heteroatoms selected from the group consisting of nitrogen, oxygen, and sulphur, or $R^1$ and $R^2$ together represent alkylene or alkenylene, where the carbon chain is optionally interrupted by 1 to 3 heteroatoms selected from the group consisting of nitrogen and oxygen and the resulting ring is optionally substituted by halogen or alkyl, X represents halogen, nitro, cyano, hydroxyl, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, cycloalkyl, aryl, arylalkyl, or saturated or unsaturated heterocyclyl having 1 to 4 heteroatoms from the group consisting of nitrogen, oxygen and sulphur; or, when n represents 2, 3 or 4, two adjacent X together optionally represent alkylene or alkenylene, where the carbon chain is optionally interrupted by 1 or 2 heteroatoms selected from the group consisting of nitrogen and oxygen, n represents 0, 1, 2, 3 or 4, with X representing identical or different radicals when n represents 2, 3 or 4, Z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$—, or —(CH$_2$)$_t$—C(R$^{12}$)=C(R$^{13}$)—(CH$_2$)$_w$—, r represents 1, 2, 3, 4, 5 or 6,
t and w independently of one another represent 0, 1, 2, 3 or 4,
R represents the group

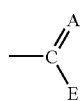

where A represents oxygen, sulphur, or NR$^{15}$ and E represents —OR$^{16}$, —SR$^{16}$, —O-M, or —S-M,
or represents a carboxylic acid bioisostere (acid mimic) selected from the group consisting of

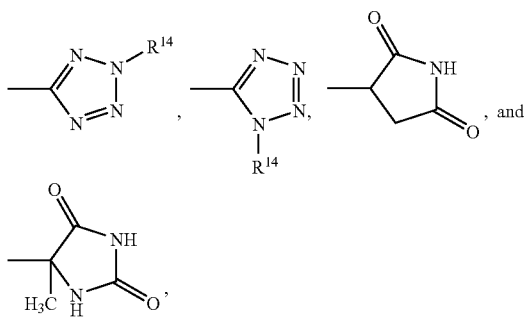

M represents ammonium that is optionally substituted by alkyl, aryl or arylalkyl; or represents an alkali metal ion, or represents an alkaline earth metal ion forming a salt with two molecules of a compound of formula (I), $R^3$ represents hydrogen, alkyl, halogenoalkyl, cycloalkyl, or cycloalkylalkyl; or represents optionally halogen-, alkyl-, halogenoalkyl-, alkoxy-, halogenoalkoxy-, alkylthio-, halogenoalkylthio-substituted aryl, arylalkyl, saturated or unsaturated heterocyclyl or heterocyclylalkyl having 1 to 4 heteroatoms selected from the group consisting of nitrogen, oxygen and sulphur, $R^4$ represents hydrogen, alkyl, halogenoalkyl, cycloalkyl or alkylcarbonyl, $R^5$ represents hydrogen, amino, formyl, alkyl, alkenyl, alkynyl, halogenoalkyl, cycloalkyl, alkoxy, alkoxyalkyl, alkylcarbonyl, alkoxycarbonyl, or oxamoyl, or $R^4$ and $R^5$ together represent alkylidene; or represent optionally halogen-, nitro-, alkyl-, or halogenoalkyl-substituted benzylidene; or $R^4$ and $R^5$ together with the nitrogen atom to which they are attached represent a saturated or unsaturated heterocycle that optionally contains a further nitrogen, oxygen or sulphur atom and is optionally be substituted by alkyl, $R^6$ represents hydrogen, alkyl, halogenoalkyl, or arylalkyl, $R^7$ represents hydrogen, alkyl, halogenoalkyl, cycloalkyl, cycloalkylalkyl, aryl, or arylalkyl, $R^8$ represents alkyl or halogenoalkyl, $R^{10}$ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, $R^{11}$ represents hydrogen or alkyl, $R^{12}$ and $R^{13}$ independently of one another represent hydrogen, hydroxyl, alkyl or alkoxy, $R^{14}$ represents hydrogen, alkyl, or halogenoalkyl, $R^{15}$ represents hydrogen, alkyl, alkoxy, cyano, or dialkylamino, $R^{16}$ represents hydrogen; represents optionally halogen-, amino-, hydroxyl-, cyano-, nitro-, alkoxy-, halogenoalkoxy-, alkylthio-, halogenoalkylthio-, alkoxycarbonyl-, alkenyloxy-carbonyl-, alkylcarbonyloxy-, alkenylcarbonyloxy-, oxyalkyleneoxy-, oxetanyl-, dioxanyl-, oxazolidinyl-, dioxolanyl-, aryloxy-, halogenoaryloxy-, —CONR$^4$R$^5$—, —NR$^4$R$^5$—, —ONR$^4$R$^5$—, or —C(R$^{14}$)=N—OR$^{14}$-substituted alkyl, alkenyl, or alkynyl; represents optionally halogen-, alkyl-, halogenoalkyl-, alkoxy-, halogenoalkoxy-, alkylthio-, halogenoalkylthio-, alkoxycarbonyl-, alkylcarbonyloxy-substituted aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen and sulphur; or represents —NR$^4$R$^5$; represents Q; or represents optionally substituted aryl, arylalkyl, cycloalkyl, cycloalkylalkyl, or saturated or unsaturated heterocyclyl or heterocyclylalkyl having 1 to 4 heteroatoms from the group consisting of nitrogen, oxygen and sulphur, where the substituents are those mentioned above or are hydroxyl or nitro, and Q represents one of the groups

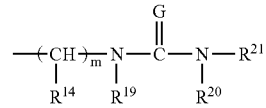 (Q$^1$)

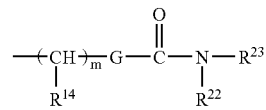 (Q$^2$)

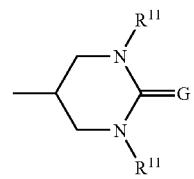 (Q$^3$)

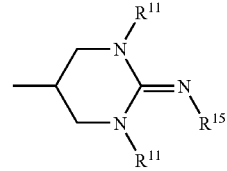 (Q$^4$)

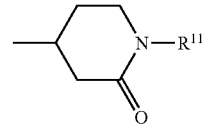 (Q$^5$)

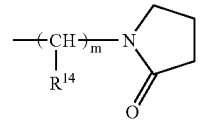 (Q$^6$)

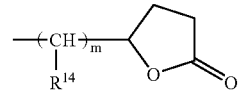 (Q$^7$)

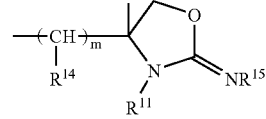 (Q$^8$)

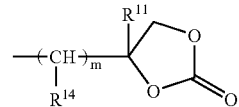 (Q$^9$)

(Q¹⁰)

$$-(CH)_m-\underset{R^{14}}{|}\text{[triazolinone ring with }R^{11}, R^{11}, G\text{]}$$

(Q¹¹)

$$-(CH)_m-\underset{R^{14}}{|}\text{[oxadiazolinone ring with }R^{11}\text{]}$$

where each $R^{11}$ may have identical or different meanings when two or more $R^{11}$ are present in the same heterocyclic group, m represents 0, 1, 2 or 3, where the repeat unit —(CHR¹⁴)— in the side chain of a heterocyclic grouping may have identical or different meanings when m represents 2 or 3, G represents oxygen or sulphur, $R^{19}$ and $R^{20}$ independently of one another represent hydrogen, alkyl or $R^{19}$ and $R^{20}$ together represent alkylene, $R^{21}$ represents hydrogen, represents optionally alkylcarbonyloxy- or alkoxy-substituted alkyl; or represents optionally halogen-, cyano-, alkyl-, halogenoalkyl-, alkylcarbonyl-, alkoxycarbonyl-, or alkylene-substituted aryl, $R^{22}$ represents hydrogen, alkyl or alkoxyalkyl, and $R^{23}$ represents hydrogen, amino, alkyl or alkoxyalkyl.

15. A pyridylpyrimidine of the formula (I-s)

(I-s)

[structure: pyridyl-pyrimidine with $X_n$, $R^1$, $R^2$, Z—R]

in which $R^1$ and $R^2$ independently of one another represent hydrogen, halogen, nitro, cyano, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)ₚR³, —NR⁴R⁵, —COR⁶, —CO₂R⁷, —CSR⁶, —CONR⁴R⁵, —NHCO₂R⁸, or cycloalkyl; or represent optionally substituted aryl, or arylalkyl, saturated or unsaturated heterocyclyl having 1 to 4 heteroatoms selected from the group consisting of nitrogen, oxygen, and sulphur, or $R^1$ and $R^2$ together represent alkylene or alkenylene, where the carbon chain is optionally interrupted by 1 to 3 heteroatoms selected from the group consisting of nitrogen and oxygen and the resulting ring is optionally substituted by halogen or alkyl, X represents halogen, nitro, cyano, hydroxyl, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)ₚR³, —NR⁴R⁵, —COR⁶, —CO₂R⁷, —CSR⁶, —CONR⁴R⁵, —NHCO₂R⁸, cycloalkyl, aryl, arylalkyl, or saturated or unsaturated heterocyclyl having 1 to 4 heteroatoms from the group consisting of nitrogen, oxygen and sulphur; or, when n represents 2, 3 or 4, two adjacent X together optionally represent alkylene or alkenylene, where the carbon chain is optionally interrupted by 1 or 2 heteroatoms selected from the group consisting of nitrogen and oxygen, n represents 0, 1, 2, 3 or 4, with X representing identical or different radicals when n represents 2, 3 or 4, Z represents —(CH₂)ᵣ—, —(CH₂)ₜ—(CHR¹⁰)—(CH₂)ᵥᵥ—, —(CH₂)ᵣ—C(O)—(CH₂)ₜ—, —(CH₂)ᵣ—O—(CH₂)ₜ—, —(CH₂)ᵣ—S(O)ₚ—(CH₂)ₜ—, —(CH₂)ᵣ—N(R¹¹)—(CH₂)ₜ—, or —(CH₂)ₜ—C(R¹²)=C(R¹³)—(CH₂)ᵥᵥ—, r represents 1, 2, 3, 4, 5 or 6, t and w independently of one another represent 0, 1, 2, 3 or 4, R represents the group $$-C\overset{A}{\underset{E}{\diagup\!\!\!\!\diagdown}}$$

where A represents oxygen, sulphur, or $NR^{15}$ and E represents —OR¹⁶, or —SR¹⁶, —O-M, or —S-M, or represents a carboxylic acid bioisostere (acid mimic) selected from the group consisting of

[tetrazole with R¹⁴], [tetrazole with R¹⁴], [succinimide-type ring with NH], and

[hydantoin-type ring with H₃C, NH],

M represents ammonium that is optionally substituted by alkyl, aryl, or arylalkyl; or represents an alkali metal ion, or represents an alkaline earth metal ion forming a salt with two molecules of a compound of formula (I), $R^3$ represents hydrogen, alkyl, halogenoalkyl, cycloalkyl, cycloalkylalkyl; or represents optionally halogen-, alkyl-, halogenoalkyl-, alkoxy-, halogenoalkoxy-, alkylthio-, halogenoalkylthio-substituted aryl, arylalkyl, saturated or unsaturated heterocyclyl or heterocyclylalkyl having 1 to 4 heteroatoms selected from the group consisting of nitrogen, oxygen, and sulphur, $R^4$ represents hydrogen, alkyl, halogenoalkyl, cycloalkyl, or alkylcarbonyl, $R^5$ represents hydrogen, amino, formyl, alkyl, alkenyl, alkynyl, halogenoalkyl, cycloalkyl, alkoxy, alkoxyalkyl, alkylcarbonyl, alkoxycarbonyl, or oxamoyl, or $R^4$ and $R^5$ together represent alkylidene; or represent optionally halogen-, nitro-, alkyl-, or halogenoalkyl-substituted benzylidene; or $R^4$ and $R^5$ together with the nitrogen atom to which they are attached represent a saturated or unsaturated heterocycle that optionally contains a further nitrogen, oxygen, or sulphur atom and is optionally be substituted by alkyl, $R^6$ represents hydrogen, alkyl, halogenoalkyl, or arylalkyl, $R^7$ represents hydrogen, alkyl, halogenoalkyl, cycloalkyl, cycloalkylalkyl, aryl, or arylalkyl, $R^8$ represents alkyl or halogenoalkyl, $R^{10}$ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, $R^{11}$ represents hydrogen or alkyl, $R^{12}$ and $R^{13}$ independently of one another represent hydrogen, hydroxyl, alkyl, or alkoxy, $R^{14}$ represents hydrogen, alkyl, or halogenoalkyl, $R^{15}$ represents hydrogen, alkyl, alkoxy, cyano, or dialkylamino, $R^{16}$ represents hydrogen; represents optionally halogen-, amino-, hydroxyl-, cyano-, nitro-, alkoxy-, halogenoalkoxy-, alkylthio-, halogenoalkylthio-, alkoxycarbonyl-, alkenyloxy-carbonyl-, alkylcarbonyloxy-, alkenylcarbonyloxy-, oxyalkyleneoxy-, oxetanyl-, dioxanyl-, oxazolidinyl-, dioxolanyl-, aryloxy-, halogenoaryloxy-, —CONR$^4$R$^5$—, —NR$^4$R$^5$—, —ONR$^4$R$^5$—, or —C(R$^{14}$)=N—OR$^{14}$-substituted alkyl, alkenyl, or alkynyl; represents optionally halogen-, alkyl-, halogenoalkyl-, alkoxy-, halogenoalkoxy-, alkylthio-, halogenoalkylthio-, alkoxycarbonyl-, alkylcarbonyloxy-substituted aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen, and sulphur; or represents —NR$^4$R$^5$; represents Q; or represents optionally substituted aryl, arylalkyl, cycloalkyl, cycloalkylalkyl, or saturated or unsaturated heterocyclyl or heterocyclylalkyl having 1 to 4 heteroatoms from the group consisting of nitrogen, oxygen and sulphur, where the substituents are those mentioned above or are hydroxyl or nitro, and Q represents one of the groups

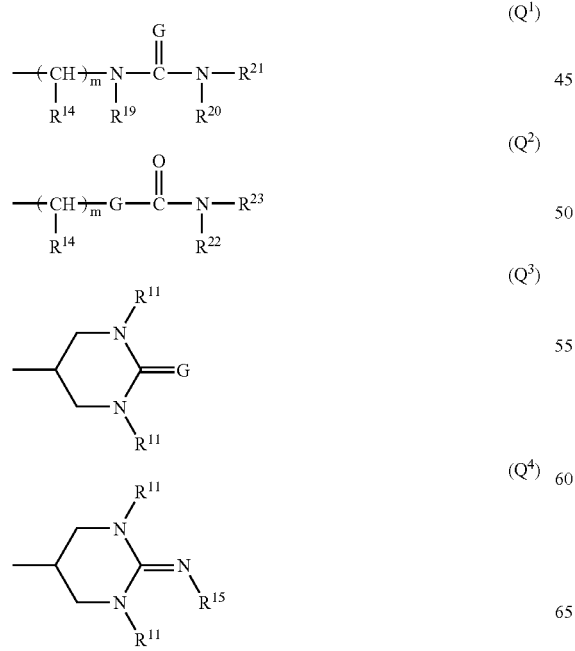

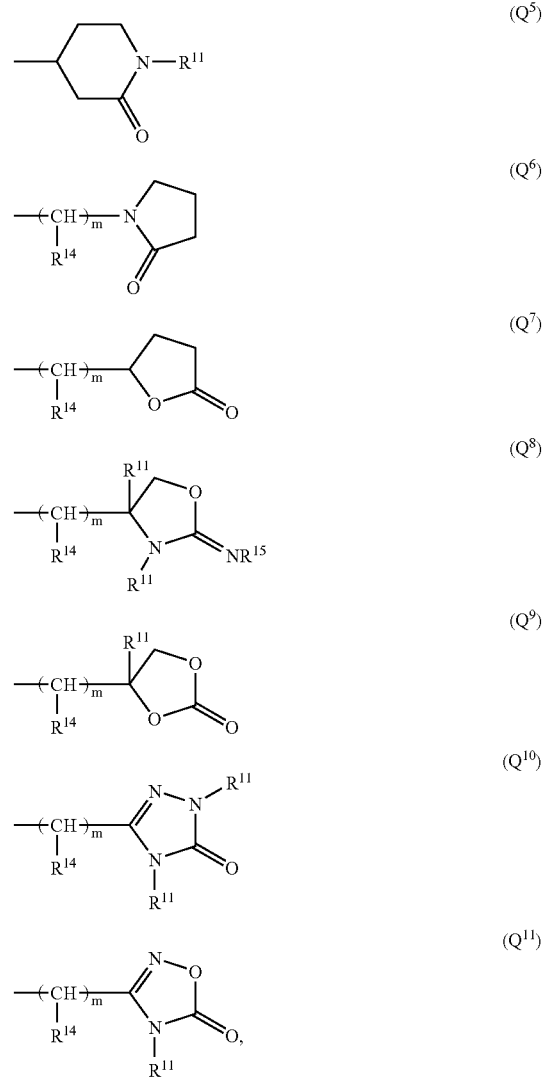

where each $R^{11}$ may have identical or different meanings when two or more $R^{11}$ are present in the same heterocyclic group, m represents 0, 1, 2 or 3, where the repeat unit —(CHR$^{14}$)— in the side chain of a heterocyclic grouping may have identical or different meanings when m represents 2 or 3, G represents oxygen or sulphur, $R^{19}$ and $R^{20}$ independently of one another represent hydrogen, alkyl or $R^{19}$ and $R^{20}$ together represent alkylene, $R^{21}$ represents hydrogen, represents optionally alkylcarbonyloxy- or alkoxy-substituted alkyl; or represents optionally halogen-, cyano-, alkyl-, halogenoalkyl-, alkylcarbonyl-, alkoxycarbonyl-, or alkylene-substituted aryl, $R^{22}$ represents hydrogen, alkyl or alkoxyalkyl, and $R^{23}$ represents hydrogen, amino, alkyl or alkoxyalkyl.

16. A pyridylpyrimidine of formula (I-n)

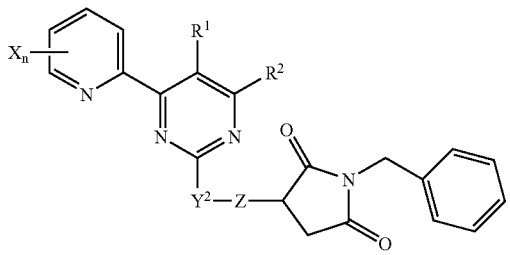

in which
R$^1$ and R$^2$ independently of one another represent hydrogen, halogen, nitro, cyano, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, or cycloalkyl; or represent optionally substituted aryl, or arylalkyl, saturated or unsaturated heterocyclyl having 1 to 4 heteroatoms selected from the group consisting of nitrogen, oxygen and sulphur, or R$^1$ and R$^2$ together represent alkylene or alkenylene, where the carbon chain is optionally interrupted by 1 to 3 heteroatoms selected from the group consisting of nitrogen and oxygen and the resulting ring is optionally substituted by halogen or alkyl, X represents halogen, nitro, cyano, hydroxyl, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, cycloalkyl, aryl, arylalkyl, or saturated or unsaturated heterocyclyl having 1 to 4 heteroatoms from the group consisting of nitrogen, oxygen and sulphur; or, when n represents 2, 3 or 4, two adjacent X together optionally represent alkylene or alkenylene, where the carbon chain is optionally interrupted by 1 or 2 heteroatoms selected from the group consisting of nitrogen and oxygen, n represents 0, 1, 2, 3 or 4, with X representing identical or different radicals when n represents 2, 3 or 4, Y$^2$ represents a direct bond, oxygen, sulphur, or —NR$^9$—, Z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$—, or —(CH$_2$)$_t$—C(R$^{12}$)=C(R$^{13}$)—(CH$_2$)$_w$—, r represents 1, 2, 3, 4, 5 or 6, t and w independently of one another represent 0, 1, 2, 3 or 4, R$^3$ represents hydrogen, alkyl, halogenoalkyl, cycloalkyl, or cycloalkylalkyl; or represents optionally halogen-, alkyl-, halogenoalkyl-, alkoxy-, halogenoalkoxy-, alkylthio-, halogenoalkylthio-substituted aryl, arylalkyl, saturated or unsaturated heterocyclyl or heterocyclylalkyl having 1 to 4 heteroatoms selected from the group consisting of nitrogen, oxygen and sulphur, R$^4$ represents hydrogen, alkyl, halogenoalkyl, cycloalkyl or alkylcarbonyl, R$^5$ represents hydrogen, amino, formyl, alkyl, alkenyl, alkynyl, halogenoalkyl, cycloalkyl, alkoxy, alkoxyalkyl, alkylcarbonyl, alkoxycarbonyl, or oxamoyl, or R$^4$ and R$^5$ together represent alkylidene; or represent optionally halogen-, nitro-, alkyl-, halogenoalkyl-substituted benzylidene; or R$^4$ and R$^5$ together with the nitrogen atom to which they are attached represent a saturated or unsaturated heterocycle that optionally contains a further nitrogen, oxygen or sulphur atom and is optionally be substituted by alkyl, R$^6$ represents hydrogen, alkyl, halogenoalkyl or arylalkyl, R$^7$ represents hydrogen, alkyl, halogenoalkyl, cycloalkyl, cycloalkylalkyl, aryl, or arylalkyl, R$^8$ represents alkyl or halogenoalkyl, R$^9$ represents hydrogen, alkyl, halogenoalkyl, cycloalkyl, or cycloalkylalkyl; or represents optionally halogen-, alkyl-, halogenoalkyl-, alkoxy-, halogenoalkoxy-, alkylthio-, halogenoalkylthio-substituted aryl, arylalkyl, or saturated or unsaturated heterocyclyl or heterocyclylalkyl having 1 to 4 heteroatoms selected from the group consisting of nitrogen, oxygen, and sulphur, R$^{10}$ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, R$^{11}$ represents hydrogen or alkyl, and R$^{12}$ and R$^{13}$ independently of one another represent hydrogen, hydroxyl, alkyl, or alkoxy.

17. A pesticide comprising one or more compounds of formula (I) according to claim 1 and one or more extenders and/or surfactants.

18. A process for preparing a pesticide comprising mixing a compound of formula (I) according to claim 1 with one or more extenders and/or surfactants.

19. A method of controlling pests comprising allowing a compound of formula (I)

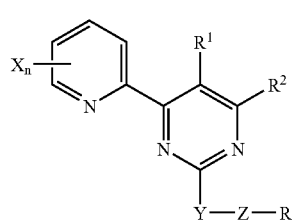

in which
R$^1$ and R$^2$ independently of one another represent hydrogen, halogen, nitro, cyano, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, or cycloalkyl; or represent optionally substituted aryl, or arylalkyl, saturated or unsaturated heterocyclyl having 1 to 4 heteroatoms selected from the group consisting of nitrogen, oxygen, and sulphur, or R$^1$ and R$^2$ together represent alkylene or alkenylene, where the carbon chain is optionally interrupted by 1 to 3 heteroatoms selected from the group consisting of nitrogen and oxygen and the resulting ring is optionally substituted by halogen or alkyl, X represents halogen, nitro, cyano, hydroxyl, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, cycloalkyl, aryl, arylalkyl, or saturated or unsaturated heterocyclyl having 1 to 4 heteroatoms from the group consisting of nitrogen, oxygen and sulphur; or, when n represents 2, 3 or 4, two adjacent X together optionally represent alkylene or alkenylene, where the carbon chain is optionally interrupted by 1 or 2 heteroatoms selected from the group consisting of nitrogen and oxygen, n represents 0, 1, 2, 3 or 4, with X representing identical or different radicals when n represents 2, 3 or 4, Y represents a direct bond, oxygen, sulphur or —NR$^9$—, p represents 0, 1 or 2, Z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$—, or —(CH$_2$)$_t$—C(R$^{12}$)=C(R$^{13}$)—(CH$_2$)$_w$—, r represents 1, 2, 3, 4, 5 or 6, t and w independently of one another represent 0, 1, 2, 3 or 4, R represents the group

or represents a carboxylic acid bioisostere (acid mimic) selected from the group consisting of

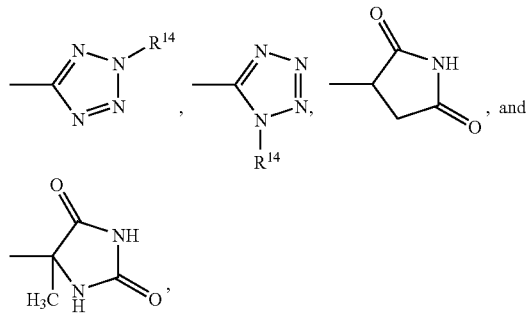

A represents oxygen, sulphur, or NR$^{15}$,

E represents —OR$^{16}$, —SR$^{16}$, —O-M, —S-M, or NR$^{17}$R$^{18}$,

M represents ammonium that is optionally substituted by alkyl, aryl or arylalkyl; or represents an alkali metal ion, or represents an alkaline earth metal ion forming a salt with two molecules of a compound of formula (I), R$^3$ represents hydrogen, alkyl, halogenoalkyl, cycloalkyl, or cycloalkylalkyl; or represents optionally halogen-, alkyl-, halogenoalkyl-, alkoxy-, halogenoalkoxy-, alkylthio-, halogenoalkylthio-substituted aryl, arylalkyl, saturated or unsaturated heterocyclyl or heterocyclylalkyl having 1 to 4 heteroatoms selected from the group consisting of nitrogen, oxygen and sulphur, R$^4$ represents hydrogen, alkyl, halogenoalkyl, cycloalkyl or alkylcarbonyl, R$^5$ represents hydrogen, amino, formyl, alkyl, alkenyl, alkynyl, halogenoalkyl, cycloalkyl, alkoxy, alkoxyalkyl, alkylcarbonyl, alkoxycarbonyl, or oxamoyl; or R$^4$ and R$^5$ together represent alkylidene; or represent optionally halogen-, nitro-, alkyl-, halogenoalkyl-substituted benzylidene; or R$^4$ and R$^5$ together with the nitrogen atom to which they are attached represent a saturated or unsaturated heterocycle that optionally contains a further nitrogen, oxygen or sulphur atom and is optionally be substituted by alkyl, R$^6$ represents hydrogen, alkyl, halogenoalkyl or arylalkyl, R$^7$ represents hydrogen, alkyl, halogenoalkyl, cycloalkyl, cycloalkylalkyl, aryl or arylalkyl, R$^8$ represents alkyl or halogenoalkyl, R$^9$ represents hydrogen, alkyl, halogenoalkyl, cycloalkyl, cycloalkylalkyl; or represents optionally halogen-, alkyl-, halogenoalkyl-, alkoxy-, halogenoalkoxy-, alkylthio-, or halogenoalkylthio-substituted aryl, arylalkyl, or saturated or unsaturated heterocyclyl or heterocyclylalkyl having 1 to 4 heteroatoms selected from the group consisting of nitrogen, oxygen and sulphur, R$^{10}$ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, R$^{11}$ represents hydrogen or alkyl, R$^{12}$ and R$^{13}$ independently of one another represent hydrogen, hydroxyl, alkyl or alkoxy, R$^{14}$ represents hydrogen, alkyl or halogenoalkyl, R$^{15}$ represents hydrogen, alkyl, alkoxy, cyano or dialkylamino, R$^{16}$ represents hydrogen; represents optionally halogen-, amino-, hydroxyl-, cyano-, nitro-, alkoxy-, halogenoalkoxy-, alkylthio-, halogenoalkylthio-, alkoxycarbonyl-, alkenyloxy-carbonyl-, alkylcarbonyloxy-, alkenylcarbonyloxy-, oxyalkyleneoxy-, oxetanyl-, dioxanyl-, oxazolidinyl-, dioxolanyl-, aryloxy-, halogenoaryloxy-, —CONR$^4$R$^5$—, —NR$^4$R$^5$—, —ONR$^4$R$^5$—, or —C(R$^{14}$)=N—OR$^{14}$-substituted alkyl, alkenyl, or alkynyl; represents optionally halogen-, alkyl-, halogenoalkyl-, alkoxy-, halogenoalkoxy-, alkylthio-, halogenoalkylthio-, alkoxycarbonyl-, alkylcarbonyloxy-substituted aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen, and sulphur; or represents —NR$^4$R$^5$; represents Q; or represents optionally substituted aryl, arylalkyl, cycloalkyl, cycloalkylalkyl, or saturated or unsaturated heterocyclyl or heterocyclylalkyl having 1 to 4 heteroatoms from the group consisting of nitrogen, oxygen and sulphur, where the substituents are those mentioned above or are hydroxyl or nitro, R$^{17}$ represents hydrogen or alkyl, R$^{18}$ represents hydrogen, hydroxyl, amino, alkyl, or alkenyl; represents optionally halogen-, hydroxyl-, alkyl-, halogenoalkyl-, alkoxy-, halogenoalkoxy-, alkylthio-, halogenoalkylthio-, or oxyalkyleneoxy-substituted cycloalkyl, cycloalkylalkyl, aryl, arylalkyl, or heteroaryl or heteroarylalkyl having 1 to 4 heteroatoms selected from the group consisting of nitrogen, oxygen, and sulphur; represents —S(O)$_p$R$^3$, —OR$^{14}$, or —NR$^4$R$^5$; represents alkyl or alkenyl, each of which is substituted by identical or different substituents selected from the group consisting of halogen, amino, hydroxyl, cyano, nitro, alkoxy, halogenoalkoxy, alkylthio, halogenoalkylthio, alkoxycarbonyl, and alkenyloxycarbonyl; or represents optionally substituted cycloalkyl, cycloalkylalkyl, aryl, arylalkyl, or heteroaryl or heteroarylalkyl having 1 to 4 heteroatoms selected from the group consisting of nitrogen, oxygen, and sulphur, where the substituents are those mentioned above or are nitro or alkoxycarbonyl, or $R^{17}$ and $R^{18}$ together with the nitrogen atom to which they are attached represent a 5- or 6-membered saturated or unsaturated heterocycle that optionally contains 1 to 2 further heteroatoms selected from the group consisting of nitrogen, oxygen, and sulphur and is optionally substituted by alkyl, and Q represents one of the groups

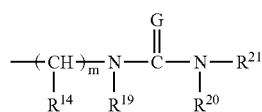 (Q¹)

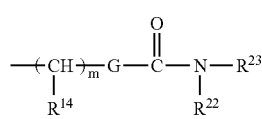 (Q²)

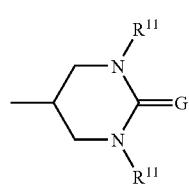 (Q³)

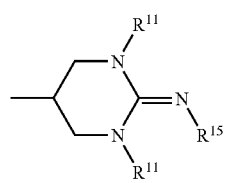 (Q⁴)

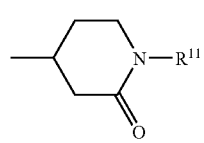 (Q⁵)

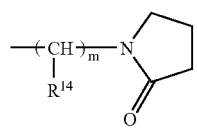 (Q⁶)

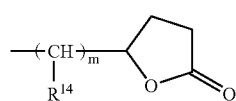 (Q⁷)

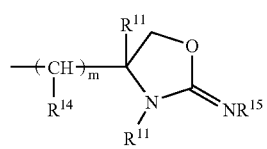 (Q⁸)

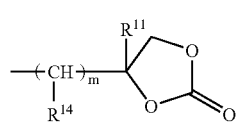 (Q⁹)

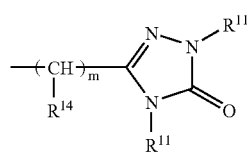 (Q¹⁰)

-continued

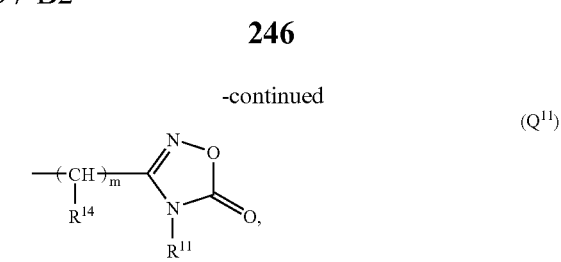 (Q¹¹)

where
each $R^{11}$ may have identical or different meanings when two or more are present in the same heterocyclic group, m represents 0, 1, 2 or 3, where the repeat unit —(CHR$^{14}$)— in the side chain of a heterocyclic grouping may have identical or different meanings when m represents 2 or 3, G represents oxygen or sulphur, $R^{19}$ and $R^{20}$ independently of one another represent hydrogen, alkyl or $R^{19}$ and $R^{20}$ together represent alkylene, $R^{21}$ represents hydrogen, represents optionally alkylcarbonyloxy- or alkoxy-substituted alkyl; or represents optionally halogen-, cyano-, alkyl-, halogenoalkyl-, alkylcarbonyl-, alkoxycarbonyl-, or alkylene-substituted aryl, $R^{22}$ represents hydrogen, alkyl, or alkoxyalkyl, and $R^{23}$ represents hydrogen, amino, alkyl, or alkoxyalkyl, to act on pests and/or their habitat.

20. A method according to claim 19 wherein R represents a carboxylic acid bioisostere selected from the group consisting of

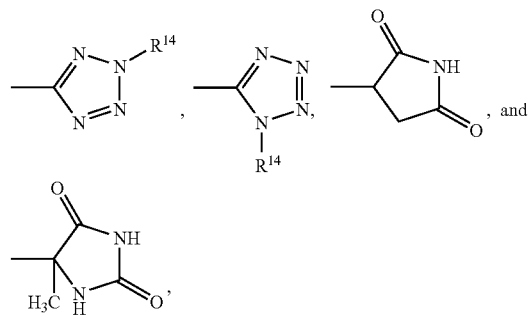

where $R^{14}$ represents hydrogen, alkyl or halogenoalkyl.

21. A method according to claim 19 wherein $R^{16}$ represents hydrogen; represents optionally halogen-, amino-, hydroxyl-, cyano-, nitro-, alkoxy-, halogenoalkoxy-, alkylthio-, halogenoalkylthio-, alkoxycarbonyl-, alkenyloxycarbonyl-, alkylcarbonyloxy-, alkenylcarbonyloxy-, oxyalkyleneoxy-, oxetanyl-, dioxanyl-, oxazolidinyl-, dioxolanyl-, aryloxy-, halogenoaryloxy-, —CONR$^4$R$^5$—, —NR$^4$R$^5$—, —ONR$^4$R$^5$—, or —C(R$^{14}$)=N—OR$^{14}$-substituted alkyl, alkenyl, or alkynyl; represents optionally halogen-, alkyl-, halogenoalkyl-, alkoxy-, halogenoalkoxy-, alkylthio-, halogenoalkylthio-, alkoxycarbonyl-, or alkylcarbonyloxy-substituted aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen and sulphur; or represents —NR$^4$R$^5$; or represents Q, and $R^{18}$ represents hydrogen, hydroxyl, amino, alkyl, or alkenyl; represents optionally halogen-, hydroxyl-, alkyl-, halogenoalkyl-, alkoxy-, halogenoalkoxy-, alkylthio-, halogenoalkylthio-, or oxyalkyleneoxy-substituted cycloalkyl, cycloalkylalkyl, aryl, arylalkyl, or heteroaryl or heteroarylalkyl having 1 to 4 heteroatoms selected from the group consisting of nitrogen, oxygen, and sulphur; represents —S(O)$_p$R$^3$, —OR$^{14}$, or —NR$^4$R$^5$.

22. A method according to claim 19 wherein $R^1$ and $R^2$ independently of one another represent hydrogen, halogen, nitro, cyano, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, $C_1$-$C_6$-halogenoalkylthio, $C_2$-$C_6$-alkenyl, $C_2$-$C_6$-alkynyl, $C_2$-$C_6$-alkenyloxy, $C_2$-$C_6$-halogenoalkenyloxy, $C_2$-$C_6$-alkynyloxy, $C_2$-$C_6$-halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, or $C_3$-$C_7$-cycloalkyl; or represent aryl, aryl-$C_1$-$C_6$-alkyl or 5- or 6-membered saturated or unsaturated heterocyclyl which contains 0 to 3 nitrogen atoms, 0 to 2 nonadjacent oxygen atoms and/or 0 to 2 nonadjacent sulphur atoms, each of which radicals is optionally mono- or polysubstituted by identical or different substituents selected from the group consisting of halogen, $C_1$-$C_6$-alkyl, $C_1$-$C_6$-halogenoalkyl, $C_1$-$C_6$-alkoxy, and $C_1$-$C_6$-halogenoalkoxy, or $R^1$ and $R^2$ together represent $C_3$-$C_5$-alkylene or $C_3$-$C_4$-alkenylene, where the carbon chain is optionally interrupted by 1 or 2 heteroatoms that are 0 to 2 nitrogen atoms and/or 0 or 1 oxygen atom, and where the resulting ring is optionally mono- or polysubstituted by identical or different substituents selected from the group consisting of halogen and $C_1$-$C_6$-alkyl, X represents halogen, nitro, cyano, hydroxyl, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, $C_1$-$C_6$-halogenoalkylthio, $C_2$-$C_6$-alkenyl, $C_2$-$C_6$-alkynyl, $C_2$-$C_6$-alkenyloxy, $C_2$-$C_6$-halogenoalkenyloxy, $C_2$-$C_6$-alkynyloxy, $C_2$-$C_6$-halogenoalkynyloxy, —S(O)$_p$R$^3$, —NR$^4$R$^5$, —COR$^6$, —CO$_2$R$^7$, —CSR$^6$, —CONR$^4$R$^5$, —NHCO$_2$R$^8$, $C_3$-$C_7$-cycloalkyl, aryl, aryl-$C_1$-$C_6$-alkyl, or 5- or 6-membered saturated or unsaturated heterocyclyl that contains 0 to 4 nitrogen atoms, 0 to 2 nonadjacent oxygen atoms, and/or 0 to 2 nonadjacent sulphur atoms; or, when n represents 2 or 3, two adjacent radicals X together optionally represent $C_3$-$C_5$-alkylene or $C_3$-$C_4$-alkenylene, where the carbon chain s optionally interrupted by 1 or 2 heteroatoms that are 0 to 2 nitrogen atoms and/or 0 or 1 oxygen atom, n represents 0, 1, 2 or 3, with X representing identical or different radicals when n represents 2 or 3, Y represents a direct bond, oxygen, —S(O)$_p$—, or —NR$^9$—, p represents 0, 1 or 2, Z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$—, or —(CH$_2$)$_t$—C(R$^{12}$)=C(R$^{13}$)—(CH$_2$)$_w$—, r represents 1, 2, 3, 4, 5 or 6, t and w independently of one another represent 0, 1, 2, 3 or 4, R represents the group

or represents a carboxylic acid bioisostere (acid mimetic), selected from the group consisting of

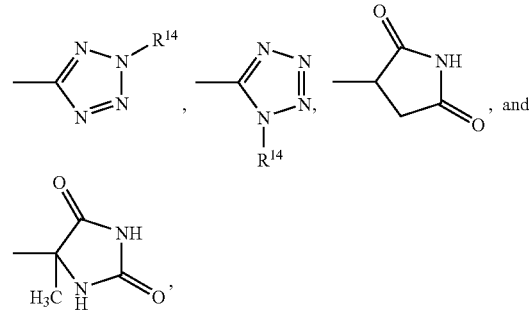

A represents oxygen, sulphur, or NR$^{15}$,

E represents —OR$^{16}$, —SR$^{16}$, —O-M, —S-M, or NR$^{17}$R$^{18}$,

M represents ammonium which is optionally mono- to tetrasubstituted by identical or different substituents selected from the group consisting of $C_1$-$C_6$-alkyl, aryl, and aryl-$C_1$-$C_6$-alkyl; or represents a lithium cation (Li$^+$), a sodium cation (Na$^+$) or a potassium cation (K$^+$); or represents a magnesium cation (Mg$^{2+}$) or a calcium cation (Ca$^{2+}$) forming a salt with two molecules of a compound of formula (I), R$^3$ represents hydrogen, $C_1$-$C_6$-alkyl, $C_1$-$C_6$-halogenoalkyl, $C_3$-$C_7$-cycloalkyl, or $C_3$-$C_7$-cycloalkyl-$C_1$-$C_6$-alkyl; or represents aryl, aryl-$C_1$-$C_6$-alkyl, or 5- or 6-membered saturated or unsaturated heterocyclyl or heterocyclyl-$C_1$-$C_6$-alkyl, each of which contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, and $C_1$-$C_6$-halogenoalkylthio, R$^4$ represents hydrogen, $C_1$-$C_6$-alkyl, $C_1$-$C_6$-halogenoalkyl, $C_3$-$C_7$-cycloalkyl, or $C_1$-$C_6$-alkylcarbonyl, R$^5$ represents hydrogen, amino, formyl, $C_1$-$C_6$-alkyl, $C_2$-$C_6$-alkenyl, $C_2$-$C_6$-alkynyl, $C_1$-$C_6$-halogenoalkyl, $C_3$-$C_7$-cycloalkyl, $C_1$-$C_6$-alkoxy, $C_1$-$C_6$-alkoxy-$C_1$-$C_6$-alkyl, $C_1$-$C_6$-alkylcarbonyl, $C_1$-$C_6$-alkoxycarbonyl, or oxamoyl, or R$^4$ and R$^5$ together represent $C_1$-$C_6$-alkylidene; or represent benzylidene that is optionally mono- or polysubstituted by identical or different substituents selected from the group consisting of halogen, nitro, $C_1$-$C_6$-alkyl, and $C_1$-$C_6$-halogenoalkyl; or R$^4$ and R$^5$ together with the nitrogen atom to which they are attached represent a 5- or 6-membered saturated or unsaturated heterocycle that optionally contain a further nitrogen, oxygen, or sulphur atom and that is optionally be mono- or polysubstituted by identical or different $C_1$-$C_6$-alkyl, R$^6$ represents hydrogen, $C_1$-$C_6$-alkyl, $C_1$-$C_6$-halogenoalkyl, or aryl-$C_1$-$C_6$-alkyl, R[7] represents hydrogen, $C_1$-$C_6$-alkyl, $C_1$-$C_6$-halogenoalkyl, $C_3$-$C_7$-cycloalkyl, $C_3$-$C_7$-cycloalkyl-$C_1$-$C_6$-alkyl, aryl, or aryl-$C_1$-$C_6$-alkyl, R[8] represents $C_1$-$C_6$-alkyl or $C_1$-$C_6$-halogenoalkyl, R[9] represents hydrogen, $C_1$-$C_6$-alkyl, $C_1$-$C_6$-halogenoalkyl, $C_3$-$C_7$-cycloalkyl, or $C_3$-$C_7$-cycloalkyl-$C_1$-$C_6$-alkyl; or represents aryl, aryl-$C_1$-$C_6$-alkyl, or 5- or 6-membered saturated or unsaturated heterocyclyl or heterocyclyl-$C_1$-$C_6$-alkyl, each of which contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, and $C_1$-$C_6$-halogenoalkylthio, R[10] represents halogen, $C_1$-$C_6$-alkyl, $C_1$-$C_6$-alkylcarbonyl, $C_1$-$C_6$-alkoxycarbonyl, $C_3$-$C_7$-cycloalkyl, $C_3$-$C_7$-cycloalkyl-$C_1$-$C_6$-alkyl; or represents aryl or aryl-$C_1$-$C_6$-alkyl which for their part may be mono- or polysubstituted in the aryl moiety by identical or different substitutents selected from the group consisting of halogen and $C_1$-$C_6$-alkyl, R[11] represents hydrogen or $C_1$-$C_6$-alkyl, R[12] and R[13] independently of one another represent hydrogen, hydroxyl, $C_1$-$C_6$-alkyl, or $C_1$-$C_6$-alkoxy, R[14] represents hydrogen, $C_1$-$C_6$-alkyl, or $C_1$-$C_6$-halogenoalkyl, R[15] represents hydrogen, $C_1$-$C_6$-alkyl, $C_1$-$C_6$-alkoxy, cyano or di($C_1$-$C_6$-alkyl)-amino, R[16] represents hydrogen; represents $C_1$-$C_{16}$-alkyl, $C_2$-$C_{10}$-alkenyl, $C_2$-$C_6$-alkynyl, each of which is optionally mono- or polysubstituted by identical or different substituents selected from the group consisting of halogen, amino, hydroxyl, cyano, nitro, $C_1$-$C_6$-alkoxy, $C_1$-$C_6$-halogenoalkoxy, $C_1$-$C_6$-alkylthio, $C_1$-$C_6$-halogenoalkylthio, $C_1$-$C_6$-alkoxycarbonyl, $C_2$-$C_6$-alkenyloxycarbonyl, $C_1$-$C_6$-alkylcarbonyloxy, $C_2$-$C_6$-alkenylcarbonyloxy, oxy($C_1$-$C_6$-alkylene)oxy, oxetanyl, dioxanyl, oxazolidinyl, dioxolanyl, aryloxy, halogenoaryloxy, —CONR[4]R[5], —NR[4]R[5], —ONR[4]R[5], and —C(R[14])=N—OR[14]; represents aryl, aryl-$C_1$-$C_6$-alkyl, $C_3$-$C_7$-cycloalkyl, $C_3$-$C_7$-cycloalkyl-$C_1$-$C_6$-alkyl, 4- to 6-membered saturated or unsaturated heterocyclyl or heterocyclyl-$C_1$-$C_6$-alkyl, each of which contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, $C_1$-$C_6$-halogenoalkylthio, $C_1$-$C_6$-alkoxycarbonyl and $C_1$-$C_6$-alkylcarbonyloxy; represents —NR[4]R[5]; represents Q; or represents aryl, aryl-$C_1$-$C_6$-alkyl, $C_3$-$C_7$-cycloalkyl, $C_3$-$C_7$-cycloalkyl-$C_1$-$C_6$-alkyl, 4- to 6-membered saturated or unsaturated heterocyclyl or heterocyclyl-$C_1$-$C_6$-alkyl, each of which contains 0 to 4 nitrogen atoms, 0 to 2 nonadjacent oxygen atoms and/or 0 to 2 nonadjacent sulphur atoms, each of which radicals is optionally mono- or polysubstituted by identical or different substituents, where the substitutents are those mentioned above or are hydroxyl or nitro, R[17] represents hydrogen or $C_1$-$C_6$-alkyl, R[18] represents hydrogen, hydroxyl, amino, $C_1$-$C_6$-alkyl, or $C_2$-$C_6$-alkenyl; represents $C_3$-$C_7$-cycloalkyl, $C_3$-$C_7$-cycloalkyl-$C_1$-$C_6$-alkyl, aryl, aryl-$C_1$-$C_6$-alkyl, or heteroaryl or heteroaryl-$C_1$-$C_6$-alkyl, each of which contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, hydroxyl, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, $C_1$-$C_6$-halogenoalkylthio, and oxy($C_1$-$C_6$-alkylene)oxy; or represents —S(O)$_p$R[3], —OR[14] or —NR[4]R[5]; represents $C_1$-$C_6$-alkyl or $C_2$-$C_6$-alkenyl, each of which is optionally mono- or polysubstituted by identical or different substituents selected from the group consisting of halogen, amino, hydroxyl, cyano, nitro, $C_1$-$C_6$-alkoxy, $C_1$-$C_6$-halogenoalkoxy, $C_1$-$C_6$-alkylthio, $C_1$-$C_6$-halogenoalkylthio, $C_1$-$C_6$-alkoxycarbonyl, and $C_2$-$C_6$-alkenyloxycarbonyl; or represents $C_3$-$C_7$-cycloalkyl, $C_3$-$C_7$-cycloalkyl-$C_1$-$C_6$-alkyl, aryl, aryl-$C_1$-$C_6$-alkyl, or heteroaryl or heteroaryl-$C_1$-$C_6$-alkyl, each of which contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents, where the substituents are those mentioned above or are nitro or $C_1$-$C_6$-alkoxycarbonyl, or R[17] and R[18] together with the nitrogen atom to which they are attached represent a 5- or 6-membered saturated or unsaturated heterocycle that optionally contains 1 to 2 further heteroatoms including 0 to 2 nitrogen atoms, 0 or 1 oxygen atom, and/or 0 or 1 sulphur atom that are optionally mono- or polysubstituted by identical or different $C_1$-$C_6$-alkyl, and Q represents one of the groups

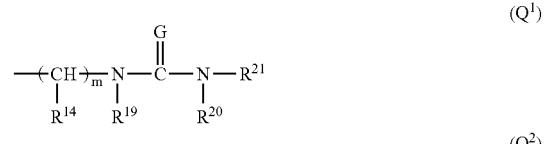

(Q¹)

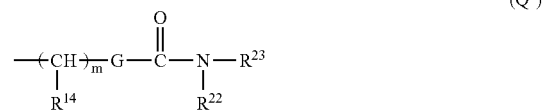

(Q²)

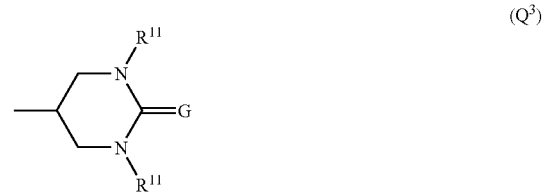

(Q³)

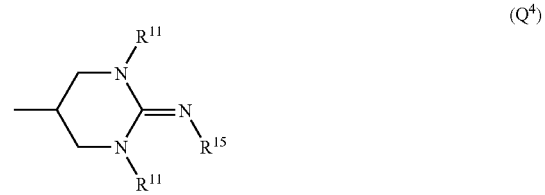

(Q⁴)

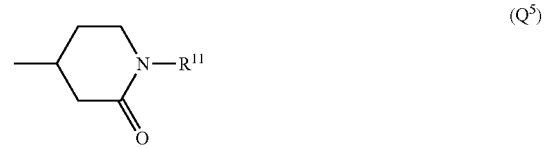

(Q⁵)

-continued

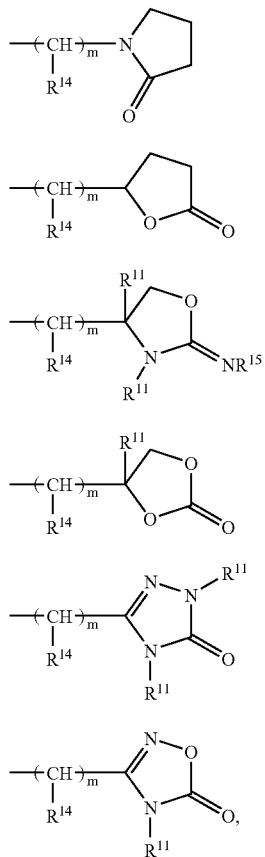

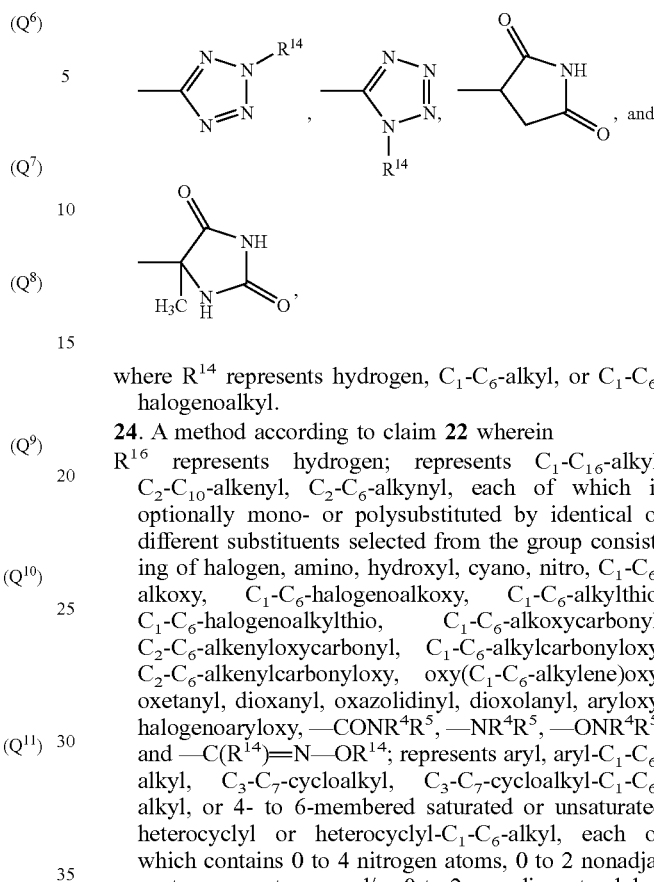

where
each $R^{11}$ may have identical or different meanings if two or more are present in the same heterocyclic group, m represents 0, 1, 2 or 3, where each repeat unit —(CHR$^{14}$)— in the side chain of a heterocyclic grouping optionally has identical or different meaning when m represents 2 or 3, G represents oxygen or sulphur, $R^{19}$ and $R^{20}$ independently of one another represent hydrogen $C_1$-$C_6$-alkyl or $R^{19}$ and $R^{20}$ together represent $C_2$-$C_4$-alkylene, $R^{21}$ represents hydrogen; represents $C_1$-$C_6$-alkyl that is optionally mono- or polysubstituted by identical or different substituents selected from the group consisting of $C_1$-$C_6$-alkylcarbonyloxy, and $C_1$-$C_6$-alkoxy; or represents aryl that is optionally mono- or polysubstituted by identical or different substituents selected from the group consisting of halogen, cyano, $C_1$-$C_6$-alkyl, $C_1$-$C_6$-halogenoalkyl, $C_1$-$C_6$-alkylcarbonyl, $C_1$-$C_{10}$-alkoxycarbonyl, and $C_3$-$C_5$-alkylene, $R^{22}$ represents hydrogen, $C_1$-$C_6$-alkyl, or $C_1$-$C_6$-alkoxy-$C_1$-$C_6$-alkyl, and $R^{23}$ represents hydrogen, amino, $C_1$-$C_6$-alkyl, or $C_1$-$C_6$-alkoxy-$C_1$-$C_6$-alkyl.

23. A method according to claim 22 wherein R represents a carboxylic acid bioisostere selected from the group consisting of where $R^{14}$ represents hydrogen, $C_1$-$C_6$-alkyl, or $C_1$-$C_6$-halogenoalkyl.

24. A method according to claim 22 wherein
$R^{16}$ represents hydrogen; represents $C_1$-$C_{16}$-alkyl, $C_2$-$C_{10}$-alkenyl, $C_2$-$C_6$-alkynyl, each of which is optionally mono- or polysubstituted by identical or different substituents selected from the group consisting of halogen, amino, hydroxyl, cyano, nitro, $C_1$-$C_6$-alkoxy, $C_1$-$C_6$-halogenoalkoxy, $C_1$-$C_6$-alkylthio, $C_1$-$C_6$-halogenoalkylthio, $C_1$-$C_6$-alkoxycarbonyl, $C_2$-$C_6$-alkenyloxycarbonyl, $C_1$-$C_6$-alkylcarbonyloxy, $C_2$-$C_6$-alkenylcarbonyloxy, oxy($C_1$-$C_6$-alkylene)oxy, oxetanyl, dioxanyl, oxazolidinyl, dioxolanyl, aryloxy, halogenoaryloxy, —CONR$^4$R$^5$, —NR$^4$R$^5$, —ONR$^4$R$^5$, and —C(R$^{14}$)=N—OR$^{14}$; represents aryl, aryl-$C_1$-$C_6$-alkyl, $C_3$-$C_7$-cycloalkyl, $C_3$-$C_7$-cycloalkyl-$C_1$-$C_6$-alkyl, or 4- to 6-membered saturated or unsaturated heterocyclyl or heterocyclyl-$C_1$-$C_6$-alkyl, each of which contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, $C_1$-$C_6$-halogenoalkylthio, $C_1$-$C_6$-alkoxycarbonyl, and $C_1$-$C_6$-alkylcarbonyloxy; represents —NR$^4$R$^5$; or represents Q, and $R^{18}$ represents hydrogen, hydroxyl, amino, $C_1$-$C_6$-alkyl, or $C_2$-$C_6$-alkenyl; represents $C_3$-$C_7$-cycloalkyl, $C_3$-$C_7$-cycloalkyl-$C_1$-$C_6$-alkyl, aryl, aryl-$C_1$-$C_6$-alkyl, or heteroaryl or heteroaryl-$C_1$-$C_6$-alkyl, each of which contains 0 to 4 nitrogen atoms, 0 to 2 nonadjacent oxygen atoms, and/or 0 to 2 nonadjacent sulphur atoms, each of which radicals is optionally mono- or polysubstituted by identical or different substituents selected from the group consisting of halogen, hydroxyl, $C_1$-$C_6$-alkyl, $C_1$-$C_6$-halogenoalkyl, $C_1$-$C_6$-alkoxy, $C_1$-$C_6$-halogenoalkoxy, $C_1$-$C_6$-alkylthio, $C_1$-$C_6$-halogenoalkylthio, and oxy($C_1$-$C_6$-alkylene)oxy; or represents —S(O)$_p$R$^3$, —OR$^{14}$, or —NR$^4$R$^5$.

25. A method according to claim 19 wherein
$R^1$ and $R^2$ independently of one another represent hydrogen, fluorine, chlorine, bromine, nitro, cyano, $C_1$-$C_4$-alkyl, $C_1$-$C_4$-halogenoalkyl having 1 to 9 fluorine, chlorine and/or bromine atoms, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine, and/or bromine atoms, $C_2$-$C_4$-alkenyl, $C_2$-$C_4$-alkynyl, —S(O)$_p$R$^3$, —NR$^4$R$^5$, —COR$^6$, —CO$_2$R$^7$, —CSR$^6$, —CONR$^4$R$^5$, —NHCO$_2$R$^8$, C$_3$-C$_6$-cycloalkyl; or represent aryl, aryl-C$_1$-C$_4$-alkyl, or 5- or 6-membered saturated or unsaturated heterocyclyl that contains 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents selected from the group consisting of fluorine, chlorine, bromine, C$_1$-C$_4$-alkyl, C$_1$-C$_4$-halogenoalkyl having 1 to 9 fluorine, chlorine, and/or bromine atoms, C$_1$-C$_4$-alkoxy, and C$_1$-C$_4$-halogenoalkoxy having 1 to 9 fluorine, chlorine, and/or bromine atoms, or R$^1$ and R$^2$ together represent C$_3$-C$_5$-alkylene or C$_3$-C$_4$-alkenylene, where the carbon chain are optionally interrupted by 1 or 2 heteroatoms that are 0 to 2 nitrogen atoms and/or 0 or 1 oxygen atom and where the resulting ring is optionally mono- to tetrasubstituted by identical or different substituents from the group consisting of fluorine, chlorine, bromine and C$_1$-C$_4$-alkyl, X represents fluorine, chlorine, bromine, nitro, cyano, hydroxyl, C$_1$-C$_4$-alkyl, C$_1$-C$_4$-halogenoalkyl having 1 to 9 fluorine, chlorine, and/or bromine atoms, C$_1$-C$_4$-alkoxy, C$_1$-C$_4$-halogenoalkoxy having 1 to 9 fluorine, chlorine, and/or bromine atoms, C$_1$-C$_4$-alkylthio, C$_1$-C$_4$-halogenoalkylthio having 1 to 9 fluorine, chlorine, and/or bromine atoms, C$_2$-C$_4$-alkenyl, C$_2$-C$_4$-alkynyl, —S(O)$_p$R$^3$, —NR$^4$R$^5$, —COR$^6$, —CO$_2$R$^7$, —CSR$^6$, —CONR$^4$R$^5$, —NHCO$_2$R$^8$, C$_3$-C$_6$-cycloalkyl, aryl, aryl-C$_1$-C$_4$-alkyl, 5- or 6-membered saturated or unsaturated heterocyclyl that contains 0 to 3 nitrogen atoms, 0 to 2 nonadjacent oxygen atoms, and/or 0 to 2 nonadjacent sulphur atoms, or when n represents 2, two adjacent radicals X together optionally represent C$_3$-C$_4$-alkylene or C$_3$-C$_4$-alkenylene, where the carbon chain may be interrupted by 1 or 2 heteroatoms that are 0 to 2 nitrogen atoms and/or 0 or 1 oxygen atom, n represents 0, 1 or 2, with X representing identical or different radicals when n represents 2, Y represents a direct bond, oxygen, —S(O)$_p$—, or —NR$^9$—, p represents 0, 1 or 2, Z represents —(CH$_2$)$_r$—, —(CH$_2$)$_t$—(CHR$^{10}$)—(CH$_2$)$_w$—, —(CH$_2$)$_r$—C(O)—(CH$_2$)$_t$—, —(CH$_2$)$_r$—O—(CH$_2$)$_t$—, —(CH$_2$)$_r$—S(O)$_p$—(CH$_2$)$_t$—, —(CH$_2$)$_r$—N(R$^{11}$)—(CH$_2$)$_t$—, or —(CH$_2$)$_t$—C(R$^{12}$)=C(R$^{13}$)—(CH$_2$)$_w$—, r represents 1, 2, 3 or 4, t and w independently of one another represent 0, 1, 2, 3 or 4, R represents the group

or represents a carboxylic acid bioisostere (acid mimic) selected from the group consisting of

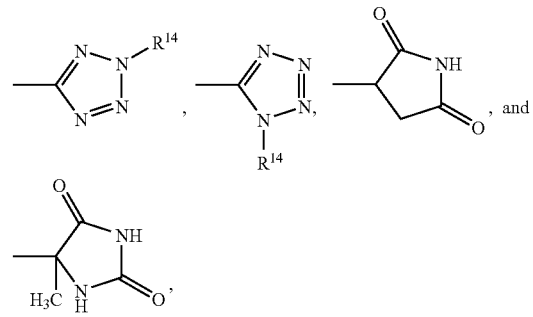

A represents oxygen or sulphur,

E represents —OR$^{16}$, —SR$^{16}$, —O-M, —S-M, or —NR$^{17}$R$^{18}$,

M represents ammonium which is optionally mono- to tetrasubstituted by identical or different substituents selected from the group consisting of C$_1$-C$_4$-alkyl, phenyl, benzyl, and phenylethyl; or represents a sodium cation (Na$^+$) or a potassium cation (K$^+$); or represents a magnesium cation (Mg$^{2+}$) or a calcium cation (Ca$^{2+}$) forming a salt with two molecules of a compound of formula (I), R$^3$ represents hydrogen, C$_1$-C$_4$-alkyl, C$_1$-C$_4$-halogenoalkyl having 1 to 9 fluorine, chlorine, and/or bromine atoms, C$_3$-C$_6$-cycloalkyl, or C$_3$-C$_6$-cycloalkyl-C$_1$-C$_4$-alkyl; represents aryl, aryl-C$_1$-C$_4$-alkyl, 5- or 6-membered saturated or unsaturated heterocyclyl or heterocyclyl-C$_1$-C$_4$-alkyl, each of which contain 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents selected from the group consisting of fluorine, chlorine, bromine, C$_1$-C$_4$-alkyl, C$_1$-C$_4$-halogenoalkyl having 1 to 9 fluorine, chlorine, and/or bromine atoms, C$_1$-C$_4$-alkoxy, C$_1$-C$_4$-halogenoalkoxy having 1 to 9 fluorine, chlorine, and/or bromine atoms, C$_1$-C$_4$-alkylthio, and C$_1$-C$_4$-halogenoalkylthio having 1 to 9 fluorine, chlorine, and/or bromine atoms, R$^4$ represents hydrogen, C$_1$-C$_4$-alkyl, C$_1$-C$_4$-halogenoalkyl having 1 to 9 fluorine, chlorine, and/or bromine atoms, C$_3$-C$_6$-cycloalkyl, C$_1$-C$_4$-alkylcarbonyl, R$^5$ represents hydrogen, amino, formyl, C$_1$-C$_4$-alkyl, C$_2$-C$_4$-alkenyl, C$_2$-C$_4$-alkynyl, C$_1$-C$_4$-halogenoalkyl having 1 to 9 fluorine, chlorine, and/or bromine atoms, C$_3$-C$_6$-cycloalkyl, C$_1$-C$_4$-alkoxy, C$_1$-C$_4$-alkoxy-C$_1$-C$_4$-alkyl, C$_1$-C$_4$-alkylcarbonyl, C$_1$-C$_4$alkoxycarbonyl, or oxamoyl, or R$^4$ and R$^5$ together represent C$_1$-C$_4$-alkylidene; or represent benzylidene that is optionally mono- to tetrasubstituted by identical or different substituents selected from the group consisting of fluorine, chlorine, bromine, nitro, C$_1$-C$_4$-alkyl, and C$_1$-C$_4$-halogenoalkyl having 1 to 9 fluorine, chlorine, and/or bromine atoms; or R$^4$ and R$^5$ together with the nitrogen atom to which they are attached represent a 5- or 6-membered saturated or unsaturated heterocycle that optionally contains a further nitrogen, oxygen, or sulphur atom and is optionally be mono- to tetrasubstituted by identical or different C$_1$-C$_4$-alkyl, $R^6$ represents hydrogen, $C_1$-$C_4$-alkyl, $C_1$-$C_4$-halogenoalkyl having 1 to 9 fluorine, chlorine, and/or bromine atoms, or aryl-$C_1$-$C_4$-alkyl, $R^7$ represents hydrogen, $C_1$-$C_4$-alkyl, $C_1$-$C_4$-halogenoalkyl having 1 to 9 fluorine, chlorine, and/or bromine atoms, $C_3$-$C_6$-cycloalkyl, $C_3$-$C_6$-cycloalkyl-$C_1$-$C_4$-alkyl, aryl, or aryl-$C_1$-$C_4$-alkyl, $R^8$ represents $C_1$-$C_4$-alkyl or $C_1$-$C_4$-halogenoalkyl having 1 to 9 fluorine, chlorine, and/or bromine atoms, $R^9$ represents hydrogen, $C_1$-$C_4$-alkyl, $C_1$-$C_4$-halogenoalkyl having 1 to 9 fluorine, chlorine, and/or bromine atoms, $C_3$-$C_6$-cycloalkyl, $C_3$-$C_6$-cycloalkyl-$C_1$-$C_4$-alkyl; or represents aryl, aryl-$C_1$-$C_4$-alkyl, 5- or 6-membered saturated or unsaturated heterocyclyl or heterocyclyl-$C_1$-$C_4$-alkyl, which contain 0 to 3 nitrogen atoms, 0 to 2 nonadjacent oxygen atoms and/or 0 to 2 nonadjacent sulphur atoms, each of which radicals is optionally mono- to tetrasubstituted by identical or different substituents selected from the group consisting of fluorine, chlorine, bromine, $C_1$-$C_4$-alkyl, $C_1$-$C_4$-halogenoalkyl having 1 to 9 fluorine, chlorine, and/or bromine atoms, $C_1$-$C_4$-alkoxy, $C_1$-$C_4$-halogenoalkoxy having 1 to 9 fluorine, chlorine, and/or bromine atoms, $C_1$-$C_4$-alkylthio and $C_1$-$C_4$-halogenoalkylthio having 1 to 9 fluorine, chlorine and/or bromine atoms, $R^{10}$ represents fluorine, chlorine, bromine, iodine, $C_1$-$C_4$-alkyl, $C_1$-$C_4$-alkylcarbonyl, $C_1$-$C_4$-alkoxycarbonyl, $C_3$-$C_6$-cycloalkyl, or $C_3$-$C_6$-cycloalkyl-$C_1$-$C_4$-alkyl; or represents aryl or aryl-$C_1$-$C_4$-alkyl that are optionally mono- to tetrasubstituted in the aryl moiety by identical or different substituents selected from the group consisting of fluorine, chlorine, bromine, and $C_1$-$C_4$-alkyl, $R^{11}$ represents hydrogen or $C_1$-$C_4$-alkyl, $R^{12}$ and $R^{13}$ independently of one another represent hydrogen, hydroxyl, $C_1$-$C_4$-alkyl, or $C_1$-$C_4$-alkoxy, $R^{14}$ represents hydrogen, $C_1$-$C_4$-alkyl or $C_1$-$C_4$-halogenoalkyl having 1 to 9 fluorine, chlorine, and/or bromine atoms, $R^{15}$ represents hydrogen, $C_1$-$C_4$-alkyl, $C_1$-$C_4$-alkoxy, cyano or di($C_1$-$C_4$-alkyl)amino, $R^{16}$ represents hydrogen; represents $C_1$-$C_6$-alkyl, decyl, dodecyl, tetradecyl, hexadecyl, $C_2$-$C_6$-alkenyl, decenyl, $C_2$-$C_4$-alkynyl, each of which is optionally mono- to tetrasubstituted by identical or different substituents selected from the group consisting of fluorine, chlorine, bromine, amino, hydroxyl, cyano, nitro, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine, and/or bromine atoms, $C_1$-$C_4$-alkoxycarbonyl, $C_2$-$C_4$-alkenyloxycarbonyl, $C_1$-$C_4$-alkylcarbonyloxy, $C_2$-$C_4$-alkenylcarbonyloxy, oxy($C_1$-$C_4$-alkylene)oxy, oxetanyl, dioxanyl, oxazolidinyl, dioxolanyl, aryloxy, halogenoaryloxy, —$CONR^4R^5$, —$NR^4R^5$, —$ONR^4R^5$, and —$C(R^{14})$=N—$OR^{14}$; represents aryl, aryl-$C_1$-$C_4$-alkyl, $C_3$-$C_6$-cycloalkyl, $C_3$-$C_6$-cycloalkyl-$C_1$-$C_4$-alkyl, 4- to 6-membered saturated or unsaturated, heterocyclyl or heterocyclyl-$C_1$-$C_4$-alkyl, each of which contains 0 to 3 nitrogen atoms, 0 to 2 nonadjacent oxygen atoms and/or 0 to 2 nonadjacent sulphur atoms, each of which radicals is optionally mono- to tetrasubstitutred by identical or different substituents selected from the group consisting of fluorine, chlorine, bromine, $C_1$-$C_4$-alkyl, $C_1$-$C_4$-halogenoalkyl having 1 to 9 fluorine, chlorine, and/or bromine atoms, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine and/or bromine atoms, $C_1$-$C_4$-alkoxycarbonyl and $C_1$-$C_4$-alkylcarbonyloxy; represents Q; represents $C_1$-$C_6$-alkyl, decyl, dodecyl, tetradecyl, hexadecyl, $C_2$-$C_6$-alkenyl, decenyl, or $C_2$-$C_4$-alkynyl, each of which is optionally substituted up to the maximum possible number by identical or different substituents from the group consisting of fluorine, chlorine and bromine; or represents aryl, aryl-$C_1$-$C_4$-alkyl, $C_3$-$C_6$-cycloalkyl, $C_3$-$C_6$-cycloalkyl-$C_1$-$C_4$-alkyl, 4- to 6-membered saturated or unsaturated heterocyclyl or heterocyclyl-$C_1$-$C_4$-alkyl, each of which contains 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents, where the substituents are those mentioned above or are hydroxyl or nitro, $R^{17}$ represents hydrogen or $C_1$-$C_6$-alkyl, $R^{18}$ represents hydrogen, hydroxyl, amino, $C_1$-$C_4$-alkyl, or $C_2$-$C_4$-alkenyl; represents $C_3$-$C_6$-cycloalkyl, $C_3$-$C_6$-cycloalkyl-$C_1$-$C_4$-alkyl, aryl, aryl-$C_1$-$C_4$-alkyl, or heteroaryl or heteroaryl-$C_1$-$C_4$-alkyl, each of which contains 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents from the group consisting of fluorine, chlorine, bromine, hydroxyl, $C_1$-$C_4$-alkyl, $C_1$-$C_4$-halogenoalkyl having 1 to 9 fluorine, chlorine and/or bromine atoms, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine, and/or bromine atoms, and oxy($C_1$-$C_4$-alkylene)oxy; represents —$S(O)_pR^3$, —$OR^{14}$ or —$NR^4R^5$; represents $C_1$-$C_4$-alkyl or $C_2$-$C_4$-alkenyl, each of which is mono- to tetrasubstituted by identical or different substituents selected from the group consisting of fluorine, chlorine, bromine, amino, hydroxyl, cyano, nitro, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine, and/or bromine atoms, $C_1$-$C_4$-alkoxycarbonyl, and $C_2$-$C_4$-alkenyloxycarbonyl; represents $C_1$-$C_4$-alkyl or $C_2$-$C_4$-alkenyl, each of which is optionally substituted up to the maximum possible number by identical or different substituents selected from the group consisting of fluorine, chlorine, and bromine; or represents $C_3$-$C_6$-cycloalkyl, $C_3$-$C_6$-cycloalkyl-$C_1$-$C_4$-alkyl, aryl, aryl-$C_1$-$C_4$-alkyl, or heteroaryl or heteroaryl-$C_1$-$C_4$-alkyl, each of which contains 0 to 3 nitrogen atoms, 0 to 2 nonadjacent oxygen atoms, and/or 0 to 2 nonadjacent sulphur atoms, each of which radicals is optionally mono- to tetrasubstituted by identical or different radicals, where the substituents are those mentioned above or are nitro or $C_1$-$C_6$-alkoxycarbonyl, or $R^{17}$ and $R^{18}$ together with the nitrogen atom to which they are attached represent a 5- or 6-membered saturated or unsaturated heterocycle that optionally contains 1 to 2 further heteroatoms including 0 to 2 nitrogen atoms, 0 or 1 oxygen atom, and/or 0 or 1 sulphur atom that are optionally mono- to trisubstituted by identical or different $C_1$-$C_4$-alkyl, and Q represents one of the groups

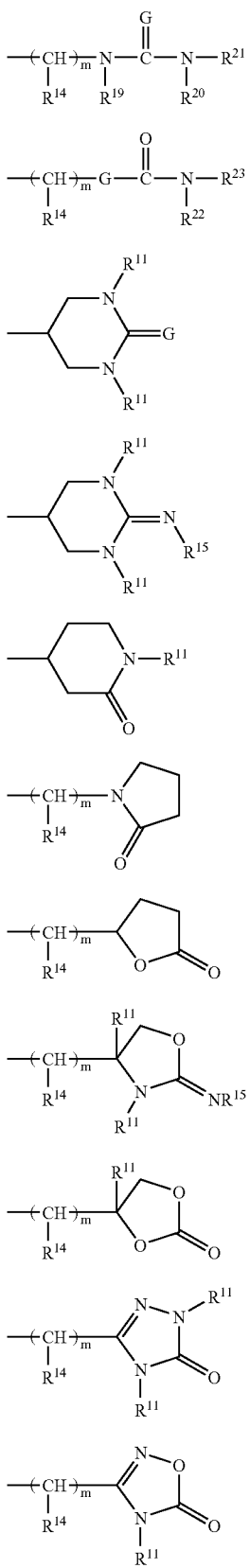

where each $R^{11}$ may have identical or different meanings when two or more $R^{11}$ are present in the same heterocyclic group, m represents 0, 1, 2 or 3, where each repeat unit —(CHR$^{14}$)— in the side chain of a heterocyclic grouping optionally has identical or different meanings when m represents 2 or 3, G represents oxygen or sulphur, $R^{19}$ and $R^{20}$ independently of one another represent hydrogen, $C_1$-$C_6$-alkyl or $R^{19}$ and $R^{20}$ together represent $C_2$-$C_3$-alkylene, $R^{21}$ represents hydrogen; represents $C_1$-$C_4$-alkyl that is optionally mono- or disubstituted by identical or different substituents selected from the group consisting of $C_1$-$C_4$-alkylcarbonyloxy and $C_1$-$C_4$-alkoxy; or represents aryl that is optionally mono- to tetrasubstituted by identical or different substituents selected from the group consisting of fluorine, chlorine, bromine, cyano, $C_1$-$C_4$-alkyl, $C_1$-$C_4$-halogenoalkyl having 1 to 9 fluorine, chlorine, and/or bromine atoms, $C_1$-$C_4$-alkylcarbonyl, $C_1$-$C_8$-alkoxycarbonyl, and $C_3$-$C_5$-alkylene, $R^{22}$ represents hydrogen, $C_1$-$C_4$-alkyl, or $C_1$-$C_4$-alkoxy-$C_1$-$C_4$-alkyl, and $R^{23}$ represents hydrogen, amino, $C_1$-$C_4$-alkyl or $C_1$-$C_4$-alkoxy-$C_1$-$C_4$-alkyl.

26. A method according to claim 25 wherein
R represents a carboxylic acid bioisostere selected from the group consisting of

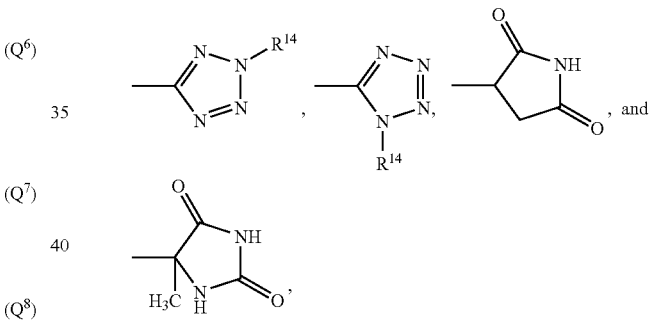

$R^{14}$ represents hydrogen, $C_1$-$C_4$-alkyl, or $C_1$-$C_4$-halogenoalkyl having 1 to 9 fluorine, chlorine, and/or bromine atoms.

27. A method according to claim 25 wherein
$R^{16}$ represents hydrogen; represents $C_1$-$C_6$-alkyl, decyl, dodecyl, tetradecyl, hexadecyl, $C_2$-$C_6$-alkenyl, decenyl, or $C_2$-$C_4$-alkynyl, each of which is optionally mono- to tetrasubstituted by identical or different substituents selected from the group consisting of fluorine, chlorine, bromine, amino, hydroxyl, cyano, nitro, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine, and/or bromine atoms, $C_1$-$C_4$-alkoxycarbonyl, $C_2$-$C_4$-alkenyloxycarbonyl, $C_1$-$C_4$-alkylcarbonyloxy, $C_2$-$C_4$-alkenylcarbonyloxy, oxy($C_1$-$C_4$-alkylene)oxy, oxetanyl, dioxanyl, oxazolidinyl, dioxolanyl, aryloxy, halogenoaryloxy, —CONR$^4$R$^5$, —NR$^4$R$^5$, —ONR$^4$R$^5$, and —C(R$^{14}$)=N—OR$^{14}$; represents aryl, aryl-$C_1$-$C_4$-alkyl, $C_3$-$C_6$-cycloalkyl, $C_3$-$C_6$-cycloalkyl-$C_1$-$C_4$-alkyl, 4- to 6-membered saturated or unsaturated, heterocyclyl or heterocyclyl-$C_1$-$C_4$-alkyl, each of which contains 0 to 3 nitrogen atoms, 0 to 2 nonadjacent oxygen atoms and/or 0 to 2 nonadjacent sulphur atoms, each of which radicals is optionally mono- to tetrasubstitutred by identical or different substituents selected from the group consisting of fluorine, chlorine, bromine, $C_1$-$C_4$-alkyl, $C_1$-$C_4$-halogenoalkyl having 1 to 9 fluorine, chlorine, and/or bromine atoms, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine, and/or bromine atoms, $C_1$-$C_4$-alkoxycarbonyl, and $C_1$-$C_4$-alkylcarbonyloxy; or represents Q, and $R^{18}$ represents hydrogen, hydroxyl, amino, $C_1$-$C_4$-alkyl, or $C_2$-$C_4$-alkenyl; represents $C_3$-$C_6$-cycloalkyl, $C_3$-$C_6$-cycloalkyl-$C_1$-$C_4$-alkyl, aryl, aryl-$C_1$-$C_4$-alkyl, or heteroaryl or heteroaryl-$C_1$-$C_4$-alkyl, each of which contains 0 to 3 nitrogen atoms, 0 to 2 nonadjacent oxygen atoms, and/or 0 to 2 nonadjacent sulphur atoms, each of which radicals is optionally mono- to tetrasubstituted by identical or different substituents from the group consisting of fluorine, chlorine, bromine, hydroxyl, $C_1$-$C_4$-alkyl, $C_1$-$C_4$-halogenoalkyl having 1 to 9 fluorine, chlorine and/or bromine atoms, $C_1$-$C_4$-alkoxy, $C_1$-$C_4$-halogenoalkoxy having 1 to 9 fluorine, chlorine, and/or bromine atoms, $C_1$-$C_4$-alkylthio, $C_1$-$C_4$-halogenoalkylthio having 1 to 9 fluorine, chlorine and/or bromine atoms, and oxy($C_1$-$C_4$-alkylene)oxy; or represents —$S(O)_pR^3$, —$OR^{14}$, or —$NR^4R^5$.

28. A method according to claim 19 wherein $R^1$ and $R^2$ independently of one another represent hydrogen, fluorine, chlorine, bromine, nitro, cyano, methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, —$CF_2CHFCF_3$, methoxy, ethoxy, n-propoxy, isopropoxy, n-butoxy, trifluoromethoxy, trichloromethoxy, —$OCH_2CF_3$, —$SCF_3$, —$SCHF_2$, —$SO_2Me$, —$SO_2CHF_2$, —$SO_2CF_3$, —$SOCHF_2$, —$SOCF_3$, —COMe, —$CO_2Me$, —$CO_2Et$, amino, cyclopentyl, or cyclohexyl; or represent phenyl, benzyl, pyridinyl, furyl, or furfuryl, each of which is optionally substituted by chlorine, bromine, methyl, ethyl, methoxy, ethoxy, trifluoromethyl, or trifluoromethoxy, or $R^1$ and $R^2$ together represent propylene, butylene, propenylene, butadienylene, —$(CH_2)_2$—O—$CH_2$—, —$(CH_2)_2$—NH—$CH_2$—, —CH=CH—N=CH—, or —CH=CCl—CH=CH—, X represents fluorine, chlorine, bromine, nitro, cyano, hydroxyl, methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$, —$CF_2CHFCF_3$, methoxy, ethoxy, n-propoxy, isopropoxy, n-butoxy, trifluoromethoxy, trichloromethoxy, —$OCH_2CF_3$, —$SCF_3$, —$SCHF_2$, —$SO_2Me$, —$SO_2CHF_2$, —$SO_2CF_3$, —$SOCHF_2$, —$SOCF_3$, —CH=$CH_2$, —C≡CH, amino, —NHMe, —$NMe_2$, —CHO, —COMe, —$CO_2Me$, —$CO_2Et$, —NHCOMe, cyclopentyl, cyclohexyl, phenyl, benzyl, furyl, thienyl, pyrrolyl, oxazolyl, isoxazyl, imidazyl, pyrazyl, thiazolyl, pyridyl, pyrimidinyl, pyridazyl, triazinyl, triazyl; or represents methylthio, ethylthio, n-propylthio, or isopropylthio; or when n represents 2, two adjacent radicals X together optionally represent propylene, butylene, propenylene or butadienylene, —$(CH_2)_2$—O—$CH_2$—, —$(CH_2)_2$—NH—$CH_2$—, or —CH=CH—N=CH—, n represents 0, 1 or 2, with X representing identical or different radicals when n represents 2, Y represents a direct bond, oxygen, —$S(O)_p$—, or —$NR^9$—, p represents 0, 1 or 2, Z represents —$CH_2$—, —$(CH_2)_2$—, —$(CH_2)_3$—, —$(CH_2)_4$—, —$(CHR^{10})$—, —$CH_2$—C(O)—$CH_2$—, —$CH_2$—NH—, —CH=CH—, —$CH_2$—CH=CH—, —CH=C(OH)—, —CH=C(OMe)—, or —$CH_2$—C(OMe)=CH—; or represents —$CH_2$—C(OEt)=CH—, R represents the group

A represents oxygen or sulphur,

E represents —$OR^{16}$, —$SR^{16}$, —O-M, —S-M, or —$NR^{17}R^{18}$,

M represents tetrabutylammonium, trimethylbenzylammonium; or represents a sodium cation ($Na^+$) or a potassium cation ($K^+$), or represents a magnesium cation ($Mg^{2+}$) or a calcium cation ($Ca^{2+}$), forming a salt with two molecules of a compound of formula (I), $R^4$ represents hydrogen, methyl, ethyl, n-propyl, isopropyl, n-butyl, sec-butyl, isobutyl, tert-butyl, or —COMe, $R^5$ represents hydrogen, amino, formyl, methyl, ethyl, n-propyl, isopropyl, n-butyl, sec-butyl, isobutyl, tert-butyl, vinyl, propargyl, methoxy, methoxymethyl, —COMe, —COEt, tert-butoxycarbonyl, or oxamoyl, or $R^4$ and $R^5$ together represent ethylidene, isopropylidene, sec-butylidene, or nitrobenzylidene; or $R^4$ and $R^5$ together with the nitrogen atom to which they are attached represent a 5- or 6-membered saturated or unsaturated heterocycle selected from the group consisting of morpholine, piperidine, thiomorpholine, pyrrolidine, tetrahydropyridine, which is optionally mono- or disubstituted by methyl, ethyl, n-propyl, isopropyl, n-butyl, sec-butyl, isobutyl, tert-butyl, $R^8$ represents methyl, ethyl, n-propyl, isopropyl, n-butyl, sec-butyl, isobutyl, tert-butyl, —$CF_3$, —$CCl_3$, —$CHF_2$, —$CClF_2$, —$CHCl_2$, —$CF_2CHFCl$, —$CF_2CH_2F$, —$CF_2CCl_3$, —$CH_2CF_3$, —$CF_2CHFCF_3$, —$CH_2CF_2H$, —$CH_2CF_2CF_3$, —$CF_2CF_2H$ or —$CF_2CHFCF_3$, $R^9$ represents hydrogen, methyl, ethyl, n-propyl, isopropyl, n-butyl, sec-butyl, isobutyl, tert-butyl, —$CH_2CF_3$, —$CH_2CF_2H$, —$CH_2CF_2CF_3$, cyclopropyl, cyclopentyl or cyclohexyl, $R^{10}$ represents fluorine, chlorine, bromine, methyl, ethyl, n-propyl, isopropyl, n-butyl, sec-butyl, isobutyl, tert-butyl, —COMe, —COEt, —$CO_2Me$, —$CO_2Et$, or cyclohexyl; represents phenyl or benzyl that are opitonally mono- to tetrasubstituted in the aryl moiety by identical or different substituents selected from the group consisting of fluorine, chlorine, bromine and methyl, $R^{11}$ represents hydrogen, methyl, ethyl, n-propyl, isopropyl, n-butyl, sec-butyl, isobutyl, tert-butyl, $R^{14}$ represents hydrogen, methyl, ethyl, n-propyl, isopropyl, n-butyl, sec-butyl, isobutyl, or tert-butyl, $R^{15}$ represents hydrogen, methyl, ethyl, n-propyl, isopropyl, n-butyl, sec-butyl, isobutyl, tert-butyl or cyano, $R^{16}$ represents hydrogen; represents methyl, ethyl, n-propyl, isopropyl, n-butyl, sec-butyl, isobutyl, tert-butyl, n-pentyl, isopentyl, siamyl, hexyl, n-decyl, n-dodecyl, n-tetradecyl, n-hexadecyl, vinyl, allyl, butenyl, 2-isopentenyl, hexenyl, n-decenyl, ethynyl, propynyl, butynyl, each of which is optionally mono- to trisubstituted by identical or different substituents selected from the group consisting of fluorine, chlorine, bromine, amino, hydroxyl, cyano, nitro, methoxy, ethoxy, isopropoxy, trifluoromethoxy, —OCH$_2$CF$_3$, trichloromethoxy, difluoromethoxy, methylthio, trifluoromethylthio, methoxycarbonyl, ethoxycarbonyl, isopropoxycarbonyl, tert-butoxycarbonyl, methylcarbonyloxy, vinylcarbonyloxy, —O—(CH$_2$)$_2$—O—, oxetanyl, dioxanyl, oxazolidinyl, dioxolanyl, phenoxy, fluorophenoxy, —CONR$^4$R$^5$, —NR$^4$R$^5$, —ONR$^4$R$^5$, and —CH=N—OCH$_3$; represents phenyl, benzyl, phenylethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, oxetanyl, oxazolanyl, dioxanyl, dioxolanyl, furyl, thienyl, pyrrolyl, oxazolyl, isoxazyl, imidazolyl, pyrazyl, thiazolyl, pyridinyl, pyrimidinyl, pyridazyl, triazinyl, triazolyl, tetrahydropyranyl, thietanyl, thietane dioxide, oxetanylmethyl, oxazolanylmethyl, dioxanylmethyl, dioxolanylmethyl, furylmethyl, thienylmethyl, pyrrolylmethyl, oxazolylmethyl, isoxazylmethyl, imidazolylmethyl, pyrazylmethyl, thiazolylmethyl, pyridinylmethyl, pyrimidinylmethyl, pyridazylmethyl, triazinylmethyl, triazolylmethyl, tetrahydropyranylmethyl, thietanylmethyl, thietane dioxide methyl, oxetanylethyl, oxazolanylethyl, dioxanylethyl, dioxolanylethyl, furylethyl, thienylethyl, pyrrolylethyl, oxazolylethyl, isoxazylethyl, imidazolylethyl, pyrazylethyl, thiazolylethyl, pyridinylethyl, pyrimidinylethyl, pyridazylethyl, triazinylethyl, triazolylethyl, tetrahydropyranylethyl, thietanylethyl, thietane dioxide ethyl, each of which is optionally mono- to trisubstituted by identical or different substituents selected from the group consisting of fluorine, chlorine, bromine, methyl, ethyl, n-propyl, isopropyl, n-butyl, sec-butyl, isobutyl, tert-butyl, —CF$_3$, —CCl$_3$, —CHF$_2$, —CClF$_2$, —CHCl$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, methoxy, ethoxy, n-propoxy, n-butoxy, trifluoromethoxy, trichloromethoxy, methylthio, trifluoromethylthio, —CO$_2$Me, —CO$_2$Et, methylcarbonyloxy and ethylcarbonyloxy; represents Q; represents methyl, ethyl, n-propyl, isopropyl, n-butyl, sec-butyl, isobutyl, tert-butyl, n-pentyl, isopentyl, siamyl, hexyl, n-decyl, n-dodecyl, n-tetradecyl, n-hexadecyl, vinyl, allyl, butenyl, 2-isopentenyl, hexenyl, n-decenyl, ethynyl, propynyl, or butynyl, each of which is optionally substituted up to the maximum possible number by identical or different radicals selected from the group consisting of fluorine, chlorine and bromine; or represents phenyl, benzyl, phenylethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, oxetanyl, oxazolanyl, dioxanyl, dioxolanyl, furyl, thienyl, pyrrolyl, oxazolyl, isoxazyl, imidazolyl, pyrazyl, thiazolyl, pyridinyl, pyrimidinyl, pyridazyl, triazinyl, triazolyl, tetrahydropyranyl, thietanyl, thietane dioxide, oxetanylmethyl, oxazolanylmethyl, dioxanylmethyl, dioxolanylmethyl, furylmethyl, thienylmethyl, pyrrolylmethyl, oxazolylmethyl, isoxazylmethyl, imidazolylmethyl, pyrazylmethyl, thiazolylmethyl, pyridinylmethyl, pyrimidinylmethyl, pyridazylmethyl, triazinylmethyl, triazolylmethyl, tetrahydropyranylmethyl, thietanylmethyl, thietane dioxide methyl, oxetanylethyl, oxazolanylethyl, dioxanylethyl, dioxolanylethyl, furylethyl, thienylethyl, pyrrolylethyl, oxazolylethyl, isoxazylethyl, imidazolylethyl, pyrazylethyl, thiazolylethyl, pyridinylethyl, pyrimidinylethyl, pyridazylethyl, triazinylethyl, triazolylethyl, tetrahydropyranylethyl, thietanylethyl, or thietane dioxide ethyl, each of which is optionally mono- to tetrasubstituted by identical or different substituents, where the substituents are those mentioned above or are hydroxyl and nitro, $R^{17}$ represents hydrogen, methyl or ethyl, $R^{18}$ represents hydrogen, hydroxyl, amino, methyl, ethyl, n-propyl, isopropyl, n-butyl, sec-butyl, isobutyl, tert-butyl, vinyl, allyl; represents cyclopropyl, cyclopropylmethyl, cyclohexyl, phenyl, benzyl, phenylethyl, pyridinyl, pyridinylmethyl, pyridinylethyl, furyl, or furfuryl, each of which is optionally mono- to trisubstituted by identical or different substituents selected from the group consisting of fluorine, chlorine, hydroxyl, methyl, ethyl, n-propyl, isopropyl, n-butyl, sec-butyl, isobutyl, tert-butyl, trifluoromethyl, trichloromethyl, methoxy, ethoxy, trifluoromethoxy, methylthio, trifluoromethylthio, and —O—CH$_2$—O—; represents —SO$_2$Me, —SO$_2$Et, or —NR$^4$R$^5$, represents methyl, ethyl, n-propyl, isopropyl, n-butyl, sec-butyl, isobutyl, tert-butyl, vinyl, or allyl, each of which is optionally mono- to trisubstituted by identical or different substituents selected from the group consisting of fluorine, chlorine, bromine, amino, hydroxyl, cyano, nitro, methoxy, ethoxy, isopropoxy, trifluoromethoxy, —OCH$_2$CF$_3$, trichloromethoxy, difluoromethoxy, methylthio, trifluoromethylthio, methoxycarbonyl, ethoxycarbonyl, isopropoxycarbonyl, and tert-butoxycarbonyl; represents methyl, ethyl, n-propyl, isopropyl, n-butyl, sec-butyl, isobutyl, tert-butyl, vinyl, allyl, each of which is optionally substituted up to the maximum possible number by identical or different substituents selected from the group consisting of fluorine, chlorine, and bromine; or represents cyclopropyl, cyclopropylmethyl, cyclohexyl, phenyl, benzyl, phenylethyl, pyridinyl, pyridinylmethyl, pyridinylethyl, furyl, furfuryl, each of which is optionally mono- to trisubstituted by identical or different substituents, where the substituents are those mentioned above or are nitro, methoxycarbonyl and ethoxycarbonyl, or $R^{17}$ and $R^{18}$ together with the nitrogen atom to which they are attached represent a 5- or 6-membered saturated heterocycle selected from the group consisting of piperazine, morpholine, piperidine, pyrrolidine, which may optionally be mono- to trisubstituted by identical or different substituents selected from the group consisting of methyl, ethyl, n-propyl and isopropyl, and Q represents one of the groups

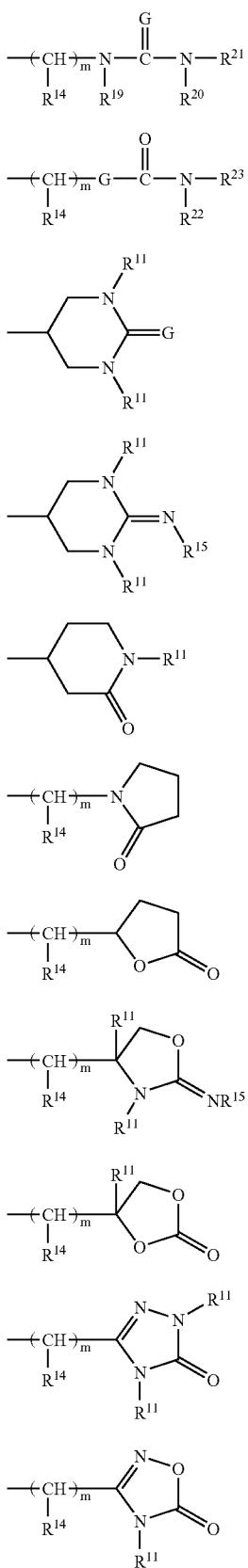

where
each $R^{11}$ may have identical or different meanings when two or more $R^{11}$ are present in the same heterocyclic group, m represents 0, 1, 2 or 3, where each repeat unit —(CHR$^{14}$)— in the side chain of a heterocyclic grouping optionally has the same or different meanings when m represents 2 or 3, G represents oxygen or sulphur, $R^{19}$ and $R^{20}$ independently of one another represent hydrogen, methyl, ethyl, n-propyl, isopropyl, n-butyl, sec-butyl, isobutyl, or tert-butyl; or $R^{19}$ and $R^{20}$ together represent —(CH$_2$)$_2$— or —(CH$_2$)$_3$—, $R^{21}$ represents hydrogen represents methyl, ethyl, n-propyl, isopropyl, n-butyl, sec-butyl, isobutyl, or tert-butyl, each of which is optionally monosubstituted by tert-butylcarbonyloxy or methoxy; or represents phenyl that is optionally mono- or disubstituted by identical or different substituents selected from the group consisting of chlorine, cyano, methyl, ethyl, tert-butyl, trifluoromethyl, sec-butyloxycarbonyl, tert-butyloxycarbonyl, n-octyloxycarbonyl, and —(CH$_2$)$_4$—, $R^{22}$ represents hydrogen, methyl, ethyl or methoxymethyl, and $R^{23}$ represents hydrogen, amino, methyl, ethyl, n-propyl, isopropyl or methoxymethyl.

29. A method according to claim 28 wherein
X represents fluorine, chlorine, bromine, nitro, cyano, hydroxyl, methyl, ethyl, n-propyl, isopropyl, n-butyl, sec-butyl, isobutyl, tert-butyl, —CF$_3$, —CCl$_3$, —CHF$_2$, —CClF$_2$, —CHCl$_2$, —CF$_2$CHFCl, —CF$_2$CH$_2$F, —CF$_2$CCl$_3$, —CH$_2$CF$_3$, —CF$_2$CHFCF$_3$, —CH$_2$CF$_2$H, —CH$_2$CF$_2$CF$_3$, —CF$_2$CF$_2$H, —CF$_2$CHFCF$_3$, methoxy, ethoxy, n-propoxy, isopropoxy, n-butoxy, trifluoromethoxy, trichloromethoxy, —OCH$_2$CF$_3$, —SCF$_3$, —SCHF$_2$, —SO$_2$Me, —SO$_2$CHF$_2$, —SO$_2$CF$_3$, —SOCHF$_2$, —SOCF$_3$, —CH=CH$_2$, —C≡CH, amino, —NHMe, —NMe$_2$, —CHO, —COMe, —CO$_2$Me, —CO$_2$Et, —NHCOMe, cyclopentyl, cyclohexyl, phenyl, benzyl, furyl, thienyl, pyrrolyl, oxazolyl, isoxazyl, imidazyl, pyrazyl, thiazolyl, pyridyl, pyrimidinyl, pyridazyl, triazinyl, or triazyl; or when n represents 2, two adjacent radicals X together optionally represent propylene, butylene, propenylene or butadienylene, —(CH$_2$)$_2$—O—CH$_2$—, —(CH$_2$)$_2$—NH—CH$_2$—, or —CH=CH—N=CH—;

Z represents —CH$_2$—, —(CH$_2$)$_2$—, —(CH$_2$)$_3$—, —(CH$_2$)$_4$—, —(CHR$^{10}$)—, —CH$_2$—C(O)—CH$_2$—, —CH$_2$—NH—, —CH=CH—, —CH$_2$—CH=CH—, —CH=C(OH)—, —CH=C(OMe)—, or —CH$_2$—C(OMe)=CH—;

$R^{16}$ represents hydrogen; represents methyl, ethyl, n-propyl, isopropyl, n-butyl, sec-butyl, isobutyl, tert-butyl, n-pentyl, isopentyl, siamyl, hexyl, n-decyl, n-dodecyl, n-tetradecyl, n-hexadecyl, vinyl, allyl, butenyl, 2-isopentenyl, hexenyl, n-decenyl, ethynyl, propynyl, or butinyl, each of which is optionally mono- to trisubstituted by identical or different substituents selected from the group consisting of fluorine, chlorine, bromine, amino, hydroxyl, cyano, nitro, methoxy, ethoxy, isopropoxy, trifluoromethoxy, —OCH$_2$CF$_3$, trichloromethoxy, difluoromethoxy, methylthio, trifluoromethylthio, methoxycarbonyl, ethoxycarbonyl, isopropoxycarbonyl, tert-butoxycarbonyl, methylcarbonyloxy, vinylcarbonyloxy, —O—(CH$_2$)$_2$—O—, oxetanyl, dioxanyl, oxazolidinyl, dioxolanyl, phenoxy, fluorophenoxy, —CONR⁴R⁵, —NR⁴R⁵, —ONR⁴R⁵ and —CH═N—OCH₃; represents phenyl, benzyl, phenylethyl, cyclopropyl, cyclobutyl, cyclopentyl, cyclohexyl, cyclopropylmethyl, cyclobutylmethyl, cyclopentylmethyl, cyclohexylmethyl, cyclopropylethyl, cyclobutylethyl, cyclopentylethyl, cyclohexylethyl, oxetanyl, oxazolanyl, dioxanyl, dioxolanyl, furyl, thienyl, pyrrolyl, oxazolyl, isoxazyl, imidazolyl, pyrazyl, thiazolyl, pyridinyl, pyrimidinyl, pyridazyl, triazinyl, triazolyl, tetrahydropyranyl, thietanyl, thietane dioxide, oxetanylmethyl, oxazolanylmethyl, dioxanylmethyl, dioxolanylmethyl, furylmethyl, thienylmethyl, pyrrolylmethyl oxazolylmethyl, isoxazylmethyl, imidazolylmethyl, pyrazylmethyl, thiazolylmethyl, pyridinylmethyl, pyrimidinylmethyl, pyridazylmethyl, triazinylmethyl, triazolylmethyl, tetrahydropyranylmethyl, thietanylmethyl, thietane dioxide methyl, oxetanylethyl, oxazolanylethyl, dioxanylethyl, dioxolanylethyl, furylethyl, thienylethyl, pyrrolylethyl, oxazolylethyl, isoxazylethyl, imidazolylethyl, pyrazylethyl, thiazolylethyl, pyridinylethyl, pyrimidinylethyl, pyridazylethyl, triazinylethyl, triazolylethyl, tetrahydropyranylethyl, thietanylethyl, thietane dioxide ethyl, each of which is optionally mono- to trisubstituted by identical or different substituents selected from the group consisting of fluorine, chlorine, bromine, methyl, ethyl, n-propyl, isopropyl, n-butyl, sec-butyl, isobutyl, tert-butyl, —CF₃, —CCl₃, —CHF₂, —CClF₂, —CHCl₂, —CF₂CHFCl, —CF₂CH₂F, —CF₂CCl₃, —CH₂CF₃, —CF₂CHFCF₃, —CH₂CF₂H, —CH₂CF₂CF₃, —CF₂CF₂H, —CF₂CHFCF₃, methoxy, ethoxy, n-propoxy, n-butoxy, trifluoromethoxy, trichloromethoxy, methylthio, trifluoromethylthio, —CO₂Me, —CO₂Et, methylcarbonyloxy and ethylcarbonyloxy; or represents Q, and R¹⁸ represents hydrogen, hydroxyl, amino, methyl, ethyl, n-propyl, isopropyl, n-butyl, sec-butyl, isobutyl, tert-butyl, vinyl, or allyl; represents cyclopropyl, cyclopropylmethyl, cyclohexyl, phenyl, benzyl, phenylethyl, pyridinyl, pyridinylmethyl, pyridinylethyl, furyl, or furfuryl, each of which is optionally mono- to trisubstituted by identical or different substituents selected from the group consisting of fluorine, chlorine, hydroxyl, methyl, ethyl, n-propyl, isopropyl, n-butyl, sec-butyl, isobutyl, tert-butyl, trifluoromethyl, trichloromethyl, methoxy, ethoxy, trifluoromethoxy, methylthio, trifluoromethylthio, and —O—CH₂—O—; or represents —SO₂Me, —SO₂Et, or —NR⁴R⁵.

30. A process for preparing pyridylpyrimidines of formula (I)

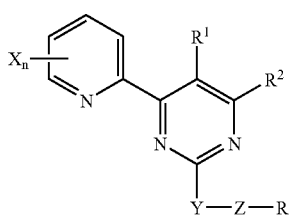

in which
R¹ and R² independently of one another represent hydrogen, halogen, nitro, cyano, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)ₚR³, —NR⁴R⁵, —COR⁶, —CO₂R⁷, —CSR⁶, —CONR⁴R⁵, —NHCO₂R⁸, or cycloalkyl; or represent optionally substituted aryl, or arylalkyl, saturated or unsaturated heterocyclyl having 1 to 4 heteroatoms from the group consisting of nitrogen, oxygen and sulphur, or R¹ and R² together represent alkylene or alkenylene, where the carbon chain is optionally interrupted by 1 to 3 heteroatoms selected from the group consisting of nitrogen and oxygen and the resulting ring is optionally substituted by halogen or alkyl, X represents halogen, nitro, cyano, hydroxyl, alkyl, halogenoalkyl, alkoxy, halogenoalkoxy, alkylthio, halogenoalkylthio, alkenyl, alkynyl, alkenyloxy, halogenoalkenyloxy, alkynyloxy, halogenoalkynyloxy, —S(O)ₚR³, —NR⁴R⁵, —COR⁶, —CO₂R⁷, —CSR⁶, —CONR⁴R⁵, —NHCO₂R⁸, cycloalkyl, aryl, arylalkyl, or saturated or unsaturated heterocyclyl having 1 to 4 heteroatoms selected from the group consisting of nitrogen, oxygen and sulphur; or, when n represents 2, 3 or 4, two adjacent X together optionally represent alkylene or alkenylene, where the carbon chain is optionally interrupted by 1 or 2 heteroatoms selected from the group consisting of nitrogen and oxygen, n represents 0, 1, 2, 3 or 4, with X representing identical or different radicals when n represents 2, 3 or 4, Y represents a direct bond, oxygen, —S(O)ₚ—, or —NR⁹—, p represents 0, 1 or 2, Z represents —(CH₂)ᵣ—, —(CH₂)ₜ—(CHR¹⁰)—(CH₂)ᵥᵥ—, —(CH₂)ᵣ—C(O)—(CH₂)ₜ—, —(CH₂)ᵣ—O—(CH₂)ₜ—, —(CH₂)ᵣ—S(O)ₚ—(CH₂)ₜ—, —(CH₂)ᵣ—N(R¹¹)—(CH₂)ₜ—, or —(CH₂)ₜ—C(R¹²)═C(R¹³)—(CH₂)ᵥᵥ—, r represents 1, 2, 3, 4, 5 or 6, t and w independently of one another represent 0, 1, 2, 3 or 4, R represents the group

or represents a carboxylic acid bioisostere (acid mimic) selected from the group consisting of

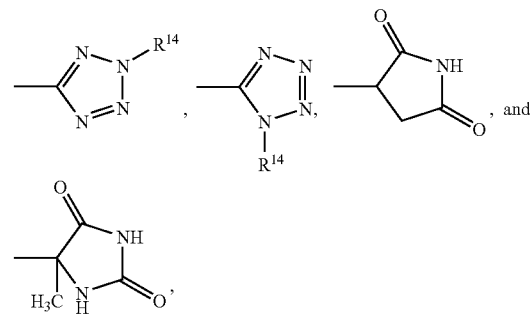

A represents oxygen, sulphur, or NR¹⁵,

E represents —OR¹⁶, —SR¹⁶, —O-M, —S-M, or NR¹⁷R¹⁸,

M represents ammonium that is optionally substituted by alkyl, aryl, or arylalkyl; or represents an alkali metal ion, or represents an alkaline earth metal ion forming a salt with two molecules of a compound of formula (I), $R^3$ represents hydrogen, alkyl, halogenoalkyl, cycloalkyl, cycloalkylalkyl; or represents optionally halogen-, alkyl-, halogenoalkyl-, alkoxy-, halogenoalkoxy-, alkylthio-, halogenoalkylthio-substituted aryl, arylalkyl, or saturated or unsaturated heterocyclyl or heterocyclylalkyl having 1 to 4 heteroatoms selected from the group consisting of nitrogen, oxygen and sulphur, $R^4$ represents hydrogen, alkyl, halogenoalkyl, cycloalkyl or alkylcarbonyl, $R^5$ represents hydrogen, amino, formyl, alkyl, alkenyl, alkynyl, halogenoalkyl, cycloalkyl, alkoxy, alkoxyalkyl, alkylcarbonyl, alkoxycarbonyl, or oxamoyl, or $R^4$ and $R^5$ together represent alkylidene; or represent optionally halogen-, nitro-, alkyl-, halogenoalkyl-substituted benzylidene; or $R^4$ and $R^5$ together with the nitrogen atom to which they are attached represent a saturated or unsaturated heterocycle that optionally contains a further nitrogen, oxygen or sulphur atom and is optionally be substituted by alkyl, $R^6$ represents hydrogen, alkyl, halogenoalkyl or arylalkyl, $R^7$ represents hydrogen, alkyl, halogenoalkyl, cycloalkyl, cycloalkylalkyl, aryl or arylalkyl, $R^8$ represents alkyl or halogenoalkyl, $R^9$ represents hydrogen, alkyl, halogenoalkyl, cycloalkyl, or cycloalkylalkyl; or represents optionally halogen-, alkyl-, halogenoalkyl-, alkoxy-, halogenoalkoxy-, alkylthio-, halogenoalkylthio-substituted aryl, arylalkyl, or saturated or unsaturated heterocyclyl or heterocyclylalkyl having 1 to 4 heteroatoms selected from the group consisting of nitrogen, oxygen and sulphur, $R^{10}$ represents halogen, alkyl, alkylcarbonyl, alkoxycarbonyl, cycloalkyl, or cycloalkylalkyl; or represents aryl or arylalkyl that are optionally substituted in the aryl moiety by halogen or alkyl, $R^{11}$ represents hydrogen or alkyl, $R^{12}$ and $R^{13}$ independently of one another represent hydrogen, hydroxyl, alkyl or alkoxy, $R^{14}$ represents hydrogen, alkyl or halogenoalkyl, $R^{15}$ represents hydrogen, alkyl, alkoxy, cyano or dialkylamino, $R^{16}$ represents hydrogen; represents optionally halogen-, amino-, hydroxyl-, cyano-, nitro-, alkoxy-, halogenoalkoxy-, alkylthio-, halogenoalkylthio-, alkoxycarbonyl-, alkenyloxy-carbonyl-, alkylcarbonyloxy-, alkenylcarbonyloxy-, oxyalkyleneoxy-, oxetanyl-, dioxanyl-, oxazolidinyl-, dioxolanyl-, aryloxy-, halogenoaryloxy-, —CONR$^4$R$^5$—, —NR$^4$R$^5$—, —ONR$^4$R$^5$—, or —C(R$^{14}$)=N—OR$^{14}$-substituted alkyl, alkenyl, or alkynyl; represents optionally halogen-, alkyl-, halogenoalkyl-, alkoxy-, halogenoalkoxy-, alkylthio-, halogenoalkylthio-, alkoxycarbonyl-, alkylcarbonyloxy-substituted aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen, and sulphur; represents —NR$^4$R$^5$; represents Q; or represents optionally substituted aryl, arylalkyl, cycloalkyl, cycloalkylalkyl, or saturated or unsaturated heterocyclyl or heterocyclylalkyl having 1 to 4 heteroatoms from the group consisting of nitrogen, oxygen and sulphur, where the substituents are those mentioned above or are hydroxyl or nitro, $R^{17}$ represents hydrogen or alkyl, $R^{18}$ represents hydrogen, hydroxyl, amino, alkyl, or alkenyl; represents optionally halogen-, hydroxyl-, alkyl-, halogenoalkyl-, alkoxy-, halogenoalkoxy-, alkylthio-, halogenoalkylthio-, or oxyalkyleneoxy-substituted cycloalkyl, cycloalkylalkyl, aryl, arylalkyl, or heteroaryl or heteroarylalkyl having 1 to 4 heteroatoms selected from the group consisting of nitrogen, oxygen, and sulphur; represents —S(O)$_p$R$^3$, —OR$^{14}$, or —NR$^4$R$^5$; represents alkyl or alkenyl, each of which is substituted by identical or different substituents selected from the group consisting of halogen, amino, hydroxyl, cyano, nitro, alkoxy, halogenoalkoxy, alkylthio, halogenoalkylthio, alkoxycarbonyl, and alkenyloxycarbonyl; or represents optionally substituted cycloalkyl, cycloalkylalkyl, aryl, arylalkyl, or heteroaryl or heteroarylalkyl having 1 to 4 heteroatoms selected from the group consisting of nitrogen, oxygen, and sulphur, where the substituents are those mentioned above or are nitro or alkoxycarbonyl, or $R^{17}$ and $R^{18}$ together with the nitrogen atom to which they are attached represent a 5- or 6-membered saturated or unsaturated heterocycle that optionally contains 1 to 2 further heteroatoms selected from the group consisting of nitrogen, oxygen, and sulphur and is optionally substituted by alkyl, and Q represents one of the groups

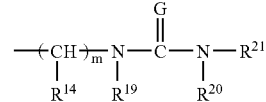
(Q$^1$)

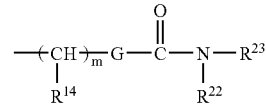
(Q$^2$)

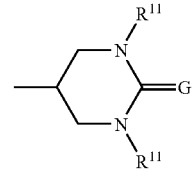
(Q$^3$)

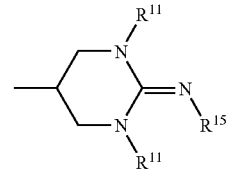
(Q$^4$)

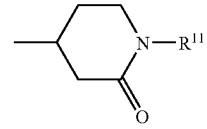
(Q$^5$)

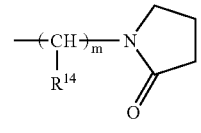
(Q$^6$)

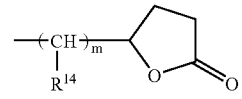
(Q$^7$)

-continued

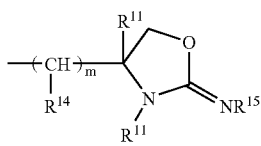
(Q⁸)

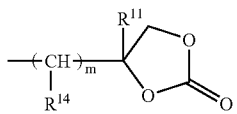
(Q⁹)

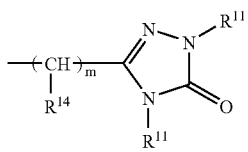
(Q¹⁰)

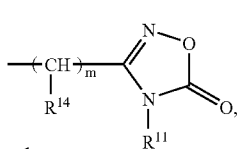
(Q¹¹)

where
each $R^{11}$ may have identical or different meanings when two or more $R^{11}$ are present in the same heterocyclic group,
m represents 0, 1, 2 or 3, where the repeat unit —(CHR$^{14}$)— in the side chain of a heterocyclic grouping may have identical or different meanings when m represents 2 or 3,
G represents oxygen or sulphur,
$R^{19}$ and $R^{20}$ independently of one another represent hydrogen, alkyl or $R^{19}$ and $R^{20}$ together represent alkylene,
$R^{21}$ represents hydrogen; represents optionally alkylcarbonyloxy- or alkoxy-substituted alkyl; or represents optionally halogen-, cyano-, alkyl-, halogenoalkyl-, alkylcarbonyl-, alkoxycarbonyl-, or alkylene-substituted aryl,
$R^{22}$ represents hydrogen, alkyl or alkoxyalkyl, and
$R^{23}$ represents hydrogen, amino, alkyl or alkoxyalkyl.
comprising
(i) for pyridylpyrimidines of the formula (I-a)

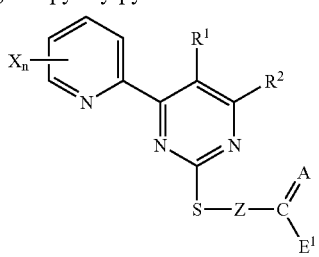
(I-a)

in which $R^1$, $R^2$, X, n, Z, A, and E have the meanings given for formula (I),
(A) reacting a thiol of formula (II)

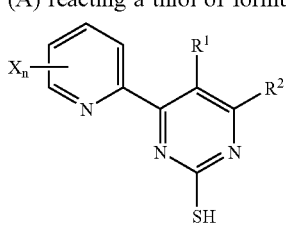
(II)

in which $R^1$, $R^2$, X, and n have the meanings given for formula (I-a),
with a halogen compound of formula (III)

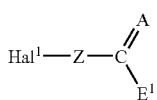
(III)

in which
Z, A, and $E^1$ have the meanings given for formula (I-a), and
Hal$^1$ represents halogen,
optionally in the presence of a diluent and optionally in the presence of an acid binder, or
(B) reacting a halogenopyrimidine of formula (IV)

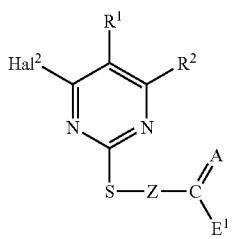
(IV)

in which
$R^1$, $R^2$, Z, A, and $E^1$ have the meanings given for formula (I-a), and
Hal$^2$ represents halogen,
with a pyridine compound of formula (V)

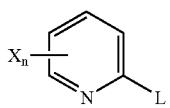
(V)

in which
X and n have the meanings for formula (I-a), and
L represents Sn(alkyl)$_3$, Sn(aryl)$_3$, ZnBr or ZnCl,
optionally in the presence of a diluent and optionally in the presence of a catalyst;
(ii) for pyridylpyrimidines of formula (I-b)

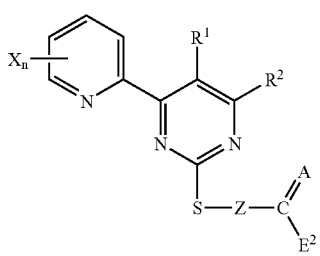
(I-b)

in which
$R^1$, $R^2$, X, n, Z, and A have the meanings given for formula (I), and
$E^2$ represents —NR$^{17}$R$^{18}$,
(1) in a first step, treating a pyridylpyrimidine of formula (I-c)

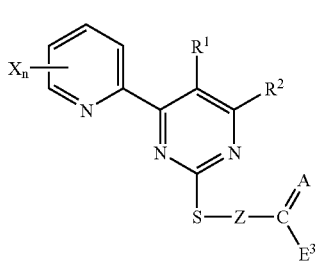
(I-c)

in which
R$^1$, R$^2$, X, n, Z and A have the meanings given for formula (I-b),
E$^3$ represents —OR$^{16}$, and
R$^{16}$ represents hydrogen; represents optionally halogen-, amino-, hydroxyl-, cyano-, nitro-, alkoxy-, halogeno alkoxy-, alkylthio-, halogenoalkylthio-, alkoxycarbonyl-, alkenyloxy-carbonyl-, alkylcarbonyloxy-, alkenyl carbonyloxy-, oxyalkyleneoxy-, oxetanyl-, dioxanyl-, oxazolidinyl-, dioxolanyl-, aryloxy-, halogenoaryloxy-, —CONR$^4$R$^5$-, —NR$^4$R$^5$-, —ONR$^4$R$^5$-, or —C(R$^{14}$)=N—OR$^{14}$-substituted alkyl, alkenyl, or alkynyl; represents optionally halogen-, alkyl-, halogenoalkyl-, alkoxy-, halogenoalkoxy-, alkylthio-, halogenoalkylthio-, alkoxycarbonyl-, alkylcarbonyloxy-substituted aryl, arylalkyl, cycloalkyl, cycloalkylalkyl, or saturated or unsaturated heterocyclyl or heterocyclylalkyl having 1 to 4 heteroatoms selected from the group consisting of nitrogen, oxygen, and sulphur; represents —NR$^4$R$^5$; represents Q; or represents optionally substituted aryl, arylalkyl, cycloalkyl, cycloalkylalkyl, or saturated or unsaturated heterocyclyl or heterocyclylalkyl having 1 to 4 heteroatoms from the group consisting of nitrogen, oxygen, and sulphur, where the substituents are those mentioned above or are hydroxyl or nitro,
with a base, optionally in the presence of a diluent, to form a compound of formula (I-d)

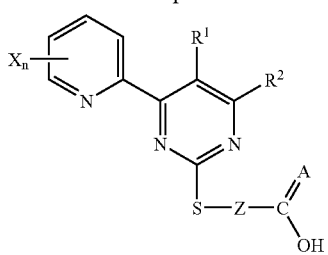
(I-d)

in which R$^1$, R$^2$, X, n, Z, and A have the meanings given for formula (I-b), and
(2) in a second step, reacting the compound of formula (I-d)
with an amine of formula (VI)

HNR$^{17}$R$^{18}$ (VI)

in which R$^{17}$ and R$^{18}$ have the meanings given for formula (I-b), optionally in the presence of a diluent and optionally in the presence of a water-absorbing reagent;
(iii) for pyridylpyrimidines of formula (I-e)

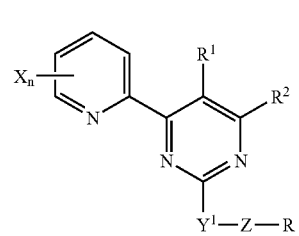
(I-e)

in which R$^1$, R$^2$, X, n, Z, and R have the meanings given for formula (I), oxidizing a pyridylpyrimidine of formula (I-f)

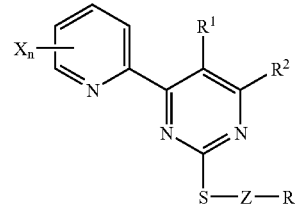
(I-f)

in which R$^1$, R$^2$, X, n, Z, and R have the meanings given for formula (I-e),
with an oxidizing agent, optionally in the presence of a diluent, optionally in the presence of an acid binder, and optionally in the presence of a catalyst;
(iv) for pyridylpyrimidines of formula (I-g)

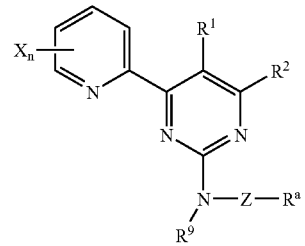
(I-g)

in which
R$^1$, R$^2$, X, n, Z, and R$^9$ have the meanings given for formula (I),
R$^a$ represents one of the groups

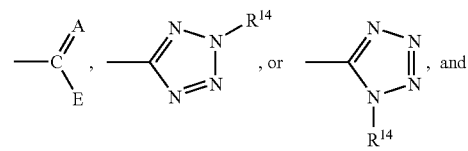

R$^{14}$ represents hydrogen, alkyl, or halogenoalkyl,
reacting a methylsulphonylpyrimidine of formula (VII)

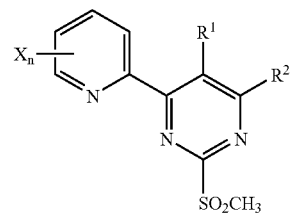
(VII)

in which $R^1$, $R^2$, X, and n have the meanings given for formula (I-g) with an amine of formula (VIII)

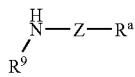
(VIII)

in which Z, $R^9$, and $R^a$ have the meanings given for formula (I-g), optionally in the presence of a diluent and optionally in the presence of a base;

(v) for pyridylpyrimidines of formula (I-h)

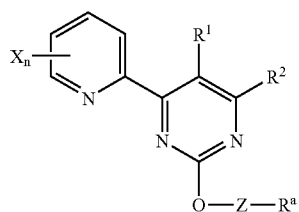
(I-h)

in which
$R^1$, $R^2$, X, n, and Z have the meanings given for formula (I),
$R^a$ represents one of the groups

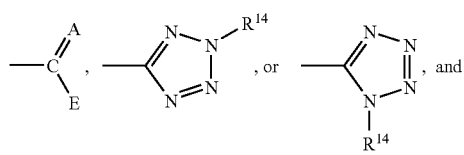

$R^{14}$ represents hydrogen, alkyl, or halogenoalkyl, reacting a methylsulphonylpyrimidine of formula (VII)

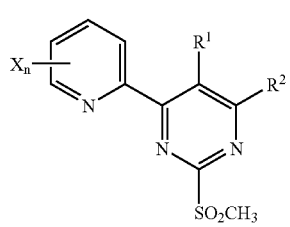
(VII)

in which $R^1$, $R^2$, X and n have the meanings given for formula (I-h), with a hydroxyl compound of formula (IX)

HO-Z-$R^a$ (IX)

in which Z and $R^a$ have the meanings given for formula (I-h), optionally in the presence of a diluent and optionally in the presence of a base;

(vi) for pyridylpyrimidines of formula (I-i)

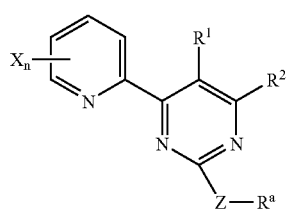
(I-i)

in which
$R^1$, $R^2$, X, n, and Z have the meanings given for formula (I),
$R^a$ represents one of the groups

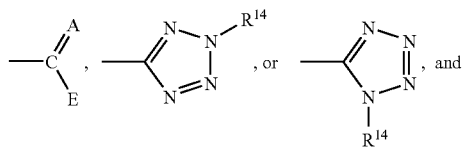

$R^{14}$ represents hydrogen, alkyl, or halogenoalkyl, reacting a pyridine derivative of formula (X)

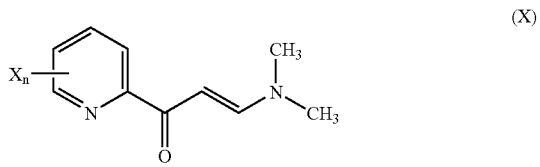
(X)

in which X and n have the meanings given for formula (I-i), or a pyridine derivative of formula (XI)

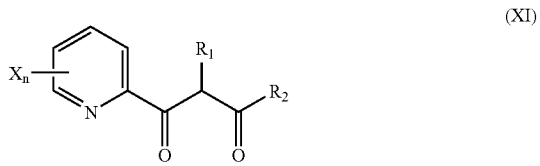
(XI)

in which $R^1$, $R^2$, X, and n have the meanings given for formula (I-i), with an amidine of formula (XII)

(XII)

in which Z and $R^a$ have the meanings given for formula (I-i), optionally in the presence of a diluent and optionally in the presence of a base;

(vii) for pyridylpyrimidines of formula (I-j)

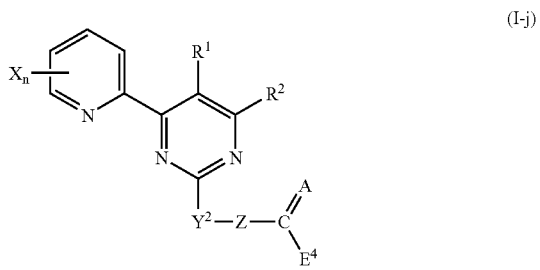
(I-j)

in which
$Y^2$ represents a direct bond, oxygen, sulphur, or —$NR^9$—,
$E^4$ represents —O-M or —S-M, and
$R^1$, $R^2$, X, n, Z, A, M, and $R^9$ have the meanings given for formula (I), reacting a pyridylpyrimidine of formula (I-k)

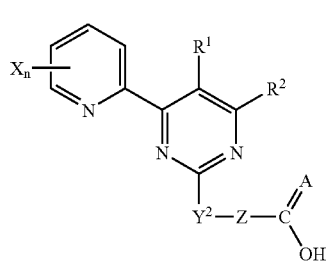
(I-k)

in which R¹, R², X, n, Z, A, and Y² have the meanings given for formula (I-j), with a hydroxide of formula (XIII)

M OH⁻      (XIII)

in which M has the meanings given for formula (I-j), optionally in the presence of a diluent;

(viii) for pyridylpyrimidines of formula (I-l)

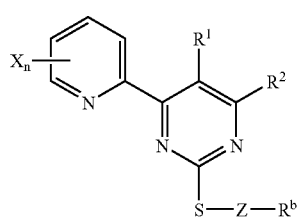
(I-l)

in which
R¹, R², X, n, and Z have the meanings given for formula (I), and
R$^b$ represents one of the groups

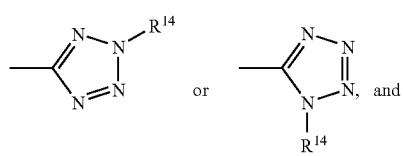
or

R$^{14}$ represents hydrogen, alkyl, or halogenoalkyl, reacting a nitrile of formula (XIV)

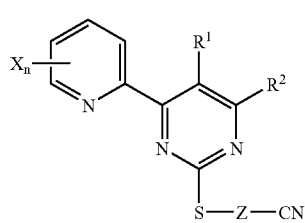
(XIV)

in which R¹, R², X, n, and Z have the meanings given for formula (I-l), with a trialkyltin azide, optionally in the presence of a diluent;

(ix) for pyridylpyrimidines of formula (I-m)

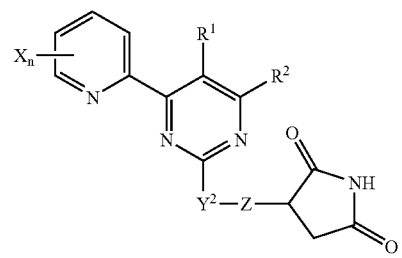
(I-m)

in which
R¹, R², X, n, and Z have the meanings given for formula (I),
Y² represents a direct bond, oxygen, sulphur, or —NR⁹-, and
R⁹ represents hydrogen, alkyl, halogenoalkyl, cycloalkyl, or cycloalkylalkyl; or represents optionally halogen-, alkyl-, halogenoalkyl-, alkoxy-, halogenoalkoxy-, alkylthio-, or halogenoalkylthio-substituted aryl, arylalkyl, or saturated or unsaturated heterocyclyl or heterocyclylalkyl having 1 to 4 heteroatoms selected from the group consisting of nitrogen, oxygen, and sulphur,
hydrogenating a pyridylpyrimidine of formula (I-n)

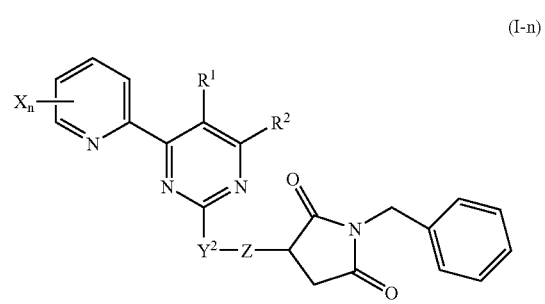
(I-n)

in which R¹, R², X, n, Z, and y² have the meanings given for formula (I-m),
optionally in the presence of a diluent and optionally in the presence of a catalyst; and (x) for pyridylpyrimidines of formula (I-o)

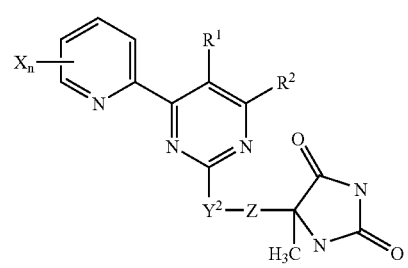
(I-o)

in which

R¹, R², X, n, and Z have the meanings given for formula (I),

Y² represents a direct bond, oxygen, sulphur, or —NR⁹-, and

R⁹ represents hydrogen, alkyl, halogenoalkyl, cycloalkyl, or cycloalkylalkyl; or represents optionally halogen-, alkyl-, halogenoalkyl-, alkoxy-, halogenoalkoxy-, alkylthio-, or halogenoalkylthio-substituted aryl, arylalkyl, or saturated or unsaturated heterocyclyl or heterocyclylalkyl having 1 to 4 heteroatoms selected from the group consisting of nitrogen, oxygen, and sulphur, reacting a keto compound of formula (XV)

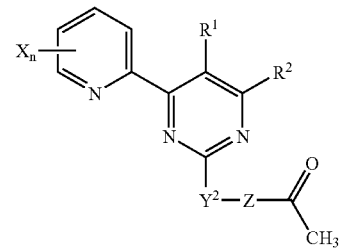

(XV)

in which R¹, R², X, n, Z, and Y² have the meanings given for formula (I-m), with ammonium carbonate and potassium cyanide, optionally in the presence of a diluent.

* * * * *